US012630647B2

(12) United States Patent
Dedi et al.

(10) Patent No.: US 12,630,647 B2
(45) Date of Patent: May 19, 2026

(54) ANTIBODIES AGAINST KLK5

(71) Applicant: UCB BIOPHARMA SRL, Brussels (BE)

(72) Inventors: Neesha Dedi, Slough (GB); Peter Charles Elliott, Slough (GB); Seppe Frans Roman Leysen, Slough (GB); Sean Mason, Slough (GB); David James McMillan, Slough (GB); Gillian Claire Ness, Slough (GB); Niccolo Pengo, Slough (GB); Martin Anthony Redhead, Slough (GB); Alison Turner, Slough (GB); Kerry Louise Tyson, Slough (GB)

(73) Assignee: UCB BIOPHARMA SRL, Brussels (BE)

(*) Notice: Subject to any disclaimer, the term of this patent is extended or adjusted under 35 U.S.C. 154(b) by 869 days.

(21) Appl. No.: 17/759,986

(22) PCT Filed: Feb. 1, 2021

(86) PCT No.: PCT/EP2021/052245

§ 371 (c)(1),
(2) Date: Aug. 2, 2022

(87) PCT Pub. No.: WO2021/156170

PCT Pub. Date: Aug. 12, 2021

(65) Prior Publication Data

US 2023/0075753 A1 Mar. 9, 2023

(30) Foreign Application Priority Data

Feb. 3, 2020 (GB) ...................................... 2001447

(51) Int. Cl.
*C07K 16/40* (2006.01)
*A61P 17/00* (2006.01)
*C12N 15/63* (2006.01)

(52) U.S. Cl.
CPC .............. *C07K 16/40* (2013.01); *A61P 17/00* (2018.01); *C12N 15/63* (2013.01); *C07K 2317/24* (2013.01); *C07K 2317/55* (2013.01); *C07K 2317/565* (2013.01); *C07K 2317/622* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 5,834,290 | A | 11/1998 | Egelrud et al. |
| 5,981,256 | A | 11/1999 | Egelrud et al. |
| 8,309,596 | B2 | 11/2012 | Flohr et al. |
| 9,642,898 | B2 | 5/2017 | Fontana et al. |
| 9,695,194 | B2 | 7/2017 | Wagberg et al. |
| 2007/0071675 | A1 | 3/2007 | Wu et al. |
| 2015/0368665 | A1 | 12/2015 | Bancel et al. |
| 2016/0311903 | A1 | 10/2016 | West et al. |
| 2019/0078160 | A1 | 3/2019 | Dressen et al. |

FOREIGN PATENT DOCUMENTS

| | | | | |
|---|---|---|---|---|
| EP | 0703985 A1 | 4/1996 | |
| EP | 1398326 A2 | 3/2004 | |
| EP | 1716248 A1 | 11/2006 | |
| EP | 1721003 A1 | 11/2006 | |
| EP | 2244728 A2 | 11/2010 | |
| EP | 2245150 A1 | 11/2010 | |
| EP | 2266612 A2 | 12/2010 | |
| EP | 2405925 A1 | 1/2012 | |
| EP | 2731604 A1 | 5/2014 | |
| EP | 2764140 A1 | 8/2014 | |
| KR | 100931997 B1 | 12/2009 | |
| KR | 101409610 B1 | 6/2014 | |
| WO | WO-9108482 A1 * | 6/1991 | ............... C12N 9/16 |
| WO | 9500651 A1 | 1/1995 | |
| WO | 0164747 A1 | 9/2001 | |
| WO | 0244736 A2 | 6/2002 | |
| WO | WO-2004041865 A2 * | 5/2004 | ................ A61P 9/08 |
| WO | 2004075723 A2 | 9/2004 | |
| WO | 2005078123 A1 | 8/2005 | |
| WO | 2007/079096 A2 | 7/2007 | |
| WO | 2013151668 A2 | 10/2013 | |
| WO | 2016/033464 A1 | 3/2016 | |
| WO | 2017123401 A1 | 7/2017 | |
| WO | WO-2018195472 A1 * | 10/2018 | .............. A61P 11/06 |
| WO | 2018232300 A1 | 12/2018 | |
| WO | WO-2019178316 A1 * | 9/2019 | ......... A61K 39/0005 |
| WO | 2021055577 A2 | 3/2021 | |

(Continued)

OTHER PUBLICATIONS

Janeway et al., Immunobiology, 3rd edition, Garland Publishing Inc, 1997, pp. 3:1-3:21.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Lescar, et al. Journal of Biological Chemistry 270.30 (1995): 18067-18076.*
Zhao, et al., "Characterization of a novel modification of aCHO-produced mAb: Evidence for the presence of tyrosine sulfation," mAbs. 9(6):85-995 (2017).

(Continued)

*Primary Examiner* — Michael Szperka
(74) *Attorney, Agent, or Firm* — MEDLER FERRO WOODHOUSE & MILLS PLLC

(57) ABSTRACT

The present invention relates to antibodies which bind and inhibit KLK5 and methods of using the same to treat diseases caused by KLK5 imbalance. In particular, the present invention relates to inhibitory antibodies binding KLK5 and their use in the treatment of Netherton disease, atopic dermatitis and cancer.

24 Claims, 16 Drawing Sheets

Specification includes a Sequence Listing.

(56) References Cited

FOREIGN PATENT DOCUMENTS

WO 2021156171 A1 8/2021
WO 2022/192647 A1 9/2022

OTHER PUBLICATIONS

Zhu, et al., "Persistent kallikrein 5 activation induces atopic dermatitis-like skin architecture independent of PAR2 activity," J Allergy Clin Immunol. 140(5):1310-1322 (2017).
Azouz et al., "Functional role of kallikrein 5 and proteinase-activated receptor 2 in eosinophilic esophagitis," Sci Transl Med 12(545):1-34 (2020).
Barry-Hamilton et al., "Allosteric inhibition of lysyl oxidase-like-2 impedes the development of a pathologic microenvironment," Nature Medicine 16(9):1009-1018 (2010).
Dragatin et al., "Secukinumab distributes into dermal interstitial fluid of psoriasis patients as demonstrated by open flow microperfusion," Experimental Dermatology 25:151-164 (2016).
Fortugno et al., "Proteolytic Activation Cascade of the Netherton Syndrome-Defective Protein, LEKTI, in the Epidermis: Implications for Skin Homeostasis," Journal of Investigative Dermatology 131:2223-2232 (2011).
De Veer et al., "Exploring the active site binding specificity of kallikrein-related peptidase 5 (KLK5) guides the design of new peptide substrates and inhibitors," Biol Chem 397(12):1237-1249 (2016).
Bitoun, et al., "Netherton Syndrome: Disease Expression and Spectrum of SPINK5 Mutations in 21 Families," Society for Investigative Dermatology Inc. 118(2):352-361 (2002).
Brattsand, et al., "A Proteolytic Cascade of Kallikreins in the Stratum Corneum," J Invest Dermatol. 124:198-203 (2005).
Briot, et al., "Kallikrein 5 induces atopic dermatitis-like lesions through PAR2-mediated thymic stromal lymphopoietin expression in Netherton syndrome," Journal of Experimental Medicine. 206(5):1135-1147 (2009).
Caubet, et al., "Degradation of Corneodesmosome Proteins by Two Serine Proteases of the Kallikrein Family, SCTE/KLK5/hK5 and SCCE/KLK7/hK7," The Journal of Investigative Dermatology. 122:1235-1244 (2004).
Corren, et al., "TSLP: from allergy to cancer," Nature Immunology. 20:1603-1609 (2019).
Debela, et al., "Structural Basis of the Zinc Inhibition of Human Tissue Kallikrein 5," J Mol Biol. 373:1017-1031 (2007).
Debela, et al., "Structures and specificity of the human kallikrein-related peptidases KLK 4, 5, 6, and 7," Biol. Chem. 389:623-632 (2008).
Deraison, et al., "LEKTI Fragments specifically inhibit KLK5, KLK7, and KLK14 and control desquamation through a pH-dependent interaction," Molecular Biology of the Cell. 18:3607-3619 (2007).
Di Paolo, et al., "The role of kallikreins in inflammatory skin disorders and their potential as therapeutic targets," Critical Reviews in Clinical Laboratory Sciences (2020).
Dorn, et al., "Assessment of kallikrein-related peptidase 5 (KLK5) protein expression in tumor tissue of advanced ovarian cancer patients by immunohistochemistry and ELISA: correlation with clinical outcome," Am J Cancer Res. 6(1):61-70 (2016).
Egawa, et al., "Multifactorial skin barrier deficiency and atopic dermatitis: Essential topics to prevent the atopic march," J Allergy Clin Immunol. 138(2):350-358 (2016).
Egawa, et al., "Barrier dysfunction in the skin allergy," Allergology International. 67:3-11 (2018).
Eissa, et al., "Human tissue kallikreins as promiscuous modulators of homeostatic skin barrier functions," Biol. Chem. 389:669-680 (2008).
Farady, et al., "Structure of an Fab-protease complex reveals a highly specific non-canonical mechanism of inhibition," J Mol Biol. 380(2):351-360 (2008).
Filippou, et al., "Kallikrein-related peptidases (KLKs) and the hallmarks of cancer," Crit Rev Clin Lab Sci. 53(4):277-291 (2016).
Furio, et al., "Netherton Syndrome: defective kallikrein inhibition in the skin leads to skin inflammation and allergy," Biol Chem. 395(9):945-958 (2014).
Furio, et al., "Transgenic kallikrein 5 mice reproduce major cutaneous and systemic hallmarks of Netherton Syndrome," J Exp Med. 211(3):499-513 (2014).
Furio, et al., "KLK5 Inactivation Reverses Cutaneous Hallmarks of Netherton Syndrome," PLOS Genetics. pp. 1-20 (2015).
Gong, et al., "Quantitative assessment and clinical relevance of kallikrein-related peptidase 5mRNA expression in advanced high-grade serous ovarian cancer," BMC Cancer. 19:696 (2019).
Goettig, et al., "Natural and synthetic inhibitors of kallikrein-related peptidases (KLKs)," Biochimie. 92:1546-1567 (2010).
Hachem, et al., "Serine Protease Activity and Residual LEKTI Expression Determine Phenotype in Netherton Syndrome," Journal of Investigative Dermatology. 126:1609-1621 (2006).
Hovnanian, A., "Netherton syndrome: skin inflammation and allergy by loss of protease inhibition," Cell tissue Res. 351:289-300 (2013).
Kapadia, et al., "Human Kallikrein 13: Production and Purification of Recombinant Protein and Monoclonal and Polyclonal Antibodies, and Development of a Sensitive and Specific Immunofluorometric Assay," Clinical Chemistry. 49(1):77-86 (2003).
Kasparek, et al., "KLK5 and KLK7 Ablation Fully Rescues Lethality of Netherton Syndrome-Like Phenotype," PLOS Genetics. pp. 1-21 (2017).
Kim, et al., "Significance of Skin Barrier Dysfunction in Atopic Dermatitis," Allergy Asthma Immunol Res. 10(3):207-215 (2018).
Komatsu, et al., "Human tissue kallikrein expression in the stratum corneum and serum of atopic dermatitis patients," Experimental Dermatology. 16:513-519 (2007).
Limon, et al., "Multifunctional Serine Protease Inhibitor-Coated Water-Soluble Gold Nanoparticles as a Novel Targeted Approach for the Treatment of inflammatory skin diseases," Bioconjugate Chemistry. 29:1060-1072 (2018).
Loessner, et al., "Kallikrein-related peptidases represent attractive therapeutic targets for ovarian cancer," Expert opinion on therapeutic targets. 22(9):745-763 (2018).
Michael, et al., "Biochemical and Enzymatic Characterization of Human Kallikrein 5 (hK5), a Novel Serine Protease Potentially Involved in Cancer Progression," Journal of Biological Chemistry. 280(15):14628-14635 (2005).
Nauroy, et al., "Kallikreins: Essential epidermal messengers for regulation of the skin microenvironment during homeostasis, repair and disease," Matrix Biology Plus. pp. 1-12 (2019).
Obiezu, et al., "Human Kallikrein 4: enzymatic activity, inhibition, and degradation of extracellular matrix proteins," Biol Chem. 387:749-759 (2006).
Oikonomopoulou, et al., "Kallikrein-mediated cell signalling: targeting proteinase-activated receptors (PARs)," Biol. Chem. 387:817-824 (2006).
Oiso, et al., "LEKTI: Netherton syndrome and Atopic Dermatitis," Current Genetics in Dermatology. Chapter 5, pp. 67-72, Published: Feb. 6, 2013.
Ovaere, et al., "The emerging roles of serine protease cascades in the epidermis," Trends in Biochemical Sciences. 34(9):453-463 (2009).
Prassas, et al., "Unleashing the therapeutic potential of human kallikrein-related serine proteases," Nature Reviews—Drug Discovery. 14:183-202 (2015).
Sarri, et al., "Netherton Syndrome: A Genotype-Phenotype Review," Mol Diagn Ther. 21:137-152 (2017).
Sexton, et al., "Specific inhibition of tissue kallikrein 1 with a human monoclonal antibody reveals a potential role in airway diseases," Biochem J. 422:383-392 (2009).
Shinoda, et al., "Association of KLK5 overexpression with invasiveness of urinary bladder carcinoma cells," Cancer Sci. 98(7):1078-1086 (2007).

(56) References Cited

OTHER PUBLICATIONS

Silverberg, et al., "Inside Out or Outside In: Does Atopic Dermatitis Disrupt Barrier Function or Does Disruption of Barrier Function Trigger Atopic Dermatitis?," Cutis. 96:359-361 (2015).
Sotiropoulou, et al., "Functional Roles of human Kallikrein-related Peptidases," Journal of Biological Chemistry. 284(48):32989-32994 (2009).
Takeichi, et al., "Inherited ichthyosis: Non-syndromic forms," Journal of Dermatology. 43:242-251 (2016).
Two, et al., "Kallikrein 5-Mediated Inflammation in Rosacea : Clinically Relevant Correlations with Acute and Chronic Manifestations in Rosacea and How Individual Treatments May Provide Therapeutic Benefit," Journal of Clinical Aesthetic Dermatology. 7(11):20-25 (2014).
Vahlquist, et al., "Inherited Nonsyndromic Ichthyoses: An Update on Pathophysiology, Diagnosis and Treatment," Am J Clin Dermatol. 19:51-66 (2018).
Voegeli, et al., "Increased mass levels of certain serine proteases in the stratum corneum in acute eczematous atopic skin," International Journal of Cosmetic Science. 33:560-565 (2011).
Weidinger, et al., "Atopic dermatitis," Nature Reviews. Disease Primers. 4:1 (2018).
Wu, et al., "Structural insight into distinct mechanisms of protease inhibition by antibodies," PNAS. 104(50):19784-19789 (2007).
Yamamoto, et al., "Clinical and molecular implications of structural changes to desmosomes and corneodesmosomes," Journal of Dermatology. 45:385-389 (2018).
Yamasaki, et al., "Kallikrein-mediated proteolysis regulates the antimicrobial effects of cathelicidins in skin," The FASEB Journal. 20:2068-2080 (2006).
Yamasaki, et al., "Increased serine protease activity and cathelicidin promotes skin inflammation in rosacea," Nature Medicine. 13(8) : 975-980 (2007).
Yang, et al., "Skin Barrier Abnormalities and Immune Dysfunction in Atopic Dermatitis," Int. J. Mol. Sci. 21:2867 (2020).

* cited by examiner

Fig. 1
A
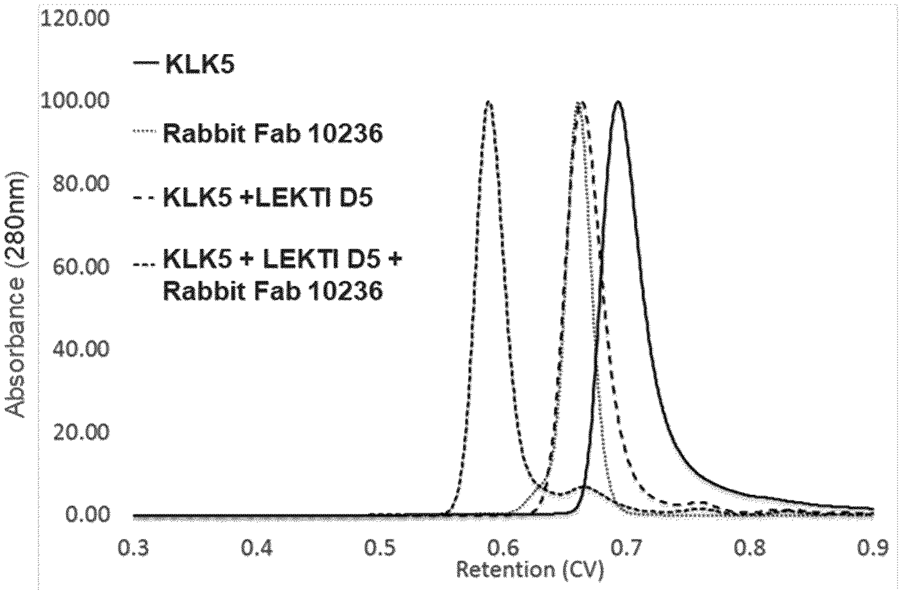
B
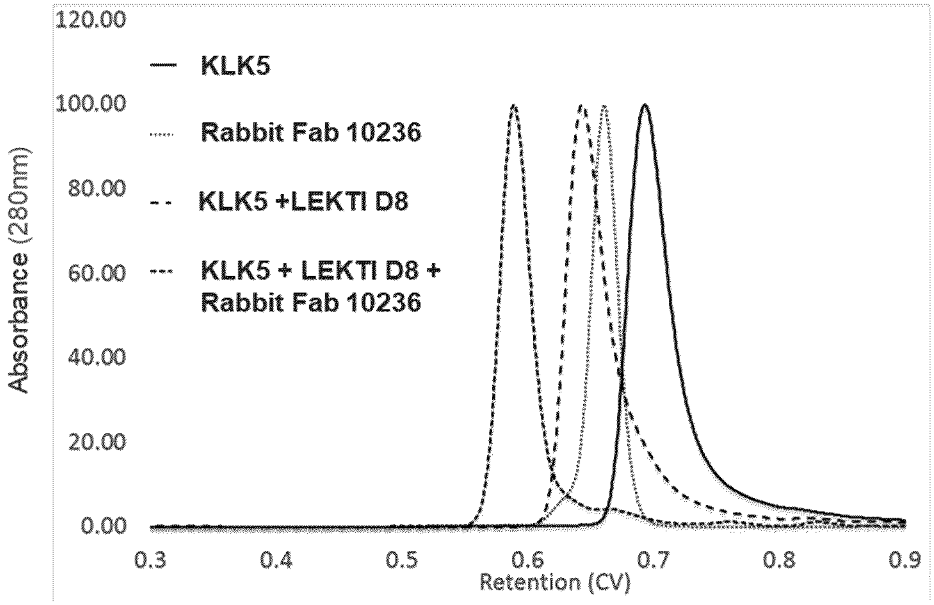

A

B

C

D

```
               1   5   10   15   20   25   30   35   40   45   50   55   60   65   70   75   80   85   90   95   100  105  110  115
Heavy 10236    ~QSVEESGGRLVTPGTPLTLTCTVSGFPLSNYA-MSWVRQAPGKGLEWIGDIYPSDIIDYASWAKGRFTISQTST--TVELKITGPTTEDTATYFCARDNNDYGLDIWGPGTLVTVSS

IGHV4-4        QVQLQESGPGLVKPSGTLSLTCAVSGGSISSSNWWSWVRQPPGKGLEWIGEIYHSGSTNYNPSLKSRVTISVDKSKNQFSLKLSSVTAADTAVYYCAR------YFDYWGQGTLVTVSS

10236gH9       EVQLQESGPGLVKPSGTLSLTCAVSGFPLSNYA-MSWVRQPPGKGLEWIGDIYPSDIIDYASWAKGRVTISQDSSKTQVSLKLSSVTAADTAVYYCARDNNDYGLDIWGQGTLVTVSS
10236gH10      EVQLQESGPGLVKPSGTLSLTCAVSGFPLSNYA-MSWVRQPPGKGLEWIGDIYPSDIIDYASWAKGRVTISVDSSKTQVSLKLSSVTAADTAVYYCARDNNDYGLDIWGQGTLVTVSS
10236gH11      EVQLQESGPGLVKPSGTLSLTCAVSGFPLSNYA-MSWVRQPPGKGLEWIGDIYPSDIIDYASWAKGRVTISQDKSKTQVSLKLSSVTAADTAVYYCARDNNDYGLDIWGQGTLVTVSS
10236gH12      EVQLQESGPGLVKPSGTLSLTCAVSGFPLSNYA-MSWVRQPPGKGLEWIGDIYPSDIIDYASWAKGRVTISQDSSKNQVSLKLSSVTAADTAVYYCARDNNDYGLDIWGQGTLVTVSS
10236gH14      EVQLQESGPGLVKPSGTLSLTCAVSGFPLSNYA-MSWVRQPPGKGLEWIGDIYPSDIIDYASWAKGRFTISQDSSKNQVSLKLSSVTAADTAVYYCARDNNDYGLDIWGQGTLVTVSS
```

Fig. 7

Fig. 10
A
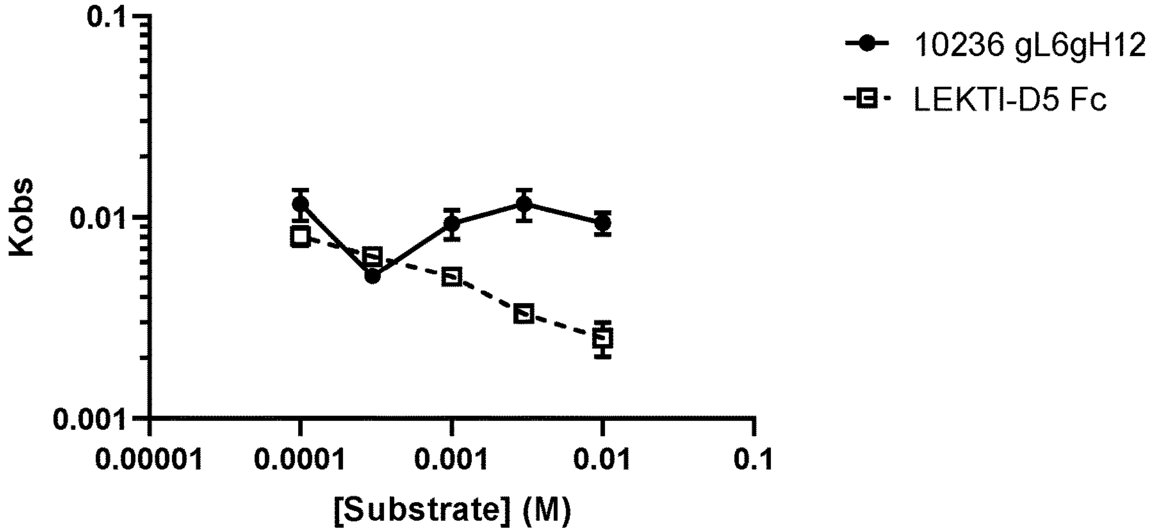
B
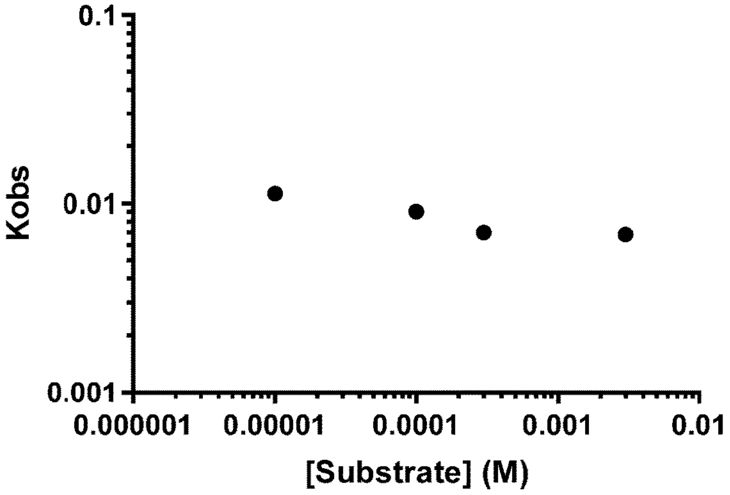

A) Atopic dermatitis skin section
+ control buffer

B) Atopic dermatitis skin section
+ Ab 10236

ANTIBODIES AGAINST KLK5

FIELD OF THE INVENTION

The present invention relates to antibodies which bind and inhibit KLK5 and methods of using the same to treat diseases caused by KLK5 dysregulation. In particular, the present invention relates to anti-KLK5 antibodies and their use in the treatment of Netherton disease, ichthyoses such as congenital ichthyosis, atopic dermatitis and cancer.

BACKGROUND OF THE INVENTION

Kallikrein-related peptidases (known as KLKs) constitute a single family of 15 highly conserved trypsin or chymotrypsin-like serine proteases encoded by the largest uninterrupted cluster of protease-encoding genes (chromosome 19q13.4) in the human genome (Sotiropoulou G. et al., 2009; JBC 284:48, 32989-94).

KLK are synthesized as inactive pre-pro-forms that are proteolytically processed to secrete inactive pro-forms. Such pro-forms are subsequently activated to mature peptidases by specific proteolytic removal of their N-terminal propeptide either by other KLKs or endopeptidase or by autocatalytic cleavage such as for kallikrein 5 (KLK5).

KLK5 is found in several tissues, but it is most abundantly expressed in skin. Along with KLK7, KLK5 is expressed in the upper spinous and granular levels of skin along with KLK7, where keratinocytes undergo terminal differentiation and are transformed in corneocytes that build the stratum corneum. The stratum corneum functions as a barrier to the outside environment and is maintained through constant replacement of corneocytes shed by the process of desquamation. Because KLK5 is capable of activating pro-KLK7 and other kallikreins, its role in desquamation is essential.

Following activation, mature KLK5 is inactivated by the endogenous inhibitor Lymphoepithelial Kazal-type inhibitor (LEKTI) which is encoded by the SPINK5 gene (Chavans P et al., 2005; Nat Genet 37, 56-65). LEKTI contains 15-domain serine protease inhibitor domains forming a tight complex with KLK5. Variation in pH govern this tight interaction with acidic pH releasing active KLK5 from the complex (Deraison C et al. 2007; Mol Biol Cell 18 3607-19).

Loss-of-function mutations in SPINK5 gene causes Netherton syndrome, a rare autosomal recessive skin disease characterized by ichthyosis features with severe inflammation, skin scaling, elevated IgE levels and constant allergic manifestations (Hovnanian A. 2013; Cell Tissue Res 351 289-300). Secondary to epidermal protease hyperactivity, lack of LEKTI causes stratum corneum detachment caused by KLK5 activity on desmoglein and desmosomes which in turn favors high permeability to various allergens causing atopic dermatitis-like lesions. KLK5 activity on KLK7 also contributes to a defective skin barrier leading to allergen and microbe penetration and production of IL-1beta.

$SPINK5^{-/-}$ mice recapitulate a phenotype highly reminiscent of Netherton syndrome replicating cutaneous and inflammatory aspects of the disease (Yant T et al.; 2004, Genes Dev 18 2354-58). $SPINK5^{-/-}$ epidermis from Netherton's syndrome patients displays unopposed KLK5 and KLK7 protease activity which appears to sustain activation of pro-inflammatory and pro-signaling pathways including the KLK5-PAR2-TSLP (thymic stromal lymphopoietin) axis.

In both $SPINK5^{-/-}$ and $KLK5^{-/-}$ mice, the KLK5 knock-out was sufficient to correct such cutaneous manifestation of LEKTI knock-out, illustrating the crucial role of KLK5 in skin homeostasis.

In recent years, several studies have reported a genetic association between atopic dermatitis (AD) and LEKTI polymorphism with abnormal variants of LEKTI being expressed (Hovnanian A. 2013; Cell Tissue Res 351 289-300).

To date, only therapies aimed at replacing LEKTI have been pursued, including gene addition by means of SPINK5 lentiviral or adenoviral vector and autologous grafts of genetically corrected patient keratinocytes (Di W L. Et al.; 2011, Mol Ther 19 408-16).

Therefore, there remains a need for anti-KLK5 therapies, such as passive-immune therapies aimed at inhibiting KLK5 that could exert therapeutic effects in diseases associated with or caused by the dysregulation of KLK5.

SUMMARY OF THE INVENTION

The present invention addresses the above-identified need by providing inhibitory anti-KLK5 antibodies according to the following embodiments.

Embodiment 1: An antibody which binds to kallikrein 5 (KLK5), wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Embodiment 2: The antibody according to Embodiment 1 wherein:

a. the variable light chain comprises a CDR-L1 comprising SEQ ID NO: 1, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Embodiment 3: An antibody which binds to kallikrein 5 (KLK5), wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

Embodiment 4: The antibody according to Embodiment 3, wherein the epitope is characterized by X-ray crystallography.

Embodiment 5: The antibody according to any one of Embodiments 1 to 4, wherein the antibody inhibits or reduces the protease activity of KLK5.

Embodiment 6: The antibody according to any one of Embodiments 1 to 5, wherein the antibody binds to KLK5 when KLK5 is bound to LEKTI, or a fragment of LEKTI.

Embodiment 7: The antibody according to any one of Embodiments 1 to 6, wherein the antibody does not compete with LEKTI, or a fragment of LEKTI, for binding KLK5.

Embodiment 8: The antibody according to any one of Embodiments 1 to 7, wherein the antibody forms a complex with KLK5 bound to LEKTI, or a fragment of LEKTI.

Embodiment 9: The antibody according to any one of Embodiments 6 to 8 wherein the fragment of LEKTI is human LEKTI domain 5 comprising amino acids 1 to 64 of SEQ ID NO: 54 or LEKTI domain 8 comprising amino acids 1 to 71 of SEQ ID NO: 61.

Embodiment 10: The antibody according to any one of the preceding Embodiments wherein the antibody binds human KLK5, preferably human KLK5 comprising SEQ ID NO: 53 and cynomolgus monkey (cyno) KLK5, preferably cyno KLK5 comprising SEQ ID NO: 60.

Embodiment 11: The antibody according to any one of the preceding Embodiments wherein the antibody does not bind human or cyno kallikrein 2 (KLK2); or human or cyno kallikrein 4 (KLK4); or human or cyno kallikrein 7 (KLK7).

Embodiment 12: The antibody according to any one of Embodiments 3 to 11, wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, preferably a CDR-L1 comprising SEQ ID NO: 1, a CDR-L2 comprising SEQ ID NO: 2 and a CDR-L3 comprising SEQ ID NO: 3; and b. the variable heavy chain comprises a CDR-H1 comprising SEQ ID NO: 4, a CDR-H2 comprising SEQ ID NO: 5 and a CDR-H3 comprising SEQ ID NO: 6.

Embodiment 13: The antibody according to any one of the preceding Embodiments wherein the antibody is a chimeric or humanized antibody.

Embodiment 14: The antibody according to any one of the preceding Embodiments, wherein the antibody is a full-length antibody.

Embodiment 15: The antibody according to Embodiment 13, wherein the full-length antibody is selected from an IgG1, IgG4 or IgG4P.

Embodiment 16: The antibody according to any one of Embodiments 1 to 13, wherein the antibody is selected from a Fab, a Fab', a $F(ab)_2$, a scFv, a dAb or a $V_{HH}$.

Embodiment 17: The antibody according to any one of Embodiments 1 to 16, wherein the antibody comprises:

a. a variable light chain comprising SEQ ID NO: 7 or 11 or 15 or 19 or 23; and/or b. a variable heavy chain comprising SEQ ID NO: 9 or 27 or 31 or 35 or 39 or 43.

Embodiment 18: The antibody according to any one of Embodiments 1 to 15 or 17, wherein the antibody comprises:

a. a light chain comprising SEQ ID NO: 13 or 17 or 21 or 25; and b. a heavy chain comprising SEQ ID NO: 29 or 33 or 37 or 41 or 45.

Embodiment 19: The antibody according to Embodiments 17 or 18, wherein amino acid residue glutamine (Gln; Q) in L-CDR1 at position 24 with reference to SEQ ID NO: 15 or 17 is replaced by arginine (Arg; R) or by lysine (Lys; K).

Embodiment 20: The antibody according to any one of the preceding Embodiments wherein KLK5 is human KLK5 comprising SEQ ID NO: 51 or 52 or 53 or cyno KLK5 comprising SEQ ID NO: 60.

Embodiment 21: An antibody which:

a. Competes for binding KLK5 with the antibody according to any one of Embodiments 1 to 20; and/or b. cross-blocks or is cross-blocked by the antibody according to any one of Embodiments 1 to 20 for binding KLK5; and/or c. binds KLK5 to the same epitope as the antibody according to any one of Embodiments 1 to 20; and/or d. comprises a heavy chain variable region having at least 90% identity or similarity to the sequence according to SEQ ID NO: 29 or 33 or 37 or 41 or 45; and/or e. comprises a light chain variable region having at least 90% identity or similarity to the sequence according to SEQ ID NO: 13 or 17 or 21 or 25.

Embodiment 22: An isolated polynucleotide encoding the antibody according to any one of Embodiments 1 to 20.

Embodiment 23: The isolated polynucleotide according to Embodiment 22, wherein the polynucleotide encodes:

a. a light chain variable region, wherein the polynucleotide:

i. is at least 90% identical to SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or ii. comprises SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or iii. consists essentially of SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or b. a heavy chain variable region, wherein the polynucleotide:

i. is at least 90% identical to SEQ ID NO: 10 or 28 or 32 or 36 or 40 or 44; or ii. comprises SEQ ID NO: 10 or 28 or 32 or 36 or 40 or 44; or iii. consists essentially of SEQ ID NO: 10 or 28 or 32 or 36 or 40 or 44; or c. a light chain, wherein the polynucleotide:

i. is at least 90% identical to SEQ ID NO: 14 or 18 or 22 or 26 or 65 or 67 or 100 or 101 or 102 or 103 or 104; or ii. comprises SEQ ID NO: 14 or 18 or 22 or 26 or 65 or 67 or 100 or 101 or 102 or 103 or 104; or iii. consists essentially of SEQ ID NO: 14 or 18 or 22 or 26 or 65 or 67 or 101 or 102 or 103 or 104; or d. a heavy chain, wherein the polynucleotide:

i. is at least 90% identical to SEQ ID NO: 30 or 34 or 38 or 42 or 46; or ii. comprises SEQ ID NO: 30 or 34 or 38 or 42 or 46; or iii. consists essentially of SEQ ID NO: 30 or 34 or 38 or 42 or 46.

Embodiment 24: A cloning or expression vector comprising one or more polynucleotides according to any one of Embodiments 22 or 23.

Embodiment 25: A host cell comprising:

a. one or more polynucleotides according to any one of Embodiments 22 or 23 or b. one or more expression vectors according to Embodiment 24.

Embodiment 26: A process for the production of an antibody according to any one of Embodiments 1 to 20, comprising culturing the host cell according to Embodiment 25 under suitable conditions for producing the antibody and isolating the antibody produced by the host cell.

Embodiment 27: A pharmaceutical composition comprising the antibody according to any one of Embodiments 1 to 20 and one or more pharmaceutically acceptable carriers, excipients of diluents.

Embodiment 28: The antibody or antigen-binding fragment thereof according to any one of Embodiments 1 to 20 or the pharmaceutical composition according to Embodiment 27 for use in therapy.

Embodiment 29: The antibody according to any one of Embodiments 1 to 20 or the pharmaceutical composition according to Embodiment 27 for use in the treatment of a disease characterized by dysregulation of KLK5 or by dysregulation of inhibition of KLK5.

Embodiment 30: The antibody for use according to Embodiment 29 wherein the disease is selected from Netherton's Syndrome, Atopic Dermatitis, Ichthyoses, Rosacea, Asthma or Cancer, such as ovarian cancer or bladder cancer or a combination thereof.

Embodiment 31: The antibody for use according to Embodiment 30 wherein the disease is Netherton's Syndrome.

Embodiment 32: The antibody for use according to Embodiment 30 wherein the disease is Atopic Dermatitis.

Embodiment 33: A method of treating diseases characterized by dysregulation of KLK5 or by dysregulation of inhibition of KLK5 in a patient comprising administering to said patient a therapeutically effective amount of an antibody according to any one of Embodiments 1 to 20 or the pharmaceutical composition according to Embodiment 27.

Embodiment 34: The method according to Embodiment 33 wherein the disease is selected from Netherton's Syndrome, Atopic Dermatitis, Ichthyoses, Rosacea, Asthma or Cancer, such as ovarian cancer or bladder cancer.

Embodiment 35: The antibody for use according to Embodiment 34 wherein the disease is Netherton's Syndrome.

Embodiment 36: The antibody for use according to Embodiment 34 wherein the disease is Atopic Dermatitis.

BRIEF DESCRIPTION OF THE DRAWINGS

FIG. 1. Size exclusion chromatography (SEC). Panels A and B show the elution profiles of human KLK5 alone (solid trace, far right), rabbit Fab antibody 10236 alone (dotted trace), human KLK5+LEKTI D5 (long dashed trace, panel A) or human KLK5+LEKTI D8 (long dashed trace, panel B) and human KLK5+LEKTI D5+rabbit Fab antibody 10236 (short dashed trace, far left, panel A) or human KLK5+LEKTI D8+rabbit Fab antibody 10236 (short dashed trace, far left, panel B).

FIG. 7. Humanization of rabbit variable heavy chain sequence of antibody 10236. Grafts 10236gH9, gH10, gH11, gH12 and gH14 are humanized grafts of rabbit variable heavy chain of antibody 10236 using IGHV4-4 human germline as the acceptor framework. CDRs are shown in bold/underlined. Donor residues are shown in bold/italic and are grey shaded: F67, Q71, S73, T76 and V78.

FIG. 10. Mechanism of action of antibody 10236 gL6gH12 (A) and the parental rabbit antibody (B). $K_{obs}$ values were plotted against substrate concentration for antibody 10236 and the LEKTI D5 rabbit Fc protein (the latter in (A) only). Data shown is for 10 nM antibody 10236 and 2 nM LEKTI D5 rabbit Fc. The slopes show that antibody 10236 is a non-competitive inhibitor whilst the LEKTI protein is a competitive inhibitor.

DETAILED DESCRIPTION OF THE INVENTION

Figure 2:
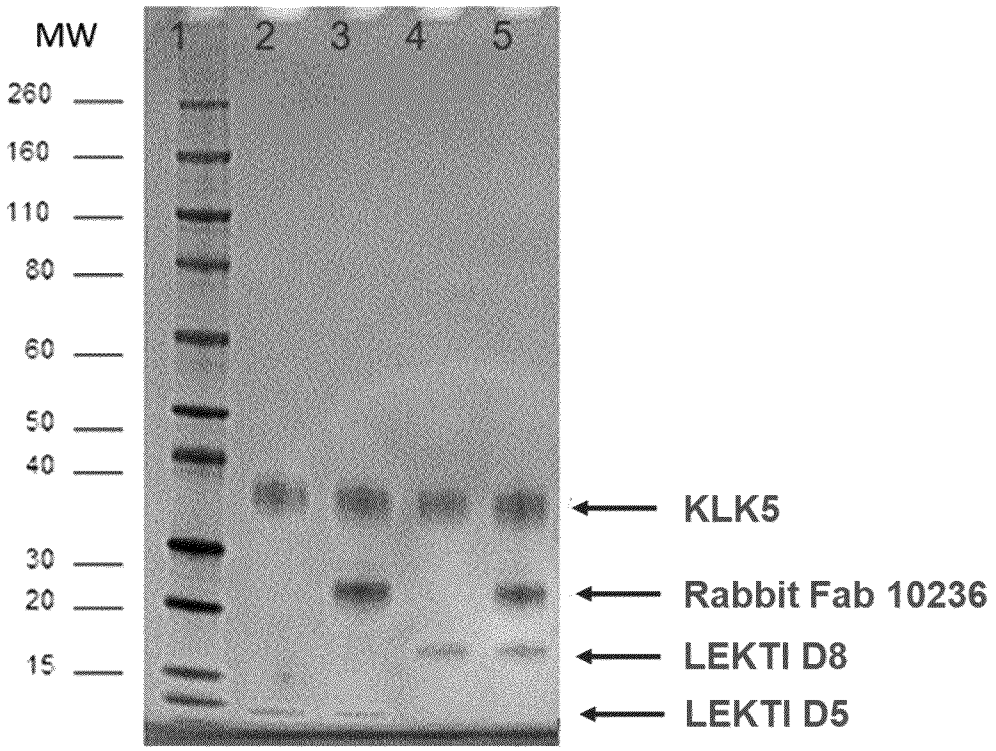
FIG. 2. SDS-PAGE of peak fractions from the SEC shown in FIGS. 1A and 1B. Lane 1, MW markers. Lane 2, peak fraction of the binary complex human KLK5+LEKTI D5. Lane 3, peak fraction of the ternary complex KLK5+LEKTI D5+rabbit Fab antibody 10236. Lane 4, peak fraction of the binary complex KLK5+LEKTI D8. Lane 5, peak fraction of the ternary complex of KLK5+LEKTI D8+rabbit Fab antibody 10236.

The present disclosure will now be described with respect to particular non-limiting aspects and embodiments thereof and with reference to certain figures and examples.

Technical terms are used by their common sense unless indicated otherwise. If a specific meaning is conveyed to certain terms, definitions of terms will be given in the context of which the terms are used.

Where the term "comprising" is used in the present description and claims, it does not exclude other elements. For the purposes of the present disclosure, the term "consisting of" is considered to be a preferred embodiment of the term "comprising of".

Where an indefinite or definite article is used when referring to a singular noun, e.g. "a", "an" or "the", this includes a plural of that noun unless something else is specifically stated.

As used herein, the terms "treatment", "treating" and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. Treatment thus covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

A "therapeutically effective amount" refers to the amount of a KLK5 antibody that, when administered to a mammal or other subject for treating a disease, is sufficient to produce such treatment for the disease. The therapeutically effective amount will vary depending on the anti-KLK5 antibody, the disease and its severity and the age, weight, etc., of the subject to be treated.

The term "isolated" means, throughout this specification, that the antibody or polynucleotide, as the case may be, exists in a physical milieu distinct from that in which it may occur in nature.

In a first aspect of the present invention, there is provided an antibody which binds to kallikrein 5 (KLK5), wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Preferably, the antibody which binds to kallikrein 5 (KLK5) and which comprises a variable light chain comprises a CDR-L1 comprising SEQ ID NO: 1.

Hence, in a preferred embodiment of the present invention, the antibody which binds to kallikrein 5 (KLK5) which antibody comprises a variable light chain and a variable heavy chain, is characterized by a variable light chain which comprises a CDR-L1 comprising SEQ ID NO: 1, a CDR-L2 comprising SEQ ID NO: 2 and a CDR-L3 comprising SEQ ID NO: 3; and a variable heavy chain which comprises a CDR-H1 comprising SEQ ID NO: 4, a CDR-H2 comprising SEQ ID NO: 5 and a CDR-H3 comprising SEQ ID NO: 6.

Kallikrein 5 (KLK5, KLK-L2, SCTE or any other known synonym) has trypsin-like activity. It is expressed in pre-pro-form and comprises a 29 amino acid signal peptide according to the bioinformatics tool SignalP 5.0 (http://www.cbs.dtu.dk/services/SignalP/index.php), followed by a 37 amino acid pro peptide sequence. Cleavage of the pro peptide produces the active mature enzyme consisting of 237 amino acids harboring an active site with a catalytic triad of residues typical of a serine-protease (Michael I. P et al., 2005; JBC 280:15, 14628-35).

Unless otherwise specified, the term KLK5 refers to any native pre- and pro-forms (i.e. unprocessed KLK5 comprising the signal sequence and activation peptide), alternative splicing or natural variants, mutants and KLK5 from other species (mouse, cynomolgus monkey, etc.,) and active KLK5 (resulting from auto-cleavage or otherwise). When human KLK5 is specified, human KLK5 comprises the sequence given in SEQ ID NO: 53 (active human KLK5). Other KLK5 sequences referred herein comprises SEQ ID NO: 52 (human KLK5 pro-form lacking the signal sequence) or SEQ ID NO: 51 (full length human KLK5 with signal and pro-peptide sequences), the sequence corresponding to Uniprot Q9Y337 or natural variants comprising mutations at positions 55 and 153 (with reference to SEQ ID NO: 51). Examples of these mutations comprises human KLK5 comprising residues 23 to 293 according to SEQ ID NO: 51 having mutations Gly to Arg change at residue 55 (G55R) and/or Asp to Asn change at residue 153 (D153N).

The antibody according to the present invention comprises complementarity determining regions (CDRs), three from a heavy chain and three from a light chain. Generally, the CDRs are in a framework and together form a variable region. By convention, the CDRs in the heavy chain variable region of an antibody or antigen-binding fragment thereof are referred as CDR-H1, CDR-H2 and CDR-H3 and in the light chain variable regions as CDR-L1, CDR-L2 and CDR-L3. They are numbered sequentially in the direction from the N-terminus to the C-terminus of each chain.

CDRs are conventionally numbered according to a system devised by Kabat et al. This system is set forth in Kabat et al., 1991, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus, unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

In addition to the CDR loops, a fourth loop exists between CDR-2 (CDR-L2 or CDR-H2) and CDR-3 (CDR-L3 or CDR-H3) which is formed by framework 3 (FR3). The Kabat numbering system defines framework 3 as positions 66-94 in a heavy chain and positions 57-88 in a light chain.

In one preferred embodiment, the antibody comprises a light chain variable region comprising a CDR-L1 comprising SEQ ID NO: 1, a CDR-L2 comprising SEQ ID NO: 2 and a CDR-L3 comprising SEQ ID NO: 3, and a heavy chain variable region comprising a CDR-H1 comprising SEQ ID NO: 4, a CDR-H2 comprising SEQ ID NO: 5 and a CDR-H3 comprising SEQ ID NO: 6.

In another embodiment, the antibody comprises a light chain variable region comprising a CDR-L1 comprising SEQ ID NO: 62; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6.

In another embodiment, the antibody comprises a light chain variable region comprising a CDR-L1 comprising SEQ ID NO: 63; a CDR-L2 comprising SEQ ID NO: 2 and a CDR-L3 comprising SEQ ID NO: 3; and a heavy chain variable region comprising a CDR-H1 comprising SEQ ID NO: 4; a CDR-H2 comprising SEQ ID NO: 5 and a CDR-H3 comprising SEQ ID NO: 6.

The antibody comprising such CDR sequences are particularly inventive because they provide for an antibody with high affinity for KLK5, preferably human KLK5, high inhibition for KLK5 biological function and high stability which is essential for manufacturability. For example, mutations of the motif "NS" to "ND" (with reference to SEQ ID NO: 15) in the CDR-L3 comprising SEQ ID NO: 3 (QQGYTNSNIINT;) resulted in a dramatic decrease in KLK5 affinity.

In a second aspect of the present invention, there is provided an antibody which binds to kallikrein 5 (KLK5), wherein the antibody binds to an epitope of human KLK5 comprising amino acid residues Arg87 (36), Ala107 (56), Arg110 (59), Lys111 (60), Lys112 (61), Val113 (62), Val137 (86), Lys138 (87), Ser139 (88), Ile140 (89), Pro141 (90), His142 (91), Pro143 (92), Tyr145 (94), Ser146 (95) and His147 (96) with reference to SEQ ID NO: 51. Preferably the epitope is characterized by X-ray crystallography. The numbers in parentheses correspond to the protease nomenclature.

In preferred embodiment, the antibody which binds to kallikrein 5 (KLK5), wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, preferably, SEQ ID NO: 1, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Within the present invention, the term "epitope" is used interchangeably for both conformational and linear epitopes. A conformational epitope is composed of discontinued sections of the antigen's amino acid primary sequence and a linear epitope is formed by a sequence formed by continuous amino acids.

The epitope can be identified by any suitable epitope mapping method known in the art in combination with any one of the antibodies provided by the present invention. Examples of such methods include screening peptides of varying lengths derived from full length KLK5 for binding to the antibody or fragment thereof of the present invention and identifying the smallest fragment that can specifically bind to the antibody containing the sequence of the epitope recognized by the antibody. KLK5 peptides may be produced synthetically or by proteolytic digestion of the KLK5. Peptides that bind the antibody can be identified by, for example, mass spectrometric analysis. Methodologies such as NMR spectroscopy or X-ray crystallography can be used to identify the epitope bound by an antibody. Typically, when the epitope determination is performed by X-ray crystallography, amino acid residues of the antigen within 4 Å from CDRs are considered to be amino acid residues part of the epitope. Once identified, the epitope may serve for preparing fragments which bind an antibody of the present invention and, if required, used as an immunogen to obtain additional antibodies which bind the same epitope.

The epitope as indicated in the aspects and embodiments describing the present invention is preferably an epitope characterized by X-ray crystallography.

The term 'antibody' as used in the context of the present disclosure includes whole antibodies and functionally active fragments thereof i.e., molecules that contain an antigen binding domain that specifically binds an antigen, also termed antigen-binding fragments. Features described herein with respect to antibodies also apply to antigen-binding fragments unless context dictates otherwise. The antibody may be (or derived from) monoclonal, multivalent, multi-specific, bispecific, fully human, humanized or chimeric.

Whole antibodies, also known as "immunoglobulins (Ig)" generally relate to intact or full-length antibodies i.e. comprising the elements of two heavy chains and two light chains, inter-connected by disulphide bonds, which assemble to define a characteristic Y-shaped three-dimensional structure. Classical natural whole antibodies are monospecific in that they bind one antigen type, and bivalent in that they have two independent antigen binding domains. The terms "intact antibody", "full-length antibody" and "whole antibody" are used interchangeably to refer to a monospecific bivalent antibody having a structure similar to a native antibody structure, including an Fc region as defined herein.

Each light chain is comprised of a light chain variable region (abbreviated herein as VL) and a light chain constant region (CL). Each heavy chain is comprised of a heavy chain variable region (abbreviated herein as VH) and a heavy chain constant region (CH) constituted of three constant domains CH1, CH2 and CH3, or four constant domains CH1, CH2, CH3 and CH4, depending on the Ig class. The "class" of an Ig or antibody refers to the type of constant region and includes IgA, IgD, IgE, IgG and IgM and several of them can be further divided into subclasses, e.g. IgG1, IgG2, IgG3, IgG4. The constant regions of the antibodies may mediate the binding of the immunoglobulin to host tissues or factors, including various cells of the immune system (e.g., effector cells) and the first component (CIq) of the classical complement system.

The term "constant region(s)" or "constant domain(s)", as used herein are used interchangeably to refer to the domain (s) of an antibody which is outside the variable regions. The constant domains are identical in all antibodies of the same isotype but are different from one isotype to another. Typically, the constant region of a heavy chain is formed, from N to C terminal, by CH1-hinge —CH2-CH3-optionally CH4, comprising three or four constant domains.

The constant region domains of the antibody molecule of the present invention, if present, may be selected having regard to the proposed function of the antibody, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody is intended for therapeutic uses and antibody effector functions are required. Alternatively, IgG2 and IgG4 isotypes may be used when the antibody is intended for therapeutic purposes and antibody effector functions are not required. It will be appreciated that sequence variants of these constant region domains may also be used. For example, IgG4 in which the serine at position 241 (numbered according to the Kabat numbering system) has been changed to proline as described in Angal et al. (Angal et al., 1993). A single amino acid substitution, which abolishes the heterogeneity of chimeric mouse/human (IgG4) antibody as observed during SDS-PAGE analysis (Mol Immunol 30, 105-108), may be used. This is termed herein IgG4P. This single amino acid substitution prevents the natural propensity for the heavy chains of IgG4 molecules to swap yielding chimeric molecules.

"Fc region", "Fc fragment" or simply "Fc", are used interchangeably to refer to the C-terminal region of an antibody comprising the constant region of an antibody excluding the first constant region immunoglobulin domain. Thus, Fc refers to the last two constant domains, CH2 and CH3, of IgA, IgD, and IgG, or the last three constant domains of IgE and IgM, and the flexible hinge N-terminal to these domains. The human IgG1 heavy chain Fc region is defined herein to comprise residues C226 to its carboxyl-terminus, wherein the numbering is according to the EU index as in Kabat. In the context of human IgG1, the lower hinge refers to positions 226-236, the CH2 domain refers to positions 237-340 and the CH3 domain refers to positions 341-447 according to the EU index as in Kabat. The corresponding Fc region of other immunoglobulins can be identified by sequence alignments.

In the context of the present disclosure, when present, the constant region or Fc region may be natural, as defined above, or else may be modified in various ways, provided that it comprises a functional FcR binding domain, and preferably a functional FcRn binding domain. Preferably, the modified constant region or Fc region lead to improve functionalities and/or pharmacokinetics. The modifications may include deletion of certain portions of the Fc fragment. The modifications may further include various amino acid substitutions able to affect the biological properties of the antibody. Mutations for increasing FcRn binding and thus in vivo half-life may also be present. The modifications may further include modifications in the glycosylation profile of the antibody. The natural Fc fragment is glycosylated in the CH2 domain with the presence, on each of the two heavy chains, of an N-glycan bound to the asparagine residue at position 297 (Asn297). In the context of the present disclosure, the antibody may be glyco-modified, i-e engineered to have a particular glycosylation profile, which, for example, lead to improved properties, e.g. improved effector function, or improved serum half-life.

Antigen-binding fragments of antibodies include single chain antibodies (e.g. scFv and dsscFv), Fab, Fab', F(ab')2, Fv, single domain antibodies or nanobodies (e.g. VH or VL, or VHH or VNAR). Other antibody fragments for use in the present invention include the Fab and Fab' fragments described in International patent applications WO2011/117648, WO2005/003169, WO2005/003170 and WO2005/003171 (which are all incorporated herein by reference).

The methods for creating and manufacturing these antibody fragments are well known in the art (see for example Verma et al., 1998, Journal of Immunological Methods, 216, 165-181).

A typical "Fab' fragment" or "Fab'" as used herein comprises a heavy and a light chain pair in which the heavy chain comprises a variable region VH, a constant domain CH1 and a natural or modified hinge region and the light chain comprises a variable region VL and a constant domain CL. Dimers of a Fab' according to the present disclosure create a F(ab')2 where, for example, dimerization may be through the hinge.

The term "single domain antibody" as used herein refers to an antibody fragment consisting of a single monomeric variable antibody domain. Examples of single domain antibodies include VH or VL or VHH or V-NAR.

The "Fv" refers to two variable domains, for example co-operative variable domains, such as a cognate pair or affinity matured variable domains, i.e. a VH and VL pair.

"Single chain variable fragment" or "scFv" as employed herein refers to a single chain variable fragment which is stabilized by a peptide linker between the VH and VL variable domains.

"Disulphide-stabilized single chain variable fragment" or "dsscFv" as employed herein refer to a single chain variable fragment which is stabilized by a peptide linker between the VH and VL variable domain and also includes an inter-domain disulphide bond between VH and VL. (see for example, Weatherill et al., Protein Engineering, Design & Selection, 25 (321-329), 2012, WO2007109254.

The disulfide bond between the variable domains VH and VL is between two of the residues listed below (unless the context indicates otherwise, Kabat numbering is employed in the list below) (Protein Science 6, 781-788 Zhu et al (1997); Weatherill et al., Protein Engineering, Design & Selection, 25 (321-329), 2012; J Biochem. 118, 825-831 Luo et al (1995); FEBS Letters 377 135-139 Young et al (1995); Proc. Natl. Acad. Sci. USA Vol. 90 pp. 7538-7542 Brinkmann et al (1993); Proteins 19, 35-47 Jung et al (1994) Biochemistry 29 1362-1367; Glockshuber et al (1990). Wherever reference is made to Kabat numbering, the relevant reference is Kabat et al., 1991 (5th edition, Bethesda, Md.), in Sequences of Proteins of Immunological Interest, US Department of Health and Human Services, NIH, USA.

VH37+VL95C;
VH44+VL100;
VH44+VL105;
VH45+VL87;
VH55+VL101;
VH100+VL50;
VH100b+VL4

VH98+VL46;
VH101+VL46;
VH105+VL43,
VH106+VL57;

and a position or positions corresponding thereto in variable region pair located in the molecule.

The term "antibody" as used herein also encompasses monovalent, i.e. antibodies comprising only one antigen binding domain (e.g. one-armed antibodies comprising a full-length heavy chain and a full-length light chain interconnected, also termed "half-antibody").

The term "antibody" also encompasses multivalent antibodies comprising multiple specificities e.g. bispecific or trispecific or multispecific antibodies.

"Multispecific" or "multi-specific antibody" as employed herein refers to an antibody as described herein which has at least two binding domains, i.e. two or more binding domains, for example two or three binding domains, wherein the at least two binding domains independently bind two different antigens or two different epitopes on the same antigen (also called multi-paratopic). Multi-specific antibodies are generally monovalent for each specificity (antigen). Multi-specific antibodies described herein encompass monovalent and multivalent, e.g. bivalent, trivalent, tetravalent multi-specific antibodies.

"Antigen-binding domain" as employed herein refers to a portion of the antibody, which comprises a part or the whole of one or more variable domains, for example a part or the whole of a pair of variable domains VH and VL, that interact specifically with the target antigen. A binding domain may comprise a single domain antibody. In one embodiment, each binding domain is monovalent. Preferably each binding domain comprises no more than one VH and one VL.

A variety of multi-specific antibody formats are known in the art. Different classifications have been proposed, but multispecific IgG antibody formats generally include bispecific IgG, appended IgG, multispecific (e.g. bispecific) antibody fragments, multispecific (e.g. bispecific) fusion proteins, and multispecific (e.g. bispecific) antibody conjugates, as described for example in Spiess et al., Mol Immunol. 67(2015):95-106.

Techniques for making bispecific antibodies include, but are not limited to, CrossMab technology (Klein et al., Methods 154 (2019) 21-31), Knobs-in-holes engineering (e.g. WO1996027011, WO1998050431), DuoBody technology (e.g. WO2011131746), Azymetric technology (e.g. WO2012058768). Further technologies for making bispecific antibodies have been described for example in Godar et al., 2018, Expert Opinion on Therapeutic Patents, 28:3, 251-276. Bispecific antibodies include in particular CrossMab antibodies, DAF (two-in-one), DAF (four-in-one), DutaMab, DT-IgG, Knobs-in-holes common LC, Knobs-in-holes assembly, Charge pair, Fab-arm exchange, SEEDbody, Triomab, LUZ-Y, Fcab, KA-body and orthogonal Fab.

Appended IgG classically comprise full-length IgG engineered by appending additional antigen-binding domain or antigen-binding fragment to the N- and/or C-terminus of the heavy and/or light chain of the IgG. Examples of such additional antigen-binding fragments include sdAb antibodies (e.g. VH or VL), Fv, scFv, dsscFv, Fab, scFav. Appended IgG antibody formats include in particular DVD-IgG, IgG(H)-scFv, scFv-(H)IgG, IgG(L)-scFv, scFv-(L)IgG, IgG(L,H)-Fv, IgG(H)-V, V(H)-IgG, IgC(L)-V, V(L)-IgG, KIH IgG-scFab, 2scFv-IgG, IgG-2scFv, scFv4-Ig, Zybody and DVI-IgG (four-in-one), for example as described in Spiess et al., Alternative molecular formats and therapeutic applications for bispecific antibodies. Mol Immunol. 67(2015):95-106.

Multispecific antibody fragments include nanobody, nanobody-HAS, BiTEs, diabody, DART, TandAb, scDiabody, sc-Diabody-CH3, Diabody-CH3, Triple Body, Miniantibody; Minibody, Tri Bi minibody, scFv-CH3 KIH, Fab-scFv, scFv-CH-CL-scFv, F(ab')2, F(ab')2-scFv2, scFv-KIH, Fab-scFv-Fc, Tetravalent HCAb, scDiabody-Fc, Diabody-Fc, Tandem scFv-Fc; and intrabody, as described, for example, Spiess et al., for bispecific antibodies. Mol Immunol. 67(2015):95-106.

Multispecific fusion proteins include Dock and Lock, ImmTAC, HSAbody, scDiabody-HAS, and Tandem scFv-Toxin. Multispecific antibody conjugates include IgG-IgG; Cov-X-Body; and scFv1-PEG-scFv2.

Additional multispecific antibody formats have been described for example in Brinkmann and Kontermann, mAbs, 9:2, 182-212 (2017), in particular in FIG. 2, for example tandem scFv, triplebody, Fab-VHH, taFv-Fc, scFv4-Ig, scFv2-Fcab, scFv4-IgG. Bibodies, tribodies and methods for producing the same are disclosed for example in WO99/37791.

Appended IgG and appended Fab comprise a whole IgG or a Fab fragment, respectively, which are engineered by appending at least one additional antigen-binding domain (e.g. two, three or four additional antigen-binding domains), for example a single domain antibody (such as VH or VL, or VHH), a scFv, a dsscFv, a dsFv to the N- and/or C-terminus of the heavy and/or light chain of said IgG or Fab, for example as described in WO2009/040562, WO2010035012, WO2011/030107, WO2011/061492, WO2011/061246 and WO2011/086091 which are all incorporated herein by reference. In particular, the Fab-Fv format was first disclosed in WO2009/040562 and the disulphide stabilized version thereof, the Fab-dsFv, first disclosed in WO2010/035012. A single linker Fab-dsFv, wherein the dsFv is connected to the Fab via a single linker between either the VL or VH domain of the Fv, and the C terminal of the LC or HC of the Fab, was first disclosed in WO2014/096390, incorporated herein by reference. An appended IgG comprising a full-length IgG1 engineered by appending a dsFv to the C-terminus of the heavy or light chain of the IgG, which was first disclosed in WO2015/197789, incorporated herein by reference.

Alternatively, another multispecific format comprises a Fab linked to two scFvs or dsscFvs, each scFv or dsscFv binding the same or a different target (e.g., one scFv or dsscFv binding a therapeutic target and one scFv or dsscFv that increases half-life by binding, for instance, albumin). Such antibody fragments are described in WO2015/197772, which is hereby incorporated by reference in its entirety. Another format comprises a Fab linked to only one scFv or dsscFv, as described for example in WO2013/068571 incorporated herein by reference, and Dave et al., Mabs, 8(7) 1319-1335 (2016).

Other well-known formats of multispecific antibodies comprise:

Diabody as employed herein refers to two Fv pairs, a first VH/VL pair and a further VH/VL pair which have two inter-Fv linkers, such that the VH of a first Fv is linked to the VL of the second Fv and the VL of the first Fv is linked to the VH of the second Fv.

Triabody as employed herein refers to a format similar to the diabody comprising three Fvs and three inter-Fv linkers.

Tetrabody as employed herein refers to a format similar to the diabody comprising fours Fvs and four inter-Fv linkers.

Tandem scFv as employed herein refers to at least two scFvs linked via a single linker such that there is a single inter-Fv linker.

Tandem scFv-Fc as employed herein refers to at least two tandem scFvs, wherein each one is appended to the N-terminus of a CH2 domain, for example via a hinge, of constant region fragment —CH2CH3.

Fab-Fv as employed herein refers to a Fv fragment with a variable region appended to the C-terminal of each of the following, the CH1 of the heavy chain and CL of the light chain. The format may be provided as a PEGylated version thereof.

Fab'-Fv as employed herein is similar to FabFv, wherein the Fab portion is replaced by a Fab'. The format may be provided as a PEGylated version thereof.

Fab-dsFv as employed herein refers to a FabFv wherein an intra-Fv disulfide bond stabilizes the appended C-terminal variable regions. The format may be provided as a PEGylated version thereof.

Fab-scFv as employed herein is a Fab molecule with a scFv appended on the C-terminal of the light or heavy chain.

Fab'-scFv as employed herein is a Fab' molecule with a scFv appended on the C-terminal of the light or heavy chain.

DiFab as employed herein refers to two Fab molecules linked via their C-terminus of the heavy chains.

DiFab' as employed herein refers to two Fab' molecules linked via one or more disulfide bonds in the hinge region thereof.

As employed herein scdiabody is a diabody comprising an intra-Fv linker, such that the molecule comprises three linkers and forms a normal scFv whose VH and VL terminals are each linked to a one of the variable regions of a further Fv pair.

Scdiabody-Fc as employed herein is two scdiabodies, wherein each one is appended to the N-terminus of a CH2 domain, for example via a hinge, of constant region fragment —CH2CH3.

ScFv-Fc-scFv as employed herein refers to four scFvs, wherein one of each is appended to the N-terminus and the C-terminus of both the heavy and light chain of a —CH2CH3 fragment.

Scdiabody-CH3 as employed herein refers to two scdiabody molecules each linked, for example via a hinge to a CH3 domain.

IgG-scFv as employed herein is a full-length antibody with a scFv on the C-terminal of each of the heavy chains or each of the light chains.

scFv-IgG as employed herein is a full-length antibody with a scFv on the N-terminal of each of the heavy chains or each of the light chains.

V-IgG as employed herein is a full-length antibody with a variable domain on the N-terminal of each of the heavy chains or each of the light chains.

IgG-V as employed herein is a full-length antibody with a variable domain on the C-terminal of each of the heavy chains or each of the light chains DVD-Ig (also known as dual V domain IgG) is a full-length antibody with 4 additional variable domains, one on the N-terminus of each heavy and each light chain.

In one preferred embodiment, the antibody which binds to kallikrein 5 (KLK5), wherein the antibody inhibits or reduces the protease activity of KLK5 and wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

In another embodiment of the present invention, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and inhibits or reduces the protease activity of KLK5.

Within the present invention, the term "inhibit" (and grammatical variations thereof) indicates the effect the antibodies according to the present invention have with respect to KLK5 biological activity. Preferably, the biological activity of KLK5 is a protease activity, preferably serine protease activity. The effect results in a complete or partial hindering of the serine protease activity of KLK5.

Without wishing to be bound by theory it is believed that the antibodies according to the present invention bind to KLK5 and:

i) inhibits (for example completely or partially) or reduces the protease activity (preferably the serine protease activity) of KLK5; and/or
ii) binds to KLK5 when KLK5 is bound to LEKTI or a fragment of LEKTI and/or
iii) does not compete with LEKTI, or a fragment of LEKTI, for binding KLK5 and/or
iv) forms a complex with KLK5 bound to LEKTI or a fragment of LEKTI (i.e. forming a complex which comprise the antibody of the present invention, KLK5 and LEKTI, or a fragment of LEKTI).

Within the present invention, the term "LEKTI" refers to the lympho-epithelial Kazal-type-related inhibitor consisting of 15 domains, and is cleaved into smaller, functional fragments by proprotein convertases such as protease furin, resulting in fragments of LEKTI comprised of one or more domains. These fragments are secreted into the extracellular space where they can form inhibitory complexes with proteases such as KLK5. LEKTI is also known as serine protease inhibitor Kazal-type 5 (SPINKS) and is a protein that in humans is encoded by the SPINKS gene. In humans, three splice variants of LEKTI mRNA are generated leading to full-length, long and short isoforms of the protein that differ in their COOH-terminal regions only.

SPINKS is a member of a gene family cluster located on chromosome 5q32 which encode inhibitors of serine proteases. This includes other epidermal proteins SPINK6 and LEKTI-2 (SPINK9) which are also included in the present invention within the term "LEKTI".

The term "form a complex" (and any grammatical variation thereof) means that the antibody according to the present invention is capable of binding KLK5 when KLK5 is already bound to another protein such as LEKTI, or a fragment of LEKTI, or another antibody or an antibody fragment such as a Fab.

The advantage associated with an antibody capable of binding KLK5 and inhibiting KLK5 biological (i.e. protease) activity, yet not-competing with LEKTI or a fragment of LEKTI for binding KLK5, may enable inhibition of KLK5 activity in conditions where LEKTI dissociates from the KLK5:LEKTI complex, such as the progressively acidic environment from the stratum basale to the stratum corneum of the epidermis.

An antibody that "competes", "cross-blocks", "is cross-blocked" or "binds to the same epitope on human KLK5"

(and any grammatical variation thereof) as the antibody of the present invention refers to an antibody that is not capable of forming a complex with KLK5 bound to the antibody of the present invention.

In one embodiment according to the present invention, the fragment of LEKTI is human LEKTI domain 5 comprising amino acids 1 to 64 of SEQ ID NO: 54 or LEKTI domain 8 comprising amino acids 1 to 71 of SEQ ID NO: 61.

Therefore, in a preferred embodiment, the antibody which binds to kallikrein 5 (KLK5):

i. binds to KLK5 when KLK5 is bound to LEKTI or a fragment of LEKTI;
ii. does not compete with LEKTI, or a fragment of LEKTI, for binding KLK5 and/or
iii. forms a complex with KLK5 bound to LEKTI or a fragment of LEKTI;

wherein preferably the fragment of LEKTI is human LEKTI domain 5 comprising amino acids 1 to 64 of SEQ ID NO: 54 or LEKTI domain 8 comprising amino acids 1 to 71 of SEQ ID NO: 61 and wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

In another embodiment according to the present invention, the antibody binds KLK5, preferably human KLK5, wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and:

i. binds to KLK5 when KLK5 is bound to LEKTI or a fragment of LEKTI;
ii. does not compete with LEKTI, or a fragment of LEKTI, for binding KLK5 and/or
iii. forms a complex with KLK5 bound to LEKTI or a fragment of LEKTI;

wherein preferably the fragment of LEKTI is human LEKTI domain 5 comprising amino acids 1 to 64 of SEQ ID NO: 54 or LEKTI domain 8 comprising amino acids 1 to 71 of SEQ ID NO: 61.

In another embodiment, the antibody according the present invention binds human KLK5, preferably comprising SEQ ID NO: 53 and also binds cyno KLK5, preferably cyno KLK5 comprising SEQ ID NO: 60.

In another embodiment, the antibody according to the present invention does not bind bind human or cynomolgus monkey (cyno) kallikrein 2 (KLK2); or human or cyno kallikrein 4 (KLK4); or human or cyno kallikrein 7 (KLK7). In other words, the antibody is specific for KLK5 and not for other kallikreins.

"Specific" as employed herein is intended to refer to an antibody that only recognizes the antigen to which it is specific or an antibody that has significantly higher binding affinity to the antigen to which it is specific (e.g. KLK5) compared to binding to antigens to which it is non-specific (such as other kallikreins), for example at least 5, 6, 7, 8, 9, 10 times higher binding affinity.

In one embodiment, according to the present invention, the binding of the antibody to KLK5 is characterized by a constant of dissociation ($K_D$) of about 500 pM or less, preferably about 172 pM.

The term "$K_D$" as used herein refers to the constant of dissociation which is obtained from the ratio of $K_d$ to $K_a$ (i.e. $K_d/K_a$) and is expressed as a molar concentration (M). $K_d$ and $K_a$ refers to the dissociation rate and association rate, respectively, of a particular antigen-antibody (or antigen-binding fragment thereof) interaction. $K_D$ values for antibodies can be determined using methods well established in the art. A method for determining the $K_D$ of an antibody is by using surface plasmon resonance, such as Biacore® system for example as described in the Examples herein, using recombinant KLK5 or a suitable fusion protein/polypeptide thereof. In one example affinity is measured using recombinant KLK5 as described in the Examples herein. For surface plasmon resonance, target molecules are immobilized on a solid phase and exposed to ligands in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al, Cancer Res. 53:2560-65 (1993)).

In one embodiment, the antibody according to the present invention has a higher binding affinity (i.e. smaller $K_D$) for human KLK5 than for cyno or mouse KLK5. The term "affinity" refers to the strength of an interaction between the antibody and KLK5.

In one embodiment, the antibody according to the present invention has an $IC_{50}$ of less than 800 pM for blocking KLK5 protease activity, preferably, the antibody according to the present invention has an $IC_{50}$ of less than 18 pM for blocking KLK5 protease activity in the in-vitro assay as described herein.

The term $IC_{50}$ as used herein refers to the half maximal inhibitory concentration which is a measure of the effectiveness of a substance, such as an antibody, in inhibiting a specific biological or biochemical function, which in the present invention is the protease activity of KLK5. The $IC_{50}$ is a quantitative measure which indicates how much of a particular substance is needed to inhibit a given biological process or function or activity by half.

The antibody according to the present invention may comprise the framework regions of the animal in which the antibody was raised. For example, if the antibody was raised in rabbit, it will comprise the CDRs as defined above and the framework regions of the rabbit antibody such as an antibody comprising a light chain variable region according to SEQ ID NO: 7 (which nucleotide sequence is shown in SEQ ID NO: 8 or nucleotides 1 to 330 of SEQ ID NO: 8) and a heavy chain variable region according to SEQ ID NO: 9 (which nucleotide sequence is shown in SEQ ID NO: 10).

In one embodiment, the antibody may be a chimeric or humanized antibody.

Chimeric antibodies are typically produced using recombinant DNA methods. The DNA may be modified by substituting the coding sequence for human L and H chain constant regions for the corresponding non-human (e.g. murine or rabbit) H and L constant regions (Morrison; PNAS 81, 6851 (1984)).

Human antibodies comprise heavy or light chain variable regions or full length heavy or light chains that are "the product of" or "derived from" a particular germline sequence if the variable regions or full-length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody or fragment thereof that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acid sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Human antibodies may be produced by a number of methods known to those of skill in the art. Human antibodies can be made by the hybridoma method using human myeloma or mouse-human heteromyeloma cells lines (Kozbor, J Immunol; (1984) 133:3001; Brodeur, Monoclonal Isolated Antibody Production Techniques and Applications, pp 51-63, Marcel Dekker Inc, 1987). Alternative methods include the use of phage libraries or transgenic mice both of which utilize human variable region repertories (Winter G; (1994) Annu Rev Immunol 12:433-455, Green LL, (1999) J Immunol Methods 231:1 1-23).

In one preferred embodiment of the present invention, the antibody according to the present invention are humanized.

Antibodies according to the present invention may be obtained using any suitable method known in the art. KLK5 including fusion proteins thereof, cells (recombinantly or naturally) expressing the KLK5 can be used to produce antibodies which specifically recognize KLK5. Various form of KLK5 as described herein may be used.

In one embodiment, the antigen used is active KLK5, preferably produced as described in the Examples below.

KLK5 or fragments thereof, for use to immunize a host, may be prepared by processes well known in the art from genetically engineered host cells comprising expression systems or they may be recovered from natural biological sources. KLK5 or a fragment thereof may in some instances be part of a larger protein such as a fusion protein for example fused to an affinity tag or similar.

Antibodies generated against KLK5 according to the present invention may be obtained, where immunization of an animal is necessary, by administering KLK5 to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15):7843-78481; WO92/02551; WO2004/051268 and WO2004/106377.

Screening for antibodies can be performed using assays to measure binding to KLK5 and/or assays to measure the inhibition of KLK5 biological activity, preferably KLK5 protease activity.

In one preferred embodiment, the antibody which binds to kallikrein 5 (KLK5), wherein the antibody is a chimeric or humanized antibody; preferably a humanized antibody; wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, preferably, SEQ ID NO: 1, a CDR-L2 comprising SEQ ID NO: 2 and a CDR-L3 comprising SEQ ID NO: 3; and b. the variable heavy chain comprises a CDR-H1 comprising SEQ ID NO: 4, a CDR-H2 comprising SEQ ID NO: 5 and a CDR-H3 comprising SEQ ID NO: 6.

In another embodiment according to the present invention, the antibody which binds to KLK5, wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51; wherein the antibody comprises a variable light chain and a variable heavy chain and wherein:

a. the light chain variable chain comprises:
    i. a CDR-L1 comprising SEQ ID NO: 1 or SEQ ID NO: 62 or SEQ ID NO: 63, preferably SEQ ID NO: 1;
    ii. a CDR-L2 comprising SEQ ID NO: 2 and
    iii. a CDR-L3 comprising to SEQ ID NO: 3; and
b. a heavy chain variable region comprising:
    iv. a CDR-H1 comprising SEQ ID NO: 4;
    v. a CDR-H2 comprising SEQ ID NO: 5 and
    vi. a CDR-H3 comprising SEQ ID NO: 6 wherein the antibody is a chimeric or humanized antibody; preferably, the antibody is a humanized antibody.

In another preferred embodiment the humanized antibody, which binds to KLK5, comprises a variable light chain and a variable heavy chain and wherein:

a. the light chain variable chain comprises:
    i. a CDR-L1 comprising SEQ ID NO: 1 or SEQ ID NO: 62 or SEQ ID NO: 63, preferably SEQ ID NO: 1;
    ii. a CDR-L2 comprising SEQ ID NO: 2 and
    iii. a CDR-L3 comprising to SEQ ID NO: 3; and b. a heavy chain variable region comprising:

iv. a CDR-H1 comprising SEQ ID NO: 4;

v. a CDR-H2 comprising SEQ ID NO: 5 and vi. a CDR-H3 comprising SEQ ID NO: 6 wherein the antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI.

More preferably, the humanized antibody binds to an epitope of human KLK5 comprising Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51; wherein the antibody comprises a variable light chain and a variable heavy chain and wherein:

a. the light chain variable chain comprises:

i. a CDR-L1 comprising SEQ ID NO: 1 or SEQ ID NO: 62 or SEQ ID NO: 63, preferably SEQ ID NO: 1;

ii. a CDR-L2 comprising SEQ ID NO: 2 and iii. a CDR-L3 comprising to SEQ ID NO: 3; and b. a heavy chain variable region comprising:

i. a CDR-H1 comprising SEQ ID NO: 4;

ii. a CDR-H2 comprising SEQ ID NO: 5 and iii. a CDR-H3 comprising SEQ ID NO: 6 wherein the antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI.

As used herein, the term "humanized" antibody refers to an antibody wherein the heavy and/or light chain contains one or more CDRs (including, if desired, one or more modified CDRs) from a donor antibody (e.g. a non-human antibody such as a murine or rabbit monoclonal antibody) grafted into a heavy and/or light chain variable region framework of an acceptor antibody (e.g. a human antibody). Fora review, see Vaughan et al, Nature Biotechnology, 16, 535-539, 1998. In one embodiment, rather than the entire CDR being transferred, only one or more of the specificities determining residues from any one of the CDRs described herein above are transferred to the human antibody framework (see for example, Kashmiri et al., 2005, Methods, 36, 25-34). In one embodiment, only the specificity determining residues from one or more of the CDRs described herein above are transferred to the human antibody framework. In another embodiment, only the specificity determining residues from each of the CDRs described herein above are transferred to the human antibody framework.

When the CDRs are grafted, any appropriate acceptor variable region framework sequence may be used having regard to the class/type of the donor antibody from which the CDRs are derived, including mouse, primate and human framework regions.

Preferably, the humanized antibody according to the present invention has a variable domain comprising human acceptor framework regions as well as one or more of the CDRs provided specifically herein. Thus, in one embodiment there is provided a blocking humanized antibody which binds KLK5, preferably human KLK5, wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://www.imgt.org/In a humanized antibody according to the present invention, the acceptor heavy and light chains do not necessarily need to be derived from the same antibody and may, if desired, comprise composite chains having framework regions derived from different chains.

A suitable framework region for the light chain of the humanized antibody according to the present invention is derived from the human germline IGKV1-6 JK4 having SEQ ID NO:47 and which nucleotide sequence is shown in SEQ ID NO: 48.

A suitable framework region for the heavy chain of the humanized antibody or antigen-binding fragment thereof according to the present invention is derived from the human germline IGHV4-4 JH4 having the sequence as shown in SEQ ID NO: 49 and which nucleotide sequence is shown in SEQ ID NO: 50.

Accordingly, in one embodiment there is provided a humanized antibody which binds to KLK5, wherein the antibody comprises a variable light chain and a variable heavy chain and wherein:

a. the light chain variable chain comprises:

i. a CDR-L1 comprising SEQ ID NO: 1 or SEQ ID NO: 62 or SEQ ID NO: 63, preferably SEQ ID NO: 1; and ii. a CDR-L2 comprising SEQ ID NO: 2 and iii. a CDR-L3 comprising to SEQ ID NO: 3; and b. a heavy chain variable region comprising:

i. a CDR-H1 comprising SEQ ID NO: 4; and ii. a CDR-H2 comprising SEQ ID NO: 5 and iii. a CDR-H3 comprising SEQ ID NO: 6 wherein the light chain framework region is derived from the human germline IGKV1-6 JK4 comprising SEQ ID NO: 47; and the heavy chain framework region is derived from the human germline IGHV4-4 JH4 comprising SEQ ID NO: 49. Preferably the antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI.

In another embodiment there is provided a humanized antibody which binds to KLK5 wherein the antibody binds to an epitope of human KLK5 comprising Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51; wherein the antibody comprises a variable light chain and a variable heavy chain and wherein:

a. the light chain variable chain comprises:

i. a CDR-L1 comprising SEQ ID NO: 1 or SEQ ID NO: 62 or SEQ ID NO: 63, preferably SEQ ID NO: 1; and ii. a CDR-L2 comprising SEQ ID NO: 2 and iii. a CDR-L3 comprising to SEQ ID NO: 3; and b. a heavy chain variable region comprising:

i. a CDR-H1 comprising SEQ ID NO: 4; and ii. a CDR-H2 comprising SEQ ID NO: 5 and iii. a CDR-H3 comprising SEQ ID NO: 6 wherein the light chain framework region is derived from the human germline IGKV1-6 JK4 comprising SEQ ID NO: 47; and the heavy chain framework region is derived from the human germline IGHV4-4 JH4 comprising SEQ ID NO: 49. Preferably the antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI; and In the humanized antibody according to the present invention, the framework regions may not have the same exact sequences as those of the acceptor antibody. For instance, unusual residues may be changed to more frequently-occurring residues for that acceptor chain class or type. Alternatively, selected residues in the acceptor framework regions may be changed so that they correspond to the residues found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO91/09967 (which is incorporated herein by reference).

Thus, in one embodiment 1, 2, 3, 4, 5, 6, 7 or 8 residues in the framework are replaced with an alternative amino acid residue.

Accordingly, in one embodiment, there is provided a humanized antibody according to the present invention, wherein residues at each of positions 2 and/or 3 and/or 63 of the variable light chain (with reference to SEQ ID NO: 47 or SEQ ID NO: 15) are donor residues. Preferably, residue at position 2 of the variable light chain is tyrosine and residue at position 3 of the variable light chain is an aspartic acid. In some embodiments, residue at position 63 of the variable light chain is lysine.

In another embodiment, there is provided a humanized antibody, wherein at least the residues at each of positions 68, 72, 74, 77 and 79 (with reference to SEQ ID NO: 49; or positions 67, 71, 73, 76 and 78 with reference to SEQ ID NO: 39) of the variable heavy chain are donor residues.

Preferably, residue at position 72 of the variable heavy chain is glutamine, residue at position 74 is serine and residue at position 79 is valine. In some embodiments, residue at position 68 of the variable heavy chain is phenylalanine, and/or residue at position 77 is threonine.

In one preferred embodiment, the humanized antibody binds to KLK5, wherein the humanized antibody comprises:

a light chain variable region comprising SEQ ID NO: 11 or 15 or 19 or 23 and a heavy chain variable region comprising SEQ ID NO: 27 or 31 or 35 or 39 or 43; or a light chain variable region comprising SEQ ID NO: 15 wherein amino acid residue at position 24 is arginine (Arg; R) or lysine (Lys; K) and a heavy chain variable region comprising SEQ ID NO: 27 or 31 or 35 or 39 or 43. Preferably the antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI.

In another embodiment, there is provided a humanized antibody which binds to KLK5 wherein the antibody binds to an epitope of human KLK5 comprising Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51; wherein the antibody comprises:

a light chain variable region comprising SEQ ID NO: 11 or 15 or 19 or 23 and a heavy chain variable region comprising SEQ ID NO: 27 or 31 or 35 or 39 or 43; or a light chain variable region comprising SEQ ID NO: 15 wherein amino acid residue at position 24 is arginine (Arg; R) or lysine (Lys; K) and a heavy chain variable region comprising SEQ ID NO: 27 or 31 or 35 or 39 or 43.

Preferably the antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI.

In one preferred embodiment of the present invention the antibody comprises a light chain variable region comprising SEQ ID NO: 15 and a heavy chain variable region comprising SEQ ID NO: 39.

More preferably, the humanized antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51; wherein the antibody comprises a light chain variable region comprising SEQ ID NO: 15 and a heavy chain variable region comprising SEQ ID NO: 39.

Even more preferably, the humanized antibody inhibits or reduces the protease activity of KLK5 and/or binds to KLK5 when KLK5 is bound to LEKTI, or a fragment of LEKTI; and/or does not compete with LEKTI, or a fragment of LEKTI, for binding KLK5 and/or forms a complex with KLK5 bound to LEKTI, or a fragment of LEKTI In one embodiment, the invention provides an antibody comprising a sequence which is 80% similar or identical to a sequence disclosed herein, for example 85%, 90%, 91%, 92%, 93%, 94%, 95% 96%, 97%, 98% or 99% over part or whole of the relevant sequence, for example a variable domain sequence, a CDR sequence or a variable domain sequence, excluding the CDRs. In one embodiment, the relevant sequence is SEQ ID NO: 15. In one embodiment the relevant sequence is SEQ ID NO: 39.

In one embodiment, the antibody, which binds KLK5, comprises a light chain and a heavy chain, wherein the variable light chain comprises a sequence having at least 80%, 85%, 90%, 91%, 92%, 93%, 94%, 95% 96%, 97%, 98% or 99% identity or similarity to the sequence comprising in SEQ ID NO:15 and/or the variable heavy chain comprises a sequence having at least 80%, 85%, 90%, 91%, 92%, 93%, 94%, 95% 96%, 97%, 98% or 99% identity or similarity to the sequence comprising in SEQ ID NO: 39.

In one embodiment, the antibody, which binds KLK5, comprises a light chain which is at least 90%, 91%, 92%, 93%, 94%, 95% 96%, 97%, 98% or 99% similar or identical to the sequence given in SEQ ID NO: 15 but wherein the antibody has the sequence comprising in SEQ ID NO: 1 (or SEQ ID NO: 62 or 63) for CDR-L1, the sequence comprising in SEQ ID NO: 2 for CDR-L2 and the sequence comprising in SEQ ID NO: 3 for CDR-L3.

"Identity", "Identical" nor grammatical variations thereof, as used herein, indicate that at any particular position in the aligned sequences, the amino acid residue is identical between the sequences. "Similarity", "similar" or grammatical variations thereof as used herein, indicate that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In one embodiment, the antibody is a full-length antibody, preferably selected from an IgG1, and IgG4 or an IgG4P.

Therefore, the present invention provides for a full-length humanized antibody which binds KLK5 and comprises:

a. a light chain variable region comprising:
   i. a CDR-L1 comprising SEQ ID NO: 1;
   ii. a CDR-L2 comprising SEQ ID NO: 2 and
   iii. a CDR-L3 comprising SEQ ID NO: 3; and
b. a heavy chain variable region comprising:
   iv. a CDR-H1 comprising SEQ ID NO: 4;
   v. a CDR-H2 comprising SEQ ID NO: 5 and
   vi. a CDR-H3 comprising SEQ ID NO: 6.

Preferably, the full-length humanized antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51, and wherein the antibody is an IgG4P isoform.

In another embodiment there is provided a full-length humanized antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and wherein the antibody is an IgG4P isoform It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. Journal of Chromatography 705: 129-134, 1995). Accordingly, the C-terminal lysine of the antibody heavy chain may be absent.

In one embodiment, a C-terminal amino acid from the antibody is cleaved during post-translation modifications.

In one embodiment, an N-terminal amino acid from the antibody is cleaved during post-translation modifications.

In one preferred embodiment, the antibody, which binds to KLK5, is a full length antibody comprising a light chain variable region comprising SEQ ID NO: 15 and a heavy chain variable region comprising SEQ ID NO: 39. Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In another embodiment, the antibody, which binds to KLK5, is a full length IgG4 antibody comprising a light chain comprising SEQ ID NO: 17 and a heavy chain comprising SEQ ID NO: 41. Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In yet another embodiment the antibody is a Fab' fragment comprising a light chain variable region comprising SEQ ID NO: 15 and a heavy chain variable region comprising SEQ ID NO: 39.

In another embodiment, the antibody comprises a light chain variable region comprising SEQ ID NO: 15 and a heavy chain variable region comprising SEQ ID NO: 27 or 31 or 35 or 39 or 43. For example, the antibody is a full length IgG4 antibody comprising a light chain variable region comprising SEQ ID NO: 15 and a heavy chain variable region comprising SEQ ID NO: 27 or 31 or 35 or 39 or 43, preferably SEQ ID NO: 39. In one embodiment, amino acids glutamine 24 (Gln; Q) with reference to SEQ ID NO: 15 is an arginine (Arg; R) Q24R or a lysine (Lys; K) Q24K.

In another embodiment, the antibody is full length IgG4 antibody comprising a light chain variable region comprising to SEQ ID NO: 11 and a heavy chain variable region comprising SEQ ID NO: 27 or 31 or 35 or 39 or 43. In another embodiment the antibody is a Fab' fragment comprising a light chain variable region according to SEQ ID NO: 11 and a heavy variable region comprising SEQ ID NO: 27 or 31 or 35 or 39 or 43.

In another embodiment, the antibody is full length IgG4 antibody comprising a light chain variable region according to SEQ ID NO: 19 and a heavy chain variable region comprising SEQ ID NO: 27 or 31 or 35 or 39 or 43. In another embodiment the antibody is a Fab' fragment comprising a light chain variable region according to SEQ ID NO: 19 and a heavy chain variable region comprising SEQ ID NO: 27 or 31 or 35 or 39 or 43.

In another embodiment, the antibody is full length IgG4 antibody comprising a light chain variable region according to SEQ ID NO: 23 and a heavy chain variable region comprising SEQ ID NO: 27 or 31 or 35 or 39 or 43.

In another embodiment the antibody is a Fab' fragment comprising a light variable region according to SEQ ID NO: 23 and a heavy variable region comprising SEQ ID NO: 27 or 31 or 35 or 39 or 43.

In another embodiment, the antibody which binds to KLK5, is full length IgG4 antibody comprising:

1. a light chain comprising SEQ ID NO: 13 and a heavy chain comprising SEQ ID NO: 29 or 33 or 37 or 41 or 45; or
2. a light chain comprising SEQ ID NO: 17 and a heavy chain comprising SEQ ID NO: 29 or 33 or 37 or 41 or 45; or
3. a light chain comprising SEQ ID NO: 17 wherein glutamine 24 (Gln; Q) is an arginine (Arg; R) Q24R or a lysine (Lys; K) Q24K and a heavy chain comprising SEQ ID NO: 29 or 33 or 37 or 41 or 45; or 4. a light chain comprising SEQ ID NO: 21 and a heavy chain comprising SEQ ID NO: 29 or 33 or 37 or 41 or 45; or
5. a light chain comprising SEQ ID NO: 25 and a heavy chain comprising SEQ ID NO: 29 or 33 or 37 or 41 or 45.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In one preferred embodiment, the antibody which binds to KLK5, is full length IgG4 antibody comprising a light chain comprising SEQ ID NO: 17 and a heavy chain comprising SEQ ID NO: 41; wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51

The present invention also provides for the antibody as described hereinabove to form a complex with KLK5, preferably human KLK5, bound to another antibody, wherein the another antibody comprises:

1. a variable light chain comprising a CDR-L1 comprising SEQ ID NO: 68, a CDR-L2 comprising SEQ ID NO: 69 and a CDR-L3 comprising SEQ ID NO: 70; and a variable heavy chain comprising a CDR-H1 comprising SEQ ID NO: 71, a CDR-H2 comprising SEQ ID NO: 72 and a CDR-H3 comprising SEQ ID NO: 73; and/or
2. a variable light chain comprising SEQ ID NO: 74 and a variable heavy chain comprising SEQ ID NO: 76; and/or
3. a variable light chain encoded by a nucleotide comprising SEQ ID NO: 75 and a variable heavy chain encoded by a nucleotide comprising SEQ ID NO: 77.

In one embodiment, the antibody, which binds KLK5, wherein the antibody preferably binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain comprising SEQ ID NO: 7 or 11 or 15 or 19 or 23; and a variable heavy chain comprising SEQ ID NO: 9 or 27 or 31 or 35 or 39 or 43;

wherein the antibody forms a complex with KLK5, preferably human KLK5, bound to another antibody, which another antibody comprises:

1. a variable light chain comprising a CDR-L1 comprising SEQ ID NO: 68, a CDR-L2 comprising SEQ ID NO: 69 and a CDR-L3 comprising SEQ ID NO: 70; and a variable heavy chain comprises a CDR-H1 comprising SEQ ID NO: 71, a CDR-H2 comprising SEQ ID NO: 72 and a CDR-H3 comprising SEQ ID NO: 73; and/or
2. a variable light chain comprising SEQ ID NO: 74 and a variable heavy chain comprising SEQ ID NO: 76; and/or
3. a variable light chain encoded by a nucleotide comprising SEQ ID NO: 75 and a variable heavy chain encoded by a nucleotide comprising SEQ ID NO: 77.

Therefore, the present invention also provides for an antibody which binds KLK5, preferably human KLK5, which comprises:

1. a variable light chain comprising a CDR-L1 comprising SEQ ID NO: 68, a CDR-L2 comprising SEQ ID NO: 69 and a CDR-L3 comprising SEQ ID NO: 70; and a variable heavy chain comprises a CDR-H1 comprising SEQ ID NO: 71, a CDR-H2 comprising SEQ ID NO: 72 and a CDR-H3 comprising SEQ ID NO: 73; wherein the antibody is optionally humanized; and/or
2. a variable light chain comprising SEQ ID NO: 74 and a variable heavy chain comprising SEQ ID NO: 76; and/or
3. a variable light chain encoded by a nucleotide comprising SEQ ID NO: 75 and a variable heavy chain encoded by a nucleotide comprising SEQ ID NO: 77.

Furthermore, the present invention also comprises a KLK5-antibody complex comprising:

a. KLK5, preferably human KLK5; and
b. an antibody which binds KLK5, wherein the antibody preferably binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and wherein the antibody comprises:
    1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
    2. a variable light chain comprising SEQ ID NO: 7 or 11 or 15 or 19 or 23; and a variable heavy chain comprising SEQ ID NO: 9 or 27 or 31 or 35 or 39 or 43; and
c. another antibody which comprises:
    1. a variable light chain comprising a CDR-L1 comprising SEQ ID NO: 68, a CDR-L2 comprising SEQ ID NO: 69 and a CDR-L3 comprising SEQ ID NO: 70; and a variable heavy chain comprises a CDR-H1 comprising SEQ ID NO: 71, a CDR-H2 comprising SEQ ID NO: 72 and a CDR-H3 comprising SEQ ID NO: 73; wherein the antibody is optionally humanized; and/or
    2. a variable light chain comprising SEQ ID NO: 74 and a variable heavy chain comprising SEQ ID NO: 76; and/or
    3. a variable light chain encoded by a nucleotide comprising SEQ ID NO: 75 and a variable heavy chain encoded by a nucleotide comprising SEQ ID NO: 77.

It should be understood that the so called "another antibody" binds KLK5, preferably human KLK5 to an epitope which is different from and not overlapping with the epitope described herein (and as comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51), as shown by the examples below. In this respect, such antibodies do not compete with one another.

Furthermore, the present invention also provides for an antibody which competes for binding KLK5, preferably human KLK5, by cross-blocking or being cross-blocked by the antibody which binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and which antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

In one embodiment, such competing antibody has a heavy chain variable region having at least 80% identity or similarity to the sequence comprising SEQ ID NO: 29 or 33 or 37 or 41 or 45; and/or has a light chain variable region having at least 80% identity or similarity to the sequence comprising SEQ ID NO: 13 or 17 or 21 or 25 or 30.

Competing antibodies can be identified using any suitable method in the art, for example by using competition ELISA or BIAcore assays where binding of KLK5 by the competing antibody by cross-blocking or by being cross-blocked prevents the binding of an antibody of the present invention or vice versa. Such competing assays may use isolated natural or recombinant KLK5 or a suitable fusion protein/polypeptide thereof. In one example competition is measured using recombinant human active KLK5 (such as for example comprising SEQ ID NO: 53).

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one example, the antibody binding KLK5, which binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 may be engineered to have an appropriate isoelectric point. This may lead to antibodies with more robust properties, in particular suitable solubility and/or stability profiles and/or improved purification characteristics.

Thus, in one aspect the invention provides the antibody binding KLK5, which preferably binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 wherein the antibody comprises:

a. a variable light chain comprising SEQ ID NO: 7 or 11 or 15 or 19 or 23; and a variable heavy chain comprising SEQ ID NO: 9 or 27 or 31 or 35 or 39 or 43; or
b. a light chain comprising SEQ ID NO: 13 or 17 or 21 or 25; and a heavy chain comprising SEQ ID NO: 29 or 33 or 37 or 41 or 45.

which is engineered to have an isoelectric point different to that of the originally identified antibody.

The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value, acidic residues may be introduced to lower the pl, as required. It is important that when manipulating the pI care must be taken to retain the desirable activity of the antibody or fragment. Thus, in one embodiment the engineered antibody has the same or substantially the same activity as the "unmodified" antibody or fragment.

Programs such as ** ExPASY http://www.expasy.ch/tools/pi_tool.html, and http://www.iut-arles.up.univ-mrs.fr/w3bb/d_abim/compo-p.html, may be used to predict the isoelectric point of the antibody.

It will be appreciated that the affinity of antibodies provided by the present invention may be altered using any suitable method known in the art. The present invention therefore also relates to variants of the antibody which have an improved affinity for KLK5, in particular human KLK5. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998).

If desired the antibody according to the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain a fragment of the antibody linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03/031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumor necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}I$, $^{131}I$, $^{111}In$ and In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

In one embodiment, the polymer is albumin or a fragment thereof, such as human serum albumin or a fragment thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumor, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example, the antibody according to the present invention are attached to poly(ethyleneglycol) (PEG) moieties. In one particular embodiment, the antibody according to the present invention and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the antibody using recombinant DNA methods (see for example U.S. Pat. Nos. 5,219,996; 5,667,425; WO98/25971, WO2008/038024). In one example the antibody of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment, Fab' fragment or diFab which is PEGylated, i.e. has PEG (poly(ethyleneglycol)) covalently attached thereto, e.g. according to the method disclosed in EP 0948544 or EP1090037 (see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545). In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido) propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA3 (wherein m in the structure below is 5) and GL2-400MA (where m is 2) and n is approximately 450:

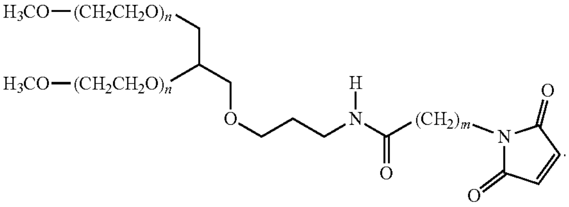

m is 2 or 5

Thus in one embodiment the PEG is 2,3-Bis(methylpolyoxyethylene-oxy)-1-{[3-(6-maleimido oxohexyl)amino] propyloxy} hexane (the 2 arm branched PEG, —CH2) 3NHCO(CH2)5-MAL, Mw 40,000 known as SUNBRIGHT GL2-400MA3.

Further alternative PEG effector molecules of the following type:

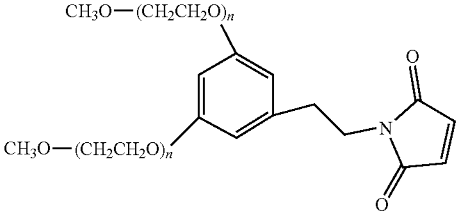

are available from Dr Reddy, NOF and Jenkem.

In one embodiment, the Fab or Fab' according to the present invention is conjugated to a PEG molecule.

In one embodiment, the present disclosure provides a Fab'PEG molecule comprising one or more PEG polymers, for example 1 or 2 polymers such as a 40 kDa polymer or polymers.

Fab'-PEG molecules according to the present disclosure may be particularly advantageous in that they have a half-life independent of the Fc fragment. In one embodiment, there is provided a Fab' conjugated to a polymer, such as a PEG molecule, a starch molecule or an albumin molecule. In one embodiment, there is provided a scFv conjugated to a polymer, such as a PEG molecule, a starch molecule or an albumin molecule. In one embodiment, the Fab or Fab' according to the present disclosure is conjugated to human serum albumin. In one embodiment, the antibody or fragment is conjugated to a starch molecule, for example to increase the half-life. Methods of conjugating starch to a protein as described in U.S. Pat. No. 8,017,739 incorporated herein by reference.

The present invention also provides for an isolated polynucleotide encoding the antibody according to the present invention. The isolated polynucleotide according to the present invention may comprise synthetic DNA, for instance produced by chemical processing, cDNA, genomic DNA or any combination thereof.

Standard techniques of molecular biology may be used to prepare DNA sequences coding for the antibody of the present invention. Desired DNA sequences may be synthesized completely or in part using oligonucleotide synthesis techniques. Site-directed mutagenesis and polymerase chain reaction (PCR) techniques may be used as appropriate.

In one embodiment, the isolated polynucleotide according to the invention encodes:

a. a light chain variable region, wherein the polynucleotide:
   i. is at least 90% identical to SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or
   ii. comprises SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or
   iii. consists essentially of SEQ ID NO: 8 (or nucleotides 1 to 330 of SEQ ID NO: 8) or 12 (or nucleotides 1 to 330 of SEQ ID NO: 12) or 16 or 20 or 24 or 64 or 66;
b. a heavy chain variable region, wherein the polynucleotide:
   i. is at least 90% identical to SEQ ID NO: 10 or 28 or 32 or 36 or 40 or 44; or
   ii. comprises SEQ ID NO: 10 or 28 or 32 or 36 or 40 or 44; or
   iii. consists essentially of SEQ ID NO: 10 or 28 or 32 or 36 or 40 or 44;
c. a light chain, wherein the polynucleotide:
   i. is at least 90% identical to SEQ ID NO: 14 or 18 or 22 or 26 or 65 or 67 or 100 or 101 or 102 or 103 or 104; or
   ii. comprises SEQ ID NO: 14 or 18 or 22 or 26 or 65 or 67 or 100 or 101 or 102 or 103 or 104; or
   iii. consists essentially of SEQ ID NO: 14 or 18 or 22 or 26 or 65 or 67 or 100 or 101 or 102 or 103 or 104;
d. a heavy chain, wherein the polynucleotide:
   i. is at least 90% identical to SEQ ID NO: 30 or 34 or 38 or 42 or 46; or
   ii. comprises SEQ ID NO: 30 or 34 or 38 or 42 or 46; or
   iii. consists essentially of SEQ ID NO: 30 or 34 or 38 or 42 or 46.

In one embodiment, the present invention provides an isolated polynucleotide encoding the heavy chain of an antibody Fab' fragment or of an IgG1 or IgG4 antibody of the present invention which comprises the sequence given in SEQ ID NO: 10 or 28 or 32 or 36 or 40 or 44. Also provided is an isolated polynucleotide encoding the light chain of an antibody Fab' fragment or of an IgG1 or IgG4 antibody of the present invention which comprises the sequence given in SEQ ID NO: 8 (or nucleotides 1 to 330 of SEQ ID NO: 8) or 12 (or nucleotides 1 to 330 of SEQ ID NO: 12) or 16 or 20 or 24 or 64 or 66.

In another embodiment, the present invention provides an isolated polynucleotide encoding the heavy chain and the light chain of an IgG4(P) antibody of the present invention in which the polynucleotide encoding the heavy chain comprises the sequence given in SEQ ID NO: 30 or 34 or 38 or 42 or 46 and the polynucleotide encoding the light chain comprises the sequence given in SEQ ID NO: 14 or 18 or 22 or 26 or 65 or 67 or 100 or 101 or 102 or 103 or 104.

The present invention also provides for a cloning or expression vector comprising one or more polynucleotides described herein. In one example, the cloning or expression vector according to the present invention comprises one or more isolated polynucleotides comprising a sequence selected from SEQ ID NO: 14 or 18 or 22 or 26 or 65 or 67 or 100 or 101 or 102 or 103 or 104 or 30 or 34 or 38 or 42 or 46.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more isolated polynucleotide sequences according to the invention or one or more cloning or expression vectors comprising one or more isolated polynucleotide sequences encoding an antibody of the present invention. Any suitable host cell/vector system may be used for expression of the polynucleotide sequences encoding the antibody of the present invention. Bacterial, for example *E. coli*, and other microbial systems may be used or eukaryotic, for example mammalian, host cell expression systems may also be used. Suitable mammalian host cells include CHO, myeloma or hybridoma cells.

Suitable types of Chinese Hamster Ovary (CHO cells) for use in the present invention may include CHO and CHO-K1 cells including dhfr− CHO cells, such as CHO-DG44 cells and CHO-DXB11 cells and which may be used with a DHFR selectable marker or CHOK1-SV cells which may be used with a glutamine synthetase selectable marker. Other cell types of use in expressing antibodies include lymphocytic cell lines, e.g., NSO myeloma cells and SP2 cells, COS cells. The host cell may be stably transformed or transfected with the isolated polynucleotide sequences or the expression vectors according to the present invention.

In one embodiment, the host cell according to the present invention is a CHO-DG44 cell stably transfected with an expression vectors comprising the isolated polynucleotide sequences of the present invention, preferably comprising the isolated polynucleotide sequences comprising SEQ ID NO: 8 (or nucleotides 1 to 330 of SEQ ID NO: 8), 10, 12 (or nucleotides 1 to 330 of SEQ ID NO: 12), 14, 16, 18, 20, 22, 24, 26, 28, 30, 32, 34, 36, 38, 40, 42, 44, 46, 64, 65, 66, 67, 100, 101, 102, 103 or 104.

The present invention also provides a process for the production of an antibody binding KLK5 according to the present invention comprising culturing a host cell according to the present invention under conditions suitable for producing the antibody and isolating the so produced antibody.

The antibody may comprise only a heavy or light chain, in which case only a heavy chain or light chain polynucleotide sequence needs to be used to transfect the host cells. For production of antibodies comprising both heavy and light chains, the cell line may be transfected with two vectors, a first vector encoding a light chain and a second vector encoding a heavy chain. Alternatively, a single vector may be used, the vector comprising polynucleotide sequences encoding the light chain and the heavy chain.

Thus, there is provided a process for culturing a host cell and expressing an antibody, isolating the latter and optionally purifying the same to provide an isolated antibody. Thus, in one embodiment there is provided an isolated antibody binding KLK5, preferably human KLK5, such as a humanized antibody, in particular an antibody according to the invention, in substantially purified from, in particular free or substantially free of endotoxin and/or host cell protein or DNA, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

In another embodiment, there is provided an isolated antibody binding KLK5, preferably human KLK5, such as a humanized antibody, in particular an antibody according to the invention, in substantially purified from, in particular free or substantially free of endotoxin and/or host cell protein or DNA, wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 pg per mg of antibody product or less such as 100 pg per mg or less, in particular 20 pg per mg, as appropriate.

As the antibodies of the present invention are useful in the treatment, diagnosis and/or prophylaxis of a pathological condition, the present invention also provides for a pharmaceutical or diagnostic composition comprising the antibody according to the present invention in combination with one or more of a pharmaceutically acceptable carrier, excipient or diluents.

Preferably, the pharmaceutical or diagnostic composition comprises an antibody which binds KLK5, preferably human KLK5, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or 6. a light chain comprising SEQ ID NO: 13 or 17 or 21 or 25 and a heavy chain comprising SEQ ID NO: 29 or 33 or 37 or 41 or 45.

Preferably the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In one embodiment, the antibody according to the present invention is the sole active ingredient. In another embodiment, the antibody according to the present invention is in combination with one or more additional active ingredients. Alternatively, the pharmaceutical compositions comprise the antibody according to the present invention which is the sole active ingredient and it may be administered individually to a patient in combination (e.g. simultaneously, sequentially or separately) with other therapeutic, diagnostic or palliative agents.

In another embodiment, the pharmaceutical composition comprises an antibody binding KLK5, preferably human KLK5, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45;

and one or more pharmaceutically acceptable carriers, excipients of diluents.

Preferably, the pharmaceutical composition comprising an antibody which binds KLK5 binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51. More preferably, the pharmaceutical composition comprising an antibody which binds KLK5 wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 and which antibody comprises a light chain variable region of SEQ ID NO: 15 and a heavy chain variable region of SEQ ID NO: 39.

The pharmaceutical compositions according to the invention may be administered suitably to a patient to identify the therapeutically effective amount required. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. Generally, a therapeutically effective amount will be from 0.01 mg/kg to 500 mg/kg, for example 0.1 mg/kg to 200 mg/kg, such as 100 mg/Kg. Pharmaceutical compositions may be conveniently presented in unit dose forms containing a predetermined amount of an active agent of the invention per dose.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion, in intravenous, inhalable or sub-cutaneous form. Where the product is for injection or infusion, it may take the form of a suspension, solution or emulsion in an oily or aqueous vehicle and it may contain formulatory agents, such as suspending, preservative, stabilizing and/or dispersing agents. Alternatively, the antibody according to the invention may be in dry form, for reconstitution before use with an appropriate sterile liquid. Solid forms suitable for solution in, or suspension in, liquid vehicles prior to injection may also be prepared.

Once formulated, the compositions of the invention can be administered directly to the subject. Accordingly, provided herein is the use of an antibody according to the invention for the manufacture of a medicament.

Preferably, the pharmaceutical composition according to the present invention is adapted for administration to human subjects.

Hence, in another aspect the present invention provides for the antibody which binds KLK5 wherein the antibody or a pharmaceutical composition comprising the antibody, for use in therapy, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or 2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

Preferably the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In a preferred embodiment, the antibody which binds KLK5 or a pharmaceutical composition comprising the antibody, for use in therapy, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising
2. a variable light chain comprising SEQ ID NO: 15; and a variable heavy chain comprising SEQ ID NO: 39; or
3. a light chain comprising SEQ ID NO: 17 and a heavy chain comprising SEQ ID NO: 41.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In another preferred embodiment, the antibody which binds KLK5 wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 or a pharmaceutical composition comprising the antibody, for use in therapy, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain comprising SEQ ID NO: 15; and a variable heavy chain comprising SEQ ID NO: 39; or
3. a light chain comprising SEQ ID NO: 17 and a heavy chain comprising SEQ ID NO: 41

In particular, the use in therapy comprises the use in the treatment of one or more diseases characterized by dysregulation of KLK5 or by dysregulation of inhibition of KLK5.

In yet another aspect, the present invention provides for method of treating one or more diseases characterized by dysregulation of KLK5 or by dysregulation of inhibition of KLK5 in a patient comprising administering to said patient a therapeutically effective amount of the antibody which binds KLK5 or a pharmaceutical composition comprising the antibody, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51

In another preferred embodiment, the present invention provides for a method of treating one or more diseases characterized by dysregulation of KLK5 or by dysregulation of inhibition of KLK5 in a patient comprising administering to said patient a therapeutically effective amount of the antibody or a pharmaceutical composition comprising the antibody, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain comprising SEQ ID NO: 15; and a variable heavy chain comprising SEQ ID NO: 39; or
3. a light chain comprising SEQ ID NO: 17 and a heavy chain comprising SEQ ID NO: 41.

Preferably the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In another aspect, the antibody which binds KLK5 or a pharmaceutical composition comprising the antibody, wherein the antibody is for use in the treatment of one or more diseases characterized by dysregulation of KLK5 or by dysregulation of inhibition of KLK5, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

In another preferred embodiment, the antibody which binds KLK5 or a pharmaceutical composition comprising the antibody, wherein the antibody is for use in the treatment of one or more diseases characterized by dysregulation of KLK5 or by dysregulation of inhibition of KLK5, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain comprising SEQ ID NO: 15; and a variable heavy chain comprising SEQ ID NO: 39; or
3. a light chain comprising SEQ ID NO: 17 and a heavy chain comprising SEQ ID NO: 41.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

Preferably, the one or more diseases characterized by dysregulation of KLK5 or by dysregulation of inhibition of KLK5 are selected from Netherton's Syndrome, Atopic Dermatitis, Ichthyoses, Rosacea, Asthma or Cancer, such as ovarian cancer or bladder cancer or a combination thereof.

Therefore, the present invention provides for a method of treating Netherton's Syndrome, Atopic Dermatitis, Ichthyoses, Rosacea, Asthma or Cancer, such as ovarian cancer or bladder cancer or a combination thereof in a patient comprising administering to said patient a therapeutically effective amount of the antibody which binds KLK5 or a pharmaceutical composition comprising the antibody, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 co comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or 6. a light chain comprising SEQ ID NO: 13 or 17 or 21 or 25 and a heavy chain comprising SEQ ID NO: 29 or 33 or 37 or 41 or 45.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

More preferably, the method is for treating Netherton's Syndrome and/or Atopic Dermatitis.

In another aspect, there is provided an antibody which binds KLK5 or a pharmaceutical composition comprising the antibody, wherein the antibody is for use in the treatment of Netherton's Syndrome, Atopic Dermatitis, Ichthyoses, Rosacea, Asthma or Cancer, such as ovarian cancer or bladder cancer or a combination thereof, and wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

More preferably, the antibody is for use in the treatment of Netherton's Syndrome and/or Atopic Dermatitis.

In another preferred embodiment, there is provided present invention provides for a method of treating Netherton's Syndrome, Atopic Dermatitis, Ichthyoses, Rosacea, Asthma or Cancer, such as ovarian cancer or bladder cancer or a combination thereof in a patient comprising administering to said patient a therapeutically effective amount of the antibody which binds KLK5 or a pharmaceutical composition comprising the antibody, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising
2. a variable light chain comprising SEQ ID NO: 15; and a variable heavy chain comprising SEQ ID NO: 39; or
3. a light chain comprising SEQ ID NO: 17 and a heavy chain comprising SEQ ID NO: 41.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

More preferably, the method is for treating Netherton's Syndrome and/or Atopic Dermatitis.

In another preferred embodiment, the antibody which binds KLK5 or a pharmaceutical composition comprising the antibody is for use in the treatment of Netherton's Syndrome, Atopic Dermatitis, Ichthyoses, Rosacea, Asthma or Cancer, such as ovarian cancer or bladder cancer, or a combination thereof, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain comprising SEQ ID NO: 15; and a variable heavy chain comprising SEQ ID NO: 39; or
3. a light chain comprising SEQ ID NO: 17 and a heavy chain comprising SEQ ID NO: 41.

Preferably, the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

More preferably, the antibody is for use in the treatment of Netherton's Syndrome and/or Atopic Dermatitis.

The present invention also provides for an antibody which binds KLK5 or a pharmaceutical composition comprising the antibody, wherein the antibody is for use in the treatment of Netherton's Syndrome, Atopic Dermatitis, Ichthyoses, Rosacea, Asthma or Cancer, such as ovarian cancer or bladder cancer or a combination thereof, wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51

Also provided by the present invention is a method of treating Netherton's Syndrome, Atopic Dermatitis, Ichthyoses, Rosacea, Asthma or Cancer, such as ovarian cancer or bladder cancer or a combination thereof in a patient comprising administering to said patient a therapeutically effective amount of the antibody which binds KLK5 or a pharmaceutical composition comprising the antibody, wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51

The present invention also provides for the use of the antibody which binds KLK5 wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 or a pharmaceutical composition comprising the antibody for the manufacture of a medicament for treating one or more diseases characterized by dysregulation of KLK5 or by dysregulation of inhibition of KLK5, wherein such dysregulation is preferably Netherton's Syndrome, Atopic Dermatitis, Ichthyoses, Rosacea, Asthma or Cancer, such as ovarian cancer or bladder cancer, or a combination thereof, more preferably Netherton's Syndrome and/or Atopic Dermatitis.

In particular, the invention also provides for the use of the antibody which binds KLK5 wherein the antibody preferably binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 or a pharmaceutical composition comprising the antibody for the manufacture of a medicament for treating one or more diseases characterized by dysregulation of KLK5 or by dysregulation of inhibition of KLK5, wherein such dysregulation is preferably Netherton's Syndrome, Atopic Dermatitis, Ichthyoses, Rosacea, Asthma or Cancer, such as ovarian cancer or bladder cancer, or a combination thereof, more preferably Netherton's Syndrome and/or Atopic Dermatitis, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

Also provided by the present invention is the use of the antibody which binds KLK5 wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51 as diagnostically active agents or in diagnostic assays, for example for diagnosing Netherton's Syndrome, Atopic Dermatitis, Ichthyoses, Rosacea, Asthma or Cancer, such as ovarian cancer or bladder cancer.

More preferably the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

The diagnosis may preferably be performed on biological samples. A "biological sample" encompasses a variety of sample types obtained from an individual and can be used in a diagnostic or monitoring assay. The definition encompasses blood such as plasma and serum, and other liquid samples of biological origin such as urine and saliva, cerebrospinal fluid, solid tissue samples such as a biopsy specimen, such as skin biopsies or tissue cultures or cells derived therefrom and the progeny thereof. The definition also includes samples that have been manipulated in any way after their procurement, such as by treatment with reagents, solubilization, or enrichment for certain components, such as polynucleotides.

Diagnostic testing may preferably be performed on biological samples which are not in contact with the human or animal body. Such diagnostic testing is also referred to as in vitro testing. In vitro diagnostic testing may rely on an in vitro method of detecting KLK5 in a biological sample which has been obtained from an individual comprising the steps of i) contacting the biological sample with the antibody as described herein; and ii) detecting binding of the antibody to KLK5. By comparing the detected KLK5 level or the presence of a specific post-translationally modified form of KLK5 (including any pro-form) with a suitable control, one or more diseases characterized by dysregulation of KLK5 or by dysregulation of inhibition of KLK5 may be identified. Such a detection method can thus be used to determine whether a subject (including an embryo or a fetus) has, or is at risk of developing, diseases characterized by dysregulation of KLK5 or by dysregulation of inhibition of KLK5.

Therefore, the present invention provides for an antibody which binds KLK5 wherein the antibody preferably binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51, wherein the antibody is for use in the diagnosis of one or more diseases characterized by dysregulation of KLK5 or by dysregulation of inhibition of KLK5, preferably in the diagnosis of Netherton's Syndrome, Atopic Dermatitis, Ichthyoses, Rosacea, Asthma or Cancer, such as ovarian cancer or bladder cancer, wherein the antibody comprises:

1. a variable light chain and a variable heavy chain, and wherein the variable light chain comprises a CDR-L1 comprising SEQ ID NO: 1, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
2. a variable light chain and a variable heavy chain, and wherein the variable light chain comprises a CDR-L1 comprising SEQ ID NO: 62, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
3. a variable light chain and a variable heavy chain, and wherein the variable light chain comprises a CDR-L1 comprising SEQ ID NO: 63, a CDR-L2 comprising SEQ ID NO: 2 and a CDR-L3 comprising SEQ ID NO: 3; and the variable heavy chain comprises a CDR-H1 comprising SEQ ID NO: 4, a CDR-H2 comprising SEQ ID NO: 5 and a CDR-H3 comprising SEQ ID NO: 6; or
4. a variable light chain comprising SEQ ID NO: 7 or 11 or 15 or 19 or 23; and a variable heavy chain comprising SEQ ID NO: 9 or 27 or 31 or 35 or 39 or 43; or
5. a variable light chain comprising SEQ ID NO: 15 wherein amino acid residue glutamine 24 (Gln; Q) with reference to SEQ ID NO: 15 is an arginine (Arg; R) or a lysine (Lys; K); and a variable heavy chain comprising SEQ ID NO: 9 or 27 or 31 or 35 or 39 or 43; or
6. a light chain comprising SEQ ID NO: 13 or 17 or 21 or 25 and a heavy chain comprising SEQ ID NO: 29 or 33 or 37 or 41 or 45.

The present invention therefore relates to the following embodiments:

Embodiment 1: An antibody which binds to kallikrein 5 (KLK5), wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Embodiment 2: The antibody according to Embodiment 1 wherein:

a. the variable light chain comprises a CDR-L1 comprising SEQ ID NO: 1, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Embodiment 3: An antibody which binds to kallikrein 5 (KLK5), wherein the antibody binds to an epitope of human KLK5 comprising amino acid residues Arg87, Ala107, Arg110, Lys111, Lys112, Val113, Val137, Lys138, Ser139, Ile140, Pro141, His142, Pro143, Tyr145, Ser146 and His147 with reference to SEQ ID NO: 51.

Embodiment 4: The antibody according to Embodiment 3, wherein the epitope is characterized by X-ray crystallography.

Embodiment 5: The antibody according to any one of Embodiments 1 to 4, wherein the antibody inhibits or reduces the protease activity of KLK5.

Embodiment 6: The antibody according to any one of Embodiments 1 to 5, wherein the antibody binds to KLK5 when KLK5 is bound to LEKTI, or a fragment of LEKTI.

Embodiment 7: The antibody according to any one of Embodiments 1 to 6, wherein the antibody does not compete with LEKTI, or a fragment of LEKTI, for binding KLK5.

Embodiment 8: The antibody according to any one of Embodiments 1 to 7, wherein the antibody forms a complex with KLK5 bound to LEKTI, or a fragment of LEKTI.

Embodiment 9: The antibody according to any one of Embodiments 6 to 8 wherein the fragment of LEKTI is human LEKTI domain 5 comprising amino acids 1 to 64 of SEQ ID NO: 54 or LEKTI domain 8 comprising amino acids 1 to 71 of SEQ ID NO: 61.

Embodiment 10: The antibody according to any one of the preceding Embodiments wherein the antibody binds human KLK5, preferably human KLK5 comprising SEQ ID NO: 53 and cynomolgus monkey (cyno) KLK5, preferably cyno KLK5 comprising SEQ ID NO: 60.

Embodiment 11: The antibody according to any one of the preceding Embodiments wherein the antibody does not bind human or cyno kallikrein 2 (KLK2); or human or cyno kallikrein 4 (KLK4); or human or cyno kallikrein 7 (KLK7).

Embodiment 12: The antibody according to any one of Embodiments 3 to 11, wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, preferably a CDR-L1 comprising SEQ ID NO: 1, a CDR-L2 comprising SEQ ID NO: 2 and a CDR-L3 comprising SEQ ID NO: 3; and
b. the variable heavy chain comprises a CDR-H1 comprising SEQ ID NO: 4, a CDR-H2 comprising SEQ ID NO: 5 and a CDR-H3 comprising SEQ ID NO: 6.

Embodiment 13: The antibody according to any one of the preceding Embodiments wherein the antibody is a chimeric or humanized antibody.

Embodiment 14: The antibody according to any one of the preceding Embodiments, wherein the antibody is a full-length antibody.

Embodiment 15: The antibody according to Embodiment 13, wherein the full-length antibody is selected from an IgG1, IgG4 or IgG4P.

Embodiment 16: The antibody according to any one of Embodiments 1 to 13, wherein the antibody is selected from a Fab, a Fab', a $F(ab)_2$, a scFv, a dAb or a $V_{HH}$.

Embodiment 17: The antibody according to any one of Embodiments 1 to 16, wherein the antibody comprises:

a. a variable light chain comprising SEQ ID NO: 7 or 11 or 15 or 19 or 23; and/or
b. a variable heavy chain comprising SEQ ID NO: 9 or 27 or 31 or 35 or 39 or 43.

Embodiment 18: The antibody according to any one of Embodiments 1 to 15 or 17, wherein the antibody comprises:
a. a light chain comprising SEQ ID NO: 13 or 17 or 21 or 25; and
b. a heavy chain comprising SEQ ID NO: 29 or 33 or 37 or 41 or 45.

Embodiment 19: The antibody according to Embodiments 17 or 18, wherein amino acid residue glutamine (Gln; Q) in L-CDR1 at position 24 with reference to SEQ ID NO: 15 or 17 is replaced by arginine (Arg; R) or by lysine (Lys; K).

Embodiment 20: The antibody according to any one of the preceding Embodiments wherein KLK5 is human KLK5 comprising SEQ ID NO: 51 or 52 or 53 or cyno KLK5 comprising SEQ ID NO: 60.

Embodiment 21: The antibody according to any one of the preceding Embodiments wherein the antibody forms a complex with KLK5, preferably human KLK5, bound to another antibody which comprises:
a. a variable light chain comprising a CDR-L1 comprising SEQ ID NO: 68, a CDR-L2 comprising SEQ ID NO: 69 and a CDR-L3 comprising SEQ ID NO: 70; and a variable heavy chain comprises a CDR-H1 comprising SEQ ID NO: 71, a CDR-H2 comprising SEQ ID NO: 72 and a CDR-H3 comprising SEQ ID NO: 73; and/or
b. a variable light chain comprising SEQ ID NO: 74 and a variable heavy chain comprising SEQ ID NO: 76; and/or
c. a variable light chain encoded by a nucleotide comprising SEQ ID NO: 75 and a variable heavy chain encoded by a nucleotide comprising SEQ ID NO: 77.

Embodiment 22: An antibody binding KLK5, preferably, human KLK5 wherein the antibody comprises:
a. a variable light chain comprising a CDR-L1 comprising SEQ ID NO: 68, a CDR-L2 comprising SEQ ID NO: 69 and a CDR-L3 comprising SEQ ID NO: 70; and a variable heavy chain comprises a CDR-H1 comprising SEQ ID NO: 71, a CDR-H2 comprising SEQ ID NO: 72 and a CDR-H3 comprising SEQ ID NO: 73; and/or
b. a variable light chain comprising SEQ ID NO: 74 and a variable heavy chain comprising SEQ ID NO: 76; and/or
c. a variable light chain encoded by a nucleotide comprising SEQ ID NO: 75 and a variable heavy chain encoded by a nucleotide comprising SEQ ID NO: 77.

Embodiment 23: A KLK5-antibody complex comprising:
a. KLK5, preferably human KLK5
b. the antibody according to any one of Embodiments 1 to 18 and
c. the antibody according to Embodiments 19 or Embodiments 20.

Embodiment 24: An antibody which:
a. Competes for binding KLK5 with the antibody according to any one of Embodiments 1 to 20; and/or
b. cross-blocks or is cross-blocked by the antibody according to any one of Embodiments 1 to 20 for binding KLK5; and/or
c. binds KLK5 to the same epitope as the antibody according to any one of Embodiments 1 to 20; and/or
d. comprises a heavy chain variable region having at least 90% identity or similarity to the sequence according to SEQ ID NO: 29 or 33 or 37 or 41 or 45; and/or
e. comprises a light chain variable region having at least 90% identity or similarity to the sequence according to SEQ ID NO: 13 or 17 or 21 or 25.

Embodiment 25: An isolated polynucleotide encoding the antibody according to any one of Embodiments 1 to 20.

Embodiment 26: The isolated polynucleotide according to Embodiment 25, wherein the polynucleotide encodes:
a. a light chain variable region, wherein the polynucleotide:
i. is at least 90% identical to SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or
ii. comprises SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or
iii. consists essentially of SEQ ID NO: 8 (or nucleotides 1 to 330 of SEQ ID NO: 8) or 12 (or nucleotides 1 to 330 of SEQ ID NO: 12) or 16 or 20 or 24 or 64 or 66; or
b. a heavy chain variable region, wherein the polynucleotide:
i. is at least 90% identical to SEQ ID NO: 10 or 28 or 32 or 36 or 40 or 44; or
ii. comprises SEQ ID NO: 10 or 28 or 32 or 36 or 40 or 44; or
iii. consists essentially of SEQ ID NO: 10 or 28 or 32 or 36 or 40 or 44; or
c. a light chain, wherein the polynucleotide:
i. is at least 90% identical to SEQ ID NO: 14 or 18 or 22 or 26 or 65 or 67 or 100 or 101 or 102 or 103 or 104; or
ii. comprises SEQ ID NO: 14 or 18 or 22 or 26 or 65 or 67 or 100 or 101 or 102 or 103 or 104; or
iii. consists essentially of SEQ ID NO: 14 or 18 or 22 or 26 or 65 or 67 or 100 or 101 or 102 or 103 or 104; or
d. a heavy chain, wherein the polynucleotide:
i. is at least 90% identical to SEQ ID NO: 30 or 34 or 38 or 42 or 46; or
ii. comprises SEQ ID NO: 30 or 34 or 38 or 42 or 46; or
iii. consists essentially of SEQ ID NO: 30 or 34 or 38 or 42 or 46.

Embodiment 27: A cloning or expression vector comprising one or more polynucleotides according to any one of Embodiments 25 or 26.

Embodiment 28: A host cell comprising:
a. one or more polynucleotides according to any one of Embodiments 25 or 26 or
b. one or more expression vectors according to Embodiment 27.

Embodiment 29: A process for the production of an antibody according to any one of Embodiments 1 to 20, comprising culturing the host cell according to Embodiment 28 under suitable conditions for producing the antibody and isolating the antibody produced by the host cell.

Embodiment 30: A pharmaceutical composition comprising the antibody according to any one of Embodiments 1 to 20 and one or more pharmaceutically acceptable carriers, excipients of diluents.

Embodiment 31: The antibody or antigen-binding fragment thereof according to any one of Embodiments 1 to 20 or the pharmaceutical composition according to Embodiment 30 for use in therapy.

Embodiment 32: The antibody according to any one of Embodiments 1 to 20 or the pharmaceutical composition according to Embodiment 30 for use in the treatment of a disease characterized by dysregulation of KLK5 or by dysregulation of inhibition of KLK5.

Embodiment 33: The antibody for use according to Embodiment 32 wherein the disease is selected from Netherton's Syndrome, Atopic Dermatitis, Ichthyoses, Rosacea, Asthma or Cancer, such as ovarian cancer or bladder cancer or a combination thereof.

Embodiment 34: The antibody for use according to Embodiment 33 wherein the disease is Netherton's Syndrome.

Embodiment 35: The antibody for use according to Embodiment 33 wherein the disease is Atopic Dermatitis.

Embodiment 36: A method of treating diseases characterized by dysregulation of KLK5 or by dysregulation of inhibition of KLK5 in a patient comprising administering to said patient a therapeutically effective amount of an antibody according to any one of Embodiments 1 to 20 or the pharmaceutical composition according to Embodiment 30.

Embodiment 37: The method according to Embodiment 34 wherein the disease is selected from Netherton's Syndrome, Atopic Dermatitis, Ichthyoses, Rosacea, Asthma or Cancer, such as ovarian cancer or bladder cancer.

Embodiment 38: The antibody for use according to Embodiment 35 wherein the disease is Netherton's Syndrome.

Embodiment 39: The antibody for use according to Embodiment 35 wherein the disease is Atopic Dermatitis.

Embodiment 40: The antibody according to any one of Embodiments 1 to 20 or the pharmaceutical composition according to Embodiment 30 for the manufacture of a medicament for treating one or more diseases characterized by dysregulation of KLK5 or by dysregulation of inhibition of KLK5.

Embodiment 41: The antibody for the manufacture according to Embodiment 40 wherein the disease is selected from Netherton's Syndrome, Atopic Dermatitis, Ichthyoses, Rosacea, Asthma or Cancer, such as ovarian cancer or bladder cancer or a combination thereof.

Embodiment 42: The antibody for the manufacture according to Embodiment 40 wherein the disease is selected from Netherton's Syndrome or Atopic Dermatitis or a combination thereof.

Embodiment 43: The antibody according to any one of Embodiments 1 to 20 for use as a diagnostic agent or for use in a diagnostic assay or a diagnostic kit for the diagnosis of one or more diseases characterized by dysregulation of KLK5 or by dysregulation of inhibition of KLK5.

Embodiment 44: The antibody according to Embodiment 43 wherein the disease is selected from Netherton's Syndrome, Atopic Dermatitis, Ichthyoses, Rosacea, Asthma or Cancer, such as ovarian cancer or bladder cancer or a combination thereof.

The sequences included in the present invention are shown in Table 1:

TABLE 1

| Name | SEQ ID NO: | SEQUENCE |
|---|---|---|
| CDR-L1 | 1 | QASQSISSWLA |
| CDR-L2 | 2 | LASTLAS |
| CDR-L3 | 3 | QQGYTNSNIINT |
| CDR-H1 | 4 | GFPLSNYAMS |
| CDR-H2 | 5 | DIYPSDIIDYASWAKG |
| CDR-H3 | 6 | DNNDYGLDI |
| Rabbit VL | 7 | AYDMTQTPASVEVAVGGTVTIKCQASQSISSWLAWYQQKPGQPPKLLIY<br>LASTLASGVSSRFKGSGSGTQFTLTISGVECADAATYYCQQGYTNSNII<br>NTFGGGTEVVVK |
| Rabbit VL nucl. | 8 | gcctatgatatgacccagactccagcctctgtggaggtagctgtgggag<br>gcacagtcaccatcaagtgccaggccagtcagagcattagcagttggtt<br>agcctggtatcagcagaaaccaggtcagcctcccaagctcctgatctat<br>ctggcatccactctggcatctggggtctcatcgcggttcaaaggcagtg<br>gatctgggacacagttcactctcaccatcagcggcgtggagtgtgccga<br>tgctgccacttactactgtcaacagggttatactaatagtaatattatt<br>aatactttcggcggagggaccgaggtggtggtcaaacgtacg |
| Rabbit VH | 9 | QSVEESGGRLVTPGTPLTLTCTVSGFPLSNYAMSWVRQAPGKGLEWIGD<br>IYPSDIIDYASWAKGRFTISQTSTTVELKITGPTTEDTATYFCARDNND<br>YGLDIWGPGTLVTVSS |
| Rabbit VH nucl. | 10 | cagtcggtggaggagtccgggggtcgcctggtcacgcctgggacacccc<br>tgacactcacctgcaccgtctctgggttccccctcagtaattatgcaat<br>gagctgggtccgccaggctccagggaaggggctggaatggatcggagac<br>atttatcctagtgatatcatagactacgcgagctgggcgaaaggccgat<br>tcaccatctcccaaacctcgaccacggtggagctgaaaatcacgggtcc<br>gacaaccgaggacacggccacctatttctgtgccagagacaacaatgac<br>tatggtctggacatctggggcccaggcaccctggtcaccgtctcgagt |
| 10236 gL5 VL | 11 | AYDMTQSPSSLSASVGDRVTITCQASQSISSWLAWYQQKPGKAPKLLIY<br>LASTLASGVPSRFKGSGSGTDFTLTISSLQPEDFATYYCQQGYTNSNII<br>NTFGGGTKVEIK |

TABLE 1-continued

| Name | SEQ ID NO: | SEQUENCE |
|---|---|---|
| 10236 gL5 VL nucl. | 12 | gcctacgacatgactcagtccccatcctccctgtccgcatccgtgggggatagagtcaccatcacctgtcaagccagccagtcaattagctcgtggctggcctggtatcagcagaagccgggaaaggctcccaagttgctgatctacctggcctcaacgctcgcgtcgggagtgcctagccgctttaagggttccggatctggcaccgacttcactctcaccatttcgagccttcaaccggaggacttcgccacttactactgccagcagggttacaccaactccaacatcatcaacaccttcggcggagggaccaaagtggaaatcaagcgtacg |
| 10236 gL5 Light chain | 13 | AYDMTQSPSSLSASVGDRVTITCQASQSISSWLAWYQQKPGKAPKLLIYLASTLASGVPSRFKGSGSGTDFTLTISSLQPEDFATYYCQQGYTNSNIINTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 10236 gL5 Light chain nucl. | 14 | gcctacgacatgactcagtccccatcctccctgtccgcatccgtgggggatagagtcaccatcacctgtcaagccagccagtcaattagctcgtggctggcctggtatcagcagaagccgggaaaggctcccaagttgctgatctacctggcctcaacgctcgcgtcgggagtgcctagccgctttaagggttccggatctggcaccgacttcactctcaccatttcgagccttcaaccggaggacttcgccacttactactgccagcagggttacaccaactccaacatcatcaacaccttcggcggagggaccaaagtggaaatcaagcgtacgcgtacggtggccgctccctccgtgttcatcttcccaccctccgacgagcagctgaagtccggcaccgcctccgtcgtgtgcctgctgaacaacttctacccccgcgaggccaaggtgcagtggaaggtggacaacgccctgcagtccggcaactcccaggaatccgtcaccgagcaggactccaaggacagcacctactccctgtcctccaccctgaccctgtccaaggccgactacgagaagcacaaggtgtacgcctgcgaagtgacccaccagggcctgtccagccccgtgaccaagtccttcaaccggggcgagtgc |
| 10236 gL6 VL | 15 | AYDMTQSPSSLSASVGDRVTITCQASQSISSWLAWYQQKPGKAPKLLIYLASTLASGVPSRFSGSGSGTDFTLTISSLQPEDFATYYCQQGYTNSNIINTFGGGTKVEIK |
| 10236 gL6 VL nucl. | 16 | gcctacgacatgactcagtccccatcctccctgtccgcatccgtgggggatagagtcaccatcacctgtcaagccagccagtcaattagctcgtggctggcctggtatcagcagaagccgggaaaggctcccaagttgctgatctacctggcctcaacgctcgcgtcgggagtgcctagccgcttttccggttccggatctggcaccgacttcactctcaccatttcgagccttcaaccggaggacttcgccacttactactgccagcagggttacaccaactccaacatcatcaacaccttcggcggagggaccaaagtggaaatcaag |
| 10236 gL6 Light chain | 17 | AYDMTQSPSSLSASVGDRVTITCQASQSISSWLAWYQQKPGKAPKLLIYLASTLASGVPSRFSGSGSGTDFTLTISSLQPEDFATYYCQQGYTNSNIINTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 10236 gL6 Light chain nucl. | 18 | gcctacgacatgactcagtccccatcctccctgtccgcatccgtgggggatagagtcaccatcacctgtcaagccagccagtcaattagctcgtggctggcctggtatcagcagaagccgggaaaggctcccaagttgctgatctacctggcctcaacgctcgcgtcgggagtgcctagccgcttttccggttccggatctggcaccgacttcactctcaccatttcgagccttcaaccggaggacttcgccacttactactgccagcagggttacaccaactccaacatcatcaacaccttcggcggagggaccaaagtggaaatcaagcgtacggtggccgctccctccgtgttcatcttcccaccctccgacgagcagctgaagtccggcaccgcctccgtcgtgtgcctgctgaacaacttctacccccgcgaggccaaggtgcagtggaaggtggacaacgccctgcagtccggcaactcccaggaatccgtcaccgagcaggactccaaggacagcacctactccctgtcctccaccctgaccctgtccaaggccgactacgagaagcacaaggtgtacgcctgcgaagtgacccaccagggcctgtccagccccgtgaccaagtccttcaaccggggcgagtgc |
| 10236 gL7 VL | 19 | AIDMTQSPSSLSASVGDRVTITCQASQSISSWLAWYQQKPGKAPKLLIYLASTLASGVPSRFSGSGSGTDFTLTISSLQPEDFATYYCQQGYTNSNIINTFGGGTKVEIK |
| 10236 gL7 VL nucl. | 20 | gcgatcgacatgactcagagcccgtccagcctgtccgcgtccgtgggagatcgcgtgactatcacgtgtcaggcctcacaatccattagctcctggctggcctggtaccagcagaagccagggaaggctccgaagctgctgatctacctggcctccacccttgcctccggcgtgccttcacggttttctggatccggctcgggaaccgacttcaccctcaccatctcgtcgctccaacccgaggacttcgcaacctactactgccaacaggggtataccaacagcaacatcatcaacaccttcggtggcggaactaaggtcgaaatcaag |

TABLE 1-continued

| Name | SEQ ID NO: | SEQUENCE |
|---|---|---|
| 10236 gL7 Light chain | 21 | AIDMTQSPSSLSASVGDRVTITCQASQSISSWLAWYQQKPGKAPKLLIY LASTLASGVPSRFSGSGSGTDFTLTISSLQPEDFATYYCQQGYTNSNII NTFGGGTKVEIKRTVAAPSVFIFPPSDEQLKSGTASVVCLLNNFYPREA KVQWKVDNALQSGNSQESVTEQDSKDSTYSLSSTLTLSKADYEKHKVYA CEVTHQGLSSPVTKSFNRGEC |
| 10236 gL7 Light chain nucl. | 22 | gcgatcgacatgactcagagcccgtccagcctgtccgcgtccgtgggag atcgcgtgactatcacgtgtcaggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaaggtggccgctccct ccgtgttcatcttcccaccctccgacgagcagctgaagtccggcaccgc ctccgtcgtgtgcctgctgaacaacttctacccccgcgaggccaaggtg cagtggaaggtggacaacgccctgcagtccggcaactcccaggaatccg tcaccgagcaggactccaaggacagcacctactccctgtcctccaccct gaccctgtccaaggccgactacgagaagcacaaggtgtacgcctgcgaa gtgacccaccagggcctgtccagccccgtgaccaagtccttcaaccggg gcgagtgc |
| 10236 gL8 VL | 23 | AYQMTQSPSSLSASVGDRVTITCQASQSISSWLAWYQQKPGKAPKLLIY LASTLASGVPSRFSGSGSGTDFTLTISSLQPEDFATYYCQQGYTNSNII NTFGGGTKVEIK |
| 10236 gL8 VL nucl. | 24 | gcgtatcagatgactcagagcccgtccagcctgtccgcgtccgtgggag atcgcgtgactatcacgtgtcaggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaag |
| 10236 gL8 Light chain | 25 | AYQMTQSPSSLSASVGDRVTITCQASQSISSWLAWYQQKPGKAPKLLIY LASTLASGVPSRFSGSGSGTDFTLTISSLQPEDFATYYCQQGYTNSNII NTFGGGTKVEIKRTVAAPSVFIFPPSDEQLKSGTASVVCLLNNFYPREA KVQWKVDNALQSGNSQESVTEQDSKDSTYSLSSTLTLSKADYEKHKVYA CEVTHQGLSSPVTKSFNRGEC |
| 10236 gL8 Light chain nucl. | 26 | gcgtatcagatgactcagagcccgtccagcctgtccgcgtccgtgggag atcgcgtgactatcacgtgtcaggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaaggtggccgctccct ccgtgttcatcttcccaccctccgacgagcagctgaagtccggcaccgc ctccgtcgtgtgcctgctgaacaacttctacccccgcgaggccaaggtg cagtggaaggtggacaacgccctgcagtccggcaactcccaggaatccg tcaccgagcaggactccaaggacagcacctactccctgtcctccaccct gaccctgtccaaggccgactacgagaagcacaaggtgtacgcctgcgaa gtgacccaccagggcctgtccagccccgtgaccaagtccttcaaccggg gcgagtgc |
| 10236 gH9 VH | 27 | EVQLQESGPGLVKPSGTLSLTCAVSGFPLSNYAMSWVRQPPGKGLEWIG DIYPSDIIDYASWAKGRVTISQDSSKTQVSLKLSSVTAADTAVYYCARD NNDYGLDIWGQGTLVTVSS |
| 10236 gH9 VH nucl. | 28 | gaagtgcagctgcaagagtcaggaccgggcttggtcaagcccagcggaa ccctgtccctgacttgtgccgtgtcggggttcccgctgtcgaactacgc gatgtcctgggtcagacagcctcccggaaagggccttgaatggatcggc gacatctacccaagcgacattattgattacgcatcctgggccaagggac gcgtgaccatctcccaggactcttccaagacccaagtgtccctcaagct gtccagcgtgaccgctgccgacactgccgtgtactattgcgcgcgggat aacaacgactacgggctggacatctggggccagggtaccctcgtgactg tctcgagc |

TABLE 1-continued

| Name | SEQ ID NO: | SEQUENCE |
|---|---|---|
| 10236 gH9 Heavy chain | 29 | EVQLQESGPGLVKPSGTLSLTCAVSGFPLSNYAMSWVRQPPGKGLEWIG<br>DIYPSDIIDYASWAKGRVTISQDSSKTQVSLKLSSVTAADTAVYYCARD<br>NNDYGLDIWGQGTLVTVSSASTKGPSVFPLAPCSRSTSESTAALGCLVK<br>DYFPEPVTVSWNSGALTSGVHTFPAVLQSSGLYSLSSVVTVPSSSLGTK<br>TYTCNVDHKPSNTKVDKRVESKYGPPCPPCPAPEFLGGPSVFLFPPKPK<br>DTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTP<br>PVLDSDGSFFLYSRLTVDKSRWQEGNVFSCSVMHEALHNHYTQKSLSLS<br>LGK |
| 10236 gH9 Heavy chain nucl. | 30 | gaagtgcagctgcaagagtcaggaccgggcttggtcaagcccagcggaa<br>ccctgtccctgacttgtgccgtgtcggggttcccgctgtcgaactacgc<br>gatgtcctgggtcagacagcctcccggaaagggccttgaatggatcggc<br>gacatctacccaagcgacattattgattacgcatcctgggccaagggac<br>gcgtgaccatctcccaggactcttccaagacccaagtgtccctcaagct<br>gtccagcgtgaccgctgccgacactgccgtgtactattgcgcgcgggat<br>aacaacgactacgggctggacatctggggccagggtaccctcgtgactg<br>tctcgagcgcttctacaaagggcccctccgtgttccctctggccccttg<br>ctcccggtccacctccgagtctaccgccgctctgggctgcctggtcaag<br>gactacttccccgagcccgtgacagtgtcctggaactctggcgccctga<br>cctccggcgtgcacaccttccctgccgtgctgcagtcctccggcctgta<br>ctccctgtcctccgtcgtgaccgtgccctcctccagcctgggcaccaag<br>acctacacctgtaacgtggaccacaagccctccaacaccaaggtggaca<br>agcgggtggaatctaagtacggccctccctgccccccctgccctgcccc<br>tgaatttctgggcggaccttccgtgttcctgttcccccccaaagcccaag<br>gacaccctgatgatctcccggacccccgaagtgacctgcgtggtggtgg<br>acgtgtcccaggaagatcccgaggtccagttcaattggtacgtggacgg<br>cgtggaagtgcacaatgccaagaccaagcccagagaggaacagttcaac<br>tccacctaccgggtggtgtccgtgctgaccgtgctgcaccaggactggc<br>tgaacggcaaagagtacaagtgcaaggtgtccaacaagggcctgccctc<br>cagcatcgaaaagaccatctccaaggccaagggccagccccgcgagccc<br>caggtgtacaccctgcccccctagccaggaagagatgaccaagaaccagg<br>tgtccctgacctgtctggtcaagggcttctacccctccgacattgccgt<br>ggaatgggagtccaacggccagcccgagaacaactacaagaccaccccc<br>cctgtgctggacagcgacggctccttcttcctgtactctcggctgaccg<br>tggacaagtcccggtggcaggaaggcaacgtcttctcctgctccgtgat<br>gcacgaggccctgcacaaccactacacccagaagtccctgtccctgagc<br>ctgggcaag |
| 10236 gH10 VH | 31 | EVQLQESGPGLVKPSGTLSLTCAVSGFPLSNYAMSWVRQPPGKGLEWIG<br>DIYPSDIIDYASWAKGRVTISVDSSKTQVSLKLSSVTAADTAVYYCARD<br>NNDYGLDIWGQGTLVTVSS |
| 10236 gH10 VH nucl. | 32 | gaagtgcagctgcaagagtcaggaccgggcttggtcaagcccagcggaa<br>ccctgtccctgacttgtgccgtgtcggggttcccgctgtcgaactacgc<br>gatgtcctgggtcagacagcctcccggaaagggccttgaatggatcggc<br>gacatctacccaagcgacattattgattacgcatcctgggccaagggac<br>gcgtgaccatctccgtggactcttccaagacccaagtgtccctcaagct<br>gtccagcgtgaccgctgccgacactgccgtgtactattgcgcgcgggat<br>aacaacgactacgggctggacatctggggccagggtaccctcgtgactg<br>tctcgagc |
| 10236 gH10 Heavy chain | 33 | EVQLQESGPGLVKPSGTLSLTCAVSGFPLSNYAMSWVRQPPGKGLEWIG<br>DIYPSDIIDYASWAKGRVTISVDSSKTQVSLKLSSVTAADTAVYYCARD<br>NNDYGLDIWGQGTLVTVSSASTKGPSVFPLAPCSRSTSESTAALGCLVK<br>DYFPEPVTVSWNSGALTSGVHTFPAVLQSSGLYSLSSVVTVPSSSLGTK<br>TYTCNVDHKPSNTKVDKRVESKYGPPCPPCPAPEFLGGPSVFLFPPKPK<br>DTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTP<br>PVLDSDGSFFLYSRLTVDKSRWQEGNVFSCSVMHEALHNHYTQKSLSLS<br>LGK |
| 10236 gH10 Heavy chain nucl. | 34 | gaagtgcagctgcaagagtcaggaccgggcttggtcaagcccagcggaa<br>ccctgtccctgacttgtgccgtgtcggggttcccgctgtcgaactacgc<br>gatgtcctgggtcagacagcctcccggaaagggccttgaatggatcggc<br>gacatctacccaagcgacattattgattacgcatcctgggccaagggac<br>gcgtgaccatctccgtggactcttccaagacccaagtgtccctcaagct<br>gtccagcgtgaccgctgccgacactgccgtgtactattgcgcgcgggat<br>aacaacgactacgggctggacatctggggccagggtaccctcgtgactg<br>tctcgagcgcttctacaaagggcccctccgtgttccctctggccccttg<br>ctcccggtccacctccgagtctaccgccgctctgggctgcctggtcaag<br>gactacttccccgagcccgtgacagtgtcctggaactctggcgccctga<br>cctccggcgtgcacaccttccctgccgtgctgcagtcctccggcctgta<br>ctccctgtcctccgtcgtgaccgtgccctcctccagcctgggcaccaag |

TABLE 1-continued

| Name | SEQ ID NO: | SEQUENCE |
|---|---|---|
| | | acctacacctgtaacgtggaccacaagccctccaacaccaaggtggaca<br>agcgggtggaatctaagtacggccctccctgccccccctgccctgcccc<br>tgaatttctgggcggaccttccgtgttcctgttcccccaaagcccaag<br>gacaccctgatgatctcccggacccccgaagtgacctgcgtggtggtgg<br>acgtgtcccaggaagatcccgaggtccagttcaattggtacgtggacgg<br>cgtggaagtgcacaatgccaagaccaagcccagagaggaacagttcaac<br>tccacctaccgggtggtgtccgtgctgaccgtgctgcaccaggactggc<br>tgaacggcaaagagtacaagtgcaaggtgtccaacaagggcctgccctc<br>cagcatcgaaaagaccatctccaaggccaagggccagccccgcgagccc<br>caggtgtacaccctgcccccctagccaggaagagatgaccaagaaccagg<br>tgtccctgacctgtctggtcaagggcttctacccctccgacattgccgt<br>ggaatgggagtccaacggccagcccgagaacaactacaagaccaccccc<br>cctgtgctggacagcgacggctccttcttcctgtactctcggctgaccg<br>tggacaagtcccggtggcaggaaggcaacgtcttctcctgctccgtgat<br>gcacgaggccctgcacaaccactacacccagaagtccctgtccctgagc<br>ctgggcaag |
| 10236 gH11<br>VH | 35 | EVQLQESGPGLVKPSGTLSLTCAVSGFPLSNYAMSWVRQPPGKGLEWIG<br>DIYPSDIIDYASWAKGRVTISQDKSKTQVSLKLSSVTAADTAVYYCARD<br>NNDYGLDIWGQGTLVTVSS |
| 10236 gH11<br>VH nucl. | 36 | gaagtgcagctgcaagagtcaggaccgggcttggtcaagcccagcggaa<br>ccctgtccctgacttgtgccgtgtcggggttcccgctgtcgaactacgc<br>gatgtcctgggtcagacagcctcccggaaagggccttgaatggatcggc<br>gacatctacccaagcgacattattgattacgcatcctgggccaagggac<br>gcgtgaccatctcccaggacaagtccaagacccaagtgtccctcaagct<br>gtccagcgtgaccgctgccgacactgccgtgtactattgcgcgcgggat<br>aacaacgactacgggctggacatctggggccagggtaccctcgtgactg<br>tctcgagc |
| 10236 gH11<br>Heavy<br>chain | 37 | EVQLQESGPGLVKPSGTLSLTCAVSGFPLSNYAMSWVRQPPGKGLEWIG<br>DIYPSDIIDYASWAKGRVTISQDKSKTQVSLKLSSVTAADTAVYYCARD<br>NNDYGLDIWGQGTLVTVSSASTKGPSVFPLAPCSRSTSESTAALGCLVK<br>DYFPEPVTVSWNSGALTSGVHTFPAVLQSSGLYSLSSVVTVPSSSLGTK<br>TYTCNVDHKPSNTKVDKRVESKYGPPCPPCPAPEFLGGPSVFLFPPKPK<br>DTLMISRTPEVTCVVVDVSQEDPEVQFNWYVDGVEVHNAKTKPREEQFN<br>STYRVVSVLTVLHQDWLNGKEYKCKVSNKGLPSSIEKTISKAKGQPREP<br>QVYTLPPSQEEMTKNQVSLTCLVKGFYPSDIAVEWESNGQPENNYKTTP<br>PVLDSDGSFFLYSRLTVDKSRWQEGNVFSCSVMHEALHNHYTQKSLSLS<br>LGK |
| 10236 gH11<br>Heavy<br>chain<br>nucl. | 38 | gaagtgcagctgcaagagtcaggaccgggcttggtcaagcccagcggaa<br>ccctgtccctgacttgtgccgtgtcggggttcccgctgtcgaactacgc<br>gatgtcctgggtcagacagcctcccggaaagggccttgaatggatcggc<br>gacatctacccaagcgacattattgattacgcatcctgggccaagggac<br>gcgtgaccatctcccaggacaagtccaagacccaagtgtccctcaagct<br>gtccagcgtgaccgctgccgacactgccgtgtactattgcgcgcgggat<br>aacaacgactacgggctggacatctggggccagggtaccctcgtgactg<br>tctcgagcgcttctacaaagggcccctccgtgttccctctggccccttg<br>ctcccggtccacctccgagtctaccgccgctctgggctgcctggtcaag<br>gactacttccccgagcccgtgacagtgtcctggaactctggcgccctga<br>cctccggcgtgcacaccttccctgccgtgctgcagtcctccggcctgta<br>ctccctgtcctccgtcgtgaccgtgccctcctccagcctgggcaccaag<br>acctacacctgtaacgtggaccacaagccctccaacaccaaggtggaca<br>agcgggtggaatctaagtacggccctccctgccccccctgccctgcccc<br>tgaatttctgggcggaccttccgtgttcctgttcccccaaagcccaag<br>gacaccctgatgatctcccggacccccgaagtgacctgcgtggtggtgg<br>acgtgtcccaggaagatcccgaggtccagttcaattggtacgtggacgg<br>cgtggaagtgcacaatgccaagaccaagcccagagaggaacagttcaac<br>tccacctaccgggtggtgtccgtgctgaccgtgctgcaccaggactggc<br>tgaacggcaaagagtacaagtgcaaggtgtccaacaagggcctgccctc<br>cagcatcgaaaagaccatctccaaggccaagggccagccccgcgagccc<br>caggtgtacaccctgcccccctagccaggaagagatgaccaagaaccagg<br>tgtccctgacctgtctggtcaagggcttctacccctccgacattgccgt<br>ggaatgggagtccaacggccagcccgagaacaactacaagaccaccccc<br>cctgtgctggacagcgacggctccttcttcctgtactctcggctgaccg<br>tggacaagtcccggtggcaggaaggcaacgtcttctcctgctccgtgat<br>gcacgaggccctgcacaaccactacacccagaagtccctgtccctgagc<br>ctgggcaag |
| 10236 gH12<br>VH | 39 | EVQLQESGPGLVKPSGTLSLTCAVSGFPLSNYAMSWVRQPPGKGLEWIG<br>DIYPSDIIDYASWAKGRVTISQDSSKNQVSLKLSSVTAADTAVYYCARD<br>NNDYGLDIWGQGTLVTVSS |
| 10236 gH12<br>VH nucl. | 40 | gaggtgcagcttcaggaatccggacccggtctggtcaagccgagcggaa<br>ccctgtcactgacttgcgcggtgtcgggcttcccccctgtccaattacgc |

TABLE 1-continued

| Name | SEQ ID NO: | SEQUENCE |
|---|---|---|
| | | catgtcatgggtccggcaaccacctgggaaagggttggagtggattggc gacatctacccgagcgacatcattgattacgcctcgtgggccaagggta gagtgaccatcagccaggactcctccaagaaccaagtgtcgctgaagct ctcctccgtgaccgcagccgataccgctgtgtactattgtgcccgcgac aacaacgactacggcctggatatctggggacagggaaccctcgtgactg tctcgagc |
| 10236 gH12 Heavy chain | 41 | EVQLQESGPGLVKPSGTLSLTCAVSGFPLSNYAMSWVRQPPGKGLEWIG DIYPSDIIDYASWAKGRVTISQDSSKNQVSLKLSSVTAADTAVYYCARD NNDYGLDIWGQGTLVTVSSASTKGPSVFPLAPCSRSTSESTAALGCLVK DYFPEPVTVSWNSGALTSGVHTFPAVLQSSGLYSLSSVVTVPSSSLGTK TYTCNVDHKPSNTKVDKRVESKYGPPCPPCPAPEFLGGPSVFLFPPKPK DTLMISRTPEVTCVVVDVSQEDPEVQFNWYVDGVEVHNAKTKPREEQFN STYRVVSVLTVLHQDWLNGKEYKCKVSNKGLPSSIEKTISKAKGQPREP QVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLS LGK |
| 10236 gH12 Heavy chain nucl. | 42 | gaggtgcagcttcaggaatccggacccggtctggtcaagccgagcggaa ccctgtcactgacttgcgcggtgtcgggcttcccccctgtccaattacgc catgtcatgggtccggcaaccacctgggaaagggttggagtggattggc gacatctacccgagcgacatcattgattacgcctcgtgggccaagggta gagtgaccatcagccaggactcctccaagaaccaagtgtcgctgaagct ctcctccgtgaccgcagccgataccgctgtgtactattgtgcccgcgac aacaacgactacggcctggatatctggggacagggaaccctcgtgactg tctcgagcgcttctacaaagggcccctccgtgttccctctggccccttg ctcccggtccacctccgagtctaccgccgctctgggctgcctggtcaag gactacttccccgagcccgtgacagtgtcctggaactctggcgccctga cctccggcgtgcacaccttccctgccgtgctgcagtcctccggcctgta ctccctgtcctccgtcgtgaccgtgccctcctccagcctgggcaccaag acctacacctgtaacgtggaccacaagccctccaacaccaaggtggaca agcgggtggaatctaagtacggccctccctgccccccctgccctgcccc tgaatttctgggcggaccttccgtgttcctgttcccccaaagcccaag gacaccctgatgatctcccggacccccgaagtgacctgcgtggtggtgg acgtgtcccaggaagatcccgaggtccagttcaattggtacgtggacgg cgtggaagtgcacaatgccaagaccaagcccagagaggaacagttcaac tccacctaccgggtggtgtccgtgctgaccgtgctgcaccaggactggc tgaacggcaaagagtacaagtgcaaggtgtccaacaagggcctgccctc cagcatcgaaaagaccatctccaaggccaagggccagccccgcgagccc caggtgtacaccctgcccccctagccaggaagagatgaccaagaaccagg tgtccctgacctgtctggtcaagggcttctaccccctccgacattgccgt ggaatgggagtccaacggccagcccgagaacaactacaagaccaccccc cctgtgctggacagcgacggctccttcttcctgtactctcggctgaccg tggacaagtcccggtggcaggaaggcaacgtcttctcctgctccgtgat gcacgaggccctgcacaaccactacacccagaagtccctgtccctgagc ctgggcaag |
| 10236 gH14 VH | 43 | EVQLQESGPGLVKPSGTLSLTCAVSGFPLSNYAMSWVRQPPGKGLEWIG DIYPSDIIDYASWAKGRFTISQDSSKNQVSLKLSSVTAADTAVYYCARD NNDYGLDIWGQGTLVTVSS |
| 10236 gH14 VH nucl. | 44 | gaagtgcagctgcaagagtcaggaccgggcttggtcaagcccagcggaa ccctgtccctgacttgtgccgtgtcggggttcccgctgtcgaactacgc gatgtcctgggtcagacagcctcccggaaagggccttgaatggatcggc gacatctacccaagcgacattattgattacgcatcctgggccaagggac gcttcaccatctcccaggactcttccaagaaccaagtgtccctcaagct gtccagcgtgaccgctgccgacactgccgtgtactattgcgcgcgggat aacaacgactacgggctggacatctggggccagggtaccctcgtgactg tctcgagc |
| 10236 gH14 Heavy chain | 45 | EVQLQESGPGLVKPSGTLSLTCAVSGFPLSNYAMSWVRQPPGKGLEWIG DIYPSDIIDYASWAKGRFTISQDSSKNQVSLKLSSVTAADTAVYYCARD NNDYGLDIWGQGTLVTVSSASTKGPSVFPLAPCSRSTSESTAALGCLVK DYFPEPVTVSWNSGALTSGVHTFPAVLQSSGLYSLSSVVTVPSSSLGTK TYTCNVDHKPSNTKVDKRVESKYGPPCPPCPAPEFLGGPSVFLFPPKPK DTLMISRTPEVTCVVVDVSQEDPEVQFNWYVDGVEVHNAKTKPREEQFN STYRVVSVLTVLHQDWLNGKEYKCKVSNKGLPSSIEKTISKAKGQPREP QVYTLPPSQEEMTKNQVSLTCLVKGFYPSDIAVEWESNGQPENNYKTTP PVLDSDGSFFLYSRLTVDKSRWQEGNVFSCSVMHEALHNHYTQKSLSLS LGK |
| 10236 gH14 Heavy chain nucl. | 46 | gaagtgcagctgcaagagtcaggaccgggcttggtcaagcccagcggaa ccctgtccctgacttgtgccgtgtcggggttcccgctgtcgaactacgc gatgtcctgggtcagacagcctcccggaaagggccttgaatggatcggc gacatctacccaagcgacattattgattacgcatcctgggccaagggac gcttcaccatctcccaggactcttccaagaaccaagtgtccctcaagct |

TABLE 1-continued

| Name | SEQ ID NO: | SEQUENCE |
|---|---|---|
| | | gtccagcgtgaccgctgccgacactgccgtgtactattgcgcgcgggat aacaacgactacgggctggacatctggggccagggtaccctcgtgactg tctcgagcgcttctacaaagggcccctccgtgttccctctggccccttg ctcccggtccacctccgagtctaccgccgctctgggctgcctggtcaag gactacttccccgagcccgtgacagtgtcctggaactctggcgccctga cctccggcgtgcacaccttccctgccgtgctgcagtcctccggcctgta ctccctgtcctccgtcgtgaccgtgccctcctccagcctgggcaccaag acctacacctgtaacgtggaccacaagccctccaacaccaaggtggaca agcgggtggaatctaagtacggccctccctgccccccctgccctgcccc tgaatttctgggcggaccttccgtgttcctgttcccccccaaagcccaag gacaccctgatgatctcccggacccccgaagtgacctgcgtggtggtgg acgtgtcccaggaagatcccgaggtccagttcaattggtacgtggacgg cgtggaagtgcacaatgccaagaccaagcccagagaggaacagttcaac tccacctaccgggtggtgtccgtgctgaccgtgctgcaccaggactggc tgaacggcaaagagtacaagtgcaaggtgtccaacaagggcctgccctc cagcatcgaaaagaccatctccaaggccaagggccagccccgcgagccc caggtgtacaccctgcccccctagccaggaagagatgaccaagaaccagg tgtccctgacctgtctggtcaagggcttctaccccctccgacattgccgt ggaatgggagtccaacggccagcccgagaacaactacaagaccaccccc cctgtgctggacagcgacggctccttcttcctgtactctcggctgaccg tggacaagtcccggtggcaggaaggcaacgtcttctcctgctccgtgat gcacgaggccctgcacaaccactacacccagaagtccctgtccctgagc ctgggcaag |
| Human IGKV1-6 JK4 acceptor framework | 47 | AIQMTQSPSSLSASVGDRVTITCRASQGIRNDLGWYQQKPGKAPKLLIY AASSLQSGVPSRFSGSGSGTDFTLTISSLQPEDFATYYCLQDYNYPLTF GGGTKVEIK |
| Human IGKV1-6 JK4 acceptor framework nucl. | 48 | gccatccagatgacccagtctccatcctccctgtctgcatctgtaggagacaga gtcaccatcacttgccgggcaagtcagggcattagaaatgatttaggctggtat cagcagaaaccagggaaagcccctaagctcctgatctatgctgcatccagttta caaagtggggtcccatcaaggttcagcggcagtggatctggcacagatttcact ctcaccatcagcagcctgcagcctgaagattttgcaacttattactgtctacaa gattacaattaccctctcactttcggcggagggaccaaggtggagatcaaa |
| Human IGHV4-4 JH4 acceptor framework | 49 | QVQLQESGPGLVKPSGTLSLTCAVSGGSISSSNWWSWVRQPPGKGLEWIGEIYH SGSTNYNPSLKSRVTISVDKSKNQFSLKLSSVTAADTAVYYCARYFDYWGQGTL VTVSS |
| Human IGHV4-4 JH4 acceptor framework nucl. | 50 | caggtgcagctgcaggagtcgggcccaggactggtgaagccttcggggaccctg tccctcacctgcgctgtctctggtggctccatcagcagtagtaactggtggagt tgggtccgccagcccccagggaaggggctggagtggattggggaaatctatcat agtgggagcaccaactacaacccgtccctcaagagtcgagtcaccatatcagta gacaagtccaagaaccagttctccctgaagctgagctctgtgaccgccgcggac acggccgtgtattactgtgcgagatactttgactactggggccaaggaaccctg gtcaccgtctcctca |
| Human KLK5 (full length with signal sequence) | 51 | MATARPPWMWVLCALITALLLGVTEHVLANNDVSCDHPSNTVPSGSNQDLGAGA GEDARSDDSSSRIINGSDCDMHTQPWQAALLLRPNQLYCGAVLVHPQWLLTAAH CRKKVFRVRLGHYSLSPVYESGQQMFQGVKSIPHPGYSHPGHSNDLMLIKLNRR IRPTKDVRPINVSSHCPSAGTKCLVSGWGTTKSPQVHFPKVLQCLNISVLSQKR CEDAYPRQIDDTMFCAGDKAGRDSCQGDSGGPVVCNGSLQGLVSWGDYPCARPN RPGVYTNLCKFTKWIQETIQANS |
| Human KLK5 pro-form | 52 | VTEHVLANNDVSCDHPSNTVPSGSNQDLGAGAGEDARSDDSSSRIINGSDCDMH TQPWQAALLLRPNQLYCGAVLVHPQWLLTAAHCRKKVFRVRLGHYSLSPVYESG QQMFQGVKSIPHPGYSHPGHSNDLMLIKLNRRIRPTKDVRPINVSSHCPSAGTK CLVSGWGTTKSPQVHFPKVLQCLNISVLSQKRCEDAYPRQIDDTMFCAGDKAGR DSCQGDSGGPVVCNGSLQGLVSWGDYPCARPNRPGVYTNLCKFTKWIQETIQAN S |
| Active human KLK5 | 53 | IINGSDCDMHTQPWQAALLLRPNQLYCGAVLVHPQWLLTAAHCRKKVFR VRLGHYSLSPVYESGQQMFQGVKSIPHPGYSHPGHSNDLMLIKLNRRIR PTKDVRPINVSSHCPSAGTKCLVSGWGTTKSPQVHFPKVLQCLNISVLS QKRCEDAYPRQIDDTMFCAGDKAGRDSCQGDSGGPVVCNGSLQGLVSWG DYPCARPNRPGVYTNLCKFTKWIQETIQANS |

TABLE 1-continued

| Name | SEQ ID NO: | SEQUENCE |
|---|---|---|
| Human LEKTI D5 Rabbit Fc | 54 | EIVKLCSQYQNQAKNGILFCTRENDPIRGPDGKMHGNLCSMCQAYFQAE NEEKKKAEARARNLEKTVAPSTCSKPTCPPPELLGGPSVFIFPPKPKDT LMISRTPEVTCVVVDVSQDDPEVQFTWYINNEQVRTARPPLREQQFNST IRVVSTLPIAHQDWLRGKEFKCKVHNKALPAPIEKTISKARGQPLEPKV YTMGPPREELSSRSVSLTCMINGFYPSDISVEWEKNGKAEDNYKTTPAV LDSDGSYFLYSKLSVPTSEWQRGDVFTCSVMHEALHNHYTQKSISRSPG K |
| Human KLK7 pro-form | 55 | EEAQGDKIIDGAPCARGSHPWQVALLSGNQLHCGGVLVNERWVLTAAHC KMNEYTVHLGSDTLGDRRAQRIKASKSFRHPGYSTQTHVNDLMLVKLNS QARLSSMVKKVRLPSRCEPPGTTCTVSGWGTTTSPDVTFPSDLMCVDVK LISPQDCTKVYKDLLENSMLCAGIPDSKKNACNGDSGGPLVCRGTLQGL VSWGTFPCGQPNDPGVYTQVCKFTKWINDTMKKHR |
| Active human KLK7 | 56 | IIDGAPCARGSHPWQVALLSGNQLHCGGVLVNERWVLTAAHCKMNEYTV HLGSDTLGDRRAQRIKASKSFRHPGYSTQTHVNDLMLVKLNSQARLSSM VKKVRLPSRCEPPGTTCTVSGWGTTTSPDVTFPSDLMCVDVKLISPQDC TKVYKDLLENSMLCAGIPDSKKNACNGDSGGPLVCRGTLQGLVSWGTFP CGQPNDPGVYTQVCKFTKWINDTMKKHR |
| Cyno KLK7 pro-form | 57 | GQEAQGDKIIDGAPCTRGSHPWQVALLSGNQLHCGGVLVNERWVLTAAH CKMNDYIVHLGSDTLGDRKAQRIKASRSFRHPGYSTQTHVNDLMLVKLN SPARLSSTVKKVRLPSRCEPPGTTCTVSGWGTTTSPDVTFPSDLMCVDV KLISSQDCTKVYKDMLGNSMLCAGIPNSKKNACNGDSGGPLVCRGTLQG LVSWGTFPCGQPNDPGVYTQVCKFTKWINDTIKKHR |
| Active Cyno KLK7 | 58 | IIDGAPCTRGSHPWQVALLSGNQLHCGGVLVNERWVLTAAHCKMNDYIV HLGSDTLGDRKAQRIKASRSFRHPGYSTQTHVNDLMLVKLNSPARLSST VKKVRLPSRCEPPGTTCTVSGWGTTTSPDVTFPSDLMCVDVKLISSQDC TKVYKDMLGNSMLCAGIPNSKKNACNGDSGGPLVCRGTLQGLVSWGTFP CGQPNDPGVYTQVCKFTKWINDTIKKHR |
| Active mouse KLK5 | 59 | IVNGSDCQKDAQPWQGALLLGPNKLYCGAVLISPQWLLTAAHCRKPVFR IRLGHHSMSPVYESGQQMFQGIKSIPHPGYSHPGHSNDLMLIKMNRKIR DSHSVKPVEIACDCATEGTRCMVSGWGTTSSSHNNFPKVLQCLNITVLS EERCKNSYPGQIDKTMFCAGDEEGRDSCQGDSGGPVVCNGKLQGLVSWG DFPCAQRNRPGVYTNLCEFVKWIKDTMNSN |
| Active cyno KLK5 | 60 | IINGSDCDEHTQPWQAALLLGPNQLYCGGVLVHPQWLLTAAHCRKKVFR VRLGHYSLSPVYESGQQMFQGIKSIPHPGYSHPGHSNDLMLIKLNRRIH STKDVRPINVSSHCPSAGTKCLVSGWGTTRSPQVHFPKVLQCLNISVLS QKRCEDAYPRQIDDTMFCAGDEAGRDSCQGDSGGPVVCNGSLQGLVSWG DYPCAKPNRPGVYTNLCKFTKWIQETIQANS |
| Human LEKTI D8 Rabbit Fc | 61 | EAAKEICSEFRDQVRNGTLICTREHNPVRGPDGKMHGNKCAMCASVFKL EEEEKKNDKEEKGKVEAEKVLEKTVAPSTCSKPTCPPPELLGGPSVFIF PPKPKDTLMISRTPEVTCVVVDVSQDDPEVQFTWYINNEQVRTARPPLR EQQFNSTIRVVSTLPIAHQDWLRGKEFKCKVHNKALPAPIEKTISKARG QPLEPKVYTMGPPREELSSRSVSLTCMINGFYPSDISVEWEKNGKAEDN YKTTPAVLDSDGSYFLYSKLSVPTSEWQRGDVFTCSVMHEALHNHYTQK SISRSPGK |
| CDR-L1 Q24R | 62 | RASQSISSWLA |
| CDR-L1 Q24K | 63 | KASQSISSWLA |
| 10236 gL6 VL nucl. Q24R | 64 | gcgtatgacatgactcagagcccgtccagcctgtccgcgtccgtgggag atcgcgtgactatcacgtgtcgggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaag |
| 10236 gL6 Light Chain nucl. Q24R | 65 | gcgtatgacatgactcagagcccgtccagcctgtccgcgtccgtgggag atcgcgtgactatcacgtgtcgggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaaggtggccgctccct ccgtgttcatcttcccaccctccgacgagcagctgaagtccggcaccgc ctccgtcgtgtgcctgctgaacaacttctacccccgcgaggccaaggtg cagtggaaggtggacaacgccctgcagtccggcaactcccaggaatccg |

TABLE 1-continued

| Name | SEQ ID NO: | SEQUENCE |
|---|---|---|
| | | tcaccgagcaggactccaaggacagcacctactccctgtcctccaccct gaccctgtccaaggccgactacgagaagcacaaggtgtacgcctgcgaa gtgacccaccagggcctgtccagccccgtgaccaagtccttcaaccggg gcgagtgc |
| 10236 gL6 VL nucl. Q24K | 66 | gcgtatgacatgactcagagcccgtccagcctgtccgcgtccgtgggag atcgcgtgactatcacgtgtaaggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaag |
| 10236 gL6 Light Chain nucl. Q24K | 67 | gcgtatgacatgactcagagcccgtccagcctgtccgcgtccgtgggag atcgcgtgactatcacgtgtaaggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaaggtggccgctccct ccgtgttcatcttcccaccctccgacgagcagctgaagtccggcaccgc ctccgtcgtgtgcctgctgaacaacttctaccccgcgaggccaaggtg cagtggaaggtggacaacgccctgcagtccggcaactcccaggaatccg tcaccgagcaggactccaaggacagcacctactccctgtcctccaccct gaccctgtccaaggccgactacgagaagcacaaggtgtacgcctgcgaa gtgacccaccagggcctgtccagccccgtgaccaagtccttcaaccggg gcgagtgc |
| 10273 CDR-L1 | 68 | QSSQSVYNNNDLA |
| 10273 CDR-L2 | 69 | RASTLAS |
| 10273 CDR-L3 | 70 | LGGYDDDVDTYT |
| 10273 CDR-H1 | 71 | GFSLSSYGMS |
| 10273 CDR-H2 | 72 | IISSSGSTYYASWAKG |
| 10273 CDR-H3 | 73 | DHIYRYDDYGDYPTYYGMXP |
| 10273 Rabbit VL | 74 | AVVLTQTPSPMSAAVGGTVTISCQSSQSVYNNNDLAWYQQKPGQPPKLL IYRASTLASGVPSRFSGSGSGTQFTLTISGVQCDDAATYYCLGGYDDDV DTYTFGGGTEVVVK |
| 10273 Rabbit VL nucleotide | 75 | gcagtcgtgctgactcagacaccatcacccatgtctgcagctgtgggag gcacagtcaccatcagttgccagtccagtcagagtgtttataataataa cgacttagcctggtatcagcagaaaccagggcagcctcctaagctcctg atctacagggcatccactctggcatctggggtcccgtcgcggttcagcg gcagtggatctgggacacagttcactctcaccatcagcggcgtgcagtg tgacgatgctgccacttactactgtctaggcggttatgatgatgatgtt gatacgtatactttcggcggagggaccgaggtggtggtcaaa |
| 10273 Rabbit VH | 76 | QSVEESGGRLVTPGTPLTLTCTVSGFSLSSYGMSWVRQAPGKGLEWIGI ISSSGSTYYASWAKGRFTISKTSTTVDLKIASPTTEDTATYFCARDHIY RYDDYGDYPTYYGMDPWGPGTLVTVSS |
| 10273 Rabbit VH nucleotide | 77 | cagtcggtggaggagtccgggggtcgcctggtcacgcctgggacacccc tgacactcacctgcacagtctctggattctccctcagtagctatggaat gagctgggtccgccaggctccagggaaggggctggaatggatcggaatt attagtagtagtggtagcacatactacgcgagctgggcgaaaggccgat tcaccatctccaagacctcgaccacggtggatctgaaaatcgccagtcc gacaaccgaggacacggccacctatttctgtgccagagatcacatttat aggtacgatgactatggtgattaccctacctactacggcatggacccct ggggcccaggcaccctggtcaccgtctcgagc |
| Rabbit 10273 mIgG Light Chain | 78 | AVVLTQTPSP MSAAVGGTVT ISCQSSQSVY NNNDLAWYQQ KPGQP PKLLI YRASTLASGV PSRFSGSGSG TQFTLTISGV QCDDAATYYC LGGYDDDVDT YTFGGGTEVV VKRTDAAPTV SIFPPSSEQL TSGG ASVVCF LNNFYPKDIN VKWKIDGSER QNGVLNSWTD QDSKDCTYS M SSTLTLTKDE YERHNSYTCE ATHKTSTSPI VKSFNRNEC |

TABLE 1-continued

| Name | SEQ ID NO: | SEQUENCE |
|---|---|---|
| Rabbit 10273 mIgG Heavy Chain | 79 | QSVEESGGRL VTPGTPLTLT CTVSGFSLSS YGMSWVRQAP GKGLE WIGII SSSGSTYYAS WAKGRFTISK TSTTVDLKIA SPTTEDTATY FCARDHIYRY DDYGDYPTYY GMDPWGPGTL VTVSSAKTTP PSVY PLAPGS AAQTNSMVTL GCLVKGYFPE PVTVTWNSGS LSSGVHTFP A VLQSDLYTLS SSVTVPSSTW PSETVTCNVA HPASSTKVDK KIV PRDCGCK PCICTVPEVS SVFIFPPKPK DVLTITLTPK VTCVVVDI SK DDPEVQFSWF VDDVEVHTAQ TQPREEQFNS TFRSVSELPI MH QDWLNGKE FKCRVNSAAF PAPIEKTISK TKGRPKAPQV YTIPPPK EQM AKDKVSLTCM ITDFFPEDIT VEWQWNGQPA ENYKNTQPIM D TDGSYFVYS KLNVQKSNWE AGNTFTCSVL HEGLHNHHTE KSLSHS PGK |
| Rabbit 10273 mIgG Light Chain Nucl. | 80 | gcagtcgtgctgactcagacaccatcacccatgtctgcagctgtgggag gcacagtcaccatcagttgccagtccagtcagagtgtttataataataa cgacttagcctggtatcagcagaaaccagggcagcctcctaagctcctg atctacagggcatccactctggcatctggggtcccgtcgcggttcagcg gcagtggatctgggacacagttcactctcaccatcagcggcgtgcagtg tgacgatgctgccacttactactgtctaggcggttatgatgatgatgtt gatacgtatactttcggcggagggaccgaggtggtggtcaaacgtacgg atgctgcaccaactgtatccatcttcccaccatccagtgagcagttaac atctggaggtgcctcagtcgtgtgcttcttgaacaacttctaccccaaa gacatcaatgtcaagtggaagattgatggcagtgaacgacaaaatggcg tcctgaacagttggactgatcaggacagcaaagactgcacctacagcat gagcagcaccctcacgttgaccaaggacgagtatgaacgacataacagc tatacctgtgaggccactcacaagacatcaacttcacccattgtcaaga gcttcaacaggaatgagtgt |
| Rabbit 10273 mIgG Heavy Chain Nucl. | 81 | cagtcggtggaggagtccgggggtcgcctggtcacgcctgggacacccc tgacactcacctgcacagtctctggattctccctcagtagctatggaat gagctgggtccgccaggctccagggaaggggctggaatggatcggaatt attagtagtagtggtagcacatactacgcgagctgggcgaaaggccgat tcaccatctccaagacctcgaccacggtggatctgaaaatcgccagtcc gacaaccgaggacacggccacctatttctgtgccagagatcacatttat aggtacgatgactatggtgattaccctacctactacggcatggacccct ggggcccaggcaccctggtcaccgtctcgagtgccaaaacgacaccccc atctgtctatccactggcccctggatctgctgcccaaactaactccatg gtgaccctgggatgcctggtcaagggctatttccctgagccagtgacag tgacctggaactctggatccctgtccagcggtgtgcacaccttcccagc tgtcctgcagtctgacctctacactctgagcagctcagtgactgtcccc tccagcacctggcccagcgagaccgtcacctgcaacgttgcccacccgg ccagcagcaccaaggtggacaagaaaattgtgcccagggattgtggttg taagccttgcatatgtacagtcccagaagtatcatctgtcttcatcttc cccccaaagcccaaggatgtgctcaccattactctgactcctaaggtca cgtgtgttgtggtagacatcagcaaggatgatcccgaggtccagttcag ctggtttgtagatgatgtggaggtgcacacagctcagacgcaaccccgg gaggagcagttcaacagcactttccgctcagtcagtgaacttcccatca tgcaccaggactggctcaatggcaaggagttcaaatgcagggtcaacag tgcagctttccctgcccccatcgagaaaaccatctccaaaaccaaaggc agaccgaaggctccacaggtgtacaccattccacctcccaaggagcaga tggccaaggataaagtcagtctgacctgcatgataacagacttcttccc tgaagacattactgtggagtggcagtggaatgggcagccagcggagaac tacaagaacactcagcccatcatggacacagatggctcttacttcgtct acagcaagctcaatgtgcagaagagcaactgggaggcaggaaatacttt cacctgctctgtgttacatgagggcctgcacaaccaccatactgagaag agcctctcccactctcctggtaaa |
| Rabbit 10236 mIgG Light Chain | 82 | AYDMTQTPAS VEVAVGGTVT IKCQASQSIS SWLAWYQQKP GQPPK LLIYL ASTLASGVSS RFKGSGSGTQ FTLTISGVEC ADAATYYCQQ GYTNSNIINT FGGGTEVVVK RTDAAPTVSI FPPSSEQLTS GGAS VVCFLN NFYPKDINVK WKIDGSERQN GVLNSWTDQD SKDCTYSMS S TLTLTKDEYE RHNSYTCEAT HKTSTSPIVK SFNRNEC |
| Rabbit 10236 mIgG Heavy Chain | 83 | QSVEESGGRL VTPGTPLTLT CTVSGFPLSN YAMSWVRQAP GKGLE WIGDI YPSDIIDYAS WAKGRFTISQ TSTTVELKIT GPTTEDTATY FCARDNNDYG LDIWGPGTLV TVSSAKTTPP SVYPLAPGSA AQTN SMVTLG CLVKGYFPEP VTVTWNSGSL SSGVHTFPAV LQSDLYTLS S SVTVPSSTWP SETVTCNVAH PASSTKVDKK IVPRDCGCKP CIC TVPEVSS VFIFPPKPKD VLTITLTPKV TCVVVDISKD DPEVQFSW FV DDVEVHTAQT QPREEQFNST FRSVSELPIM HQDWLNGKEF KC RVNSAAFP APIEKTISKT KGRPKAPQVY TIPPPKEQMA KDKVSLT CMI TDFFPEDITV EWQWNGQPAE NYKNTQPIMD TDGSYFVYSK L NVQKSNWEA GNTFTCSVLH EGLHNHHTEK SLSHSPGK |

TABLE 1-continued

| Name | SEQ ID NO: | SEQUENCE |
|---|---|---|
| Rabbit 10236 mIgG Light Chain Nucl. | 84 | gcctatgatatgacccagactccagcctctgtggaggtagctgtgggag gcacagtcaccatcaagtgccaggccagtcagagcattagcagttggtt agcctggtatcagcagaaaccaggtcagcctcccaagctcctgatctat ctggcatccactctggcatctggggtctcatcgcggttcaaaggcagtg gatctgggacacagttcactctcaccatcagcggcgtggagtgtgccga tgctgccacttactactgtcaacagggttatactaatagtaatattatt aatactttcggcggagggaccgaggtggtggtcaaacgtacggatgctg caccaactgtatccatcttcccaccatccagtgagcagttaacatctgg aggtgcctcagtcgtgtgcttcttgaacaacttctaccccaaagacatc aatgtcaagtggaagattgatggcagtgaacgacaaaatggcgtcctga acagttggactgatcaggacagcaaagactgcacctacagcatgagcag caccctcacgttgaccaaggacgagtatgaacgacataacagctatacc tgtgaggccactcacaagacatcaacttcacccattgtcaagagcttca acaggaatgagtgt |
| Rabbit 10236 mIgG Heavy Chain Nucl. | 85 | cagtcggtggaggagtccgggggtcgcctggtcacgcctgggacacccc tgacactcacctgcaccgtctctgggttccccctcagtaattatgcaat gagctgggtccgccaggctccagggaaggggctggaatggatcggagac atttatcctagtgatatcatagactacgcgagctgggcgaaaggccgat tcaccatctcccaaacctcgaccacggtggagctgaaaatcacgggtcc gacaaccgaggacacggccacctatttctgtgccagagacaacaatgac tatggtctggacatctggggcccaggcaccctggtcaccgtctcgagtg ccaaaacgacacccccatctgtctatccactggcccctggatctgctgc ccaaactaactccatggtgaccctgggatgcctggtcaagggctatttc cctgagccagtgacagtgacctggaactctggatccctgtccagcggtg tgcacaccttcccagctgtcctgcagtctgacctctacactctgagcag ctcagtgactgtcccctccagcacctggcccagcgagaccgtcacctgc aacgttgcccacccggccagcagcaccaaggtggacaagaaaattgtgc ccagggattgtggttgtaagccttgcatatgtacagtcccagaagtatc atctgtcttcatcttccccccaaagcccaaggatgtgctcaccattact ctgactcctaaggtcacgtgtgttgtggtagacatcagcaaggatgatc ccgaggtccagttcagctggtttgtagatgatgtggaggtgcacacagc tcagacgcaacccccgggaggagcagttcaacagcactttccgctcagtc agtgaacttcccatcatgcaccaggactggctcaatggcaaggagttca aatgcagggtcaacagtgcagctttccctgcccccatcgagaaaaccat ctccaaaaccaaaggcagaccgaaggctccacaggtgtacaccattcca cctcccaaggagcagatggccaaggataaagtcagtctgacctgcatga taacagacttcttccctgaagacattactgtggagtggcagtggaatgg gcagccagcggagaactacaagaacactcagcccatcatggacacagat ggctcttacttcgtctacagcaagctcaatgtgcagaagagcaactggg aggcaggaaatactttcacctgctctgtgttacatgagggcctgcacaa ccaccatactgagaagagcctctcccactctcctggtaaatgatcccag tgtccttggagccctctggtcctacaggactctgacacctacctccacc cctccctgtataaa |
| 10236 Light chain Fab | 86 | AYDMTQTPASVEVAVGGTVTIKCQASQSISSWLAWYQQKPGQPPKLLIY LASTLASGVSSRFKGSGSGTQFTLTISGVECADAATYYCQQGYTNSNII NTFGGGTEVVVKRTPVAPTVLIFPPAADQVATGTVTIVCVANKYFPDVT VTWEVDGTTQTTGIENSKTPQNSADCTYNLSSTLTLTSTQYNSHKEYTC KVTQGTTSVVQSFNRGDC |
| 10236 Light Chain Fab Nucl. | 87 | gcctatgatatgacccagactccagcctctgtggaggtagctgtgggag gcacagtcaccatcaagtgccaggccagtcagagcattagcagttggtt agcctggtatcagcagaaaccaggtcagcctcccaagctcctgatctat ctggcatccactctggcatctggggtctcatcgcggttcaaaggcagtg gatctgggacacagttcactctcaccatcagcggcgtggagtgtgccga tgctgccacttactactgtcaacagggttatactaatagtaatattatt aatactttcggcggagggaccgaggtggtggtcaaacgtacgccagttg cacctactgtcctcatcttcccaccagctgctgatcaggtggcaactgg aacagtcaccatcgtgtgtgtggcgaataaatactttcccgatgtcacc gtcacctgggaggtggatggcaccacccaaacaactggcatcgagaaca gtaaaacaccgcagaattctgcagattgtacctacaacctcagcagcac tctgacactgaccagcacacagtacaacagccacaaagagtacacctgc aaggtgacccagggcacgacctcagtcgtccagagcttcaatagggggtg actgt |
| 10236 heavy chain Fab | 88 | QSVEESGGRLVTPGTPLTLTCTVSGFPLSNYAMSWVRQAPGKGLEWIGD IYPSDIIDYASWAKGRFTISQTSTTVELKITGPTTEDTATYFCARDNND YGLDIWGPGTLVTVSSGQPKAPSVFPLAPCCGDTPSSTVTLGCLVKGYL PEPVTVTWNSGTLTNGVRTFPSVRQSSGLYSLSSVVSVTSSSQPVTCNV AHPATNTKVDKTVAPSTCSKP |
| 10236 heavy chain Fab Nucl. | 89 | cagtcggtggaggagtccgggggtcgcctggtcacgcctgggacacccc tgacactcacctgcaccgtctctgggttccccctcagtaattatgcaat gagctgggtccgccaggctccagggaaggggctggaatggatcggagac atttatcctagtgatatcatagactacgcgagctgggcgaaaggccgat |

TABLE 1-continued

| Name | SEQ ID NO: | SEQUENCE |
|---|---|---|
| | | tcaccatctcccaaacctcgaccacggtggagctgaaaatcacgggtcc<br>gacaaccgaggacacggccacctatttctgtgccagagacaacaatgac<br>tatggtctggacatctggggcccaggcaccctggtcaccgtctcgagtg<br>ggcaacctaaggctccatcagtcttcccactggcccccctgctgcgggga<br>cacacccagctccacggtgaccctgggctgcctggtcaaaggctacctc<br>ccggagccagtgaccgtgacctggaactcgggcaccctcaccaatgggg<br>tacgcaccttcccgtccgtccggcagtcctcaggcctctactcgctgag<br>cagcgtggtgagcgtgacctcaagcagccagcccgtcacctgcaacgtg<br>gcccacccagccaccaacaccaaagtggacaagaccgttgcgccctcga<br>catgcagcaagccc |
| 10273 Light chain Fab | 90 | AVVLTQTPSPMSAAVGGTVTISCQSSQSVYNNNDLAWYQQKPGQPPKLL<br>IYRASTLASGVPSRFSGSGSGTQFTLTISGVQCDDAATYYCLGGYDDDV<br>DTYTFGGGTEVVVKRTPVAPTVLIFPPAADQVATGTVTIVCVANKYFPD<br>VTVTWEVDGTTQTTGIENSKTPQNSADCTYNLSSTLTLTSTQYNSHKEY<br>TCKVTQGTTSVVQSFNRGDC |
| 10273 Light Chain Fab Nucl. | 91 | gcagtcgtgctgactcagacaccatcacccatgtctgcagctgtgggag<br>gcacagtcaccatcagttgccagtccagtcagagtgtttataataataa<br>cgacttagcctggtatcagcagaaaccagggcagcctcctaagctcctg<br>atctacagggcatccactctggcatctggggtcccgtcgcggttcagcg<br>gcagtggatctgggacacagttcactctcaccatcagcggcgtgcagtg<br>tgacgatgctgccacttactactgtctaggcggttatgatgatgatgtt<br>gatacgtatactttcggcggagggaccgaggtggtggtcaaacgtacgc<br>cagttgcacctactgtcctcatcttcccaccagctgctgatcaggtggc<br>aactggaacagtcaccatcgtgtgtgtggcgaataaatactttcccgat<br>gtcaccgtcacctgggaggtggatggcaccacccaaacaactggcatcg<br>agaacagtaaaacaccgcagaattctgcagattgtacctacaacctcag<br>cagcactctgacactgaccagcacacagtacaacagccacaaagagtac<br>acctgcaaggtgacccagggcacgacctcagtcgtccagagcttcaata<br>ggggtgactgt |
| 10273 heavy chain Fab | 92 | QSVEESGGRLVTPGTPLTLTCTVSGFSLSSYGMSWVRQAPGKGLEWIGI<br>ISSSGSTYYASWAKGRFTISKTSTTVDLKIASPTTEDTATYFCARDHIY<br>RYDDYGDYPTYYGMDPWGPGTLVTVSSGQPKAPSVFPLAPCCGDTPSST<br>VTLGCLVKGYLPEPVTVTWNSGTLTNGVRTFPSVRQSSGLYSLSSVVSV<br>TSSSQPVTCNVAHPATNTKVDKTVAPSTCSKP |
| 10273 heavy chain Fab Nucl. | 93 | cagtcggtggaggagtccgggggtcgcctggtcacgcctgggacacccc<br>tgacactcacctgcacagtctctggattctccctcagtagctatggaat<br>gagctgggtccgccaggctccagggaaggggctggaatggatcggaatt<br>attagtagtagtggtagcacatactacgcgagctgggcgaaaggccgat<br>tcaccatctccaagacctcgaccacggtggatctgaaaatcgccagtcc<br>gacaaccgaggacacggccacctatttctgtgccagagatcacatttat<br>aggtacgatgactatggtgattaccctacctactacggcatggacccct<br>ggggcccaggcaccctggtcaccgtctcgagtgggcaacctaaggctcc<br>atcagtcttcccactggcccccctgctgcggggacacacccagctccacg<br>gtgaccctgggctgcctggtcaaaggctacctcccggagccagtgaccg<br>tgacctggaactcgggcaccctcaccaatggggtacgcaccttcccgtc<br>cgtccggcagtcctcaggcctctactcgctgagcagcgtggtgagcgtg<br>acctcaagcagccagcccgtcacctgcaacgtggcccacccagccacca<br>acaccaaagtggacaagaccgttgcgccctcgacatgcagcaagccc |
| Human LEKTI D5 Fab H chain | 94 | EVQLLESGGGLVQPGGSLRLSCAVSGIDLSNYAINWVRQAPGKGLEWIG<br>IIWASGTTFYATWAKGRFTISRDNSGGGGSGGGGSREIVKLCSQYQNQA<br>KNGILFCTRENDPIRGPDGKMHGNLCSMCQAYFQAENEEKKKAEARARS<br>GGGGGGGGSKNTVYLQMNSLRAEDTAVYYCARTVPGYSTAPYFDLWGQG<br>TLVTVSSASTKGPSVFPLAPSSKSTSGGTAALGCLVKDYFPEPVTVSWN<br>SGALTSGVHTFPAVLQSSGLYSLSSVVTVPSSSLGTQTYICNVNHKPSN<br>TKVDKKVEPKSCHHHHHHHHH |
| Human LEKTI D5 Fab L chain | 95 | DIQMTQSPSSVSASVGDRVTITCQSSPSVWSNFLSWYQQKPGKAPKLLI<br>YEASKLTSGVPSRFSGSGSGTDFTLTISSLQPEDFATYYCGGGYSSISD<br>TTFGGGTKVEIKRTVAAPSVFIFPPSDEQLKSGTASVVCLLNNFYPREA<br>KVQWKVDNALQSGNSQESVTEQDSKDSTYSLSSTLTLSKADYEKHKVYA<br>CEVTHQGLSSPVTKSFNRGEC |
| Rabbit/ human chimeric light chain (hCK S171C) 10236 | 96 | AYDMTQTPASVEVAVGGTVTIKCQASQSISSWLAWYQQKPGQPPKLLIY<br>LASTLASGVSSRFKGSGSGTQFTLTISGVECADAATYYCQQGYTNSNII<br>NTFGGGTEVVVKRTVAAPSVFIFPPSDEQLKSGTASVVCLLNNFYPREA<br>KVQWKVDNALQSGNSQESVTEQDSKDCTYSLSSTLTLSKADYEKHKVYA<br>CEVTHQGLSSPVTKSFNRGEC |

TABLE 1-continued

| Name | SEQ ID NO: | SEQUENCE |
|---|---|---|
| Rabbit/ human chimeric heavy chain 10236 | 97 | QSVEESGGRLVTPGTPLTLTCTVSGFPLSNYAMSWVRQAPGKGLEWIGD<br>IYPSDIIDYASWAKGRFTISQTSTTVELKITGPTTEDTATYFCARDNND<br>YGLDIWGPGTLVTVSSASTKGPSVFPLAPCSRSTSESTAALGCLVKDYF<br>PEPVTVSWNSGALTSGVHTFPAVLQSSGLYSLSSVVTVPSSSLGTKTYT<br>CNVDHKPSNTKVDKRVESKYGPPCPPCPAPEFLGGPSVFLFPPKPKDTL<br>MISRTPEVTCVVVDVSQEDPEVQFNWYVDGVEVHNAKTKPREEQFNSTY<br>RVVSVLTVLHQDWLNGKEYKCKVSNKGLPSSIEKTISKAKGQPREPQVY<br>TLPPSQEEMTKNQVSLTCLVKGFYPSDIAVEWESNGQPENNYKTTPPVL<br>DSDGSFFLYSRLTVDKSRWQEGNVFSCSVMHEALHNHYTQKSLSLSLGK |
| LEKTI-D5- Fc TEV | 98 | EIVKLCSQYQNQAKNGILFCTRENDPIRGPDGKMHGNLCSMCQAYFQAE<br>NEEKKKAEARARNLEENLYFQGVDKKVEPKSCDKTHTCPPCPAPELLGG<br>PSVFLFPPKPKDTLMISRTPEVTCVVVDVSHEDPEVKFNWYVDGVEVHN<br>AKTKPREEQYNSTYRVVSVLTVLHQDWLNGKEYKCKVSNKALPAPIEKT<br>ISKAKGQPREPQVYTLPPSRDELTKNQVSLTCLVKGFYPSDIAVEWESN<br>GQPENNYKTTPPVLDSDGSFFLYSKLTVDKSRWQQGNVFSCSVMHEALH<br>NHYTQKSLSLSPGK |
| LEKTI-D8- Fc TEV | 99 | EAAKEICSEFRDQVRNGTLICTREHNPVRGPDGKMHGNKCAMCASVFKL<br>EEEEKKNDKEEKGKVEAEKVLEENLYFQGVDKKVEPKSCDKTHTCPPCP<br>APELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKAL<br>PAPIEKTISKAKGQPREPQVYTLPPSRDELTKNQVSLTCLVKGFYPSDI<br>AVEWESNGQPENNYKTTPPVLDSDGSFFLYSKLTVDKSRWQQGNVFSCS<br>VMHEALHNHYTQKSLSLSPGK |
| 10236 gL5 Light chain nucl. Minus RS | 100 | gcgtatgacatgactcagagcccgtccagcctgtccgcgtccgtgggag<br>atcgcgtgactatcacgtgtcaggcctcacaatccattagctcctggct<br>ggcctggtaccagcagaagccagggaaggctccgaagctgctgatctac<br>ctggcctccacccttgcctccggcgtgccttcacggtttaaaggatccg<br>gctcgggaaccgacttcaccctcaccatctcgtcgctccaacccgagga<br>cttcgcaacctactactgccaacaggggtataccaacagcaacatcatc<br>aacaccttcggtggcggaactaaggtcgaaatcaagcgtacggtggccg<br>ctccctccgtgttcatcttcccaccctccgacgagcagctgaagtccgg<br>caccgcctccgtcgtgtgcctgctgaacaacttctacccccgcgaggcc<br>aaggtgcagtggaaggtggacaacgccctgcagtccggcaactcccagg<br>aatccgtcaccgagcaggactccaaggacagcacctactccctgtcctc<br>caccctgaccctgtccaaggccgactacgagaagcacaaggtgtacgcc<br>tgcgaagtgacccaccagggcctgtccagccccgtgaccaagtccttca<br>accggggcgagtgc |
| 10236 gL7 Light chain nucl. Plus RS | 101 | gcgatcgacatgactcagagcccgtccagcctgtccgcgtccgtgggag<br>atcgcgtgactatcacgtgtcaggcctcacaatccattagctcctggct<br>ggcctggtaccagcagaagccagggaaggctccgaagctgctgatctac<br>ctggcctccacccttgcctccggcgtgccttcacggttttctggatccg<br>gctcgggaaccgacttcaccctcaccatctcgtcgctccaacccgagga<br>cttcgcaacctactactgccaacaggggtataccaacagcaacatcatc<br>aacaccttcggtggcggaactaaggtcgaaatcaagcgtacggtggccg<br>ctccctccgtgttcatcttcccaccctccgacgagcagctgaagtccgg<br>caccgcctccgtcgtgtgcctgctgaacaacttctacccccgcgaggcc<br>aaggtgcagtggaaggtggacaacgccctgcagtccggcaactcccagg<br>aatccgtcaccgagcaggactccaaggacagcacctactccctgtcctc<br>caccctgaccctgtccaaggccgactacgagaagcacaaggtgtacgcc<br>tgcgaagtgacccaccagggcctgtccagccccgtgaccaagtccttca<br>accggggcgagtgc |
| 10236 gL8 Light chain nucl. Plus RS | 102 | gcgtatcagatgactcagagcccgtccagcctgtccgcgtccgtgggag<br>atcgcgtgactatcacgtgtcaggcctcacaatccattagctcctggct<br>ggcctggtaccagcagaagccagggaaggctccgaagctgctgatctac<br>ctggcctccacccttgcctccggcgtgccttcacggttttctggatccg<br>gctcgggaaccgacttcaccctcaccatctcgtcgctccaacccgagga<br>cttcgcaacctactactgccaacaggggtataccaacagcaacatcatc<br>aacaccttcggtggcggaactaaggtcgaaatcaagcgtacggtggccg<br>ctccctccgtgttcatcttcccaccctccgacgagcagctgaagtccgg<br>caccgcctccgtcgtgtgcctgctgaacaacttctacccccgcgaggcc<br>aaggtgcagtggaaggtggacaacgccctgcagtccggcaactcccagg<br>aatccgtcaccgagcaggactccaaggacagcacctactccctgtcctc<br>caccctgaccctgtccaaggccgactacgagaagcacaaggtgtacgcc<br>tgcgaagtgacccaccagggcctgtccagccccgtgaccaagtccttca<br>accggggcgagtgc |
| 10236 gL6 Light Chain nucl. Q24R Plus | 103 | gcgtatgacatgactcagagcccgtccagcctgtccgcgtccgtgggag<br>atcgcgtgactatcacgtgtcgggcctcacaatccattagctcctggct<br>ggcctggtaccagcagaagccagggaaggctccgaagctgctgatctac<br>ctggcctccacccttgcctccggcgtgccttcacggttttctggatccg<br>gctcgggaaccgacttcaccctcaccatctcgtcgctccaacccgagga |

TABLE 1-continued

| Name | SEQ ID NO: | SEQUENCE |
|---|---|---|
| RS | | cttcgcaacctactactgccaacaggggtataccaacagcaacatcatc aacaccttcggtggcggaactaaggtcgaaatcaagcgtacggtggccg ctccctccgtgttcatcttcccaccctccgacgagcagctgaagtccgg caccgcctccgtcgtgtgcctgctgaacaacttctacccccgcgaggcc aaggtgcagtggaaggtggacaacgccctgcagtccggcaactcccagg aatccgtcaccgagcaggactccaaggacagcacctactccctgtcctc caccctgaccctgtccaaggccgactacgagaagcacaaggtgtacgcc tgcgaagtgacccaccagggcctgtccagccccgtgaccaagtccttca accggggcgagtgc |
| 10236 gL6 Light Chain nucl. Q24K Plus RS | 104 | gcgtatgacatgactcagagcccgtccagcctgtccgcgtccgtgggag atcgcgtgactatcacgtgtaaggcctcacaatccattagctcctggct ggcctggtaccagcagaagccagggaaggctccgaagctgctgatctac ctggcctccacccttgcctccggcgtgccttcacggttttctggatccg gctcgggaaccgacttcaccctcaccatctcgtcgctccaacccgagga cttcgcaacctactactgccaacaggggtataccaacagcaacatcatc aacaccttcggtggcggaactaaggtcgaaatcaagcgtacggtggccg ctccctccgtgttcatcttcccaccctccgacgagcagctgaagtccgg caccgcctccgtcgtgtgcctgctgaacaacttctacccccgcgaggcc aaggtgcagtggaaggtggacaacgccctgcagtccggcaactcccagg aatccgtcaccgagcaggactccaaggacagcacctactccctgtcctc caccctgaccctgtccaaggccgactacgagaagcacaaggtgtacgcc tgcgaagtgacccaccagggcctgtccagccccgtgaccaagtccttca accggggcgagtgc |

The invention will now be further described by way of examples with references to embodiments illustrated in the accompanying drawings.

EXAMPLES

Example 1: Cloning, Expression and Purification of Kallikrein Proteins and LEKTI Domains An optimized nucleotide sequence encoding a protein according to SEQ ID NO: 51, cloned into an in-house mammalian expression vector, using HindIII/EcoRI sites, generating a vector encoding the human KLK5 protein with no tags.

The mouse and cynomolgus monkey (cyno) KLK5 sequences were similarly cloned to enable generation of the active forms of the proteins comprising SEQ ID NO: 59 and 60, respectively.

Domain 5 (D5) and Domain 8 (D8) of human LEKTI (Uniprot Q9NQ38) comprising residues 292-353 and 490-558 respectively (according to the numbering in Uniprot), were cloned and expressed for utilization as reference proteins in in vitro assays.

The human LEKTI Domain 5 and Domain 8 nucleotide sequences, both optimized for expression in mammalian cells, were separately cloned into an in-house mammalian expression vector encoding a rabbit Fc tag, using HindIII/XhoI sites, generating vectors encoding either the LEKTI domain 5 sequence with a C-terminal rabbit Fc tag (SEQ ID NO: 54) or the LEKTI domain 8 sequence with a C-terminal rabbit Fc tag (SEQ ID NO: 61). The encoded proteins will be referred to as LEKTI D5 rabbit Fc and LEKTI D8 rabbit Fc respectively The KLK5, LEKTI Domain 5 and LEKTI Domain 8 rabbit Fc fusion proteins were expressed by transient transfection using the Expi293™ Expression System (Life Technologies™) following manufacturer's protocol. During expression, KLK5 auto-activates to yield active KLK5 (comprising SEQ ID NO: 53 or residues 167-S293 of SEQ ID NO: 51) in the supernatant. Cells were harvested 5 days post transfection and supernatants used immediately for purification. Supernatants comprising human (or mouse or cyno) active KLK5 were diluted 4-fold with Buffer A (50 mM Tris pH 7.0, 50 mM NaCl) and loaded onto HiTrap SP HP cation exchange column. Bound proteins were eluted with a salt gradient generated over a total of 10 column volumes using Buffer A (50 mM Tris pH 7.0, 50 mM NaCl) and Buffer B (50 mM Tris pH 7.0, 1M NaCl). Fractions containing purified human (or mouse or cyno) active KLK5 were pooled, concentrated and purified further by size exclusion chromatography on an S200 26/60 column which had been equilibrated with a buffer composed of 20 mM Tris, 150 mM NaCl, 5% glycerol at pH 7.2. SDS-PAGE analysis indicated that the proteins underwent glycosylation during expression. Analysis by mass spectrometry resulted in the expected molecular weight. Supernatants comprising human LEKTI D5 rabbit Fc fusion protein (according to SEQ ID NO: 54) were first subjected to Protein A affinity chromatography. The supernatants were loaded onto a 5 ml Hitrap™ Protein A columns. Bound proteins were eluted with 1M citric acid buffer, pH 2.0 and fractions neutralized with 2M Tris-HCl pH8.5. Fractions containing LEKTI D5 rabbit Fc fusion protein were pooled, concentrated and further purified by size exclusion chromatography using a S200 26/60 column which had been equilibrated with PBS. Fractions containing purified human LEKTI D5 rabbit Fc fusion protein were then pooled and concentrated. LEKTI D8 rabbit Fc fusion protein (according to SEQ ID NO: 61) was similarly purified from transfected cell culture supernatants.

A LEKTI D5 Fab fusion molecule (according to SEQ ID NO: 94 and 95) was expressed and purified by cation exchange chromatography. The LEKTI Domain 5 nucleotide sequence, flanked at the 5' and 3' termini by sequences encoding $Gly_4Ser$ linkers was integrated into framework 3 of a heavy chain sequence of a Fab specific for albumin (as described in WO2020011868 which is incorporated herein by reference); a tag encoding a 10×His sequence was also placed at the 3' end of the Fab H chain. The LEKTI D5 Fab fusion heavy chain sequence was optimized for expression in mammalian cells, cloned into an in-house expression vector and co-transfected with the appropriate light chain, also optimized for mammalian expression, in CHO SXE cells. Transfected cells were cultured in a vented flask at 32° C. for 13 days. Supernatant was harvested, concentrated and buffer exchanged into 20 mM Tris, 50 mM NaCl, pH7.0 before loading onto a SP Sepharose HP column. Bound proteins were eluted with a salt gradient generated over a total of 10 column volumes using Buffer A (50 mM Tris pH 7.0, 50 mM NaCl) and Buffer B (50 mM Tris pH 7.0, 1M NaCl). Fractions containing LEKTI D5 Fab fusion protein were pooled and further purified by size exclusion chromatography using an S200 column equilibrated with PBS pH 7.4. Relevant fractions were pooled.

The human and cyno nucleotide sequences encoding full-length KLK7 proteins were expressed in a similar manner to human KLK5 generating pro-KLK7 (comprising SEQ ID NO: 55 and 57, respectively). Unlike KLK5, KLK7 does not auto-activate during expression and so the active forms of human and cyno KLK7 (comprising SEQ ID NO: 56, 58 respectively) were generated using thermolysin to cleave the pro-peptide sequence from the respective purified proteins. Human and cyno pro-KLK7 proteins (comprising SEQ ID NO: 55 and 57), were diluted to 1 mg/ml with activation buffer (50 mM Tris pH 7.5, 10 mM $CaCl_2$), 150 mM NaCl, 0.05% Brij 35). Thermolysin from Sigma™ (25 mg) was resuspended in 25 ml digestion buffer (50 mM Tris pH8.0, 0.5 mM $CaCl_2$), added at a ratio of 1:10 to the pro-KLK7 proteins for 45 minutes at 37° C. before mixing with anion exchange DEAE resin (GE Life Sciences™) to bind and remove the thermolysin. The flow-through was collected as active (human or cyno) KLK7, buffer exchanged into 50 mM Tris pH7.5, 150 mM NaCl, 5% glycerol, 1 mM EDTA and concentrated to circa 3.2 mg/ml. Mouse pro-KLK7 was similarly generated and cleaved to produce the active enzyme.

Human KLK2 was sourced from R&D Systems™ (Catalog #4104-SE-010) as active protein.

Human KLK4 was sourced from R&D Systems™ (Catalog #1719-SE) as pro-form and activated as follows. Human pro-KLK4 was diluted to 200 pg/mL in 50 mM Tris, 10 mM $CaCl_2$, 150 mM NaCl, pH 7.5. Bacterial thermolysin was sourced from R&D Systems™ (Catalog #3097-ZN) and diluted in the same buffer to 2 μg/mL. Equal volumes of pro-human KLK4 and thermolysin were combined and incubated at room temperature for 10 minutes to allow activation. The reaction was stopped with EDTA to a final concentration of 10 mM.

Example 2: Generation of Antibodies by Immunization with KLK5

Female New Zealand White rabbits (>2 kg) received sub-cutaneous immunization with 100 pg of 0.4 mg/mL of human active KLK5 and human active KLK7 (expressed according to example 1) mixed with an equal volume of complete Freund's adjuvant (Sigma™). Animals received boost injections at intervals of 21 days comprising of 100 pg of the same immunogen mixed in an equal volume of incomplete Freund's adjuvant (Sigma™). Termination occurred 14 days after the final boost when single cell suspensions of spleen, bone marrow, and peripheral blood mononuclear cells (PBMCs) were prepared and frozen in 10% dimethyl sulfoxide (DMSO) in fetal calf serum (FCS) at −80° C.

B cell cultures were prepared using a method similar to that described by Tickle et al., 2015 J Biomol Screen: 20(4), 492-497. Briefly, lymph node cells, splenocytes, or peripheral blood mononuclear cells (PBMC) from immunized animals were cultured at a density of 2000 cells per well in barcoded 96-well tissue culture plates with 200 pl/well RPMI 1640 medium (Gibco™) supplemented with 10% FCS (Sigma Aldrich™) 2% HEPES solution (Sigma Aldrich™) 2% L-Glutamine solution (Gibco™), 1% penicillin/streptomycin solution (Gibco™), 0.2% Normocin (Invivogen™), 0.1% β-mercaptoethanol (Gibco™), and using a feeder cell expressing CD40L and IL-2 in the presence or absence of B-cell stimulating supernatant (BSS). BSS is generated by culturing PBMC in the presence of the mitogenic agents Phorbol-12-myristate-13-acetate (PMA) and Phytohemagglutinin-L (PHA-L) for 6 days before harvesting the supernatant. Plates were incubated six days at 37° C. and 5% $CO_2$. Cultures were set up using B cells from all immunized animals, and in total, approximately $1\times10^9$ B cells were screened.

After six days, supernatants were screened for binding to human KLK5 (produced as in example 1) by a multiplex homogeneous fluorescence-based binding assay using Sol-R2 streptavidin beads (TTP Labtech™) coated with biotinylated human KLK5 as a source of target antigen and Sol-R4 streptavidin beads (TTP Labtech™) coated with the related KLK7 for counter-screening. Lightning-Link Rapid Biotin Type B (Expedeon™) was used to biotinylate proteins using a 5-fold molar excess of protein compared to the provider's protocol to avoid complete modifications of all lysine residues. A total of 10 μL of supernatant from the barcoded 96-well tissue culture plates were transferred using an Agilent Bravo liquid handler into barcoded 384-well black-walled assay plates containing biotinylated KLK coated Sol-R beads as above and a FITC conjugated goat anti-rabbit Fc fragment specific (Jackson ImmunoResearch™). After 1 h incubation plates were read on a mirror-ball instrument (TTP-Labtech™).

Following primary screening, supernatants positive for binding to KLK5 were consolidated on 96-well bar-coded master plates using a Beckman Coulter BiomekNXP™ hit-picking robot and B cells in cell culture plates were frozen at −80° C. First, consolidated supernatants were re-screened to confirm binding to human KLK5 by Fluorometric Microvolume Assay Technology (FMAT). Briefly 10 μL of supernatant were transferred to barcoded black Greiner plates. 50 μL/plate of 10 μm superavidin (Bangs Beads™) were coated with human biotinylated KLK5, mixed with Alexa647™ goat anti-rabbit IgG Fc fragment specific (Jackson ImmunoResearch™). The supernatant was then added and the plates read on an Applied Biosystems™ Cellular Detection System 8200.

A number of antibodies were selected for binding to KLK5 and were subsequently investigated for their ability to specifically inhibit KLK5 and their specificity for KLK5 over other kallikreins.

Example 3: Identification of KLK5 Inhibitory Antibodies

To identify antibodies capable of inhibiting specifically KLK5 activity among the proteases and protease inhibitors present in the complex B cell supernatant, a screening assay was developed. Nunc Maxisorp black 384 (Sigma Aldrich™) were coated with $F(ab')_2$ Fragment Goat Anti-Rabbit IgG Fc Fragment Specific (Jackson ImmunoResearch™) at 10 pg/mL in carbonate buffer and left overnight at 4° C. Plates were washed 3 times on a Biotek™ plate washer with PBS/0.1% Tween-20 and blocked with 20

μL/well PBS/1% BSA for 1 h at room temperature. B-cell supernatants were added to the plates with 25 μl of 1 nM LEKTI D5 rabbit Fc fusion protein added to control wells as a positive control for inhibition and assay buffer A (50 mM Tris, 150 mM NaCl, 0.05% (v/v) Tween-20, pH 7.6) added to a separate set of control wells as a negative control for inhibition. The plates were incubated overnight at room temperature and then washed three times on a Biotek™ plate washer with PBS/0.1% Tween-20. 10 μL of 250 pM human KLK5 in assay buffer A were added to each well and the plates incubated overnight at room temperature to allow full association. Boc-VPR-AMC substrate (Cambridge Research Biochemicals™) in assay buffer A was added to the wells to a final concentration of 600 pM and the fluorescence ($\lambda_{ex}$380 nm $\lambda_{em}$430 nm) determined after 4 hours using a PHERAStar FSX (BMG Labtech™) plate reader.

Data were analyzed to determine the percentage inhibition of KLK5 activity using the following equation:

$$\%\ \text{Inhibition} = 100 \cdot \left(1 - \frac{\text{Test} - \text{Positive}}{\text{Negative} - \text{Positive}}\right)$$

where Test is the fluorescence value for a test antibody, Positive is the average of the fluorescence values of the positive control for inhibition wells and Negative is the average fluorescence values of the negative control for inhibition wells.

Supernatants that showed >40% inhibition were considered hits. This amounted to about 4% of all of the screened supernatants. These antibodies were selected for variable region recovery.

In order to identify the specific antibody secreting cells to allow recovery of antibody variable region genes from an heterogenous population of activated B cells, a deconvolution step had to be performed. The fluorescent foci method (Clargo et al., 2014) was used. Briefly, antibody secreting cells were statically incubated at 37° C. for 1 hour in the presence of streptavidin beads (New England Biolabs™) coated with biotinylated human KLK5 and a goat anti-rabbit Fc fragment-specific FITC conjugate (Jackson ImmunoResearch™). Antigen-specific antibody secreting cells were then identified from the fluorescent halo surrounding them. A number of these individual B cell clones, identified using an Olympus microscope, were then picked with an Eppendorf™ micromanipulator and deposited into a PCR tube. cDNA from the single cells was obtained by standard RT-PCR and subsequent PCR of the variable immunoglobulin sequences for the heavy and light chains were performed using immunoglobulin gene specific primers, followed by a nested PCR incorporating overlapping vector sites allowing for direct cloning of the variable region into a rabbit IgG (VH) or rabbit kappa (VL) mammalian expression vector. Heavy and light chain constructs were co-transfected into ExpiHEK-293 cells using ExpiFectamine™ (Life Technologies™) and recombinant antibody expressed in 125 ml Erlenmeyer™ flask in a volume of 30 ml. After 5-7 days of culture, supernatants were harvested, and antibodies purified by Protein A affinity capture using the AKTA pure chromatography system. 1 ml Protein A HiTrap MabSelect™ SuRe™ column (GE Healthcare) was attached to the system and the column equilibrated in PBS pH 7.4 before applying cell culture supernatant to the column at a flow rate of 0.25 ml/min. The column was then washed with PBS pH 7.4, bound material eluted with sodium citrate pH 3.4 and neutralised with an appropriate volume of 2M Tris-HCL pH 8.5. The eluted fractions were buffer exchanged into PBS (Sigma), pH7.4 and passed through a 0.22 μm filter. Final purified material was assayed by A280 scan, SE-UPLC (BEH200 method), and for endotoxin using the Endosafe® PTS™ system.

From this analysis, rabbit antibodies 10236 and 10273 showed potent inhibition and were selected for further characterization.

Example 4: Identification of KLK5 Specific Inhibitory Antibodies

Purified rabbit antibodies 10236 and 10273 were then screened to confirm their inhibitory activity against KLK5 and determine specificity for KLK5 by using a panel of other human sequence kallikrein family members including KLK2, KLK4 and KLK7 together with murine and cyno KLK5 and KLK7. A 10-point half log dilution series with a range of 600 nM to 20 pM was prepared for each antibody and 5 uL transferred to black 384 well assay plates (Corning™, cat n.3575) using a Beckman Coulter FX™ and a Multidrop System. 15 μL of the active recombinant human kallikrein proteins were added to the relevant wells achieve the following final assay concentrations: 60 pM KLK5, 250 pM KLK7, 500 pM KLK2, 30 pM KLK4, 30 pM cynoKLK5, 500 pM cyno KLK7, 30 pM mouse KLK5 or 10 nM mouse KLK7 in assay buffer A (50 mM Tris, 150 mM NaCl, 200 pM EDTA, 0.05% (v/v) Tween-20, pH 7.6). As controls, 20 μL assay buffer A only (no KLK protein) was added to wells for 0% activity. LEKTI D5 rabbit Fc was used as a positive control for inhibition (tested over the same concentration range as the antibodies), whilst 15 μL of the respective active human kallilkrein proteins were added to 5 μL assay buffer A for 100% activity references. Plates were incubated at room temperature overnight before addition of the following peptide substrates using a multidrop device: Boc-VPR-AMC (Cambridge Research Biochemicals™) for human KLK5 (300 μM), human KLK2 (30 μM), murine KLK5 (300 μM) and cyno KLK5 (450 μM); KHLF-AMC (Cambridge Research Biochemicals™) for human and cyno KLK7 (90 μM and 150 μM, respectively), PFR-AMC (R&D Systems™) for human KLK4 (200 μM), and Mca-RPKPVE-Nval-WRK(Dnp)-NH2 (R&D Systems™) for murine KLK7 (150 μM). Samples were incubated for 4 hours and read on a Pherastar FSX Plate Reader (BMG Labtech™) at $\lambda_{ex}$380 nm and $\lambda_{em}$430 nm for Boc-VPR-AMC, PFR-AMC and KHLF-AMC; and at $\lambda_{ex}$320 nm and $\lambda_{em}$400 nm for Mca-RPKPVE-Nval-WRK(Dnp)-NH2. Data were analysed to determine percentage inhibition as described in Example 3. Data were plotted against concentration of test antibody and a 4-parameter sigmoid curve fitted to determine IC50 (Genedata Screener™).

In addition to rabbit antibody 10236, for this measurement, the polynucleotide sequences of rabbit variable regions of antibodies 10236 and 10273 were cloned on a modified version of the mouse C Kappa vector comprising the S171C mutation, to re-create the additional disulphide bond found in rabbit VK light chains not present in the mouse constant regions (SEQ ID NO: 80 and 81 for rabbit antibody 10273 mIgG and SEQ ID NO: 84 and 85 (or nucleotides 1-1314 of SEQ ID NO: 85) for rabbit antibody 10236 mIgG). This resulted in antibodies comprising SEQ ID NO: 82 and 83 for rabbit antibody 10236 mIgG and SEQ ID NO: 78 and 79 for rabbit antibody 10273 mIgG.

Rabbit antibodies 10236 and 10237 mIgGs showed potent inhibition of human KLK5 with no activity (i.e. below the 40% threshold as per selection criteria in example 2) against the other human family members tested (human KLK2, 4 and 7). Potent inhibition of cyno KLK5 but not cyno KLK7 was also demonstrated. No inhibitory activity was evident against either mouse KLK5 or KLK7. $IC_{50}$ results for rabbit antibody 10236, 10273 and LEKTI D5 rabbit Fc are shown in Table 2.

TABLE 2

| Antibody descriptor | Hu KLK5 | Hu KLK2 | Hu KLK4 | Hu KLK7 | Cyno KLK5 | Cyno KLK7 | Mouse KLK5 | Mouse KLK7 |
|---|---|---|---|---|---|---|---|---|
| | IC50 (M) | | | | | | | |
| 10236 mIgG | 2.40E−10 | NI | NI | NI | 3.30E−11 | NI | NI | NI |
| Rabbit 10236 IgG | 1.74E−10 | NI | NI | NI | 2.76E−11 | NI | NI | NI |
| 10273 mIgG | 3.48E−11 | NI | NI | NI | 3.01E−10 | NI | NI | NI |
| LEKTI D5 Fc | 1.03E−10 | n/a | n/a | n/a | n/a | n/a | n/a | n/a |

NI = No Inhibition;
Hu = human;
Cy = cyno;
Mu = mouse;
n/a = not available

Example 5: Determination of Affinity of KLK5 Specific Abs

The kinetics of murine IgG molecules binding to human KLK5 were assessed by surface plasmon resonance (Biacore T200, (GE Life Sciences™) at 25° C.

A goat anti-mouse IgG Fc specific antibody (Jackson ImmunoResearch) was immobilised on a CM5 Sensor Chip via amine coupling chemistry to a level of approximately 7000RU. Each analysis cycle consisted of capture of the anti-KLK5 IgG molecules to the anti Fc surface, injection of KLK5 analyte (prepared in house) for 300 s at 30 μl/min followed by 600 s dissociation. At the end of each cycle the surface was regenerated at a flowrate of 10 μL/min using a 60 s injection of 50 mM HCl followed by a 30 s injection of 5 mM NaOH and a final 60 s injection of 50 mM HCl. Human KLK5 was titrated from 20 nM to 0.25 nM (4×3-fold serial dilutions) in HBS-EP+ running buffer (GE Healthcare) supplemented with NaCl to a final concentration of 300 mM. Buffer blank injections were included to subtract instrument noise and drift.

Kinetic parameters were determined using a 1:1 binding model using Biacore T200 Evaluation software.

The affinities of rabbit antibodies 10236 and 10273 are shown in Table 3.

TABLE 3

| Rabbit/mouse antibodies | ka (Ms^−1) | kd (s^−1) | KD (pM) |
|---|---|---|---|
| 10236 | 3.00E+06 | 5.17E−04 | 172.3 |
| 10273 | 1.14E+06 | 1.84E−04 | 160.0 |

Example 6: Characterization of Antibody 10236

LEKTI Binding to KLK5 in the Presence of Antibody 10236

Surface plasmon resonance (SPR) experiments were carried out to determine whether antibody 10236 competed with the LEKTI D5 protein for binding to human KLK5. These assays enabled comparison of the affinity of LEKTI D5 Fab fusion for KLK5 protein alone to human KLK5 complexed with antibody 10236.

Kinetic measurements for the binding of LEKTI D5 Fab fusion protein to human KLK5 were obtained using a Biacore T200 (GE Life Sciences™). To prepare the surface, CM5 chips (GE Life Sciences™) were first activated with a 5-minute injection (30 μL $min^{-1}$) of a mixture of EDC/NHS (GE Life Sciences™) followed by injection of 100 μg $mL^{-1}$ LEKTI D5 Fab fusion (UCB) in acetate buffer, pH 5.0 (GE Life Sciences™) to achieve 80 RU immobilised LEKTI D5 Fab fusion on the chip surface. Finally, an injection of 1 M Ethanolamine hydrochloride-NaOH pH 8.5 was utilised to deactivate the surface. Increasing concentrations of human KLK5 from 0.32 to 32 nM in HBS-EP buffer (GE Life Sciences™) were then injected in the single cycle kinetics mode. Values resulting from buffer only injections were subtracted from those obtained for the KLK5 injections and kinetics determined by fitting to a 1:1 binding model in BIAcore evaluation software (GE Life Sciences™)

To determine whether human LEKTI was capable of binding human KLK5 when human KLK5 was bound by rabbit antibody 10236, antibody capture surfaces were prepared using a Goat anti-Rabbit Fc polyclonal and Ab 10236 captured as described in Example 4. 20 nM of human KLK5 was then injected until the surface reached saturation. LEKTI D5 Fab fusion protein (generated as described in example 1) was then injected at concentrations between 30 μM and 100 nM. Values from buffer only injections were first subtracted from those obtained with the analytes before fitting to a 1:1 binding kinetic model in Biacore™ evaluation software (GE Life Sciences™)

As reference, LEKTI D5 Fab fusion protein was immobilised to the chip surface prior to monitoring the interaction with human KLK5. Human LEKTI D5 Fab fusion protein was able to bind to human KLK5 when human KLK5 is already in complex with rabbit antibody 10236 with an affinity of 120 nM (Table 4A). Whilst the affinity of human LEKTI to human KLK5 in the absence of rabbit antibody 10236 is higher (40 μM), this analysis demonstrates that, by binding human KLK5 in the presence or absence of human LEKTI, rabbit antibody 10236 may provide additional inhibitory activity to human KLK5.

TABLE 4A

| | ka (Ms^−1) | kd (s^−1) | KD (pM) |
|---|---|---|---|
| Human KLK5 only | 5.70E+05 | 2.30E−05 | 4.00E−11 |
| 10236 + Human KLK5 | 5.90E+04 | 7.30E−03 | 1.20E−07 |

LEKTI-KLK5-Antibody 10236 Complex Formation

KLK5 was produced in HEK293 cells as a secreted protein with a N-terminal, TEV-cleavable 8×His-tag. The protein was first purified from conditioned media by $Ni^{2+}$ affinity chromatography. Fractions from the $Ni^{2+}$ column containing KLK5 were pooled and digested with TEV protease to remove the His tag then a second Ni affinity step was performed to remove the TEV protease, letting the cleaved KLK5 flow through the column. The flow through fraction from the second $Ni^{2+}$ column was concentrated and run on a size exclusion column in 50 mM Tris pH 7, 50 mM NaCl, 1 mM EDTA, 5% glycerol. KLK5 fractions from the SEC were pooled and concentrated to approximately 10 mg/ml and stored at −80° C.

LEKTI domain 5 (LEKTI D5 Fc) according to SEQ ID NO: 98 and LEKTI domain 8 (LEKTI D8 Fc) according to SEQ ID NO; 99 were produced in HEK293 cells as secreted proteins with a C-terminal, TEV-cleavable Fc tag. These proteins were purified by passing conditioned media over Protein A beads. Bound protein was eluted with 0.1 M Citric acid, pH2.0 and fractions neutralized by the addition of 2M Tris-HCl, pH 8.5. Fractions from the Protein A column containing either LEKTI domain 5 or domain 8 were pooled and the Fc tag removed with TEV protease to give LEKTI D5 or LEKTI D8. The cleaved protein was concentrated to ~15 mg/ml for size exclusion chromatography. SEC was carried out in PBS, pH 7.2. LEKTI containing fractions were pooled and concentrated to ~10 mg/ml and stored frozen at −80° C.

Rabbit Fab antibody 10236 was expressed in HEK293 cells as a secreted protein. Expression constructs comprising SEQ ID NO: 87 and 89 were co-transfected at a 1:1 molar ratio. The secreted Fab (comprising SEQ ID NO: 86 and 88) was purified by passing conditioned media over Protein G beads and eluted with 0.1M glycine, pH 2.7. Fractions were neutralized by the addition of 2M Tris-HCl, pH8.5. The protein was dialyzed into PBS, pH 7.2 then concentrated to ~10 mg/ml and stored frozen at −80° C.

Complexes of KLK5, LEKTI D5 or LEKTI D8, and rabbit Fab antibody 10236 were formed by first incubating 25 μM KLK5 with 25 μM LEKTI D5 or LEKTI D8 for 60 minutes on ice then adding 25 μM rabbit Fab antibody 10236 and continuing the incubation for another 60 minutes on ice. The mixture was injected onto a Superdex 200® size exclusion column equilibrated with PBS, pH 7.2. which was connected in series to an HPLC. Peak fractions were collected for analysis by SDS-PAGE. FIGS. 1A and 1B show the SEC chromatograms of human KLK5 alone (solid trace, far right), rabbit Fab antibody 10236 alone (dotted trace), the binary complex of human KLK+LEKTI D5 or D8 (FIG. 1A or 1B respectively, long dash), and the ternary complex of KLK5+LEKTI D5 or D8+rabbit Fab antibody 10236 (FIG. 3A or 3B respectively, short dash, far left).

The molecular weight (MW) of the components of each peak was confirmed by SDS-PAGE as shown in FIG. 2.

Overall, complexes between KLK5, LEKTI D5 or LEKTI D8, and rabbit Fab antibody 10236 formed readily when mixed in a 1:1:1 ratio by mixing human KLK5 with each LEKTI fragment individually then incubating the binary complexes with rabbit Fab antibody 10236. Binary and ternary complexes were observed on SEC and by SDS-PAGE of peak fractions, indicating they were stable and suitable for isolation/purification from the other species.

Example 7: Crystallization of KLK5/Fab Antibody 10236 Complex

Human KLK5 was expressed by transient transfection using the Expi293™ Expression System (Life Technologies™) following manufacturer's protocol, with the addition of kifunensine (Sigma®) at a 5 mM final concentration. Kifunensine is a potent inhibitor of the mannosidase I enzyme and is primarily used in cell culture to make high mannose glycoproteins.

During expression of KLK5, the protein auto-activates to yield active KLK5 protein (residues 167-S293 (UniProt Q9Y337 numbering) of SEQ ID NO: 53) in the supernatant. Cells were harvested 5 days post transfection and supernatants used immediately for purification. Supernatants comprising human active KLK5 were diluted 4-fold with Buffer A (50 mM Tris pH 7.0, 50 mM NaCl) and loaded onto a HiTrap SP HP cation exchange column. Bound proteins were eluted with a salt gradient generated over a total of 10 column volumes using Buffer A (50 mM Tris pH 7.0, 50 mM NaCl) and Buffer B (50 mM Tris pH 7.0, 1M NaCl). Fractions containing purified human active KLK5 were pooled, concentrated and purified further by size exclusion chromatography on an S200 26/60 column which had been equilibrated with 20 mM Tris, 150 mM NaCl, at pH 7.2.

Figure 3:
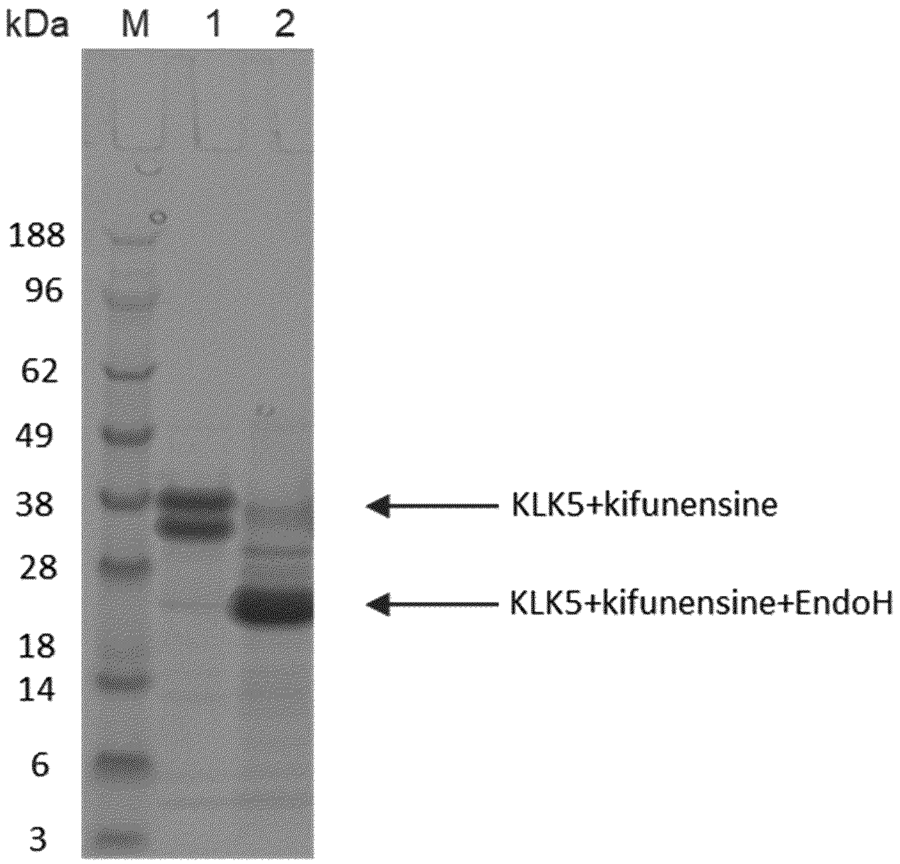
FIG. 3. SDS-PAGE of KLK5 produced for X-ray crystallography studies. Lane M, MW markers. Lane 1, human KLK5 purified from cultures grown in presence of kifunensine (kif). Lane 2, human KLK5 purified from kifunensine cultures and treated with Endoglycosidase H (Endo H).

KLK5 was characterized by SDS-PAGE and migrated to a position on the gel consistent with the expected molecular weight (MW) of the high mannose glycosylated protein ~35-38 kDa (FIG. 3).

Human KLK5 protein was then treated with Endoglycosidase H (Endo H) protein at ratio of 1:100 and incubated at 4° C. overnight to form a homogenous de-glycosylated KLK5 protein for structural studies. Endoglycosidase H (Endo H) is a recombinant glycosidase cloned from *Streptomyces plicatus* and overexpressed in *E. coli*. Endo H cleaves the chitobiose core of high mannose and a limited number of hybrid oligosaccharides from N-linked glycoproteins. It does not cleave complex glycans. Enzymatic cleavage is between the two N-acetylglucosamine residues in the diacetylchitobiose core of the oligosaccharide, leaving one N-acetylglucosamine residue on the asparagine. This step was performed to ensure that a homogenous human KLK5 was available for crystallographic studies. KLK5 was characterized by SDS-PAGE (FIG. 3) and migrated to a position on the gel consistent with the expected molecular weight (MW) of the de-glycosylated protein ~25 kDa.

Rabbit Fab antibody 10236 was expressed as described in Example 6. Rabbit Fab antibody 10236 (comprising SEQ ID NO: 86 and 88) was expressed as described in example 6. In short, expression constructs comprising SEQ ID NO: 87 and 89 were co-transfected at a 1:1 molar ratio. Rabbit Fab antibody 10236 was purified by passing conditioned medium over Protein G beads and eluted with 0.1 M glycine, pH 2.7. Fractions were neutralized by the addition of 2M Tris-HCl, pH8.5. The respective, individual proteins were dialyzed into PBS, pH 7.2, concentrated to ~10 mg/ml and stored frozen at −80° C.

A 1.5:1 molar ratio human KLK5/rabbit Fab antibody 10236 mixture was made, incubated at 4° C. overnight and purified by size exclusion chromatography (20 mM Tris, 150 mM NaCl, pH 7.2 elution buffer). The formed complex was isolated and concentrated to ~10.0 mg/ml prior to crystallization.

Crystallization conditions for the human KLK5/rabbit Fab antibody 10236 complex were identified using several commercially available crystallization screens. These were carried out in sitting drop format, using Swissci 96-well 2-drop MRC Crystallization plates (sourced from Molecular Dimensions, Cat No. MD11-00-100). First, the reservoirs were filled with 75 μL of each crystallization solution in the screens using a Microlab STAR liquid handling system (Hamilton). Then, 300 nL of the human KLK5/rabbit Fab antibody 10236 complex and 300 nL of the reservoir solutions were dispensed in the wells of the crystallization plates using a Mosquito liquid handler (TTP LabTech). A single crystal was obtained in condition 88 (well H4) of the ProComplex Suite, Qiagen). This condition contains 1.4 M sodium malonate. Crystals were briefly transferred to a drop containing 1.4 M sodium malonate and 25% glycerol. The crystal was flash frozen in liquid nitrogen and diffraction data were collected at beamline 103 (Diamond Light Source, UK). The data was indexed and integrated using XDS (Kabsch, W. XDS. Acta Cryst. D66, 125-132 (2010)), followed by scaling using AIMLESS (Evans P R, Murshudov G N. How good are my data and what is the resolution? Acta Crystallogr D Biot Crystallogr. 2013; 69(Pt 7):1204-1214). The human KLK5/rabbit Fab antibody 10236 complex structure was solved by molecular replacement using Phaser (McCoy, A. J., Grosse-Kunstleve, R. W., Adams, P. D., Winn, M. D., Storoni, L. C., & Read, R. J. Phaser crystallographic software. J. Appl. Cryst. (2007). 40, 658-674) in the Phenix software suite (Adams P D, Afonine P V, Bunkoczi G, et al. The Phenix software for automated determination of macromolecular structures. Methods. 2011; 55(1): 94-106). In this procedure, the structures of KLK5 and rabbit Fab antibody 10236 observed in our crystal structure of KLK5 in complex with rabbit Fab antibodies 10273 and 10236 were used as molecular replacement models. Coot (P. Emsley; B. Lohkamp; W. G. Scott; Cowtan (2010). "Features and Development of Coot". Acta Crystallographica. D66: 486-501) and phenix.refine (Towards automated crystallographic structure refinement with phenix.refine. P. V. Afonine, R. W. Grosse-Kunstleve, N. Echols, J. J. Headd, N. W. Moriarty, M. Mustyakimov, T. C. Terwilliger, A. Urzhumtsev, P. H. Zwart, and P. D. Adams. Acta Crystallogr D Biol Crystallogr 68, 352-67 (2012)) were used in the following cycles of manual model completion and refinement. Table 4B shows the refinement statistics at the time the invention was first described.

TABLE 4B

| Data collection | |
|---|---|
| Resolution (Å) | 123.01-2.70 (2.83-2.70) |
| Space group | 1 2 3 |
| Cell parameters | |
| a = b = c (Å) | 137.96 |
| α = β = γ (°) | 90.00 |
| $R_{merge}$ (%) | 5.70 (75.4) |
| $R_{meas}$ (%) | 5.80 (77.4) |
| $R_{pim}$ | 1.30 (16.7) |
| Average I/σ(I) | 48.5 (6.6) |
| Completeness (%) | 100.0 (100.0) |
| No. of unique reflections | 24174 (3190) |
| Multiplicity | 40.8 (41.5) |
| Wilson B-factor (Å$^2$) | 77.528 |
| **Refinement statistics** | |
| Number of protein/solvent atoms | 4826/12 |
| Rwork/free (%) | 21.19/25.8 |
| Number of reflections in the 'free' set | 3302 |
| R.m.s. deviations from ideal values | |
| Bonds (Å) | 0.004 |
| Angles (°) | 0.764 |
| Average protein B factor (Å$^2$) | 89.06 |

Figure 4:
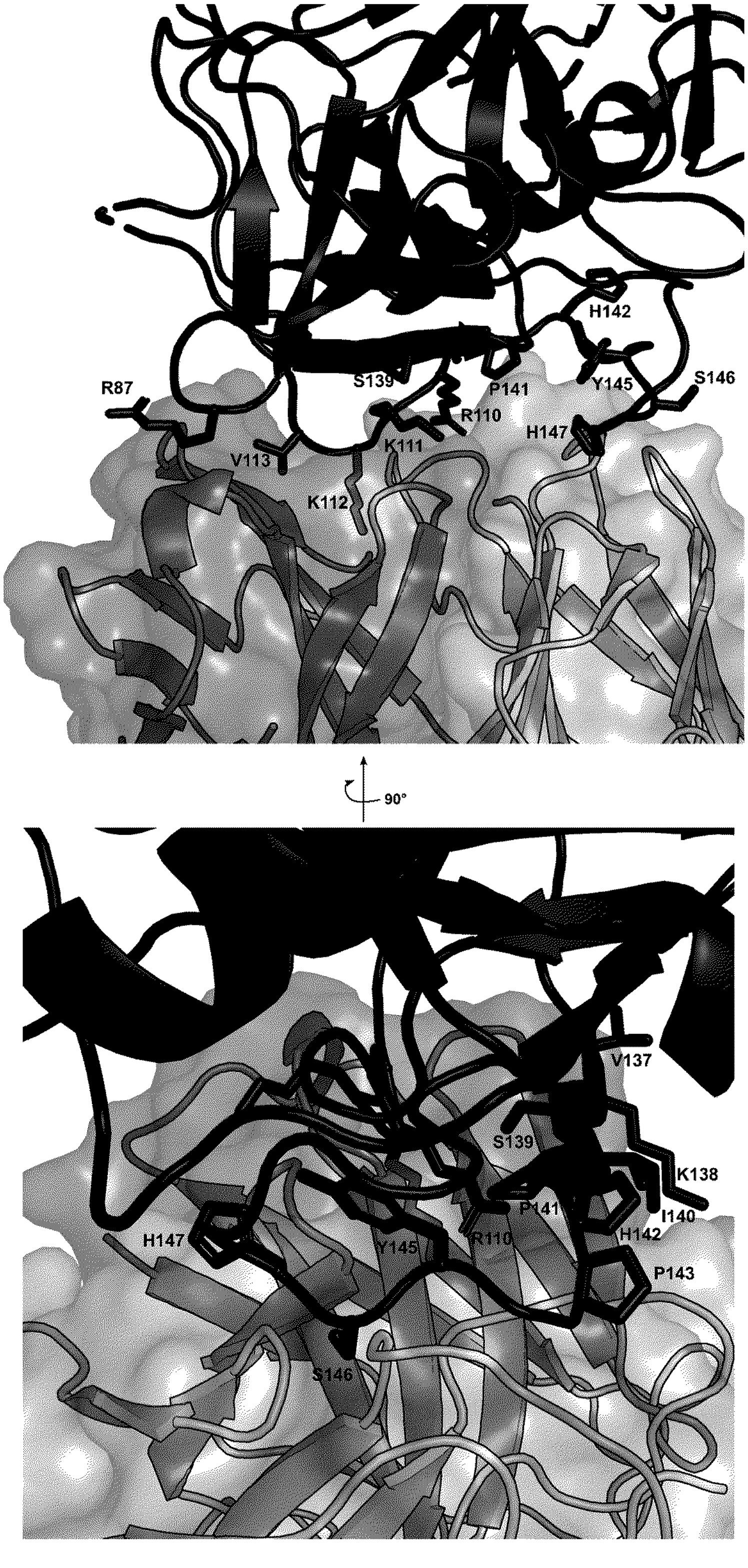
FIG. 4. Schematic representation of the human KLK5 epitope in complex with rabbit Fab antibody 10236. A) Fab heavy (dark grey) and light (light grey) chains are shown in cartoon and transparent surface. KLK5 is shown as black ribbon. Residues of KLK5 which are part of the epitope on human KLK5 bound by antibody 10236 are depicted as black sticks. B) Leupeptin (surface and sticks) modelled in the crystal structure of KLK5 (ribbon) bound to rabbit Fab10236 (surface rendered). Fab10236 makes contact with the 99-loop on KLK5. C) Superposition of crystal structures 2PSX (white, no zinc) and 2PSY (grey, with zinc), highlighting movements in the 99-loop and side chain positions of His147 and His150 on KLK5, in the presence of zinc. Leupeptin is shown in white surface and sticks. D) Superposition of crystal structure 2PSX (KLK5 bound to Leupeptin) on the crystal structure of KLK5 in complex with Fab10236. Movements in the 99-loop and side chain positions of His147 and His150, upon comparison of both structures, are highlighted. The conformations of the loop and His residues in crystal structure 2PSX and the crystal structure of Fab10236 bound to KLK5, are shown in white and black respectively. The white, dashed rectangle around His147 (crystal structure 2PSX) indicates that this conformation would clash with Fab10236 (grey surface). His147 is in a different conformation in the KLK5-Fab10236 structure. The white, dashed circle around His150 (black, as observed in the complex of KLK5 with Fab10236) indicates that it points towards the S2 pocket of the KLK5 active site, where a substrate such as leupeptin would bind. Leupeptin (grey surface and sticks), from crystal structure 2PSX, shows where substrate is expected to bind in the KLK5 active site.
Figure 4:
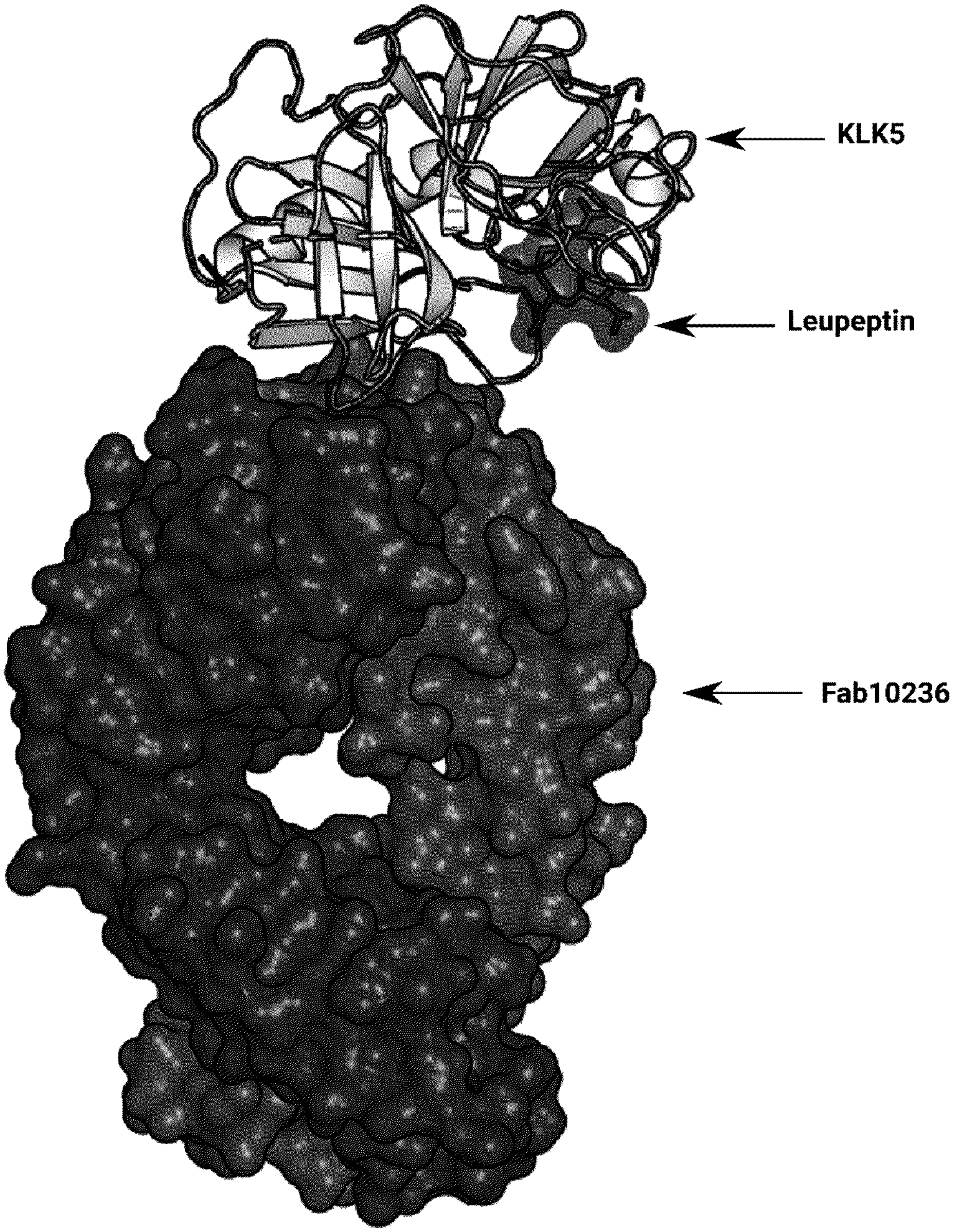
Figure 4:
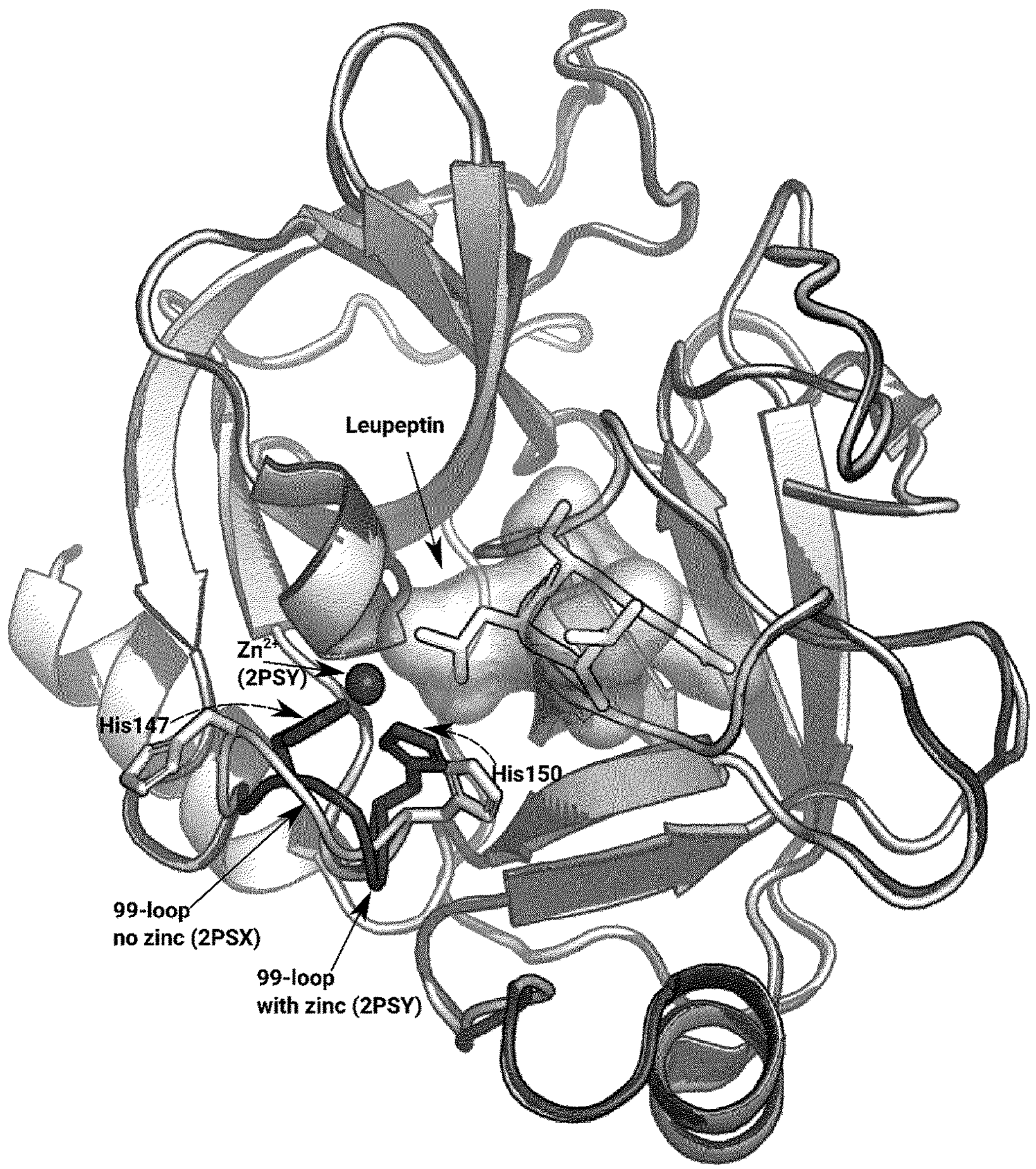
Figure 4:
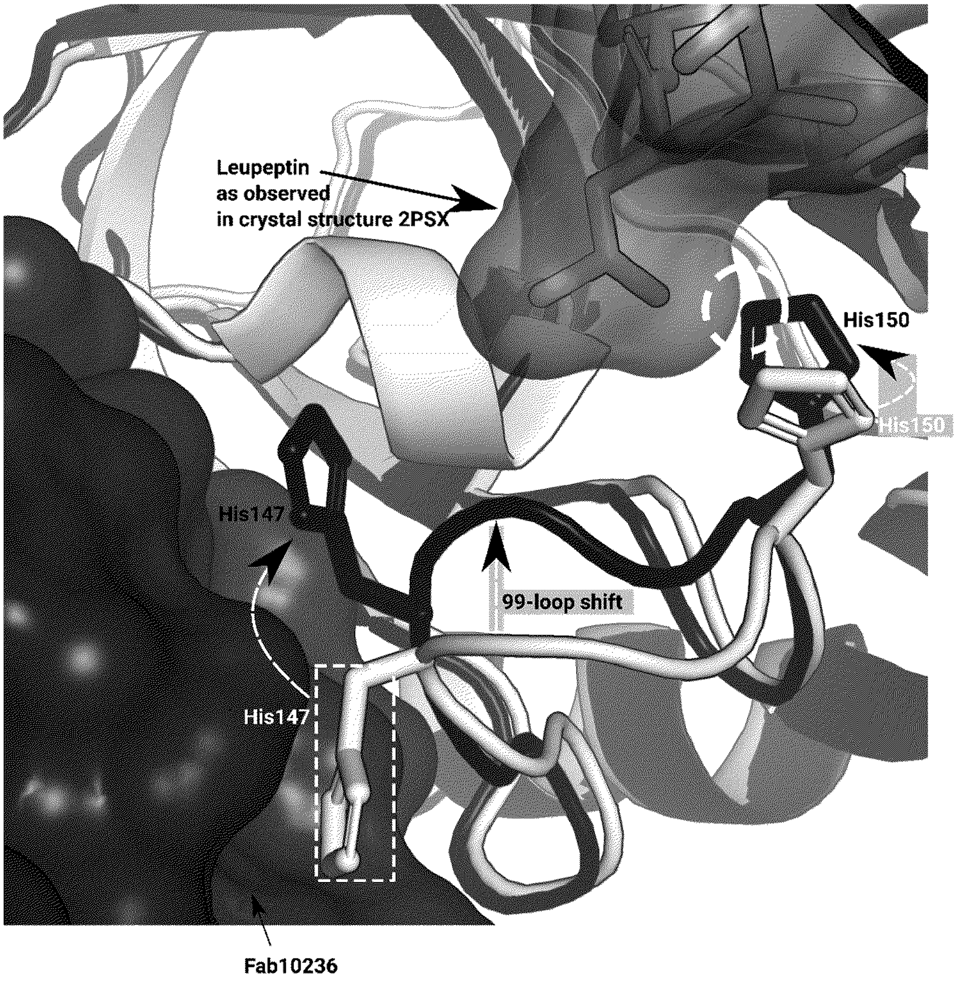

A single human KLK5/rabbit Fab antibody 10236 complex was observed in the crystal asymmetric unit. FIG. 4B shows that the antibody binding site to KLK5 is distinct from the substrate binding site. NCONT in the CCP4 software suite was used to define the epitope on KLK5, recognized by the Fab10236 molecule. The KLK5 amino acid numbering is based on UnitProtKB entry Q9Y337 with standard protease numbering based on chymotrypsinogen in brackets.

The human KLK5 epitope bound by rabbit Fab antibody 10236 at 4 A contact distance is composed of residues Arg87 (36), Ala107 (56), Arg110 (59), Lys111 (60), Lys112 (61), Val113 (62), Val137 (86), Lys138 (87), Ser139 (88), Ile140 (89), Pro141 (90), His142 (91), Pro143 (92), Tyr145 (94), Ser146 (95), His147 (96) with reference to SEQ ID NO: 51, whilst the numbers in parentheses correspond to the protease nomenclature. The binding site is shown in more detail in FIG. 4A.

In order to visualize the binding site of Fab10236 in relation to the active site of KLK5, a structural overlay of the KLK5-Fab10236 structure presented herein with the published structure of KLK5 with leupeptin bound in the active site (2PSX) was made (FIG. 4B). The overlay shows that Fab10236 does not bind KLK5 at the core of the active site as indicated by the position of Leupeptin (FIG. 4B), however the light chain of Fab10236 forms a contact with the 99-loop which shapes part of the active site cleft on KLK5. A comparison was made of the KLK5-Fab10236 structure presented herein with previously published structures of KLK5, such as those disclosed as PDB IDs 2PSX and 2PSY. The crystal structure 2PSX shows KLK5 bound to the peptidic protease inhibitor leupeptin in its active site, while crystal structure 2PSY shows KLK5 bound to leupeptin, as well as a zinc ion adjacent to the active site. Zinc is known to inhibit KLK5 in a non-competitive manner. Comparing structures 2PSX and 2PSY revealed that zinc affects the protease activity by inducing a shift in the backbone conformation of the 99-loop, accompanied with substantial positional changes in the side chains of His147(96) and His150(99). The backbone 99-loop movement is shown in the structural overlay (FIG. 4C, white no zinc and black plus zinc) as well as the histidine sidechain movements, in particular the shift of His147(99) from an outward position in the absence of zinc to an inward position when zinc is bound (FIG. 4C, dashed arrows indicate histidine sidechain movements).

A structural overlay of the KLK5-Fab10236 structure with the KLK leupeptin structure without zinc (2PSX), highlights backbone movements of the 99-loop and sidechain movements of His147(96) and His150(99) (FIG. 4D, 99-loop and histidine sidechains shown in detail—black is KLK5-Fab10236 structure and white is KLK5-leupeptin no zinc structure).

Upon binding of Fab10236 to KLK5, His147(96) located in the 99-loop cannot adopt the conformation previously observed in crystal structure 2PSX as this would cause steric clashes with the Fab light chain (dashed square, FIG. 4D). In order to accommodate binding of Fab10236, the 99-loop adopts a different conformation with His147(96) swinging from an outward position to an inward position (similar to that observed when zinc binds; FIG. 4D, dashed arrow indicating His147(96) movement). Concomitantly, the side chain of His150(99) undergoes a positional change shifting it towards the S2 pocket where it may block substrate binding. As shown in FIG. 4D, the S2 pocket is occupied by modelled leupeptin and the clash between the His150(99) side chain and leupeptin is highlighted by a white, dashed circle.

Example 8: Crystallization of KLK5/Fab Antibody 10236/Fab Antibody 10273 Complex Human KLK5 was expressed as in Example 7 except that once the supernatant was loaded onto HiTrap SP HP cation exchange column, the bound proteins were eluted with a Buffer B (50 mM Tris pH 7.0, 1M NaCl) gradient over 10 column volumes. Further purification, endoglycosidase treatment and analytical characterization were performed as in Example 7.

Rabbit Fab antibody 10236 was expressed as in Example 6. Rabbit Fab antibody 10273 (comprising SEQ ID NO: 90 and 92) was cloned as described for rabbit Fab antibody 10236. In short, expression constructs comprising SEQ ID NO: 91 and 93 were co-transformed at a 1:1 molar ratio. The secreted proteins were purified by passing conditioned media over Protein G beads and eluted with 0.1 M glycine, pH 2.7. Fractions were neutralized by the addition of 2M Tris-HCl, pH8.5. The protein was dialyzed into PBS, pH 7.2 then concentrated to ~10 mg/ml and stored frozen at −80° C.

A 1:1.5:1.5 human KLK5/rabbit Fab antibody 10273/rabbit Fab antibody 10236 complex was made, incubated at 4° C. overnight and purified by size exclusion chromatography (20 mM Tris, 150 mM NaCl, pH 7.2 elution buffer). A single peak containing the complex was concentrated to ~10.8 mg/ml prior to crystallization.

Crystallization conditions for the human KLK5/rabbit Fab antibody 10273/rabbit Fab antibody 10236 complex were identified using several commercially available crystallization screens. These were carried out in sitting drop format, using Swissci 96-well 2-drop MRC Crystallization plates (sourced from Molecular Dimensions, Cat No. MD11-00-100). First, the reservoirs were filled with 75 μL of each crystallization solution in the screens using a Microlab STAR liquid handling system (Hamilton). Then, 300 nL of the human KLK5/rabbit Fab antibody 10273/rabbit Fab antibody 10236 complex and 300 nL of the reservoir solutions were dispensed in the wells of the crystallization plates using a Mosquito liquid handler (TTP LabTech). A single crystal was obtained in condition 16 (well B4) of the MIDAS+ HT-96 screen (Molecular Dimensions, Cat No. MD1-107). This condition contains 45% v/v Pentaerythritol Propoxylate (5/4), 0.2 M NaCl and 0.1 M MES monohydrate pH 6.0. The crystal was flash frozen in liquid nitrogen and diffraction data were collected at beamline 103 (Diamond Light Source, UK). The data was indexed and integrated using XDS (Kabsch, W. XDS. Acta Cryst. D66, 125-132 (2010)), followed by scaling using AIMLESS (2. Evans P R, Murshudov G N. How good are my data and what is the resolution? Acta Crystallogr D Biol Crystallogr. 2013; 69(Pt 7):1204-1214). The human KLK5/rabbit Fab antibody 10273/rabbit Fab antibody 10236 complex structure was solved by molecular replacement using Phaser (McCoy, A. J., Grosse-Kunstleve, R. W., Adams, P. D., Winn, M. D., Storoni, L. C., & Read, R. J. Phaser crystallographic software. J. Appl. Cryst. (2007). 40, 658-674) in the Phenix software suite (Adams P D, Afonine P V, Bunkoczi G, et al. The Phenix software for automated determination of macromolecular structures. Methods. 2011; 55(1):94-106). In this procedure, KLK5 structure 2PSX (Debela M, Goettig P, Magdolen V, Huber R, Schechter N M, Bode W. Structural basis of the zinc inhibition of human tissue kallikrein 5. J Mol Biol. 2007 Nov. 2; 373(4):1017-31) and a proprietary Fab model were used as molecular replacement templates. Coot (P. Emsley; B. Lohkamp; W. G. Scott; Cowtan (2010). "Features and Development of Coot". Acta Crystallographica. D66: 486-501) and phenix.refine (Towards automated crystallographic structure refinement with phenix.refine. P. V. Afonine, R. W. Grosse-Kunstleve, N. Echols, J. J. Headd, N. W. Moriarty, M. Mustyakimov, T. C. Terwilliger, A. Urzhumtsev, P. H. Zwart, and P. D. Adams. Acta Crystallogr D Biol Crystallogr 68, 352-67 (2012)) were used in the following cycles of manual model completion and refinement until acceptable Rwork, Rfree and Ramachandran statistics (as analysed by Molprobity (Williams et al. (2018) MolProbity: More and better reference data for improved all-atom structure validation. Protein Science 27: 293-315)) were obtained.

The human KLK5/rabbit Fab antibody 10273/rabbit Fab antibody 10236 complex was observed in the crystal asymmetric unit. NCONT in the CCP4 software suite was used to determine the epitopes on KLK5, recognized by the Fab10273 and Fab10236 molecules. The KLK5 amino acid numbering is based on UnitProtKB entry Q9Y337 with standard protease numbering based on chymotrypsinogen in brackets. Table 4C shows the refinement statistics at the time the invention was firstly described.

TABLE 4C

| Data collection | |
|---|---|
| Resolution (Å) | 87.77-2.45 (2.51-2.45) |
| Space group | I 1 2 1 |
| Cell parameters | |
| a, b, c (Å) | 76.97, 93.19, 261.27 |
| β (°) | 91.00 |
| $R_{merge}$ (%) | 4.10 (52.9) |
| $R_{meas}$ (%) | 5.70 (72.4) |
| $R_{pim}$ | 4.00 (49.2) |
| Average I/σ(I) | 13.3 (1.9) |
| Completeness | 99.3 (99.9) |
| No. of unique reflections | 67522 (4551) |
| Multiplicity | 3.5 (3.4) |
| Wilson B-factor ($Å^2$) | 62.535 |
| **Refinement statistics** | |
| Number of protein/solvent atoms | 7924/84 |
| Rwork/free (%) | 22.89/27.68 |
| Number of reflections in the 'free' set | 3302 |
| R.m.s. deviations from ideal values | |
| Bonds (Å) | 0.011 |
| Angles (°) | 1.158 |
| Average protein B factor ($Å^2$) | 69.33 |

At 4 A contact distance, the human KLK5 epitope bound by rabbit Fab antibody 10236 is composed of residues Arg87 (36), Ala107 (56), Arg110 (59), Lys111 (60), Lys112 (61), Val113 (62), Val137 (86), Lys138 (87), Ser139 (88), Ile140 (89), Pro141 (90), His142 (91), Pro143 (92), Tyr145 (94), Ser146 (95) and His147 (96) with reference to SEQ ID NO: 51, whilst the numbers in parentheses correspond to the protease nomenclature. The binding site is shown in more details in FIG. 4D.

Figure 5:
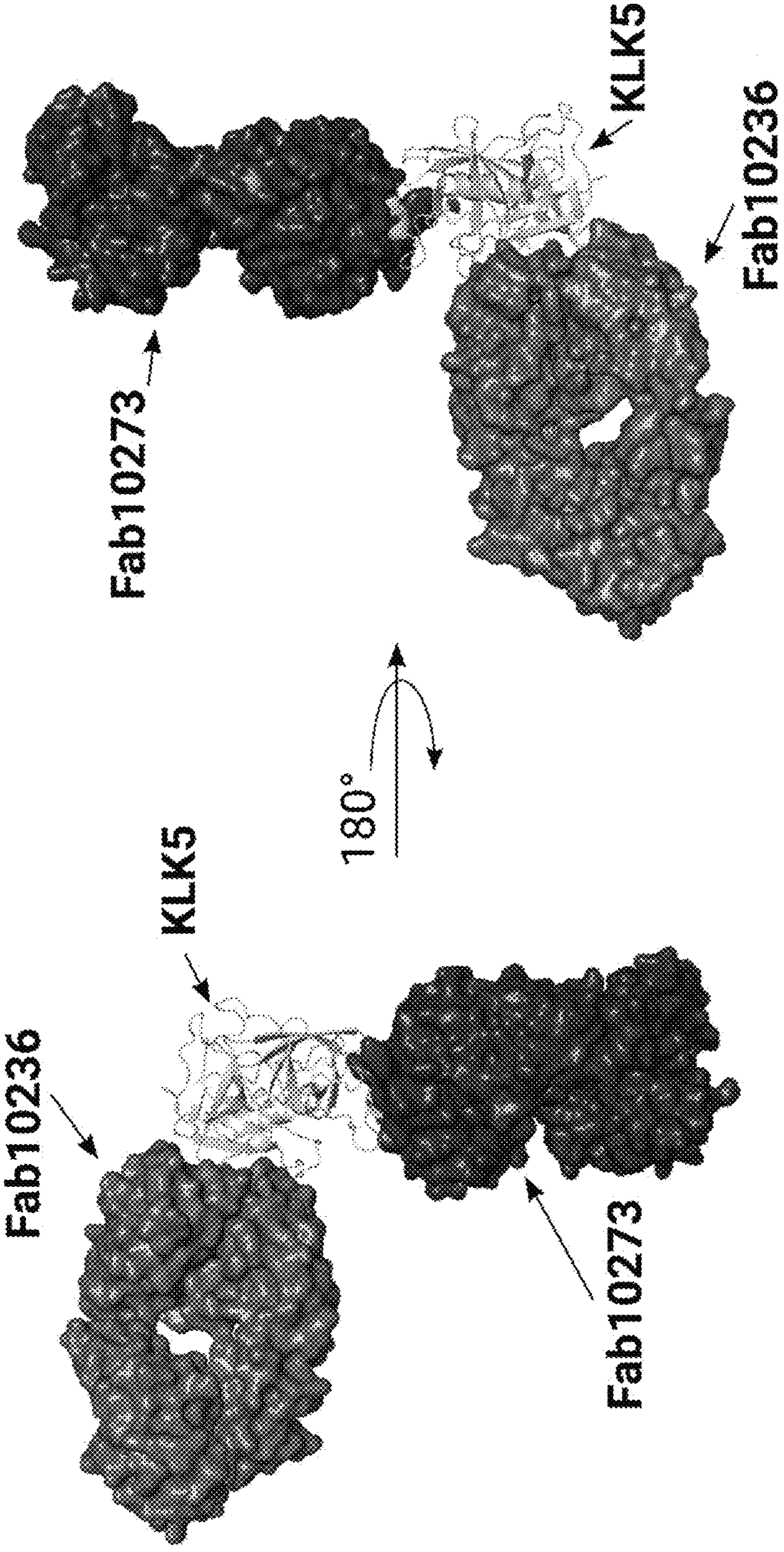
FIG. 5. Two orientations of the crystal structure of the human KLK5 in complex with rabbit Fab antibodies 10236 and 10273. Human KLK5 is shown as ribbon representation, rabbit Fab antibodies 10236 and 10273 are shown as solid surfaces.

As shown in FIG. 5, antibodies 10236 and 10273 have very distinct, non-overlapping binding sites and bind different epitopes on human KLK5.

Example 9: Antibody 10236 Humanization and Characterization

Humanization of Ab 10236

Rabbit antibody 10236 was humanized by grafting the CDRs from the rabbit V-regions onto human germline antibody V-region frameworks. In order to recover the activity of the antibodies, a number of framework residues from the rabbit V-regions were also retained in the humanized sequence. These residues were selected using the protocol outlined by Adair et al. (1991) (Humanized antibodies. WO91/09967). Alignments of the rabbit antibody (donor) V-region sequences with the human germline (acceptor)

Figure 6:
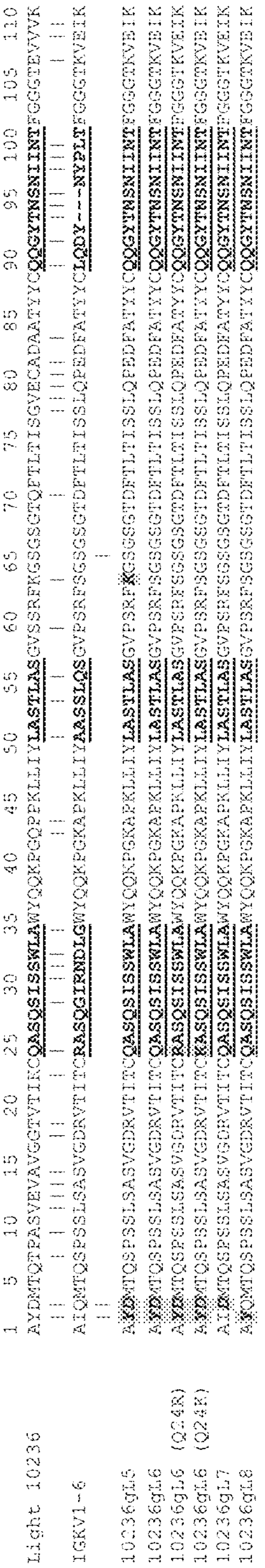
FIG. 6. Humanization of rabbit variable light chain sequence of antibody 10236. Grafts 10236gL5, gL6, gL7 and gL8 are humanized grafts of rabbit variable light chain of antibody 10236 using IGKV1-6 human germline as the acceptor framework. Donor residues are shown in bold/italic and are grey shaded: Y2, D3 and K63. The CDRs are shown in bold/underlined. Mutations in CDRL1 to increase the pI are shown in bold/underlined and are highlighted: Q24R or Q24K.

V-region sequences are shown in FIGS. 6 and 7, together with the designed humanized sequences. The CDRs grafted from the donor to the acceptor sequences are as defined by Kabat (Kabat et al., 1987), with the exception of CDR-H1 where the combined Chothia/Kabat definition is used (see Adair et al., 1991 Humanized antibodies. WO91/09967).

For antibody 10236, the human V-region IGKV1-6 plus JK4 J-region (IMGT, http://www.imgt.org/) was chosen as the acceptor for the light chain CDRs. The framework residues in the humanized grafts of 10236 light chain are all from the human germline gene, with the exception of one or more residues from the group comprising residues 2, 3 and 63, where the donor residues Tyrosine (Y2), Aspartic acid (D3) and Lysine (K63), with respect to SEQ ID NO: 15 were retained, respectively (FIG. 6). Retention of donor residues Y2 and D3 was essential for the highest affinity binding to human KLK-5.

Human V-region IGHV4-4 plus JH4 J-region (IMGT, http://www.imgt.org/) was chosen as the acceptor for the heavy chain CDRs of antibody 10236. In common with many rabbit antibodies, the VH gene of antibody 10236 is shorter than the selected human acceptor. When aligned with the human acceptor sequence, framework 1 of the VH region of antibody 10236 lacks the N-terminal residue, which is retained in the humanized antibody (FIG. 7). Framework 3 of the 10236 rabbit VH region also lacks two residues (75 and 76) in the loop between beta sheet strands D and E: in the humanized grafts the gap is filled with the corresponding residues (Lysine 75, K75; Asparagine 76, N76) from the selected human acceptor sequence (FIG. 7), or alternatively with Lysine and Threonine (Lysine 75, K75; Threonine 76, T76). The framework residues in the humanized grafts of 10236 heavy chain are all derived from the human germline gene sequence, with the exception of one or more residues from the group comprising residues 67, 71, 73 and 78, where the donor residues Phenylalanine (F67), Glutamine (Q71), Serine (S73) and Valine (V78), with respect to SEQ ID NO: 39, were retained, respectively. Retention of donor residues Q71, S73 and V78 was essential for the highest affinity binding to human KLK-5. The Glutamine residue at position 1 of the human framework was replaced with Glutamic acid (E1) to afford the expression and purification of a homogeneous product: the conversion of Glutamine to pyroGlutamate at the N-terminus of antibodies and antibody fragments is widely reported. The theoretical pI of the humanized 10236 antibodies is ~6.3 to 6.6. To facilitate the removal of impurities by ion-exchange chromatography during downstream processing, the pI was increased by mutation of residue 24 in CDRL1 of graft gL6 from a glutamine (Q) to either an Arginine (R) or a Lysine (K) residue.

The humanized grafts were tested with rabbit/human antibody 10236 to assess if their affinities had been affected by the humanization procedures. Rabbit/human antibody 10236 was cloned on a modified version of the human C Kappa vector comprising the S171C mutation, to re-create the additional disulphide bond found in rabbit VK light chains not present in the human constant regions leading to rabbit/human antibody 10236 according to SEQ ID NO: 96 and 97.

Affinity Measurement of Ab 10236 Humanized Drafts.

A goat anti-human IgG Fc specific antibody (Jackson ImmunoResearch) was immobilized on a CM5 Sensor Chip via amine coupling chemistry to a level of approximately 6000RU. Each analysis cycle consisted of capture of the anti-KLK5 IgG from supernatants to the anti Fc surface, injection of KLK5 analyte (prepared in house) for 180 s at 30 µl/min followed by 600 s dissociation. At the end of each cycle the surface was regenerated at a flowrate of 10 µL/min using a 60 s injection of 50 mM HCl followed by a 30 s injection of 5 mM NaOH and a final 60 s injection of 50 mM HCl. Human KLK5 was titrated from 20 nM to 0.08 nM (5×3-fold serial dilutions) for the supernatant in HBS-EP+ running buffer (GE Healthcare®) supplemented to a final concentration of 300 mM NaCl. Buffer blank injections were included to subtract instrument noise and drift. Kinetic parameters were determined using a 1:1 binding model using Biacore T200 Evaluation software (version 3.0). Experiments were carried out at 25° C.

Rabbit/human chimera antibodies were analyzed at the start and end of the assay and showed good precision. High quality data was generated for all samples as summarized in Table 5.

TABLE 5

| Antibody 10236 | Light chain Donor residues | Light chain Mutation | Heavy chain Donor residues | ka (1/Ms) | kd (1/s) | KD (pM) |
|---|---|---|---|---|---|---|
| Chimera Rabbit/human 10236 | — | | — | 2.69E+06 | 4.51E−04 | 167.9 |
| Chimera Rabbit/human 10236 | — | | — | 2.70E+06 | 44.09E−04 | 151.7 |
| Chimera Rabbit/mouse 10236* | | | | 3.00E+06 | 5.17E−04 | 172.3 |
| gL5 gH9 | Y2, D3, K63 | | Q71, S73, T76, V78 | 1.92E+06 | 9.29E−04 | 484.5 |
| gL5 gH10 | Y2, D3, K63 | | S73, T76, V78 | 1.97E+06 | 1.07E−03 | 545.6 |
| gL5 gH11 | Y2, D3, K63 | | Q71, T76, V78 | 1.69E+06 | 8.11E−04 | 480.6 |
| gL5 gH12 | Y2, D3, K63 | | Q71, S73, V78 | 2.03E+06 | 6.69E−04 | 330.6 |
| gL6 gH9 | Y2, D3 | | Q71, S73, T76, V78 | 1.91E+06 | 9.10E−04 | 475.2 |
| gL6 gH10 | Y2, D3 | | S73, T76, V78 | 1.93E+06 | 1.05E−03 | 541.5 |
| gL6 gH11 | Y2, D3 | | Q71, T76, V78 | 1.69E+06 | 8.02E−04 | 475.4 |
| gL6 gH12 | Y2, D3 | | Q71, S73, V78 | 2.04E+06 | 6.60E−04 | 323.9 |
| gL6 gH12$ | Y2, D3 | | Q71, S73, V78 | | | 299 |
| gL6 Q24R gH12 | Y2, D3 | Q24R | Q71, S73, V78 | 2.01E+06 | 6.69E−04 | 333.4 |

TABLE 5-continued

| Antibody 10236 | Light chain Donor residues | Light chain Mutation | Heavy chain Donor residues | ka (1/Ms) | kd (1/s) | KD (pM) |
|---|---|---|---|---|---|---|
| gL6 Q24K gH12 | Y2, D3 | Q24K | Q71, S73, V78 | 2.04E+06 | 6.87E−04 | 336.5 |

*as described in example 4 and Table 3;
$average of 2 runs (Table 15).

As shown in Table 5, graft 10236gL6gH12, with or without the Q24R/K mutations, retained high affinity for human KLK5.

Profiling of Humanized Antibodies

KLK5 Selectivity

A series of investigations were performed to ensure the humanization of rabbit antibody 10236 did not alter the KLK5 selectivity over other kallikreins, did not reduce affinity or inhibition activity. Purified antibodies were then screened to confirm their inhibitory activity against KLK5 according to the methods described in example 4. Antibodies were tested on a 10-point half log dilution series with a range of 600 nM to 20 μM. Using a Beckman Coulter FX™ and a Multidrop System, 5 μL of each antibody was transferred to black 384 well assay plates (Corning™, cat no. 3575) and 15 μL of the selected active recombinant kallikrein enzymes in assay buffer A (150 mM NaCl, 50 mM Tris, 200 μM EDTA, 0.05% (v/v) Tween-20, pH7.6 were added to appropriate wells to achieve the following final assay concentrations: 60 μM human KLK5(UCB), 250 μM KLK7 (UCB), 500 μM KLK2 (R&D Systems™), 30 μM KLK4 (UCB), 30 μM cyno KLK5 (UCB), 500 μM cyno KLK7, 30 μM mouse KLK5 (UCB) and 5 nM mouse KLK7 (UCB). Enzymes prepared at UCB are indicated in brackets and prepared as described above in Example 1. The source of commercially available enzymes is indicated in brackets.

20 μL assay buffer A alone was added to wells for 0% activity. LEKTI D5 rabbit Fc (UCB prepared, as described above) was used as a reference for inhibitory activity; 5 μl LEKTI D5 rabbit Fc at the same concentration range utilized for the 10236 antibody was added to 15 μl of the kallikrein enzymes. 15 μL of human KLK5 added to 5 μL assay buffer A was used as a 100% activity reference.

Antibodies and kallikreins were incubated at room temperature overnight. The following peptide substrates were added using a multidrop: Boc-VPR-AMC (Cambridge Research Biochemicals™) for human KLK5 (300 μM), human KLK2 (30 μM), murine KLK5 (300 μM) and cyno KLK5 (450 μM); KHLF-AMC (Cambridge Research Biochemicals™) for human and cyno KLK7 (90 μM and 150 μM, respectively), PFR-AMC (R&D Systems™) for human KLK4 (200 μM), and Mca-RPKPVE-Nval-WRK(Dnp)-NH2 (R&D Systems™) for murine KLK7 (150 μM). Samples were incubated for 4 hours and read on a Pherastar FSX Plate Reader (BMG Labtech™) at $\lambda_{ex}$380 nm and $\lambda_{em}$430 nm for Boc-VPR-AMC, PFR-AMC and KHLF-AMC; and at $\lambda_{ex}$320 nm and $\lambda_{em}$400 nm for Mca-RPKPVE-Nval-WRK(Dnp)-NH2. Data were analysed to determine percentage inhibition as described in example 3. Data were plotted against concentration of test antibody and a 4-parameter sigmoid fitted to determine IC50 (Genedata Screener™).

Figure 8:
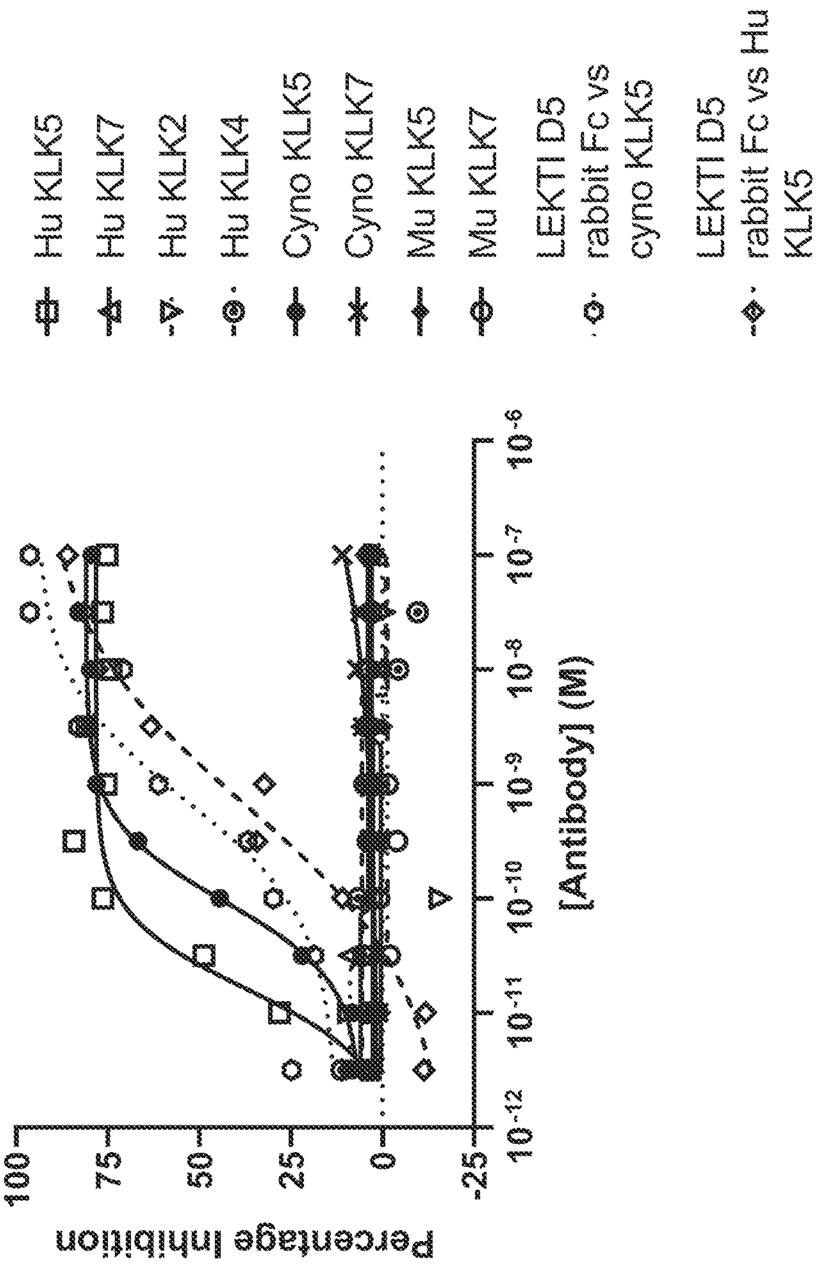
FIG. 8. Inhibitory activity of antibody 10236 gL6gH12 vs the kallikrein panel and of LEKTI D5 rabbit Fc vs human and cyno KLK5.

The humanised grafts of Ab 10236 retained specific inhibitory activity for KLK5 and showed little or no inhibition of the other KLK family members tested. Ab 10236 gL6gH12 is a potent inhibitor of human and cyno KLK5 (Table 6, each value being an individual measurement) retaining similar potency to the parental, non-humanized antibody. No activity (i.e. below the 40% threshold as per selection criteria in example 2) was evident against human KLK2, 4 and 7, cyno KLK7, mouse KLK5 or mouse KLK7 (FIG. 8).

TABLE 6

| | Hu KLK5 IC50 | Cyno KLK5 IC50 |
|---|---|---|
| Ab10236gL6gH12 | 7.65E−10 | 1.05E−10 |
| | 1.42E−10 | 4.77E−10 |
| | 6.63E−10 | 1.30E−10 |
| | 5.86E−10 | 8.24E−11 |
| LEKTI D5 Rabbit Fc | 1.03E−10 | n/a |
| | 7.44E−11 | |

n/a = not available

LEKTI Binding to KLK5 in the Presence of Humanized Antibody 10236

Surface plasmon resonance (SPR) experiments as described in Example 5 were carried out to determine the affinity of LEKTI for KLK5 complexed with humanized antibody 10236 gL6gH12 as was performed for the parental rabbit antibody 10236.

The experimental conditions described in example 5 were used with the exception that an anti-human Fc chip surface was prepared, and the results are reported in Table 6.

Similar to the parental rabbit 10236 antibody, LEKTI D5 Fab fusion protein was able to bind to KLK5 which is already in complex with antibody 10236 gL6gH12 but with a lower the affinity than human KLK5 alone (Table 7, 540 nM versus 40 pM).

TABLE 7

| | ka (Ms^−1) | kd (s^−1) | KD (M) |
|---|---|---|---|
| Human KLK5 only | 5.70E+05 | 2.30E−05 | 4.00E−11 |
| 10236 gL6gH12 + Human KLK5 | 2.90E+04 | 1.60E−03 | 5.40E−07 |

KLK5-PAR2 Cellular Assay

KLK5 has been shown to activate protease activated receptor-2 (PAR2) receptors at the surface of keratinocytes (K. Oikonomopoulou et al. Kallikrein-mediated cell signaling: targeting proteinase-activated receptors (PARs). Biol Chem, 387 (2006), pp. 817-824). This results in an NFkB-driven inflammatory cascade and the release of relevant cytokines such as TSLP.

As PAR2 is a Gq-coupled G-protein coupled receptor (GPCR), activation leads to phospholipase signaling and generation of inositol monophosphate (IP-1). Activation of endogenous PAR2 expressed on HaCat keratinocytes by exposure to KLK5, was monitored by detection of IP1 using an assay kit from Cisbio.

Confluent HaCat cells were harvested and plated in a 384 Fluoblock plate (Corning™) at 10,000 cells/well and cultured in DMEM Medium+10% FBS+2 mM L-glutamine+Pen/Strep (Life Technologies™) at 37° C., 5% $CO_2$ overnight, after which they were treated according to the IP-One Gq Assay protocol (Cisbio™). Antibodies (antibody 10236 gL6gH12 and negative human IgG4 A33) to be tested were serially diluted in 1× Stimulation Buffer B (IP-One Gq Assay kit, Cisbio™) from a top concentration of 2 μM and incubated for 1 h at 37° C. in the presence of 200 nM human KLK5. The antibody/KLK5 mix was added to HaCat cells and inositol 1 phosphate (IP1) was detected following the IP-One Gq assay protocol with fluorescence read at 665 nM and 620 nM on a Synergy Neo plate reader.

Figure 9:
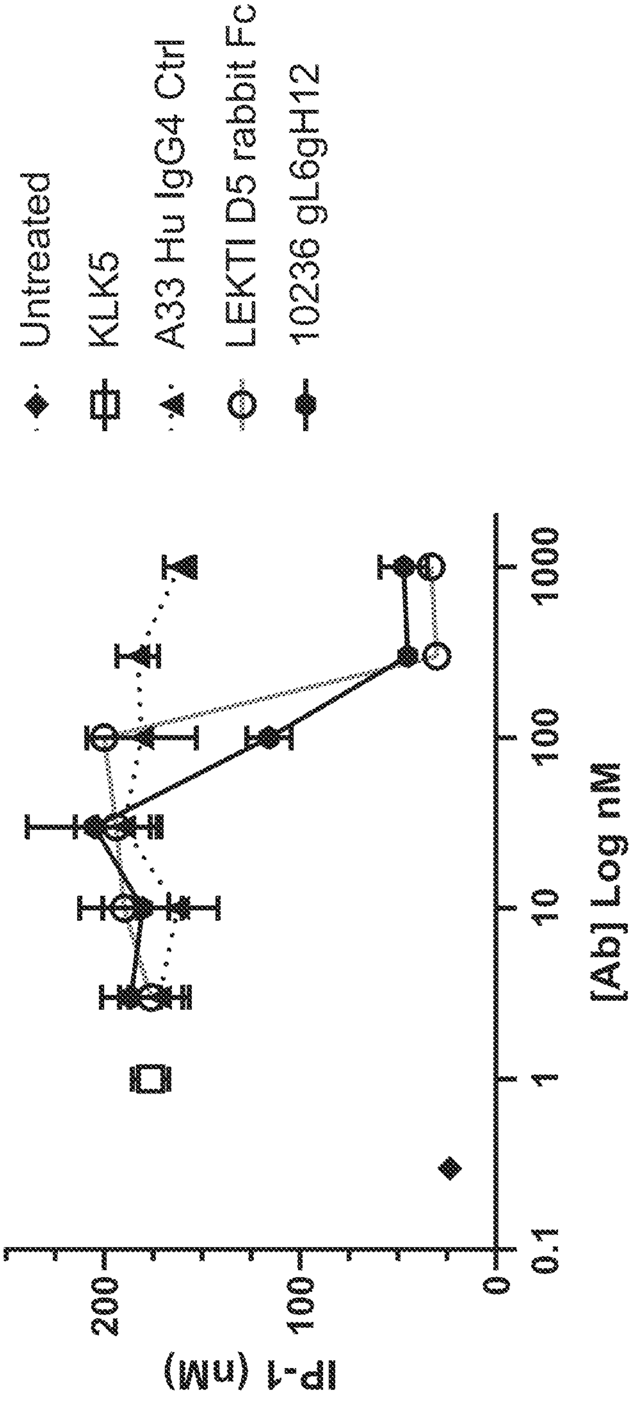
FIG. 9. Inhibition of IP-1 release from HaCat cells by Ab 10236 gL6gH12. IP-1 release was stimulated by addition of KLK5 to the HaCat cells. Antibody 10236 gL6gH12 achieved almost complete inhibition of IP-1, to a level comparable to the reference LEKTI D5 rabbit Fc protein. A33 Hu IgG4 is an isotype control.

Antibody 10236 gL6gH12 was able to almost completely inhibit IP1 release from KLK5 treated HaCat cells (FIG. 9), showing similar maximum inhibition of IP1 release to the LEKTI D5 rabbit Fc protein.

Antibody 10236 Mechanism of Action

Experiments were carried out to determine the mechanism of action of inhibitory antibodies. Non-competitive enzyme inhibitors reduce the activity of an enzyme but are able to bind the enzyme equally well in the presence or absence of substrate. Inhibitor and substrate are both able to bind the enzyme concurrently, but product cannot be formed, resulting in the enzyme-substrate-inhibitor complex only being able to resolve into either enzyme-substrate or enzyme-inhibitor complexes. With non-competitive inhibitors, the rate of inhibition will be unaffected by increasing substrate concentration.

Antibody 10236 gL6gH12 or LEKTI D5 rabbit Fc protein were prepared in assay buffer (150 mM NaCl, 50 mM Tris, 200 μM EDTA, 0.05% (v/v) Tween-20, pH 7.6) at either 300, 30 or 3 times the IC50 for human KLK5. 10 μL of antibody 10236 gL6gH12 were added to a Corning low binding black low flange 384 well assay plate (Corning®). 10 μL of a 5-point serial dilution of 30 mM-300 μM Boc-VPR-AMC (Cambridge Research Biochemicals™) was added to the plate. A Pherastar FSX plate reader (BMG Labtech™) was used to simultaneously start the reaction, via injection of 10 μL of either 1.8 nM human KLK5 (Boc-VPR-AMC <1 mM) or 180 μM KLK5 (Boc-VPR-AMC >1 mM) and monitor fluorescence (λex380 nm $\lambda_{em}$430 nm) every 30 seconds. The final reaction conditions contained antibody 10236 gL6gH12 or LEKTI D5 rabbit Fc protein at either 100, 10 or 1 times the IC50 for human KLK5 determined, a serial dilution of Boc-VPR-AMC between 10 mM and 100 μM and either 60 or 600 μM human KLK5. Antibody was replaced with assay buffer to set an uninhibited control and enzyme was replaced with buffer to set a background control.

Data were analysed by subtracting the background fluorescence at each time point and plotting the fluorescence against time. Data were fit to the following equation (GraphPad Prism®, GraphPad Software):

$$y = v_s \cdot x + \left(\frac{v_i - v_s}{k_{obs}} \cdot \left(1 - e^{-k_{obs} \cdot x}\right)\right)$$

This enabled $k_{obs}$ to be determined, the observed rate of time dependent inhibition, where $v_i$ is the initial reaction velocity and $v_s$ is the final velocity. Values for $k_{obs}$ were plotted against substrate concentration to determine the mechanism of inhibition.

The rate of inhibition of human KLK5 by antibody 10236 gL6gH12 (FIG. 10A) and the rabbit antibody 10236 (FIG. 10B) is unchanged with increasing substrate concentration, demonstrating that antibody 10236 gL6gH12 is a non-competitive inhibitor of human KLK5. In contrast, the LEKTI D5 rabbit Fc protein shows a decrease in the rate of inhibition with increasing substrate concentration demonstrating that it is a competitive inhibitor of human KLK5.

Example 10: In-Vitro Skin System Studies

A human in vitro full thickness skin system EpiDermFT (MatTek™ corporation; Morizane, Shin et al. "Kallikrein expression and cathelicidin processing are independently controlled in keratinocytes by calcium, vitamin D(3), and retinoic acid." The Journal of investigative dermatology vol. 130, 5 (2010): 1297-306. doi:10.1038/jid.2009.435) was used to demonstrate the functional effect of antibody 10236 gL6gH12 IgG4P on human KLK5.

MC903, a vitamin D3 analogue, was used to treat the in vitro skin system as it induces atopic dermatitis-like phenotype in vivo (Naidoo, Karmella et al. "Eosinophils Determine Dermal Thickening and Water Loss in an MC903 Model of Atopic Dermatitis." *The Journal of investigative dermatology* vol. 138, 12 (2018): 2606-2616. doi:10.1016/j.jid.2018.06.168).

EpiDermFT™ full thickness reconstituted skin tissue was equilibrated in EFT-400-ASY assay medium (MatTek Corporation™) at 37° C. 5% $CO_2$ overnight. On day 0, media was removed from wells and replaced with 2.5 ml EFT-400-ASY media. Tissues were treated topically with 25 μl of: medium alone; MC903 (Tocris Bioscience®) diluted in EFT-400-ASY media to give a final concentration of 2 nmol; MC903 diluted in media (2 nmol) plus either 10 μg/ml antibody 10236 gL6gH12 IgG4P or hIgG4P Isotype control (produced in-house). Plates were incubated at 37° C. 5% CO2. Basal medium was replaced every day and topical treatments were applied every day. The experiment was stopped on day 4.

Tissues were removed from transwells (Costar Snapwell™), bisected using a scalpel on a sterile petri dish, and placed in OCT tissue embedding matrix (Cellpath™) in preparation for histological analysis. Sections of 6 μm were cut and stained to assess architectural integrity using Haematoxylin and Eosin, detect KLK5 by immunofluorescence and assess protease activity via an in situ zymography assay.

For KLK5 immunofluorescence staining, sections were air dried for 10 minutes at room temperature, washed in 0.1% Tween 20 in PBS 3 times and once in PBS. Sections were then blocked in 5% BSA in PBS for 10 minutes. Sections were circled using a PAP pen and incubated with mouse anti-huKLK5 antibody (Abeam®) at 10 μg/ml for 1 hour at 37° C. in a humidified chamber. After antibody incubation sections were washed again and fixed in 4% PFA for 10 minutes. sections were then incubated with a secondary goat anti mouse IgG Alexa 546 (Life Technologies®) for 1 hour at 37° C. in a humidified chamber. Sections were washed and mounted using mounting media containing DAPI (Vector Labs™). Fluorescent images were acquired on a Zeiss Axio Scan at 20× magnification.

For in situ zymography, sections were air dried for 10 minutes at room temperature, washed in once in 2% tween in PBS and 3 times in PBS. Sections were then incubated with casein-BODIPY-FL fluorescent substrate (Invitrogen®) at 10 μg/ml for 3 hours at 37° C. in a humidified chamber. Sections were washed 3 times in PBS and mounted using mounting media containing DAPI (Vector Labs™). Fluorescent images were acquired immediately on a Zeiss Axio Scan at 20× magnification.

Figure 11:
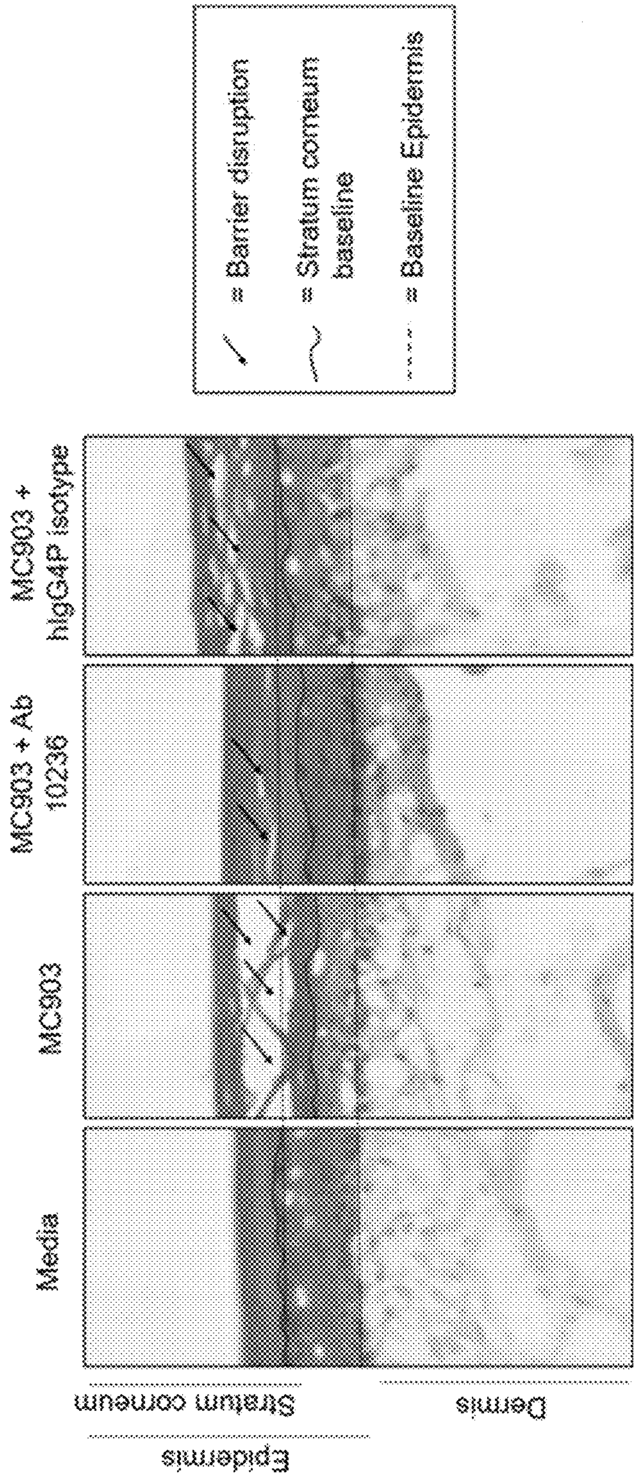
FIG. 11. Haematoxylin and eosin staining showing skin architecture and stratum corneum integrity in the reconstituted human skin epidermis model. Effect of media, MC903 with and without antibody 10236 gL6gH12 IgG4P (Ab 10236) or Isotype control (hIgG4P).

Comparison of tissue architecture after MC903 treatment with and without antibody 10236 gL6gH12 IgG4P demonstrates that KLK inhibition can prevent stratum corneum disruption in the human skin model (FIG. 11).

Moreover, although KLK5 expression was not altered serine protease activity was decreased in the skin systems treated with antibody 10236 gL6gH12 IgG4P (data not shown).

Example 11: In-Situ Zymography in Atopic Dermatitis Samples

Skin punch biopsies (National Bioservice Russia) from moderate to severe atopic dermatitis patients were tested to assess the inhibitory effect of anti KLK5 antibodies Biopsies (4 mm) were embedded in OCT tissue embedding matrix (Cellpath™) and stored at −80° C. Tissue sections were cut (6 μm) and used for in situ zymography analysis as previously described in example 9 using, instead of casein-BODIPY-FL, fluorescently quenched substrate [5-FAM]-FVNRSYPP-Lys(Dabcyl)-amide at 20 μm final assay concentration. Cleavage of the substrate in tissue sections results in fluorescence which is detected as fluorescent images on a Zeiss Axio Scan™ at 20× magnification.

Figure 12:
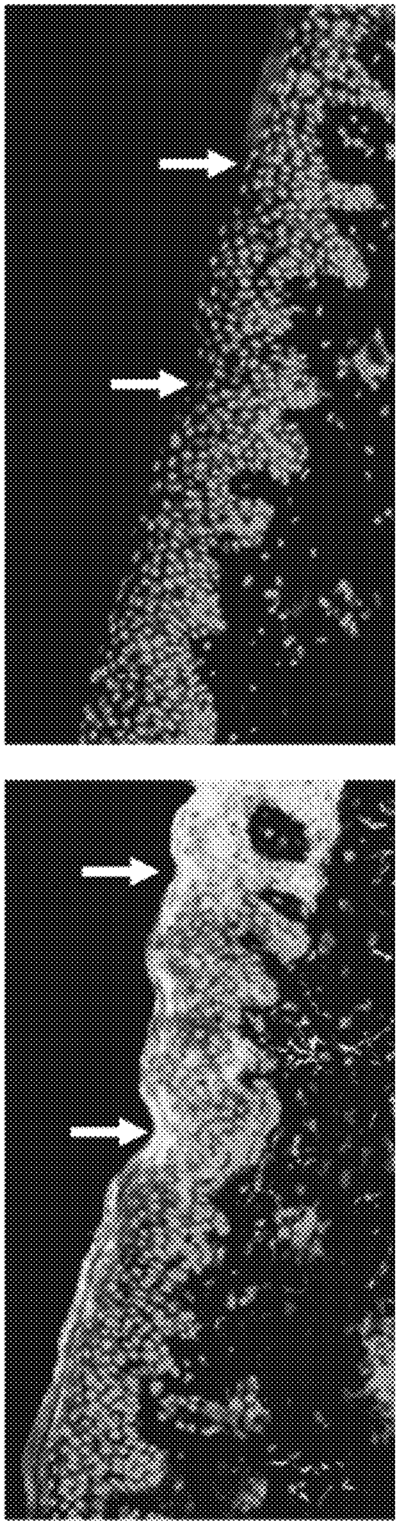
FIG. 12. In situ zymography assay showing serine protease activity in atopic dermatitis skin sections treated with control buffer (A) or antibody 10236 gL6gH12 IgGP4 (B).

Data show that pre-incubation of atopic dermatitis tissue sections with antibody 10236 gL6gH12 IgG4P can reduce serine protease activity levels compared to sections treated without an inhibitor (FIG. 12), as shown by the substantially reduced white staining in the stratum corneum (most upper layer of the epidermis) and in the stratum *granulosum* (immediately below the stratum corneum).

Example 12: Biophysical Characterization of Humanized Antibodies

The biophysical properties of 10236 gL6gH12, (as IgG4P and IgG1 isotypes) were determined to assess developability. This included thermal stability (™), experimental pl, apparent hydrophobicity, solubility (PEG precipitation assay) and assessment of self-interaction (aggregation propensity) by AC-SINS.

Additionally, antibody 10236 gL6N94D gH12 mutant was tested to assess the chemical stability, that is the deamidation propensity of the Asn(94)Ser motif (with reference to SEQ ID NO: 15) in the light chain CDR3 (Table 8).

TABLE 8

| | Descriptor |
|---|---|
| IgG4P | 10236 gL6gH12 |
| | 10236 gL6-N94DgH12 |
| IgG1 | 10236 gL6gH12 |

Characterization by Mass Spectrometry

Identity of antibodies 10236 IgG1 and IgG4P was confirmed by intact mass measurement of the heavy and light chains by LC-MS using a Waters ACQUITY UPLC System with a Xevo® G2 Q-ToF mass spectrometer. Samples (~5 pg) were reduced with 5 mM tris(2-carboxyethyl) phosphine (TCEP) in 150 mM ammonium acetate at 37° C. for 40 minutes. The LC column was a Waters BioResolve™ RP mAb Polyphenyl, 450 A, 2.7 μm held at 80° C., equilibrated with 95% solvent A (water/0.02% trifluoroacetic acid (TFA)/0.08% formic acid) and 5% Solvent B (95% acetonitrile/5% water/0.02% TFA/0.08% formic acid) at a flow rate of 0.6 mL/minute. Proteins were eluted with a gradient from 5% to 50% solvent B over 8.8 minutes followed by a 95% solvent B wash and re-equilibration. UV data were acquired at 280 nm. MS conditions were as follows: Ion mode: ESI positive ion, resolution mode, mass range: 400-5000 m/z and external calibration with NaI. Data were analysed using Waters MassLynx™ and MaxEnt Software.

No difference was observed between expected and observed molecular mass as judged by intact mass spectrometry (Table 9).

TABLE 9

| Antibody description | | Light Chain (Da) | | | Heavy Chain (Da) | | |
|---|---|---|---|---|---|---|---|
| | | Expected | Observed | Delta | Expected | Observed | Delta |
| hIgG4P | 10236gL6gH12 | 23476.1 | 23475.4 | −0.7 | 49792.7 | 49793.6 | 0.9 |
| hIgG1 | 10236gL6gH12 | 23474.6 | 23476.1 | −1.5 | 49947.2 | 49948 | −0.8 |

Thermal Stability (™) Measurements

The melting temperature (Tm) or temperature at the midpoint of unfolding was determined using the Thermal Shift Assay.

For this assay, the fluorescent dye SYPRO® orange was used to monitor the protein unfolding process by binding to hydrophobic regions that become exposed as the temperature increases. The reaction mix contained 5 μL of 30×SYPRO® Orange Protein Gel Stain (Thermofisher scientific, S6651), diluted from 5000× concentrate with test buffer. 45 μL of sample at 0.2 mg/mL, in PBS pH 7.4, or 50 mM sodium acetate 125 mM sodium chloride pH 5.0, was added to the dye and mixed (being common pre-formulation buffers) 10 μL of this solution was dispensed in quadruplicate into a 384 PCR optical well plate and was run on a QuantStudio 7 Real-Time PCR System (Thermofisher™). The PCR system heating device was set at 20° C. and increased to 99° C. at a rate of 1.1° C./min. A charge-coupled device monitored fluorescence changes in the wells. Fluorescence intensity increases were plotted, the inflection point of the slope(s) was used to generate apparent midpoint temperatures (™). The data is shown in Table 10.

Two unfolding transitions were observed for 10236gL6gH12 (IgG4P). The first can be attributed to the CH2 domain and the second can be attributed to an average of the Tm of the Fab unfolding domain and CH3 domain. For the IgG1 molecule, one unfolding domain was observed attributed to an average of the Tm of the CH2 and Fab domains. This is in accordance with the literature (Garber E. Demerest S J. Biochem Biophys Res Commun. 2007 April; 355(3):751-7).

TABLE 10

| | PBS pH 7.4 | | | | |
|---|---|---|---|---|---|
| Antibody description | Fab domain Tm (° C.) | SD | CH2 domain Tm (° C.) | SD | CH3 domain Tm (° C.) |
| hIgG4P 10236 gL6gH12 | 74 | 0.0 | 66.3 | 0.1 | not measured |
| hIgG1 10236 gL6gH12 | 71.5 | 0.9 | overlaid with Fab domain | | not measured |

Experimental Isoelectric Point (PI) Measurement

An iCE3™ whole-capillary imaged capillary isoelectric focusing (cIEF) system (ProteinSimple) was used to experimentally determine pl. Samples were prepared by mixing the following: 30 μL sample (from a 1 mg/mL stock in HPLC grade water), 35 μL of 1% methylcellulose solution (ProteinSimple, 101876), 4 μL pH 3-10 pharmalytes (ProteinSimple, 042-848), 0.5 μL of 4.65, 0.5 μl 9.77 synthetic pI markers (ProteinSimple, 102223 and 102219), and 12.5 μL of 8 M urea solution (Sigma Aldrich®). HPLC grade water was used to make up the final volume to 100 μl. Samples were focused for 1 min at 1.5 kV, followed by 5 min at 3 kV, 280 nm images of the capillary were taken using the Protein Simple software. The resulting electropherograms were analysed using iCE3 software and pI values were assigned (linear relationship between the pl markers). The data is summarized in Table 11.

The pI of 10236gL6gH12 (hIgG4P) was found to be lower than the corresponding IgG1 molecule. It would be envisaged that there would be no developability/manufacturing issues for either molecules and the pI is above that of buffers generally used for formulation (~pH 5).

TABLE 11

| Antibody description | | pl |
|---|---|---|
| IgG4P | 10236 gL6gH12 | 6.7 |
| IgG1 | 10236 gL6gH12 | 7.5 |

Hydrophobic Interaction Chromatography (HIC)

Hydrophobic Interaction chromatography (HIC) separates molecules in order of increasing hydrophobicity. Molecules bind to the hydrophobic stationary phase in the presence of high concentrations of polar salts and desorb into the mobile phase as the concentration of salt decreases. A longer retention time equates to a greater hydrophobicity.

The two isotypes (IgG4P and IgG1) of 10236 gL6gH12 at 2 mg/mL were diluted 1:2 with 1.6 M ammonium sulphate and PBS (pH 7.4).10 pg (10 μL) of sample was injected onto a Dionex ProPac™ HIC-10 column (100 mm×4.6 mm) connected in series to an Agilent 1200 binary HPLC with a fluorescence detector. The separation was monitored by intrinsic fluorescence (excitation and emission wavelengths, 280 nm and 340 nm respectively). Using Buffer A (0.8 M ammonium sulphate 100 mM Phosphate pH7.4) and Buffer B (100 mM Phosphate pH7.4) the sample was analysed using gradient elution as follows, (i) 2 minute hold at 0% B, (ii) linear gradient from 0 to 100% B in 30 minutes (0.8 mL/minute) (iii) the column was washed with 100% B for 2 minutes and re-equilibrated in 0% B for 10 minutes prior to next sample injection. The column temperature was maintained at 20° C. The retention time (in minutes) is shown in Table 12.

TABLE 12

| Antibody description | | Main Peak retention time (min) |
|---|---|---|
| IgG4P | 10236gL6gH12 | 12.8 |
| IgG1 | 10236 gL6gH12 | 11.0 |

There was a small difference in retention time between the two molecules, where 10236 gL6gH12 (IgG4P) showed a slightly greater apparent hydrophobicity than the corresponding IgG1 format. Both molecules would be expected to have an average propensity to aggregate based on results of other commercial antibodies. (Jain et al "Biophysical properties of the clinical-stage antibody landscape" Proc Natl Acad Sci USA. 2017 Jan. 31; 114(5):944-949. doi: 10.1073/pnas.1616408114. Epub 2017 Jan. 17).

Solubility Measurement Using Polyethylene Glycol (PEG) Measurement

An understanding of colloidal stability (solubility) can be derived from examining the effect of polyethylene glycol (PEG) precipitation. PEG was used to reduce protein solubility in a quantitatively definable manner, by increasing the concentrations of PEG (w/v) and measuring the amount of protein remaining in solution. This assay serves to mimic the effect of high concentration solubility without using conventional concentration methods.

Stock 40% PEG 3350 (Merck, 202444) solutions (w/v) were prepared in PBS pH 7.4; 50 mM sodium acetate 125 mM sodium chloride pH 5.0 (common pre-formulation storage buffers) and 50 mM histidine, 250 mM proline pH 5.5 (common formulation buffer). A serial titration was performed by an Assist Plus liquid handling robot (INTEGRA, 4505), resulting in a range of 40% to 15.4% PEG 3350. To minimize non-equilibrium precipitation, sample preparation consisted of mixing protein and PEG solutions at a 1:1 volume ratio. 35 μL of the PEG 3350 stock solutions was added to a 96 well v bottom PCR plate (A1 to H1) by a liquid handling robot. 35 μL of a 2 mg/mL sample solution was added to the PEG stock solutions resulting in a 1 mg/mL test concentration. This solution was mixed by automated slow repeat pipetting and incubated at 37° C. for 0.5 h to re-dissolve any non-equilibrium aggregates. Samples were then incubated at 20° C. for 24 h. The sample plate was subsequently centrifuged at 4000×g for 1 h at 20° C. 50 μL of supernatant was dispensed into a UV-Star®, half area, 96 well, μClear®, microplate (Greiner, 675801). Protein concentrations were determined by UV spectrophotometry at 280 nm using a FLUOstar® Omega multi-detection microplate reader (BMG LABTECH). The resulting values were plotted using Graphpad prism ver 7.04, PEG midpoint (PEGmdpnt) score was derived from the midpoint of the sigmoidal dose-response (variable slope) fit.

The data is shown in Table 13 The higher the PEG midpoint (%); the greater probability for high concentration stability/solubility.

Differences were observed between the two isotypes depending on the buffer conditions. In PBS pH 7.4, 10236gL6gH12 (IgG4P) showed greater solubility than 10236gL6gH12 (IgG1); whereas in 50 mM sodium acetate, 125 mM sodium chloride pH 5, the reverse was observed. The solubility of 10236gL6gH12 (IgG4P) could be improved by using a more typical formulation buffer, that is 50 mM Histidine, 250 mM proline pH 5.5.

TABLE 13

| Antibody description | | PEG mid-point (%) PBS pH 7.4 | 50 mM sodium acetate, 125 mM sodium chloride pH 5 | 50 mM Histidine, 250 mM Proline pH 5.5 |
|---|---|---|---|---|
| IgG4P | 10236gL6gH12 | 10.5 | 10.4 | 11.5 |
| IgG1 | 10236gL6gH12 | 9.9 | 11.3 | not done |

Assessment of Self-Interaction Using AC-SINS (Affinity Capture Self-Interaction Nanoparticle Spectroscopy).

The AC-SINS assay (Liu Y. MAbs. 2014 March-April; 6(2):483-92) was used to assess developability of 10236gL6gH12 by determining self-interaction propensity and hence informing on potential aggregation stability. This was performed in PBS pH 7.4.

Goat anti human-Fcγ specific capture antibody (Jackson ImmunoResearch) was buffer exchanged into 20 mM sodium acetate, pH4.3, diluted to 0.4 mg/mL and 50 μL added to 450 μL citrate-stabilized 20 nm gold nanoparticles (TedPella, USA) and left overnight at room temp. The conjugated nanoparticles were blocked with 55 μL PEG-thiol for 1 hour, centrifuged at 21,000×g for 6 min, the supernatant removed and resuspended in 20 mM sodium acetate, pH4.3 to a final volume of 150 μL.

10236gL6gH12 (IgG4P and IgG1) were diluted to 22 pg/mL in PBS, pH7.4 (200 μL) and added to an equal volume non-specific whole IgG (Jackson ImmunoResearch), vortexed briefly and 72 μL added to a 96-well plate. 8 μL of nanoparticles were added to each well (n=4). Absorbance were read on a BMG plate reader from 500-600 nm, fitted to Lorenzian curves (RShiny) and PBS-only subtracted from the samples to give Δλmax. The data is summarized on Table 14.

Both 10236gL6gH12 as IgG4P and IgG1 isotypes showed a low λmax and Δλmax (from PBS background) suggesting a low propensity of self-interaction and low risk of aggregation in PBS pH 7.4.

TABLE 14

| Antibody description | | λmax | Δλmax |
|---|---|---|---|
| IgG4P | 10236 gL6gH12 | 531.37 | 1.88 |
| IgG1 | 10236 gL6gH12 | 530.27 | 1.17 |

Accelerated Stress Study for Assessment of Deamidation Propensity at Asn (94) (Light Chain CDR3)

A deamidation motif Asn(94)Ser is present on the light chain CDR3 of 10236gL6gH12. The propensity/rate of deamidation cannot be predicted as it is dependent on primary sequence and 3D structure as well as solution properties (R. C. Stephenson and S. Clarke (1989); K. Diepold et al (2012); Jasmin F. Sydow et al (2014); N. E Robinson et al (2004). Hence, an accelerated stress study was set up to determine the deamidation propensity of 10236 gL6gH12 at Asn(94). This was performed on 10236gL6gH12 (IgG4P) only; the rate of deamidation was assumed to be the same for IgG1 since the deamidation motif is present in the variable region.

The basal deamidation level (non-stressed sample) was also measured; low levels indicate low susceptibility to deamidation, but these can vary due to different manufacturing batches/conditions.

Antibody 10236 gL6gH12 (IgG4P) was buffer exchanged into conditions (i) known to favor deamidation of Asn(N) residues (Tris pH 8.0/125 mM NaCl at 37° C.) and (ii) a control buffer (acetate, pH 5.0/125 mM NaCl at 37° C.). The final concentration of sample in each of the buffers was 5.9 mg/mL at pH 8.0 and 6.6 mg/mL at pH 5.0 and then split into two aliquots where one was stored at 4° C. and one at 37° C. for up to 2 weeks. An aliquot was removed immediately (TO) and at 2 weeks and stored at −20° C.

The basal deamidation was obtained by analyzing the stock sample, that had been stored in PBS pH 7.4 at −20° C.

All samples were thawed and analyzed by peptide mapping with mass spectrometry (MS) using the following method:

Samples of stressed proteins were reduced with TCEP and alkylated with chloroacetic acid in Tris-HCL buffer pH 8.0 containing 0.1% w/v Rapigest™ detergent. Trypsin/LysC mix was added (1:50 w/w) and samples were digested for 1 hour at 37° C. then chymotrypsin (1:50 w/w) as added and the digestion continued overnight at room temperature. Proteolysis was stopped by adding formic acid to 1% v/v and samples were diluted to 0.5 mg/ml before centrifuging to remove precipitated Rapigest™. The resulting peptide pools were separated and analysed on a Waters BEH C18 column interfaced to a Thermo Fusion mass spectrometer running a positive-ion, data-dependent orbitrap-orbitrap method with CID fragmentation. LC-MS data was analysed using Thermo Xcalibur™ and Pepfinder™ software.

Figure 13:
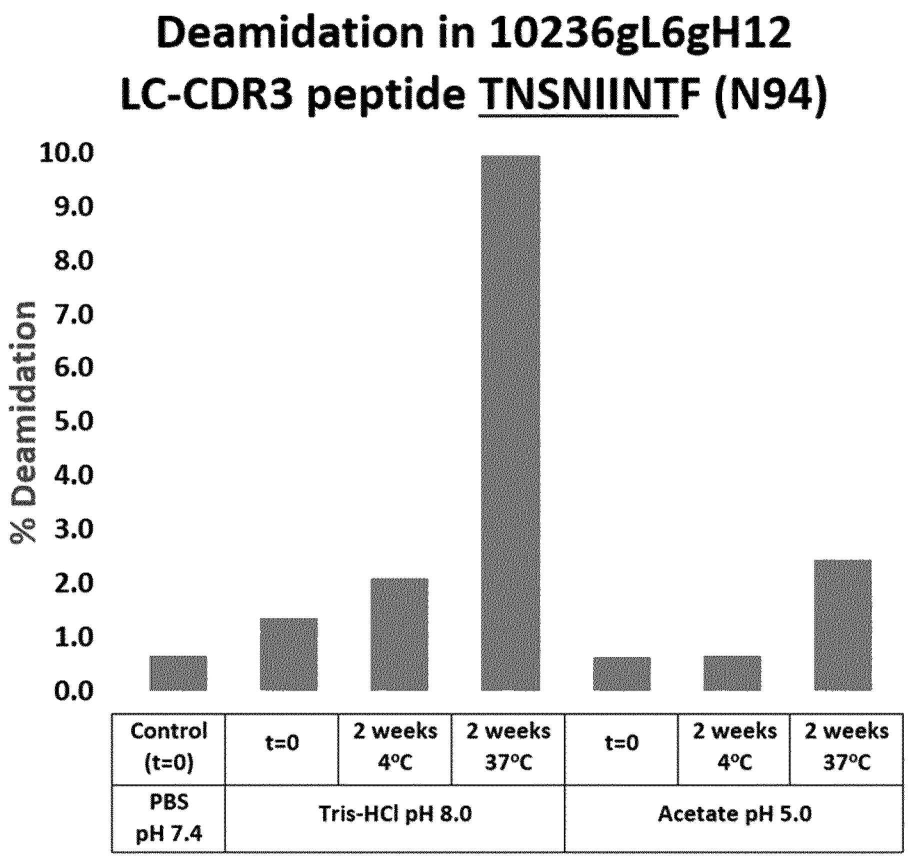
FIG. 13. Stress study of antibody 10236 gL6gH12 IgG4P (named 10236gL6gH12) to assess deamidation propensity at the Asn(94)Ser motif on light chain CDR3.

The basal level of deamidation in KLK5 10236 L-CDR3 was 0.7% at Asn94 (calculated using Pepfinder™). This increased to a maximum of 10% for the sample incubated at 37° C. in Tris pH8.0 for 2 weeks (FIG. 13).

The propensity of deamidation was low and could be controlled by minimizing the use of high pH buffers during manufacture, storage and formulation.

Affinity Measurement of a Fully Deamidated Product: 10236 gL6-N94DgH12 (NS to DS Mutation on Light Chain CDR3)

The light chain of 10236gL6gH12 was mutated to replace Asn 94 with Asp (Asn94Asp), to generate a surrogate molecule for a fully deamidated product of 10236gL6gH12.

The kinetics of binding of both antibodies 10236gL6gH12 and 10236gL6-N94DgH12 to human KLK5 were assessed by surface plasmon resonance (Biacore T200, GE Life Sciences™) at 25° C. to assess the impact of 100% deamidation.

A goat anti-human IgG Fc specific antibody (Jackson ImmunoResearch) was immobilized on a CM5 Sensor Chip via amine coupling chemistry to a level of approximately 6000RU. Each analysis cycle consisted of capture of the anti-KLK5 IgG molecules to the anti Fc surface, injection of KLK5 analyte (prepared in house) for 300 s at 30 μl/min followed by 600 s dissociation. At the end of each cycle the surface was regenerated at a flowrate of 10 μL/min using a 60 s injection of 50 mM HCl followed by a 30 s injection of 5 mM NaOH and a final 60 s injection of 50 mM HCl. Human KLK5 was titrated from 20 nM to 0.03 nM (6×3-fold serial dilutions) in HBS-EP+ running buffer (GE Healthcare) supplemented to a final concentration of 300 mM NaCl. Buffer blank injections were included to subtract instrument noise and drift. Kinetic parameters were determined using a 1:1 binding model using Biacore T200 Evaluation software (version 3.0). The data is summarized on Table 15.

Two replicates of 10236gL6gH12 were included to demonstrate experimental reproducibility. The Asn94Asp mutation in the light chain CDR3 decreased the affinity to KLK5 by 4.5-fold.

Extensive deamidation could therefore impact on the efficacy of 10236gL6gH12 if the manufacturing, storage and formulation conditions are not monitored and controlled. The accelerated stress experiment indicated a low propensity for deamidation at the Asn94 residue and hence de-risked the molecule.

TABLE 15

| Antibody description | ka (1/Ms) | kd (1/s) | KD (pM) |
|---|---|---|---|
| 10236gL6gH12 run 1$ | 2.26E+06 | 7.11E−04 | 314.3 |
| 10236gL6gH12 run 2$ | 2.33E+06 | 6.58E−04 | 283.0 |
| 10236gL6N94DgH12 | 3.89E+06 | 4.86E−03 | 1249.2 |

$average of run 1 and run 2 = 299 pM

Viscosity Assessment at Different Concentrations for Antibody 10236 gL6gH12 (hIgG4P)

Low viscosity at high antibody concentration is important for sub cutaneous administration of therapeutic molecules. The viscosity at increasing concentrations of antibody 10236 gL6gH12 in a common pre-formulation buffer, 50 mM Histidine/250 mM Proline pH 5.5 was measured to investigate its viscosity behavior.

The study was performed by (i) initial concentration of the samples and (ii) viscosity measurement as detailed below.

(i) Concentration

A total of 23 mL of antibody 10236 gL6gH12 (hIgG4P) was spin concentrated using a Vivaspin® 20 MWCO 30 kD) centrifugal filter (Z14637, Sigma-Aldrich) at 4000×g at 20° C. to concentrate the antibody until the retentate volume was approximately 950 μL. The retentate solution was recovered and the final concentration of antibody 10236 gL6gH12 (hIgG4P) was determined using UV absorbance measurement at 280 nm and an extinction coefficient of 1.46 mL/(mg cm) using a NanoDrop™ 1000 instrument. The concentrated sample was determined to be 185 mg/mL (mean of triplicates), giving 84% recovery of the theoretical concentration. Losses were within the expected range for this method.

The antibody sample was then diluted using 50 mM histidine, 250 mM proline pH 5.5 to give a range of concentrations suitable for viscosity measurement. The diluted sample concentrations were confirmed by UV absorbance measurements at 280 nm to be 159.8 mg/mL, 63.6 mg/mL and 33.2 mg/mL.

(ii) Viscosity Measurement

The viscosity at each concentration was measured using Discovery Hybrid Rheometer-1 (DHR-1, TA Instruments) with Peltier plate and liquid cooling system for temperature control, and 20 mm stainless steel parallel plate geometry for measurement. The sample (80 μL) at the different concentrations (33.2 mg/mL, 63.6 mg/mL, and 159.8 mg/mL), was placed on the centre of the Peltier plate, and the viscosity (in mPa·s, or cP) was measured with steady state flow sweep procedure setting at 20° C. with varying shear rates, from 2.87918 to 287.918 $s^{-1}$. The measured viscosity was averaged when the values at each shear rate points were constant (SD±5%). The viscosity of 10236 gL6gH12 (IgG4P) at different concentrations is summarized in Table 16.

An increasing trend was observed for antibody 10236 gL6gH12 (hIgG4P) between the concentration and the viscosity coefficient. The viscosity increased from 2.8 to 6.4 cP in the range of concentration from 33.2 mg/mL to 159.8 mg/ml. All these samples showed a constant viscosity coefficient (variability less than 5%) at different shear rates. The study showed that antibody 10236 gL6gH12 (hIgG4P) exhibited low viscosity at a high concentration (~150 mg/mL) in 50 mM Histidine/250 mM Proline pH 5.5 and therefore could be envisaged to be suitable for subcutaneous administration.

TABLE 16

| Concentration (mg/mL) | Average viscosity (cP) | SD (cP) | % RSD |
|---|---|---|---|
| 33.2 | 2.8 | 0.08 | 2.99 |
| 63.6 | 3.6 | 0.08 | 2.29 |
| 159.8 | 6.4 | 0.16 | 2.54 |

The invention claimed is:

1. An antibody which binds to kallikrein 5 (KLK5), wherein the antibody comprises a variable light chain and a variable heavy chain, and wherein:

a. the variable light chain comprises a CDR-L1 comprising SEQ ID NO: 1 or SEQ ID NO: 62 or SEQ ID NO: 63, a CDR-L2 comprising SEQ ID NO: 2 and a CDR-L3 comprising SEQ ID NO: 3; and b. the variable heavy chain comprises a CDR-H1 comprising SEQ ID NO: 4, a CDR-H2 comprising SEQ ID NO: 5 and a CDR-H3 comprising SEQ ID NO: 6.

2. The antibody according to claim 1 wherein:

a. the variable light chain comprises a CDR-L1 comprising SEQ ID NO: 1, a CDR-L2 comprising SEQ ID NO: 2 and a CDR-L3 comprising SEQ ID NO: 3; and b. the variable heavy chain comprises a CDR-H1 comprising SEQ ID NO: 4, a CDR-H2 comprising SEQ ID NO: 5 and a CDR-H3 comprising SEQ ID NO: 6.

3. The antibody according to claim 1, wherein the antibody inhibits or reduces the protease activity of KLK5.

4. The antibody according to claim 1, wherein the antibody binds to KLK5 when KLK5 is bound to LEKTI, or a fragment of LEKTI.

5. The antibody according to claim 1, wherein the antibody does not compete with LEKTI, or a fragment of LEKTI, for binding KLK5.

6. The antibody according to claim 1, wherein the antibody forms a complex with KLK5 bound to LEKTI, or a fragment of LEKTI.

7. The antibody according to claim 6 wherein the fragment of LEKTI is human LEKTI domain 5 comprising amino acids 1 to 64 of SEQ ID NO: 54 or LEKTI domain 8 comprising amino acids 1 to 71 of SEQ ID NO: 61.

8. The antibody according to claim 1 wherein the antibody binds human KLK5 and cynomolgus monkey (cyno) KLK5.

9. The antibody according to claim 1 wherein the antibody does not bind human or cyno kallikrein 2 (KLK2); or human or cyno kallikrein 4 (KLK4); or human or cyno kallikrein 7 (KLK7).

10. The antibody according to claim 1 wherein the antibody is a chimeric or humanized antibody.

11. The antibody according to claim 1, wherein the antibody is a full-length antibody.

12. The antibody according to claim 1, wherein the antibody is selected from a Fab, a Fab', a $F(ab')_2$ or a scFv.

13. The antibody according to claim 1, wherein the antibody comprises:

a. a variable light chain comprising SEQ ID NO: 7 or 11 or 15 or 19 or 23; and/or b. a variable heavy chain comprising SEQ ID NO: 9 or 27 or 31 or 35 or 39 or 43; and/or c. a light chain comprising SEQ ID NO: 13 or 17 or 21 or 25; and d. a heavy chain comprising SEQ ID NO: 29 or 33 or 37 or 41 or 45.

14. The antibody according to claim 1, wherein amino acid residue glutamine (Gln; Q) in L-CDR1 at position 24 with reference to SEQ ID NO: 15 or 17 is replaced by arginine (Arg; R) or by lysine (Lys; K).

15. The antibody according to claim 1 wherein KLK5 is human KLK5 comprising SEQ ID NO: 51 or 52 or 53 or cyno KLK5 comprising SEQ ID NO: 60.

16. An isolated polynucleotide encoding the antibody according to claim 1.

17. A cloning or expression vector comprising one or more polynucleotides according to claim 16.

18. A host cell comprising:

a. one or more polynucleotides according to claim 16 or b. one or more cloning or expression vectors comprising the one or more polynucleotides.

19. A process for the production of an antibody according to claim 1, comprising culturing a host cell comprising one or more polynucleotides encoding the antibody or an expression vector comprising the one or more polynucleotides under suitable conditions for producing the antibody and isolating the antibody produced by the host cell.

20. A pharmaceutical composition comprising the antibody according to claim 1 and one or more pharmaceutically acceptable carriers, excipients or diluents.

21. A method of treating diseases characterized by dysregulation of KLK5 or by dysregulation of inhibition of KLK5 in a patient comprising administering to said patient a therapeutically effective amount of an antibody according to claim 1 or a pharmaceutical composition comprising the antibody and one or more pharmaceutically acceptable carriers, excipients or diluents, wherein the disease is selected from Netherton's Syndrome, Atopic Dermatitis, Ichthyoses, Rosacea, Asthma or Cancer.

22. The method according to claim 21 wherein the disease is Netherton's Syndrome.

23. The method according to claim 21 wherein the disease is Atopic Dermatitis.

24. The antibody according to claim 11, wherein the full-length antibody is selected from an IgG1, IgG4 or IgG4P.

* * * * *

SEQUENCE LISTING

```
<160> NUMBER OF SEQ ID NOS: 104

<210> SEQ ID NO 1
<211> LENGTH: 11
<212> TYPE: PRT
<213> ORGANISM: Artificial Sequence
<220> FEATURE:
<223> OTHER INFORMATION: CDR-L1

<400> SEQUENCE: 1

Gln Ala Ser Gln Ser Ile Ser Ser Trp Leu Ala
1               5                   10


<210> SEQ ID NO 2
<211> LENGTH: 7
<212> TYPE: PRT
<213> ORGANISM: Artificial Sequence
<220> FEATURE:
<223> OTHER INFORMATION: CDR-L2

<400> SEQUENCE: 2
```

Leu Ala Ser Thr Leu Ala Ser
1               5

<210> SEQ ID NO 3
<211> LENGTH: 12
<212> TYPE: PRT
<213> ORGANISM: Artificial Sequence
<220> FEATURE:
<223> OTHER INFORMATION: CDR-L3

<400> SEQUENCE: 3

Gln Gln Gly Tyr Thr Asn Ser Asn Ile Ile Asn Thr
1               5                   10

<210> SEQ ID NO 4
<211> LENGTH: 10
<212> TYPE: PRT
<213> ORGANISM: Artificial Sequence
<220> FEATURE:
<223> OTHER INFORMATION: CDR-H1

<400> SEQUENCE: 4

Gly Phe Pro Leu Ser Asn Tyr Ala Met Ser
1               5                   10

<210> SEQ ID NO 5
<211> LENGTH: 16
<212> TYPE: PRT
<213> ORGANISM: Artificial Sequence
<220> FEATURE:
<223> OTHER INFORMATION: CDR-H2

<400> SEQUENCE: 5

Asp Ile Tyr Pro Ser Asp Ile Ile Asp Tyr Ala Ser Trp Ala Lys Gly
1               5                   10                  15

<210> SEQ ID NO 6
<211> LENGTH: 9
<212> TYPE: PRT
<213> ORGANISM: Artificial Sequence
<220> FEATURE:
<223> OTHER INFORMATION: CDR-H3

<400> SEQUENCE: 6

Asp Asn Asn Asp Tyr Gly Leu Asp Ile
1               5

<210> SEQ ID NO 7
<211> LENGTH: 110
<212> TYPE: PRT
<213> ORGANISM: Artificial Sequence
<220> FEATURE:
<223> OTHER INFORMATION: Rabbit VL

<400> SEQUENCE: 7

Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys

```
65                  70                  75                  80

Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys
            100                 105                 110


<210> SEQ ID NO 8
<211> LENGTH: 336
<212> TYPE: DNA
<213> ORGANISM: Artificial Sequence
<220> FEATURE:
<223> OTHER INFORMATION: Rabbit VL nucl.

<400> SEQUENCE: 8

gcctatgata tgacccagac tccagcctct gtggaggtag ctgtgggagg cacagtcacc      60

atcaagtgcc aggccagtca gagcattagc agttggttag cctggtatca gcagaaacca     120

ggtcagcctc ccaagctcct gatctatctg gcatccactc tggcatctgg ggtctcatcg     180

cggttcaaag gcagtggatc tgggacacag ttcactctca ccatcagcgg cgtggagtgt     240

gccgatgctg ccacttacta ctgtcaacag ggttatacta atagtaatat tattaatact     300

ttcggcggag ggaccgaggt ggtggtcaaa cgtacg                               336


<210> SEQ ID NO 9
<211> LENGTH: 114
<212> TYPE: PRT
<213> ORGANISM: Artificial Sequence
<220> FEATURE:
<223> OTHER INFORMATION: Rabbit VH

<400> SEQUENCE: 9

Gln Ser Val Glu Glu Ser Gly Gly Arg Leu Val Thr Pro Gly Thr Pro
1               5                   10                  15

Leu Thr Leu Thr Cys Thr Val Ser Gly Phe Pro Leu Ser Asn Tyr Ala
            20                  25                  30

Met Ser Trp Val Arg Gln Ala Pro Gly Lys Gly Leu Glu Trp Ile Gly
        35                  40                  45

Asp Ile Tyr Pro Ser Asp Ile Ile Asp Tyr Ala Ser Trp Ala Lys Gly
    50                  55                  60

Arg Phe Thr Ile Ser Gln Thr Ser Thr Thr Val Glu Leu Lys Ile Thr
65                  70                  75                  80

Gly Pro Thr Thr Glu Asp Thr Ala Thr Tyr Phe Cys Ala Arg Asp Asn
                85                  90                  95

Asn Asp Tyr Gly Leu Asp Ile Trp Gly Pro Gly Thr Leu Val Thr Val
            100                 105                 110

Ser Ser


<210> SEQ ID NO 10
<211> LENGTH: 342
<212> TYPE: DNA
<213> ORGANISM: Artificial Sequence
<220> FEATURE:
<223> OTHER INFORMATION: Rabbit VH nucl.

<400> SEQUENCE: 10

cagtcggtgg aggagtccgg gggtcgcctg gtcacgcctg ggacacccct gacactcacc      60

tgcaccgtct ctgggttccc cctcagtaat tatgcaatga gctgggtccg ccaggctcca     120

gggaaggggc tggaatggat cggagacatt tatcctagtg atatcataga ctacgcgagc     180
```

-continued

```
tgggcgaaag gccgattcac catctcccaa acctcgacca cggtggagct gaaaatcacg    240

ggtccgacaa ccgaggacac ggccacctat ttctgtgcca gagacaacaa tgactatggt    300

ctggacatct ggggcccagg caccctggtc accgtctcga gt                       342
```

<210> SEQ ID NO 11
<211> LENGTH: 110
<212> TYPE: PRT
<213> ORGANISM: Artificial Sequence
<220> FEATURE:
<223> OTHER INFORMATION: 10236 gL5 VL

<400> SEQUENCE: 11

```
Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Lys Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys
            100                 105                 110
```

<210> SEQ ID NO 12
<211> LENGTH: 336
<212> TYPE: DNA
<213> ORGANISM: Artificial Sequence
<220> FEATURE:
<223> OTHER INFORMATION: 10236 gL5 VL nucl.

<400> SEQUENCE: 12

```
gcctacgaca tgactcagtc cccatcctcc ctgtccgcat ccgtggggga tagagtcacc     60

atcacctgtc aagccagcca gtcaattagc tcgtggctgg cctggtatca gcagaagccg    120

ggaaaggctc ccaagttgct gatctacctg gcctcaacgc tcgcgtcggg agtgcctagc    180

cgctttaagg gttccggatc tggcaccgac ttcactctca ccatttcgag ccttcaaccg    240

gaggacttcg ccacttacta ctgccagcag ggttacacca actccaacat catcaacacc    300

ttcggcggag ggaccaaagt ggaaatcaag cgtacg                              336
```

<210> SEQ ID NO 13
<211> LENGTH: 217
<212> TYPE: PRT
<213> ORGANISM: Artificial Sequence
<220> FEATURE:
<223> OTHER INFORMATION: 10236 gL5 Light Chain

<400> SEQUENCE: 13

```
Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Lys Gly
```

-continued

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 14
<211> LENGTH: 657
<212> TYPE: DNA
<213> ORGANISM: Artificial Sequence
<220> FEATURE:
<223> OTHER INFORMATION: 10236 gL5 Light chain nucl.

<400> SEQUENCE: 14

gcctacgaca tgactcagtc cccatcctcc ctgtccgcat ccgtggggga tagagtcacc     60

atcacctgtc aagccagcca gtcaattagc tcgtggctgg cctggtatca gcagaagccg    120

ggaaaggctc ccaagttgct gatctacctg gcctcaacgc tcgcgtcggg agtgcctagc    180

cgctttaagg gttccggatc tggcaccgac ttcactctca ccatttcgag ccttcaaccg    240

gaggacttcg ccacttacta ctgccagcag ggttacacca actccaacat catcaacacc    300

ttcggcggag ggaccaaagt ggaaatcaag cgtacgcgta cggtggccgc tccctccgtg    360

ttcatcttcc caccctccga cgagcagctg aagtccggca ccgcctccgt cgtgtgcctg    420

ctgaacaact tctacccccg cgaggccaag gtgcagtgga aggtggacaa cgccctgcag    480

tccggcaact cccaggaatc cgtcaccgag caggactcca aggacagcac ctactccctg    540

tcctccaccc tgaccctgtc caaggccgac tacgagaagc acaaggtgta cgcctgcgaa    600

gtgacccacc agggcctgtc cagccccgtg accaagtcct tcaaccgggg cgagtgc       657


<210> SEQ ID NO 15
<211> LENGTH: 110
<212> TYPE: PRT
<213> ORGANISM: Artificial Sequence
<220> FEATURE:
<223> OTHER INFORMATION: 10236 gL6 VL

<400> SEQUENCE: 15

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30
```

-continued

```
Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys
            100                 105                 110


<210> SEQ ID NO 16
<211> LENGTH: 330
<212> TYPE: DNA
<213> ORGANISM: Artificial Sequence
<220> FEATURE:
<223> OTHER INFORMATION: 10236 gL6 VL nucl.

<400> SEQUENCE: 16

gcctacgaca tgactcagtc cccatcctcc ctgtccgcat ccgtgggggga tagagtcacc     60

atcacctgtc aagccagcca gtcaattagc tcgtggctgg cctggtatca gcagaagccg    120

ggaaaggctc ccaagttgct gatctacctg gcctcaacgc tcgcgtcggg agtgcctagc    180

cgcttttccg gttccggatc tggcaccgac ttcactctca ccatttcgag ccttcaaccg    240

gaggacttcg ccacttacta ctgccagcag ggttacacca actccaacat catcaacacc    300

ttcggcggag ggaccaaagt ggaaatcaag                                     330


<210> SEQ ID NO 17
<211> LENGTH: 217
<212> TYPE: PRT
<213> ORGANISM: Artificial Sequence
<220> FEATURE:
<223> OTHER INFORMATION: 10236 gL6 Light Chain

<400> SEQUENCE: 17

Ala Tyr Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
```

```
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 18
<211> LENGTH: 651
<212> TYPE: DNA
<213> ORGANISM: Artificial Sequence
<220> FEATURE:
<223> OTHER INFORMATION: 10236 gL6 Light Chain nucl.

<400> SEQUENCE: 18

gcctacgaca tgactcagtc cccatcctcc ctgtccgcat ccgtggggga tagagtcacc      60

atcacctgtc aagccagcca gtcaattagc tcgtggctgg cctggtatca gcagaagccg     120

ggaaaggctc ccaagttgct gatctacctg gcctcaacgc tcgcgtcggg agtgcctagc     180

cgcttttccg gttccggatc tggcaccgac ttcactctca ccatttcgag ccttcaaccg     240

gaggacttcg ccacttacta ctgccagcag ggttacacca actccaacat catcaacacc     300

ttcggcggag ggaccaaagt ggaaatcaag cgtacggtgg ccgctccctc cgtgttcatc     360

ttcccaccct ccgacgagca gctgaagtcc ggcaccgcct ccgtcgtgtg cctgctgaac     420

aacttctacc cccgcgaggc caaggtgcag tggaaggtgg acaacgccct gcagtccggc     480

aactcccagg aatccgtcac cgagcaggac tccaaggaca gcacctactc cctgtcctcc     540

accctgaccc tgtccaaggc cgactacgag aagcacaagg tgtacgcctg cgaagtgacc     600

caccagggcc tgtccagccc cgtgaccaag tccttcaacc ggggcgagtg c              651


<210> SEQ ID NO 19
<211> LENGTH: 110
<212> TYPE: PRT
<213> ORGANISM: Artificial Sequence
<220> FEATURE:
<223> OTHER INFORMATION: 10236 gL7 VL

<400> SEQUENCE: 19

Ala Ile Asp Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys
            100                 105                 110


<210> SEQ ID NO 20
<211> LENGTH: 330
<212> TYPE: DNA
<213> ORGANISM: Artificial Sequence
```

-continued

<220> FEATURE:
<223> OTHER INFORMATION: 10236 gL7 VL nucl.

<400> SEQUENCE: 20
gcgatcgaca tgactcagag cccgtccagc ctgtccgcgt ccgtgggaga tcgcgtgact 60
atcacgtgtc aggcctcaca atccattagc tcctggctgg cctggtacca gcagaagcca 120
gggaaggctc cgaagctgct gatctacctg gcctccaccc ttgcctccgg cgtgccttca 180
cggttttctg gatccggctc gggaaccgac ttcaccctca ccatctcgtc gctccaaccc 240
gaggacttcg caacctacta ctgccaacag gggtatacca acagcaacat catcaacacc 300
ttcggtggcg gaactaaggt cgaaatcaag 330

<210> SEQ ID NO 21
<211> LENGTH: 217
<212> TYPE: PRT
<213> ORGANISM: Artificial Sequence
<220> FEATURE:
<223> OTHER INFORMATION: 10236 gL7 Light Chain

<400> SEQUENCE: 21

Ala Ile Asp Met Thr Gln Ser Pro Ser Ser Leu Ser Ala Ser Val Gly
1 5 10 15

Asp Arg Val Thr Ile Thr Cys Gln Ala Ser Gln Ser Ile Ser Ser Trp
20 25 30

Leu Ala Trp Tyr Gln Gln Lys Pro Gly Lys Ala Pro Lys Leu Leu Ile
35 40 45

Tyr Leu Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Gly Tyr Thr Asn Ser Asn
85 90 95

Ile Ile Asn Thr Phe Gly Gly Gly Thr Lys Val Glu Ile Lys Arg Thr
100 105 110

Val Ala Ala Pro Ser Val Phe Ile Phe Pro Pro Ser Asp Glu Gln Leu
115 120 125

Lys Ser Gly Thr Ala Ser Val Val Cys Leu Leu Asn Asn Phe Tyr Pro
130 135 140

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Ser Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 22
<211> LENGTH: 645
<212> TYPE: DNA
<213> ORGANISM: Artificial Sequence
<220> FEATURE:
<223> OTHER INFORMATION: 10236 gL7 Light Chain nucl.

<400> SEQUENCE: 22

```
gcgatcgaca tgactcagag cccgtccagc ctgtccgcgt ccgtgggaga tcgcgtgact      60

atcacgtgtc aggcctcaca atccattagc tcctggctgg cctggtacca gcagaagcca     120

gggaaggctc cgaagctgct gatctacctg gcctccaccc ttgcctccgg cgtgccttca     180

cggttttctg gatccggctc gggaaccgac ttcaccctca ccatctcgtc gctccaaccc     240

gaggacttcg caacctacta ctgccaacag ggtataccca acagcaacat catcaacacc     300

ttcggtggcg gaactaaggt cgaaatcaag gtggccgctc cctccgtgtt catcttccca     360

ccctccgacg agcagctgaa gtccggcacc gcctccgtcg tgtgcctgct gaacaacttc     420

taccccgcg aggccaaggt gcagtggaag gtggacaacg ccctgcagtc cggcaactcc     480

caggaatccg tcaccgagca ggactccaag gacagcacct actccctgtc ctccaccctg     540

accctgtcca aggccgacta cgagaagcac aaggtgtacg cctgcgaagt gacccaccag     600

ggcctgtcca gccccgtgac caagtccttc aaccggggcg agtgc                     645


<210> SEQ ID NO 23
<211> LENGTH: 110
<212> TYPE: PRT
<213> ORGANISM: Artificial Sequence
<220> FEATURE:
<223> OTHER INFORMATION: 10236 gL8 VL

<400> SEQUENCE: 23

Ala Tyr Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys
            100                 105                 110


<210> SEQ ID NO 24
<211> LENGTH: 330
<212> TYPE: DNA
<213> ORGANISM: Artificial Sequence
<220> FEATURE:
<223> OTHER INFORMATION: 10236 gL8 VL nucl.

<400> SEQUENCE: 24

gcgtatcaga tgactcagag cccgtccagc ctgtccgcgt ccgtgggaga tcgcgtgact      60

atcacgtgtc aggcctcaca atccattagc tcctggctgg cctggtacca gcagaagcca     120

gggaaggctc cgaagctgct gatctacctg gcctccaccc ttgcctccgg cgtgccttca     180

cggttttctg gatccggctc gggaaccgac ttcaccctca ccatctcgtc gctccaaccc     240

gaggacttcg caacctacta ctgccaacag ggtataccca acagcaacat catcaacacc     300

ttcggtggcg gaactaaggt cgaaatcaag                                      330


<210> SEQ ID NO 25
<211> LENGTH: 217
<212> TYPE: PRT
```

<213> ORGANISM: Artificial Sequence
<220> FEATURE:
<223> OTHER INFORMATION: 10236 gL8 Light Chain

<400> SEQUENCE: 25

```
Ala Tyr Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Leu Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Thr Asn Ser Asn
                85                  90                  95

Ile Ile Asn Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 26
<211> LENGTH: 645
<212> TYPE: DNA
<213> ORGANISM: Artificial Sequence
<220> FEATURE:
<223> OTHER INFORMATION: 10236 gL8 Light Chain nucl.

<400> SEQUENCE: 26

```
gcgtatcaga tgactcagag cccgtccagc ctgtccgcgt ccgtgggaga tcgcgtgact     60

atcacgtgtc aggcctcaca atccattagc tcctggctgg cctggtacca gcagaagcca    120

gggaaggctc cgaagctgct gatctacctg gcctccaccc ttgcctccgg cgtgccttca    180

cggttttctg gatccggctc gggaaccgac ttcaccctca ccatctcgtc gctccaaccc    240

gaggacttcg caacctacta ctgccaacag ggtataccca acagcaacat catcaacacc    300

ttcggtggcg gaactaaggt cgaaatcaag gtggccgctc cctccgtgtt catcttccca    360

ccctccgacg agcagctgaa gtccggcacc gcctccgtcg tgtgcctgct gaacaacttc    420

tacccccgcg aggccaaggt gcagtggaag gtggacaacg ccctgcagtc cggcaactcc    480

caggaatccg tcaccgagca ggactccaag gacagcacct actccctgtc ctccaccctg    540

accctgtcca aggccgacta cgagaagcac aaggtgtacg cctgcgaagt gacccaccag    600

ggcctgtcca gccccgtgac caagtccttc aaccggggcg agtgc                    645
```

<210> SEQ ID NO 27
<211> LENGTH: 117
<212> TYPE: PRT
<213> ORGANISM: Artificial Sequence
<220> FEATURE:
<223> OTHER INFORMATION: 10236 gH9 VH

<400> SEQUENCE: 27

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Val Thr Ile Ser Gln Asp Ser Ser Lys Thr Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser
        115

<210> SEQ ID NO 28
<211> LENGTH: 351
<212> TYPE: DNA
<213> ORGANISM: Artificial Sequence
<220> FEATURE:
<223> OTHER INFORMATION: 10236 gH9 VH nucl.

<400> SEQUENCE: 28
gaagtgcagc tgcaagagtc aggaccgggc ttggtcaagc ccagcggaac cctgtccctg 60
acttgtgccg tgtcggggtt cccgctgtcg aactacgcga tgtcctgggt cagacagcct 120
cccggaaagg gccttgaatg gatcggcgac atctacccaa gcgacattat tgattacgca 180
tcctgggcca agggacgcgt gaccatctcc caggactctt ccaagaccca agtgtccctc 240
aagctgtcca gcgtgaccgc tgccgacact gccgtgtact attgcgcgcg ggataacaac 300
gactacgggc tggacatctg gggccagggt accctcgtga ctgtctcgag c 351

<210> SEQ ID NO 29
<211> LENGTH: 444
<212> TYPE: PRT
<213> ORGANISM: Artificial Sequence
<220> FEATURE:
<223> OTHER INFORMATION: 10236 gH9 Heavy Chain

<400> SEQUENCE: 29

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

```
Gly Arg Val Thr Ile Ser Gln Asp Ser Ser Lys Thr Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 30
<211> LENGTH: 1332
<212> TYPE: DNA
<213> ORGANISM: Artificial Sequence
<220> FEATURE:
<223> OTHER INFORMATION: 10236 gH9 Heavy chain nucl.

<400> SEQUENCE: 30
gaagtgcagc tgcaagagtc aggaccgggc ttggtcaagc ccagcggaac cctgtccctg 60
acttgtgccg tgtcggggtt cccgctgtcg aactacgcga tgtcctgggt cagacagcct 120
cccggaaagg gccttgaatg gatcggcgac atctacccaa gcgacattat tgattacgca 180
tcctgggcca agggacgcgt gaccatctcc caggactctt ccaagaccca agtgtccctc 240
aagctgtcca gcgtgaccgc tgccgacact gccgtgtact attgcgcgcg ggataacaac 300
gactacgggc tggacatctg gggccagggt accctcgtga ctgtctcgag cgcttctaca 360
aagggcccct ccgtgttccc tctggcccct tgctcccggt ccacctccga gtctaccgcc 420
gctctgggct gcctggtcaa ggactacttc cccgagcccg tgacagtgtc ctggaactct 480
ggcgccctga cctccggcgt gcacaccttc cctgccgtgc tgcagtcctc cggcctgtac 540
tccctgtcct ccgtcgtgac cgtgccctcc tccagcctgg gcaccaagac ctacacctgt 600
aacgtggacc acaagccctc caacaccaag gtggacaagc gggtggaatc taagtacggc 660
cctccctgcc ccccctgccc tgcccctgaa tttctgggcg gaccttccgt gttcctgttc 720
cccccaaagc ccaaggacac cctgatgatc tcccggaccc ccgaagtgac ctgcgtggtg 780
gtggacgtgt cccaggaaga tcccgaggtc cagttcaatt ggtacgtgga cggcgtggaa 840
gtgcacaatg ccaagaccaa gcccagagag gaacagttca actccaccta ccgggtggtg 900
tccgtgctga ccgtgctgca ccaggactgg ctgaacggca aagagtacaa gtgcaaggtg 960
tccaacaagg gcctgccctc cagcatcgaa aagaccatct ccaaggccaa gggccagccc 1020
cgcgagcccc aggtgtacac cctgcccccct agccaggaag agatgaccaa gaaccaggtg 1080
tccctgacct gtctggtcaa gggcttctac ccctccgaca ttgccgtgga atgggagtcc 1140
aacggccagc ccgagaacaa ctacaagacc acccccccctg tgctggacag cgacggctcc 1200
ttcttcctgt actctcggct gaccgtggac aagtcccggt ggcaggaagg caacgtcttc 1260
tcctgctccg tgatgcacga ggccctgcac aaccactaca cccagaagtc cctgtccctg 1320
agcctgggca ag 1332

<210> SEQ ID NO 31
<211> LENGTH: 117
<212> TYPE: PRT
<213> ORGANISM: Artificial Sequence
<220> FEATURE:
<223> OTHER INFORMATION: 10236 gH10 VH nucl.

<400> SEQUENCE: 31

Glu Val Gln Leu Gln Glu Ser Gly Pro Gly Leu Val Lys Pro Ser Gly
1 5 10 15

Thr Leu Ser Leu Thr Cys Ala Val Ser Gly Phe Pro Leu Ser Asn Tyr
20 25 30

Ala Met Ser Trp Val Arg Gln Pro Pro Gly Lys Gly Leu Glu Trp Ile
35 40 45

Gly Asp Ile Tyr Pro Ser Asp Ile Ile Asp Tyr Ala Ser Trp Ala Lys
50 55 60

Gly Arg Val Thr Ile Ser Val Asp Ser Ser Lys Thr Gln Val Ser Leu
65 70 75 80

Lys Leu Ser Ser Val Thr Ala Ala Asp Thr Ala Val Tyr Tyr Cys Ala
85 90 95

Arg Asp Asn Asn Asp Tyr Gly Leu Asp Ile Trp Gly Gln Gly Thr Leu
100 105 110

```
Val Thr Val Ser Ser
        115


<210> SEQ ID NO 32
<211> LENGTH: 351
<212> TYPE: DNA
<213> ORGANISM: Artificial Sequence
<220> FEATURE:
<223> OTHER INFORMATION: 10236 gH10 VH nucl.

<400> SEQUENCE: 32

gaagtgcagc tgcaagagtc aggaccgggc ttggtcaagc ccagcggaac cctgtccctg     60

acttgtgccg tgtcggggtt cccgctgtcg aactacgcga tgtcctgggt cagacagcct    120

cccggaaagg gccttgaatg gatcggcgac atctacccaa gcgacattat tgattacgca    180

tcctgggcca agggacgcgt gaccatctcc gtggactctt ccaagaccca agtgtccctc    240

aagctgtcca gcgtgaccgc tgccgacact gccgtgtact attgcgcgcg ggataacaac    300

gactacgggc tggacatctg gggccagggt accctcgtga ctgtctcgag c             351


<210> SEQ ID NO 33
<211> LENGTH: 444
<212> TYPE: PRT
<213> ORGANISM: Artificial Sequence
<220> FEATURE:
<223> OTHER INFORMATION: 10236 gH10 Heavy Chain

<400> SEQUENCE: 33

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Val Thr Ile Ser Val Asp Ser Ser Lys Thr Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
```

-continued

```
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 34
<211> LENGTH: 1332
<212> TYPE: DNA
<213> ORGANISM: Artificial Sequence
<220> FEATURE:
<223> OTHER INFORMATION: 10236 gH10 Heavy Chain nucl.

<400> SEQUENCE: 34

```
gaagtgcagc tgcaagagtc aggaccgggc ttggtcaagc ccagcggaac cctgtccctg      60

acttgtgccg tgtcggggtt cccgctgtcg aactacgcga tgtcctgggt cagacagcct     120

cccggaaagg gccttgaatg gatcggcgac atctacccaa gcgacattat tgattacgca     180

tcctgggcca agggacgcgt gaccatctcc gtggactctt ccaagaccca agtgtccctc     240

aagctgtcca gcgtgaccgc tgccgacact gccgtgtact attgcgcgcg ggataacaac     300

gactacgggc tggacatctg gggccagggt accctcgtga ctgtctcgag cgcttctaca     360

aagggcccct ccgtgttccc tctggcccct tgctcccggt ccacctccga gtctaccgcc     420

gctctgggct gcctggtcaa ggactacttc cccgagcccg tgacagtgtc ctggaactct     480

ggcgccctga cctccggcgt gcacaccttc cctgccgtgc tgcagtcctc cggcctgtac     540

tccctgtcct ccgtcgtgac cgtgccctcc tccagcctgg gcaccaagac ctacacctgt     600

aacgtggacc acaagccctc caacaccaag gtggacaagc gggtggaatc taagtacggc     660

cctccctgcc ccccctgccc tgcccctgaa tttctgggcg gaccttccgt gttcctgttc     720

cccccaaagc ccaaggacac cctgatgatc tcccggaccc ccgaagtgac ctgcgtggtg     780

gtggacgtgt cccaggaaga tcccgaggtc cagttcaatt ggtacgtgga cggcgtggaa     840
```

-continued

```
gtgcacaatg ccaagaccaa gcccagagag gaacagttca actccaccta ccgggtggtg    900

tccgtgctga ccgtgctgca ccaggactgg ctgaacggca aagagtacaa gtgcaaggtg    960

tccaacaagg gcctgccctc cagcatcgaa aagaccatct ccaaggccaa gggccagccc   1020

cgcgagcccc aggtgtacac cctgcccccct agccaggaag agatgaccaa gaaccaggtg   1080

tccctgacct gtctggtcaa gggcttctac ccctccgaca ttgccgtgga atgggagtcc   1140

aacggccagc ccgagaacaa ctacaagacc acccccccctg tgctggacag cgacggctcc   1200

ttcttcctgt actctcggct gaccgtggac aagtcccggt ggcaggaagg caacgtcttc   1260

tcctgctccg tgatgcacga ggccctgcac aaccactaca cccagaagtc cctgtccctg   1320

agcctgggca ag                                                       1332
```

```
<210> SEQ ID NO 35
<211> LENGTH: 117
<212> TYPE: PRT
<213> ORGANISM: Artificial Sequence
<220> FEATURE:
<223> OTHER INFORMATION: 10236 gH11 VH nucl.

<400> SEQUENCE: 35

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Val Thr Ile Ser Gln Asp Lys Ser Lys Thr Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser
        115


<210> SEQ ID NO 36
<211> LENGTH: 351
<212> TYPE: DNA
<213> ORGANISM: Artificial Sequence
<220> FEATURE:
<223> OTHER INFORMATION: 10236 gH11 VH nucl.

<400> SEQUENCE: 36

gaagtgcagc tgcaagagtc aggaccgggc ttggtcaagc ccagcggaac cctgtccctg     60

acttgtgccg tgtcggggtt cccgctgtcg aactacgcga tgtcctgggt cagacagcct    120

cccggaaagg gccttgaatg gatcggcgac atctacccaa gcgacattat tgattacgca    180

tcctgggcca agggacgcgt gaccatctcc caggacaagt ccaagaccca agtgtccctc    240

aagctgtcca gcgtgaccgc tgccgacact gccgtgtact attgcgcgcg ggataacaac    300

gactacgggc tggacatctg gggccagggt accctcgtga ctgtctcgag c             351


<210> SEQ ID NO 37
<211> LENGTH: 444
<212> TYPE: PRT
<213> ORGANISM: Artificial Sequence
```

```
<220> FEATURE:
<223> OTHER INFORMATION: 10236 hG11 Heavy Chain

<400> SEQUENCE: 37

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Val Thr Ile Ser Gln Asp Lys Ser Lys Thr Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400
```

```
Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 38
<211> LENGTH: 1332
<212> TYPE: DNA
<213> ORGANISM: Artificial Sequence
<220> FEATURE:
<223> OTHER INFORMATION: 10236 gH11 Heavy Chain nucl.

<400> SEQUENCE: 38

```
gaagtgcagc tgcaagagtc aggaccgggc ttggtcaagc ccagcggaac cctgtccctg      60

acttgtgccg tgtcggggtt cccgctgtcg aactacgcga tgtcctgggt cagacagcct     120

cccggaaagg gccttgaatg gatcggcgac atctacccaa gcgacattat tgattacgca     180

tcctgggcca agggacgcgt gaccatctcc caggacaagt ccaagaccca agtgtccctc     240

aagctgtcca gcgtgaccgc tgccgacact gccgtgtact attgcgcgcg ggataacaac     300

gactacgggc tggacatctg gggccagggt accctcgtga ctgtctcgag cgcttctaca     360

aagggcccct ccgtgttccc tctggcccct tgctcccggt ccacctccga gtctaccgcc     420

gctctgggct gcctggtcaa ggactacttc cccgagcccg tgacagtgtc ctggaactct     480

ggcgccctga cctccggcgt gcacaccttc cctgccgtgc tgcagtcctc cggcctgtac     540

tccctgtcct ccgtcgtgac cgtgccctcc tccagcctgg gcaccaagac ctacacctgt     600

aacgtggacc acaagccctc caacaccaag gtggacaagc gggtggaatc taagtacggc     660

cctccctgcc ccccctgccc tgcccctgaa tttctgggcg gaccttccgt gttcctgttc     720

cccccaaagc ccaaggacac cctgatgatc tcccggaccc ccgaagtgac ctgcgtggtg     780

gtggacgtgt cccaggaaga tcccgaggtc cagttcaatt ggtacgtgga cggcgtggaa     840

gtgcacaatg ccaagaccaa gcccagagag gaacagttca actccaccta ccgggtggtg     900

tccgtgctga ccgtgctgca ccaggactgg ctgaacggca aagagtacaa gtgcaaggtg     960

tccaacaagg gcctgccctc cagcatcgaa aagaccatct ccaaggccaa gggccagccc    1020

cgcgagcccc aggtgtacac cctgccccct agccaggaag agatgaccaa gaaccaggtg    1080

tccctgacct gtctggtcaa gggcttctac ccctccgaca ttgccgtgga atgggagtcc    1140

aacggccagc ccgagaacaa ctacaagacc acccccccctg tgctggacag cgacggctcc    1200

ttcttcctgt actctcggct gaccgtggac aagtcccggt ggcaggaagg caacgtcttc    1260

tcctgctccg tgatgcacga ggccctgcac aaccactaca cccagaagtc cctgtccctg    1320

agcctgggca ag                                                        1332
```

<210> SEQ ID NO 39
<211> LENGTH: 117
<212> TYPE: PRT
<213> ORGANISM: Artificial Sequence
<220> FEATURE:
<223> OTHER INFORMATION: 10236 gH12 VH

<400> SEQUENCE: 39

```
Glu Val Gln Leu Gln Glu Ser Gly Pro Gly Leu Val Lys Pro Ser Gly
1               5                   10                  15
```

```
Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Val Thr Ile Ser Gln Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser
        115
```

<210> SEQ ID NO 40
<211> LENGTH: 351
<212> TYPE: DNA
<213> ORGANISM: Artificial Sequence
<220> FEATURE:
<223> OTHER INFORMATION: 10236 gH12 VH nucl.

<400> SEQUENCE: 40

```
gaggtgcagc ttcaggaatc cggacccggt ctggtcaagc cgagcggaac cctgtcactg      60

acttgcgcgg tgtcgggctt ccccctgtcc aattacgcca tgtcatgggt ccggcaacca     120

cctgggaaag ggttggagtg gattggcgac atctacccga gcgacatcat tgattacgcc     180

tcgtgggcca agggtagagt gaccatcagc caggactcct ccaagaacca agtgtcgctg     240

aagctctcct ccgtgaccgc agccgatacc gctgtgtact attgtgcccg cgacaacaac     300

gactacggcc tggatatctg gggacaggga accctcgtga ctgtctcgag c              351
```

<210> SEQ ID NO 41
<211> LENGTH: 444
<212> TYPE: PRT
<213> ORGANISM: Artificial Sequence
<220> FEATURE:
<223> OTHER INFORMATION: 10236 gH12 Heavy Chain

<400> SEQUENCE: 41

```
Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Val Thr Ile Ser Gln Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140
```

-continued

```
Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 42
<211> LENGTH: 1332
<212> TYPE: DNA
<213> ORGANISM: Artificial Sequence
<220> FEATURE:
<223> OTHER INFORMATION: 10236 gH12 Heavy Chain nucl.

<400> SEQUENCE: 42

```
gaggtgcagc ttcaggaatc cggacccggt ctggtcaagc cgagcggaac cctgtcactg      60

acttgcgcgg tgtcgggctt ccccctgtcc aattacgcca tgtcatgggt ccggcaacca     120

cctgggaaag ggttggagtg gattggcgac atctacccga gcgacatcat tgattacgcc     180

tcgtgggcca agggtagagt gaccatcagc caggactcct ccaagaacca agtgtcgctg     240

aagctctcct ccgtgaccgc agccgatacc gctgtgtact attgtgcccg cgacaacaac     300

gactacggcc tggatatctg gggacaggga accctcgtga ctgtctcgag cgcttctaca     360
```

aagggcccct ccgtgttccc tctggcccct tgctcccggt ccacctccga gtctaccgcc 420
gctctgggct gcctggtcaa ggactacttc cccgagcccg tgacagtgtc ctggaactct 480
ggcgccctga cctccggcgt gcacaccttc cctgccgtgc tgcagtcctc cggcctgtac 540
tccctgtcct ccgtcgtgac cgtgccctcc tccagcctgg gcaccaagac ctacacctgt 600
aacgtggacc acaagccctc caacaccaag gtggacaagc gggtggaatc taagtacggc 660
cctccctgcc ccccctgccc tgcccctgaa tttctgggcg gaccttccgt gttcctgttc 720
cccccaaagc ccaaggacac cctgatgatc tcccggaccc ccgaagtgac ctgcgtggtg 780
gtggacgtgt cccaggaaga tcccgaggtc cagttcaatt ggtacgtgga cggcgtggaa 840
gtgcacaatg ccaagaccaa gcccagagag gaacagttca actccaccta ccgggtggtg 900
tccgtgctga ccgtgctgca ccaggactgg ctgaacggca aagagtacaa gtgcaaggtg 960
tccaacaagg gcctgccctc cagcatcgaa aagaccatct ccaaggccaa gggccagccc 1020
cgcgagcccc aggtgtacac cctgccccct agccaggaag agatgaccaa gaaccaggtg 1080
tccctgacct gtctggtcaa gggcttctac ccctccgaca ttgccgtgga atgggagtcc 1140
aacggccagc ccgagaacaa ctacaagacc acccccccctg tgctggacag cgacggctcc 1200
ttcttcctgt actctcggct gaccgtggac aagtcccggt ggcaggaagg caacgtcttc 1260
tcctgctccg tgatgcacga ggccctgcac aaccactaca cccagaagtc cctgtccctg 1320
agcctgggca ag 1332

<210> SEQ ID NO 43
<211> LENGTH: 117
<212> TYPE: PRT
<213> ORGANISM: Artificial Sequence
<220> FEATURE:
<223> OTHER INFORMATION: 10236 gH14 VH

<400> SEQUENCE: 43

Glu Val Gln Leu Gln Glu Ser Gly Pro Gly Leu Val Lys Pro Ser Gly
1 5 10 15

Thr Leu Ser Leu Thr Cys Ala Val Ser Gly Phe Pro Leu Ser Asn Tyr
20 25 30

Ala Met Ser Trp Val Arg Gln Pro Pro Gly Lys Gly Leu Glu Trp Ile
35 40 45

Gly Asp Ile Tyr Pro Ser Asp Ile Ile Asp Tyr Ala Ser Trp Ala Lys
50 55 60

Gly Arg Phe Thr Ile Ser Gln Asp Ser Ser Lys Asn Gln Val Ser Leu
65 70 75 80

Lys Leu Ser Ser Val Thr Ala Ala Asp Thr Ala Val Tyr Tyr Cys Ala
85 90 95

Arg Asp Asn Asn Asp Tyr Gly Leu Asp Ile Trp Gly Gln Gly Thr Leu
100 105 110

Val Thr Val Ser Ser
115

<210> SEQ ID NO 44
<211> LENGTH: 351
<212> TYPE: DNA
<213> ORGANISM: Artificial Sequence
<220> FEATURE:
<223> OTHER INFORMATION: 10236 gH14 VH nucl.

<400> SEQUENCE: 44

-continued

```
gaagtgcagc tgcaagagtc aggaccgggc ttggtcaagc ccagcggaac cctgtccctg      60

acttgtgccg tgtcggggtt cccgctgtcg aactacgcga tgtcctgggt cagacagcct    120

cccggaaagg gccttgaatg gatcggcgac atctacccaa gcgacattat tgattacgca    180

tcctgggcca agggacgctt caccatctcc caggactctt ccaagaacca agtgtccctc    240

aagctgtcca gcgtgaccgc tgccgacact gccgtgtact attgcgcgcg ggataacaac    300

gactacgggc tggacatctg gggccagggt accctcgtga ctgtctcgag c             351


<210> SEQ ID NO 45
<211> LENGTH: 444
<212> TYPE: PRT
<213> ORGANISM: Artificial Sequence
<220> FEATURE:
<223> OTHER INFORMATION: 10236 gH14 Heavy Chain

<400> SEQUENCE: 45

Glu Val Gln Leu Gln Glu Ser Gly Pro Gly Leu Val Lys Pro Ser Gly
1               5                   10                  15

Thr Leu Ser Leu Thr Cys Ala Val Ser Gly Phe Pro Leu Ser Asn Tyr
            20                  25                  30

Ala Met Ser Trp Val Arg Gln Pro Pro Gly Lys Gly Leu Glu Trp Ile
        35                  40                  45

Gly Asp Ile Tyr Pro Ser Asp Ile Ile Asp Tyr Ala Ser Trp Ala Lys
    50                  55                  60

Gly Arg Phe Thr Ile Ser Gln Asp Ser Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Asn Asn Asp Tyr Gly Leu Asp Ile Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300
```

```
Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440
```

<210> SEQ ID NO 46
<211> LENGTH: 1332
<212> TYPE: DNA
<213> ORGANISM: Artificial Sequence
<220> FEATURE:
<223> OTHER INFORMATION: 10236 gH14 Heavy Chain nucl.

<400> SEQUENCE: 46

```
gaagtgcagc tgcaagagtc aggaccgggc ttggtcaagc ccagcggaac cctgtccctg     60

acttgtgccg tgtcggggtt cccgctgtcg aactacgcga tgtcctgggt cagacagcct    120

cccggaaagg gccttgaatg gatcggcgac atctacccaa gcgacattat tgattacgca    180

tcctgggcca agggacgctt caccatctcc caggactctt ccaagaacca agtgtccctc    240

aagctgtcca gcgtgaccgc tgccgacact gccgtgtact attgcgcgcg ggataacaac    300

gactacgggc tggacatctg gggccagggt accctcgtga ctgtctcgag cgcttctaca    360

aagggcccct ccgtgttccc tctggcccct tgctcccggt ccacctccga gtctaccgcc    420

gctctgggct gcctggtcaa ggactacttc cccgagcccg tgacagtgtc ctggaactct    480

ggcgccctga cctccggcgt gcacaccttc cctgccgtgc tgcagtcctc cggcctgtac    540

tccctgtcct ccgtcgtgac cgtgccctcc tccagcctgg gcaccaagac ctacacctgt    600

aacgtggacc acaagccctc caacaccaag gtggacaagc gggtggaatc taagtacggc    660

cctccctgcc ccccctgccc tgcccctgaa tttctgggcg gaccttccgt gttcctgttc    720

cccccaaagc ccaaggacac cctgatgatc tcccggaccc ccgaagtgac ctgcgtggtg    780

gtggacgtgt cccaggaaga tcccgaggtc cagttcaatt ggtacgtgga cggcgtggaa    840

gtgcacaatg ccaagaccaa gcccagagag gaacagttca actccaccta ccgggtggtg    900

tccgtgctga ccgtgctgca ccaggactgg ctgaacggca aagagtacaa gtgcaaggtg    960

tccaacaagg gcctgccctc cagcatcgaa aagaccatct ccaaggccaa gggccagccc   1020

cgcgagcccc aggtgtacac cctgccccct agccaggaag agatgaccaa gaaccaggtg   1080

tccctgacct gtctggtcaa gggcttctac ccctccgaca ttgccgtgga atgggagtcc   1140

aacggccagc ccgagaacaa ctacaagacc accccccctg tgctggacag cgacggctcc   1200

ttcttcctgt actctcggct gaccgtggac aagtcccggt ggcaggaagg caacgtcttc   1260
```

```
tcctgctccg tgatgcacga ggccctgcac aaccactaca cccagaagtc cctgtccctg   1320

agcctgggca ag                                                       1332


<210> SEQ ID NO 47
<211> LENGTH: 107
<212> TYPE: PRT
<213> ORGANISM: Artificial Sequence
<220> FEATURE:
<223> OTHER INFORMATION: Human IGKV1-6 JK4 acceptor framework

<400> SEQUENCE: 47

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Leu
                85                  90                  95

Thr Phe Gly Gly Gly Thr Lys Val Glu Ile Lys
            100                 105


<210> SEQ ID NO 48
<211> LENGTH: 321
<212> TYPE: DNA
<213> ORGANISM: Artificial Sequence
<220> FEATURE:
<223> OTHER INFORMATION: Human IGKV1-6 JK4 acceptor framework nucl.

<400> SEQUENCE: 48

gccatccaga tgacccagtc tccatcctcc ctgtctgcat ctgtaggaga cagagtcacc     60

atcacttgcc gggcaagtca gggcattaga aatgatttag gctggtatca gcagaaacca    120

gggaaagccc ctaagctcct gatctatgct gcatccagtt tacaaagtgg ggtcccatca    180

aggttcagcg gcagtggatc tggcacagat ttcactctca ccatcagcag cctgcagcct    240

gaagattttg caacttatta ctgtctacaa gattacaatt accctctcac tttcggcgga    300

gggaccaagg tggagatcaa a                                              321


<210> SEQ ID NO 49
<211> LENGTH: 113
<212> TYPE: PRT
<213> ORGANISM: Artificial Sequence
<220> FEATURE:
<223> OTHER INFORMATION: Human IGHV4-4 JH4 acceptor framework

<400> SEQUENCE: 49

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60
```

-continued

```
Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser


<210> SEQ ID NO 50
<211> LENGTH: 339
<212> TYPE: DNA
<213> ORGANISM: Artificial Sequence
<220> FEATURE:
<223> OTHER INFORMATION: Human IGHV4-4 JH5 acceptor framework nucl.

<400> SEQUENCE: 50

caggtgcagc tgcaggagtc gggcccagga ctggtgaagc cttcggggac cctgtccctc      60

acctgcgctg tctctggtgg ctccatcagc agtagtaact ggtggagttg ggtccgccag     120

cccccaggga aggggctgga gtggattggg gaaatctatc atagtgggag caccaactac     180

aacccgtccc tcaagagtcg agtcaccata tcagtagaca agtccaagaa ccagttctcc     240

ctgaagctga gctctgtgac cgccgcggac acggccgtgt attactgtgc gagatacttt     300

gactactggg gccaaggaac cctggtcacc gtctcctca                            339


<210> SEQ ID NO 51
<211> LENGTH: 293
<212> TYPE: PRT
<213> ORGANISM: Artificial Sequence
<220> FEATURE:
<223> OTHER INFORMATION: Human KLK5 (full length with signal sequence)

<400> SEQUENCE: 51

Met Ala Thr Ala Arg Pro Pro Trp Met Trp Val Leu Cys Ala Leu Ile
1               5                   10                  15

Thr Ala Leu Leu Leu Gly Val Thr Glu His Val Leu Ala Asn Asn Asp
            20                  25                  30

Val Ser Cys Asp His Pro Ser Asn Thr Val Pro Ser Gly Ser Asn Gln
        35                  40                  45

Asp Leu Gly Ala Gly Ala Gly Glu Asp Ala Arg Ser Asp Asp Ser Ser
    50                  55                  60

Ser Arg Ile Ile Asn Gly Ser Asp Cys Asp Met His Thr Gln Pro Trp
65                  70                  75                  80

Gln Ala Ala Leu Leu Leu Arg Pro Asn Gln Leu Tyr Cys Gly Ala Val
                85                  90                  95

Leu Val His Pro Gln Trp Leu Leu Thr Ala Ala His Cys Arg Lys Lys
            100                 105                 110

Val Phe Arg Val Arg Leu Gly His Tyr Ser Leu Ser Pro Val Tyr Glu
        115                 120                 125

Ser Gly Gln Gln Met Phe Gln Gly Val Lys Ser Ile Pro His Pro Gly
    130                 135                 140

Tyr Ser His Pro Gly His Ser Asn Asp Leu Met Leu Ile Lys Leu Asn
145                 150                 155                 160

Arg Arg Ile Arg Pro Thr Lys Asp Val Arg Pro Ile Asn Val Ser Ser
                165                 170                 175

His Cys Pro Ser Ala Gly Thr Lys Cys Leu Val Ser Gly Trp Gly Thr
            180                 185                 190
```

```
Thr Lys Ser Pro Gln Val His Phe Pro Lys Val Leu Gln Cys Leu Asn
        195                 200                 205

Ile Ser Val Leu Ser Gln Lys Arg Cys Glu Asp Ala Tyr Pro Arg Gln
    210                 215                 220

Ile Asp Asp Thr Met Phe Cys Ala Gly Asp Lys Ala Gly Arg Asp Ser
225                 230                 235                 240

Cys Gln Gly Asp Ser Gly Gly Pro Val Val Cys Asn Gly Ser Leu Gln
                245                 250                 255

Gly Leu Val Ser Trp Gly Asp Tyr Pro Cys Ala Arg Pro Asn Arg Pro
            260                 265                 270

Gly Val Tyr Thr Asn Leu Cys Lys Phe Thr Lys Trp Ile Gln Glu Thr
        275                 280                 285

Ile Gln Ala Asn Ser
    290


<210> SEQ ID NO 52
<211> LENGTH: 271
<212> TYPE: PRT
<213> ORGANISM: Artificial Sequence
<220> FEATURE:
<223> OTHER INFORMATION: Human KLK5 pro-form

<400> SEQUENCE: 52

Val Thr Glu His Val Leu Ala Asn Asn Asp Val Ser Cys Asp His Pro
1               5                   10                  15

Ser Asn Thr Val Pro Ser Gly Ser Asn Gln Asp Leu Gly Ala Gly Ala
            20                  25                  30

Gly Glu Asp Ala Arg Ser Asp Asp Ser Ser Ser Arg Ile Ile Asn Gly
        35                  40                  45

Ser Asp Cys Asp Met His Thr Gln Pro Trp Gln Ala Ala Leu Leu Leu
    50                  55                  60

Arg Pro Asn Gln Leu Tyr Cys Gly Ala Val Leu Val His Pro Gln Trp
65                  70                  75                  80

Leu Leu Thr Ala Ala His Cys Arg Lys Lys Val Phe Arg Val Arg Leu
                85                  90                  95

Gly His Tyr Ser Leu Ser Pro Val Tyr Glu Ser Gly Gln Gln Met Phe
            100                 105                 110

Gln Gly Val Lys Ser Ile Pro His Pro Gly Tyr Ser His Pro Gly His
        115                 120                 125

Ser Asn Asp Leu Met Leu Ile Lys Leu Asn Arg Arg Ile Arg Pro Thr
    130                 135                 140

Lys Asp Val Arg Pro Ile Asn Val Ser Ser His Cys Pro Ser Ala Gly
145                 150                 155                 160

Thr Lys Cys Leu Val Ser Gly Trp Gly Thr Thr Lys Ser Pro Gln Val
                165                 170                 175

His Phe Pro Lys Val Leu Gln Cys Leu Asn Ile Ser Val Leu Ser Gln
            180                 185                 190

Lys Arg Cys Glu Asp Ala Tyr Pro Arg Gln Ile Asp Asp Thr Met Phe
        195                 200                 205

Cys Ala Gly Asp Lys Ala Gly Arg Asp Ser Cys Gln Gly Asp Ser Gly
    210                 215                 220

Gly Pro Val Val Cys Asn Gly Ser Leu Gln Gly Leu Val Ser Trp Gly
225                 230                 235                 240

Asp Tyr Pro Cys Ala Arg Pro Asn Arg Pro Gly Val Tyr Thr Asn Leu
                245                 250                 255
```

```
Cys Lys Phe Thr Lys Trp Ile Gln Glu Thr Ile Gln Ala Asn Ser
            260                 265                 270


<210> SEQ ID NO 53
<211> LENGTH: 227
<212> TYPE: PRT
<213> ORGANISM: Artificial Sequence
<220> FEATURE:
<223> OTHER INFORMATION: Active human KLK5

<400> SEQUENCE: 53

Ile Ile Asn Gly Ser Asp Cys Asp Met His Thr Gln Pro Trp Gln Ala
1               5                   10                  15

Ala Leu Leu Leu Arg Pro Asn Gln Leu Tyr Cys Gly Ala Val Leu Val
            20                  25                  30

His Pro Gln Trp Leu Leu Thr Ala Ala His Cys Arg Lys Lys Val Phe
        35                  40                  45

Arg Val Arg Leu Gly His Tyr Ser Leu Ser Pro Val Tyr Glu Ser Gly
    50                  55                  60

Gln Gln Met Phe Gln Gly Val Lys Ser Ile Pro His Pro Gly Tyr Ser
65                  70                  75                  80

His Pro Gly His Ser Asn Asp Leu Met Leu Ile Lys Leu Asn Arg Arg
                85                  90                  95

Ile Arg Pro Thr Lys Asp Val Arg Pro Ile Asn Val Ser Ser His Cys
            100                 105                 110

Pro Ser Ala Gly Thr Lys Cys Leu Val Ser Gly Trp Gly Thr Thr Lys
        115                 120                 125

Ser Pro Gln Val His Phe Pro Lys Val Leu Gln Cys Leu Asn Ile Ser
    130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Lys Ala Gly Arg Asp Ser Cys Gln
                165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Arg Pro Asn Arg Pro Gly Val
        195                 200                 205

Tyr Thr Asn Leu Cys Lys Phe Thr Lys Trp Ile Gln Glu Thr Ile Gln
    210                 215                 220

Ala Asn Ser
225


<210> SEQ ID NO 54
<211> LENGTH: 295
<212> TYPE: PRT
<213> ORGANISM: Artificial Sequence
<220> FEATURE:
<223> OTHER INFORMATION: Human LEKTI D5 Rabbit Fc

<400> SEQUENCE: 54

Glu Ile Val Lys Leu Cys Ser Gln Tyr Gln Asn Gln Ala Lys Asn Gly
1               5                   10                  15

Ile Leu Phe Cys Thr Arg Glu Asn Asp Pro Ile Arg Gly Pro Asp Gly
            20                  25                  30

Lys Met His Gly Asn Leu Cys Ser Met Cys Gln Ala Tyr Phe Gln Ala
        35                  40                  45

Glu Asn Glu Glu Lys Lys Lys Ala Glu Ala Arg Ala Arg Asn Leu Glu
    50                  55                  60
```

```
Lys Thr Val Ala Pro Ser Thr Cys Ser Lys Pro Thr Cys Pro Pro Pro
65                  70                  75                  80

Glu Leu Leu Gly Gly Pro Ser Val Phe Ile Phe Pro Pro Lys Pro Lys
                85                  90                  95

Asp Thr Leu Met Ile Ser Arg Thr Pro Glu Val Thr Cys Val Val Val
            100                 105                 110

Asp Val Ser Gln Asp Asp Pro Glu Val Gln Phe Thr Trp Tyr Ile Asn
        115                 120                 125

Asn Glu Gln Val Arg Thr Ala Arg Pro Pro Leu Arg Glu Gln Gln Phe
    130                 135                 140

Asn Ser Thr Ile Arg Val Val Ser Thr Leu Pro Ile Ala His Gln Asp
145                 150                 155                 160

Trp Leu Arg Gly Lys Glu Phe Lys Cys Lys Val His Asn Lys Ala Leu
                165                 170                 175

Pro Ala Pro Ile Glu Lys Thr Ile Ser Lys Ala Arg Gly Gln Pro Leu
            180                 185                 190

Glu Pro Lys Val Tyr Thr Met Gly Pro Pro Arg Glu Glu Leu Ser Ser
        195                 200                 205

Arg Ser Val Ser Leu Thr Cys Met Ile Asn Gly Phe Tyr Pro Ser Asp
    210                 215                 220

Ile Ser Val Glu Trp Glu Lys Asn Gly Lys Ala Glu Asp Asn Tyr Lys
225                 230                 235                 240

Thr Thr Pro Ala Val Leu Asp Ser Asp Gly Ser Tyr Phe Leu Tyr Ser
                245                 250                 255

Lys Leu Ser Val Pro Thr Ser Glu Trp Gln Arg Gly Asp Val Phe Thr
            260                 265                 270

Cys Ser Val Met His Glu Ala Leu His Asn His Tyr Thr Gln Lys Ser
        275                 280                 285

Ile Ser Arg Ser Pro Gly Lys
    290                 295


<210> SEQ ID NO 55
<211> LENGTH: 231
<212> TYPE: PRT
<213> ORGANISM: Artificial Sequence
<220> FEATURE:
<223> OTHER INFORMATION: Human KLK7 pro-form

<400> SEQUENCE: 55

Glu Glu Ala Gln Gly Asp Lys Ile Ile Asp Gly Ala Pro Cys Ala Arg
1               5                   10                  15

Gly Ser His Pro Trp Gln Val Ala Leu Leu Ser Gly Asn Gln Leu His
            20                  25                  30

Cys Gly Gly Val Leu Val Asn Glu Arg Trp Val Leu Thr Ala Ala His
        35                  40                  45

Cys Lys Met Asn Glu Tyr Thr Val His Leu Gly Ser Asp Thr Leu Gly
    50                  55                  60

Asp Arg Arg Ala Gln Arg Ile Lys Ala Ser Lys Ser Phe Arg His Pro
65                  70                  75                  80

Gly Tyr Ser Thr Gln Thr His Val Asn Asp Leu Met Leu Val Lys Leu
                85                  90                  95

Asn Ser Gln Ala Arg Leu Ser Ser Met Val Lys Lys Val Arg Leu Pro
            100                 105                 110

Ser Arg Cys Glu Pro Pro Gly Thr Thr Cys Thr Val Ser Gly Trp Gly
        115                 120                 125
```

```
Thr Thr Thr Ser Pro Asp Val Thr Phe Pro Ser Asp Leu Met Cys Val
    130                 135                 140

Asp Val Lys Leu Ile Ser Pro Gln Asp Cys Thr Lys Val Tyr Lys Asp
145                 150                 155                 160

Leu Leu Glu Asn Ser Met Leu Cys Ala Gly Ile Pro Asp Ser Lys Lys
                165                 170                 175

Asn Ala Cys Asn Gly Asp Ser Gly Gly Pro Leu Val Cys Arg Gly Thr
            180                 185                 190

Leu Gln Gly Leu Val Ser Trp Gly Thr Phe Pro Cys Gly Gln Pro Asn
        195                 200                 205

Asp Pro Gly Val Tyr Thr Gln Val Cys Lys Phe Thr Lys Trp Ile Asn
    210                 215                 220

Asp Thr Met Lys Lys His Arg
225                 230


<210> SEQ ID NO 56
<211> LENGTH: 224
<212> TYPE: PRT
<213> ORGANISM: Artificial Sequence
<220> FEATURE:
<223> OTHER INFORMATION: Active human KLK7

<400> SEQUENCE: 56

Ile Ile Asp Gly Ala Pro Cys Ala Arg Gly Ser His Pro Trp Gln Val
1               5                   10                  15

Ala Leu Leu Ser Gly Asn Gln Leu His Cys Gly Gly Val Leu Val Asn
            20                  25                  30

Glu Arg Trp Val Leu Thr Ala Ala His Cys Lys Met Asn Glu Tyr Thr
        35                  40                  45

Val His Leu Gly Ser Asp Thr Leu Gly Asp Arg Arg Ala Gln Arg Ile
    50                  55                  60

Lys Ala Ser Lys Ser Phe Arg His Pro Gly Tyr Ser Thr Gln Thr His
65                  70                  75                  80

Val Asn Asp Leu Met Leu Val Lys Leu Asn Ser Gln Ala Arg Leu Ser
                85                  90                  95

Ser Met Val Lys Lys Val Arg Leu Pro Ser Arg Cys Glu Pro Pro Gly
            100                 105                 110

Thr Thr Cys Thr Val Ser Gly Trp Gly Thr Thr Thr Ser Pro Asp Val
        115                 120                 125

Thr Phe Pro Ser Asp Leu Met Cys Val Asp Val Lys Leu Ile Ser Pro
    130                 135                 140

Gln Asp Cys Thr Lys Val Tyr Lys Asp Leu Leu Glu Asn Ser Met Leu
145                 150                 155                 160

Cys Ala Gly Ile Pro Asp Ser Lys Lys Asn Ala Cys Asn Gly Asp Ser
                165                 170                 175

Gly Gly Pro Leu Val Cys Arg Gly Thr Leu Gln Gly Leu Val Ser Trp
            180                 185                 190

Gly Thr Phe Pro Cys Gly Gln Pro Asn Asp Pro Gly Val Tyr Thr Gln
        195                 200                 205

Val Cys Lys Phe Thr Lys Trp Ile Asn Asp Thr Met Lys Lys His Arg
    210                 215                 220


<210> SEQ ID NO 57
<211> LENGTH: 232
<212> TYPE: PRT
<213> ORGANISM: Artificial Sequence
```

<220> FEATURE:
<223> OTHER INFORMATION: Cyno KLK7 pro-form

<400> SEQUENCE: 57

Gly Gln Glu Ala Gln Gly Asp Lys Ile Ile Asp Gly Ala Pro Cys Thr
1               5                   10                  15

Arg Gly Ser His Pro Trp Gln Val Ala Leu Leu Ser Gly Asn Gln Leu
            20                  25                  30

His Cys Gly Gly Val Leu Val Asn Glu Arg Trp Val Leu Thr Ala Ala
        35                  40                  45

His Cys Lys Met Asn Asp Tyr Ile Val His Leu Gly Ser Asp Thr Leu
    50                  55                  60

Gly Asp Arg Lys Ala Gln Arg Ile Lys Ala Ser Arg Ser Phe Arg His
65                  70                  75                  80

Pro Gly Tyr Ser Thr Gln Thr His Val Asn Asp Leu Met Leu Val Lys
                85                  90                  95

Leu Asn Ser Pro Ala Arg Leu Ser Ser Thr Val Lys Lys Val Arg Leu
            100                 105                 110

Pro Ser Arg Cys Glu Pro Pro Gly Thr Thr Cys Thr Val Ser Gly Trp
        115                 120                 125

Gly Thr Thr Thr Ser Pro Asp Val Thr Phe Pro Ser Asp Leu Met Cys
    130                 135                 140

Val Asp Val Lys Leu Ile Ser Ser Gln Asp Cys Thr Lys Val Tyr Lys
145                 150                 155                 160

Asp Met Leu Gly Asn Ser Met Leu Cys Ala Gly Ile Pro Asn Ser Lys
                165                 170                 175

Lys Asn Ala Cys Asn Gly Asp Ser Gly Gly Pro Leu Val Cys Arg Gly
            180                 185                 190

Thr Leu Gln Gly Leu Val Ser Trp Gly Thr Phe Pro Cys Gly Gln Pro
        195                 200                 205

Asn Asp Pro Gly Val Tyr Thr Gln Val Cys Lys Phe Thr Lys Trp Ile
    210                 215                 220

Asn Asp Thr Ile Lys Lys His Arg
225                 230

<210> SEQ ID NO 58
<211> LENGTH: 224
<212> TYPE: PRT
<213> ORGANISM: Artificial Sequence
<220> FEATURE:
<223> OTHER INFORMATION: Active Cyno KLK7

<400> SEQUENCE: 58

Ile Ile Asp Gly Ala Pro Cys Thr Arg Gly Ser His Pro Trp Gln Val
1               5                   10                  15

Ala Leu Leu Ser Gly Asn Gln Leu His Cys Gly Gly Val Leu Val Asn
            20                  25                  30

Glu Arg Trp Val Leu Thr Ala Ala His Cys Lys Met Asn Asp Tyr Ile
        35                  40                  45

Val His Leu Gly Ser Asp Thr Leu Gly Asp Arg Lys Ala Gln Arg Ile
    50                  55                  60

Lys Ala Ser Arg Ser Phe Arg His Pro Gly Tyr Ser Thr Gln Thr His
65                  70                  75                  80

Val Asn Asp Leu Met Leu Val Lys Leu Asn Ser Pro Ala Arg Leu Ser
                85                  90                  95

Ser Thr Val Lys Lys Val Arg Leu Pro Ser Arg Cys Glu Pro Pro Gly

-continued

```
            100                 105                 110

Thr Thr Cys Thr Val Ser Gly Trp Gly Thr Thr Thr Ser Pro Asp Val
        115                 120                 125

Thr Phe Pro Ser Asp Leu Met Cys Val Asp Val Lys Leu Ile Ser Ser
    130                 135                 140

Gln Asp Cys Thr Lys Val Tyr Lys Asp Met Leu Gly Asn Ser Met Leu
145                 150                 155                 160

Cys Ala Gly Ile Pro Asn Ser Lys Lys Asn Ala Cys Asn Gly Asp Ser
                165                 170                 175

Gly Gly Pro Leu Val Cys Arg Gly Thr Leu Gln Gly Leu Val Ser Trp
            180                 185                 190

Gly Thr Phe Pro Cys Gly Gln Pro Asn Asp Pro Gly Val Tyr Thr Gln
        195                 200                 205

Val Cys Lys Phe Thr Lys Trp Ile Asn Asp Thr Ile Lys Lys His Arg
    210                 215                 220


<210> SEQ ID NO 59
<211> LENGTH: 226
<212> TYPE: PRT
<213> ORGANISM: Artificial Sequence
<220> FEATURE:
<223> OTHER INFORMATION: Active mouse KLK5

<400> SEQUENCE: 59

Ile Val Asn Gly Ser Asp Cys Gln Lys Asp Ala Gln Pro Trp Gln Gly
1               5                   10                  15

Ala Leu Leu Leu Gly Pro Asn Lys Leu Tyr Cys Gly Ala Val Leu Ile
            20                  25                  30

Ser Pro Gln Trp Leu Leu Thr Ala Ala His Cys Arg Lys Pro Val Phe
        35                  40                  45

Arg Ile Arg Leu Gly His His Ser Met Ser Pro Val Tyr Glu Ser Gly
    50                  55                  60

Gln Gln Met Phe Gln Gly Ile Lys Ser Ile Pro His Pro Gly Tyr Ser
65                  70                  75                  80

His Pro Gly His Ser Asn Asp Leu Met Leu Ile Lys Met Asn Arg Lys
                85                  90                  95

Ile Arg Asp Ser His Ser Val Lys Pro Val Glu Ile Ala Cys Asp Cys
            100                 105                 110

Ala Thr Glu Gly Thr Arg Cys Met Val Ser Gly Trp Gly Thr Thr Ser
        115                 120                 125

Ser Ser His Asn Asn Phe Pro Lys Val Leu Gln Cys Leu Asn Ile Thr
    130                 135                 140

Val Leu Ser Glu Glu Arg Cys Lys Asn Ser Tyr Pro Gly Gln Ile Asp
145                 150                 155                 160

Lys Thr Met Phe Cys Ala Gly Asp Glu Glu Gly Arg Asp Ser Cys Gln
                165                 170                 175

Gly Asp Ser Gly Gly Pro Val Val Cys Asn Gly Lys Leu Gln Gly Leu
            180                 185                 190

Val Ser Trp Gly Asp Phe Pro Cys Ala Gln Arg Asn Arg Pro Gly Val
        195                 200                 205

Tyr Thr Asn Leu Cys Glu Phe Val Lys Trp Ile Lys Asp Thr Met Asn
    210                 215                 220

Ser Asn
225
```

<210> SEQ ID NO 60
<211> LENGTH: 227
<212> TYPE: PRT
<213> ORGANISM: Artificial Sequence
<220> FEATURE:
<223> OTHER INFORMATION: Active cyno KLK5

<400> SEQUENCE: 60

```
Ile Ile Asn Gly Ser Asp Cys Asp Glu His Thr Gln Pro Trp Gln Ala
1               5                   10                  15

Ala Leu Leu Leu Gly Pro Asn Gln Leu Tyr Cys Gly Gly Val Leu Val
            20                  25                  30

His Pro Gln Trp Leu Leu Thr Ala Ala His Cys Arg Lys Lys Val Phe
        35                  40                  45

Arg Val Arg Leu Gly His Tyr Ser Leu Ser Pro Val Tyr Glu Ser Gly
    50                  55                  60

Gln Gln Met Phe Gln Gly Ile Lys Ser Ile Pro His Pro Gly Tyr Ser
65                  70                  75                  80

His Pro Gly His Ser Asn Asp Leu Met Leu Ile Lys Leu Asn Arg Arg
                85                  90                  95

Ile His Ser Thr Lys Asp Val Arg Pro Ile Asn Val Ser Ser His Cys
            100                 105                 110

Pro Ser Ala Gly Thr Lys Cys Leu Val Ser Gly Trp Gly Thr Thr Arg
        115                 120                 125

Ser Pro Gln Val His Phe Pro Lys Val Leu Gln Cys Leu Asn Ile Ser
    130                 135                 140

Val Leu Ser Gln Lys Arg Cys Glu Asp Ala Tyr Pro Arg Gln Ile Asp
145                 150                 155                 160

Asp Thr Met Phe Cys Ala Gly Asp Glu Ala Gly Arg Asp Ser Cys Gln
                165                 170                 175

Gly Asp Ser Gly Gly Pro Val Val Cys Asn Gly Ser Leu Gln Gly Leu
            180                 185                 190

Val Ser Trp Gly Asp Tyr Pro Cys Ala Lys Pro Asn Arg Pro Gly Val
        195                 200                 205

Tyr Thr Asn Leu Cys Lys Phe Thr Lys Trp Ile Gln Glu Thr Ile Gln
    210                 215                 220

Ala Asn Ser
225
```

<210> SEQ ID NO 61
<211> LENGTH: 302
<212> TYPE: PRT
<213> ORGANISM: Artificial Sequence
<220> FEATURE:
<223> OTHER INFORMATION: Human LEKTI D8 Rabbit Fc

<400> SEQUENCE: 61

```
Glu Ala Ala Lys Glu Ile Cys Ser Glu Phe Arg Asp Gln Val Arg Asn
1               5                   10                  15

Gly Thr Leu Ile Cys Thr Arg Glu His Asn Pro Val Arg Gly Pro Asp
            20                  25                  30

Gly Lys Met His Gly Asn Lys Cys Ala Met Cys Ala Ser Val Phe Lys
        35                  40                  45

Leu Glu Glu Glu Glu Lys Lys Asn Asp Lys Glu Glu Lys Gly Lys Val
    50                  55                  60

Glu Ala Glu Lys Val Leu Glu Lys Thr Val Ala Pro Ser Thr Cys Ser
65                  70                  75                  80
```

-continued

```
Lys Pro Thr Cys Pro Pro Pro Glu Leu Leu Gly Gly Pro Ser Val Phe
                85                  90                  95

Ile Phe Pro Pro Lys Pro Lys Asp Thr Leu Met Ile Ser Arg Thr Pro
            100                 105                 110

Glu Val Thr Cys Val Val Val Asp Val Ser Gln Asp Asp Pro Glu Val
        115                 120                 125

Gln Phe Thr Trp Tyr Ile Asn Asn Glu Gln Val Arg Thr Ala Arg Pro
    130                 135                 140

Pro Leu Arg Glu Gln Gln Phe Asn Ser Thr Ile Arg Val Val Ser Thr
145                 150                 155                 160

Leu Pro Ile Ala His Gln Asp Trp Leu Arg Gly Lys Glu Phe Lys Cys
                165                 170                 175

Lys Val His Asn Lys Ala Leu Pro Ala Pro Ile Glu Lys Thr Ile Ser
            180                 185                 190

Lys Ala Arg Gly Gln Pro Leu Glu Pro Lys Val Tyr Thr Met Gly Pro
        195                 200                 205

Pro Arg Glu Glu Leu Ser Ser Arg Ser Val Ser Leu Thr Cys Met Ile
    210                 215                 220

Asn Gly Phe Tyr Pro Ser Asp Ile Ser Val Glu Trp Glu Lys Asn Gly
225                 230                 235                 240

Lys Ala Glu Asp Asn Tyr Lys Thr Thr Pro Ala Val Leu Asp Ser Asp
                245                 250                 255

Gly Ser Tyr Phe Leu Tyr Ser Lys Leu Ser Val Pro Thr Ser Glu Trp
            260                 265                 270

Gln Arg Gly Asp Val Phe Thr Cys Ser Val Met His Glu Ala Leu His
        275                 280                 285

Asn His Tyr Thr Gln Lys Ser Ile Ser Arg Ser Pro Gly Lys
    290                 295                 300


<210> SEQ ID NO 62
<211> LENGTH: 11
<212> TYPE: PRT
<213> ORGANISM: Artificial Sequence
<220> FEATURE:
<223> OTHER INFORMATION: CDR-L1 Q24R

<400> SEQUENCE: 62

Arg Ala Ser Gln Ser Ile Ser Ser Trp Leu Ala
1               5                   10


<210> SEQ ID NO 63
<211> LENGTH: 11
<212> TYPE: PRT
<213> ORGANISM: Artificial Sequence
<220> FEATURE:
<223> OTHER INFORMATION: CDR-L1 Q24K

<400> SEQUENCE: 63

Lys Ala Ser Gln Ser Ile Ser Ser Trp Leu Ala
1               5                   10


<210> SEQ ID NO 64
<211> LENGTH: 330
<212> TYPE: DNA
<213> ORGANISM: Artificial Sequence
<220> FEATURE:
<223> OTHER INFORMATION: 10236 gL6 VL nucl. Q24R

<400> SEQUENCE: 64

gcgtatgaca tgactcagag cccgtccagc ctgtccgcgt ccgtgggaga tcgcgtgact     60
```

-continued

```
atcacgtgtc gggcctcaca atccattagc tcctggctgg cctggtacca gcagaagcca      120

gggaaggctc cgaagctgct gatctacctg gcctccaccc ttgcctccgg cgtgccttca      180

cggttttctg gatccggctc gggaaccgac ttcaccctca ccatctcgtc gctccaaccc      240

gaggacttcg caacctacta ctgccaacag gggtatacca acagcaacat catcaacacc      300

ttcggtggcg gaactaaggt cgaaatcaag                                       330

<210> SEQ ID NO 65
<211> LENGTH: 645
<212> TYPE: DNA
<213> ORGANISM: Artificial Sequence
<220> FEATURE:
<223> OTHER INFORMATION: 10236 gL6 Light Chain nucl. Q24R

<400> SEQUENCE: 65

gcgtatgaca tgactcagag cccgtccagc ctgtccgcgt ccgtgggaga tcgcgtgact      60

atcacgtgtc gggcctcaca atccattagc tcctggctgg cctggtacca gcagaagcca      120

gggaaggctc cgaagctgct gatctacctg gcctccaccc ttgcctccgg cgtgccttca      180

cggttttctg gatccggctc gggaaccgac ttcaccctca ccatctcgtc gctccaaccc      240

gaggacttcg caacctacta ctgccaacag gggtatacca acagcaacat catcaacacc      300

ttcggtggcg gaactaaggt cgaaatcaag gtggccgctc cctccgtgtt catcttccca      360

ccctccgacg agcagctgaa gtccggcacc gcctccgtcg tgtgcctgct gaacaacttc      420

tacccccgcg aggccaaggt gcagtggaag gtggacaacg ccctgcagtc cggcaactcc      480

caggaatccg tcaccgagca ggactccaag gacagcacct actccctgtc ctccaccctg      540

accctgtcca aggccgacta cgagaagcac aaggtgtacg cctgcgaagt gacccaccag      600

ggcctgtcca gccccgtgac caagtccttc aaccggggcg agtgc                     645

<210> SEQ ID NO 66
<211> LENGTH: 330
<212> TYPE: DNA
<213> ORGANISM: Artificial Sequence
<220> FEATURE:
<223> OTHER INFORMATION: 10236 gL6 VL nucl. Q24K

<400> SEQUENCE: 66

gcgtatgaca tgactcagag cccgtccagc ctgtccgcgt ccgtgggaga tcgcgtgact      60

atcacgtgta aggcctcaca atccattagc tcctggctgg cctggtacca gcagaagcca      120

gggaaggctc cgaagctgct gatctacctg gcctccaccc ttgcctccgg cgtgccttca      180

cggttttctg gatccggctc gggaaccgac ttcaccctca ccatctcgtc gctccaaccc      240

gaggacttcg caacctacta ctgccaacag gggtatacca acagcaacat catcaacacc      300

ttcggtggcg gaactaaggt cgaaatcaag                                       330

<210> SEQ ID NO 67
<211> LENGTH: 645
<212> TYPE: DNA
<213> ORGANISM: Artificial Sequence
<220> FEATURE:
<223> OTHER INFORMATION: 10236 gL6 Light Chain nucl. Q24K

<400> SEQUENCE: 67

gcgtatgaca tgactcagag cccgtccagc ctgtccgcgt ccgtgggaga tcgcgtgact      60

atcacgtgta aggcctcaca atccattagc tcctggctgg cctggtacca gcagaagcca      120
```

-continued

```
gggaaggctc cgaagctgct gatctacctg gcctccaccc ttgcctccgg cgtgccttca    180

cggttttctg gatccggctc gggaaccgac ttcaccctca ccatctcgtc gctccaaccc    240

gaggacttcg caacctacta ctgccaacag ggtataccca acagcaacat catcaacacc    300

ttcggtggcg gaactaaggt cgaaatcaag gtggccgctc cctccgtgtt catcttccca    360

ccctccgacg agcagctgaa gtccggcacc gcctccgtcg tgtgcctgct gaacaacttc    420

taccccccgcg aggccaaggt gcagtggaag gtggacaacg ccctgcagtc cggcaactcc    480

caggaatccg tcaccgagca ggactccaag gacagcacct actccctgtc ctccaccctg    540

accctgtcca aggccgacta cgagaagcac aaggtgtacg cctgcgaagt gacccaccag    600

ggcctgtcca gccccgtgac caagtccttc aaccggggcg agtgc                    645
```

<210> SEQ ID NO 68
<211> LENGTH: 13
<212> TYPE: PRT
<213> ORGANISM: Artificial Sequence
<220> FEATURE:
<223> OTHER INFORMATION: 10273 CDR-L1

<400> SEQUENCE: 68

```
Gln Ser Ser Gln Ser Val Tyr Asn Asn Asn Asp Leu Ala
1               5                   10
```

<210> SEQ ID NO 69
<211> LENGTH: 7
<212> TYPE: PRT
<213> ORGANISM: Artificial Sequence
<220> FEATURE:
<223> OTHER INFORMATION: 10273 CDR-L2

<400> SEQUENCE: 69

```
Arg Ala Ser Thr Leu Ala Ser
1               5
```

<210> SEQ ID NO 70
<211> LENGTH: 12
<212> TYPE: PRT
<213> ORGANISM: Artificial Sequence
<220> FEATURE:
<223> OTHER INFORMATION: 10273 CDR-L3

<400> SEQUENCE: 70

```
Leu Gly Gly Tyr Asp Asp Asp Val Asp Thr Tyr Thr
1               5                   10
```

<210> SEQ ID NO 71
<211> LENGTH: 10
<212> TYPE: PRT
<213> ORGANISM: Artificial Sequence
<220> FEATURE:
<223> OTHER INFORMATION: 10273 CDR-H1

<400> SEQUENCE: 71

```
Gly Phe Ser Leu Ser Ser Tyr Gly Met Ser
1               5                   10
```

<210> SEQ ID NO 72
<211> LENGTH: 16
<212> TYPE: PRT
<213> ORGANISM: Artificial Sequence
<220> FEATURE:
<223> OTHER INFORMATION: 10273 CDR-H2

<400> SEQUENCE: 72

Ile Ile Ser Ser Ser Gly Ser Thr Tyr Tyr Ala Ser Trp Ala Lys Gly
1 5 10 15

<210> SEQ ID NO 73
<211> LENGTH: 20
<212> TYPE: PRT
<213> ORGANISM: Artificial Sequence
<220> FEATURE:
<223> OTHER INFORMATION: 10273 CDR-H3
<220> FEATURE:
<221> NAME/KEY: misc_feature
<222> LOCATION: (19)..(19)
<223> OTHER INFORMATION: Xaa can be any naturally occurring amino acid

<400> SEQUENCE: 73

Asp His Ile Tyr Arg Tyr Asp Asp Tyr Gly Asp Tyr Pro Thr Tyr Tyr
1 5 10 15

Gly Met Xaa Pro
20

<210> SEQ ID NO 74
<211> LENGTH: 112
<212> TYPE: PRT
<213> ORGANISM: Artificial Sequence
<220> FEATURE:
<223> OTHER INFORMATION: 10273 Rabbit VL

<400> SEQUENCE: 74

Ala Val Val Leu Thr Gln Thr Pro Ser Pro Met Ser Ala Ala Val Gly
1 5 10 15

Gly Thr Val Thr Ile Ser Cys Gln Ser Ser Gln Ser Val Tyr Asn Asn
20 25 30

Asn Asp Leu Ala Trp Tyr Gln Gln Lys Pro Gly Gln Pro Pro Lys Leu
35 40 45

Leu Ile Tyr Arg Ala Ser Thr Leu Ala Ser Gly Val Pro Ser Arg Phe
50 55 60

Ser Gly Ser Gly Ser Gly Thr Gln Phe Thr Leu Thr Ile Ser Gly Val
65 70 75 80

Gln Cys Asp Asp Ala Ala Thr Tyr Tyr Cys Leu Gly Gly Tyr Asp Asp
85 90 95

Asp Val Asp Thr Tyr Thr Phe Gly Gly Gly Thr Glu Val Val Val Lys
100 105 110

<210> SEQ ID NO 75
<211> LENGTH: 336
<212> TYPE: DNA
<213> ORGANISM: Artificial Sequence
<220> FEATURE:
<223> OTHER INFORMATION: 10273 Rabbit VL nucl.

<400> SEQUENCE: 75
gcagtcgtgc tgactcagac accatcaccc atgtctgcag ctgtgggagg cacagtcacc 60
atcagttgcc agtccagtca gagtgtttat aataataacg acttagcctg gtatcagcag 120
aaaccagggc agcctcctaa gctcctgatc tacagggcat ccactctggc atctggggtc 180
ccgtcgcggt tcagcggcag tggatctggg acacagttca ctctcaccat cagcggcgtg 240
cagtgtgacg atgctgccac ttactactgt ctaggcggtt atgatgatga tgttgatacg 300
tatactttcg gcggagggac cgaggtggtg gtcaaa 336

<210> SEQ ID NO 76

<211> LENGTH: 125
<212> TYPE: PRT
<213> ORGANISM: Artificial Sequence
<220> FEATURE:
<223> OTHER INFORMATION: 10273 VH

<400> SEQUENCE: 76

Gln Ser Val Glu Glu Ser Gly Gly Arg Leu Val Thr Pro Gly Thr Pro
1 5 10 15

Leu Thr Leu Thr Cys Thr Val Ser Gly Phe Ser Leu Ser Ser Tyr Gly
20 25 30

Met Ser Trp Val Arg Gln Ala Pro Gly Lys Gly Leu Glu Trp Ile Gly
35 40 45

Ile Ile Ser Ser Ser Gly Ser Thr Tyr Tyr Ala Ser Trp Ala Lys Gly
50 55 60

Arg Phe Thr Ile Ser Lys Thr Ser Thr Thr Val Asp Leu Lys Ile Ala
65 70 75 80

Ser Pro Thr Thr Glu Asp Thr Ala Thr Tyr Phe Cys Ala Arg Asp His
85 90 95

Ile Tyr Arg Tyr Asp Asp Tyr Gly Asp Tyr Pro Thr Tyr Tyr Gly Met
100 105 110

Asp Pro Trp Gly Pro Gly Thr Leu Val Thr Val Ser Ser
115 120 125

<210> SEQ ID NO 77
<211> LENGTH: 375
<212> TYPE: DNA
<213> ORGANISM: Artificial Sequence
<220> FEATURE:
<223> OTHER INFORMATION: 10273 Rabbit VH nucl.

<400> SEQUENCE: 77
cagtcggtgg aggagtccgg gggtcgcctg gtcacgcctg ggacacccct gacactcacc 60
tgcacagtct ctggattctc cctcagtagc tatggaatga gctgggtccg ccaggctcca 120
gggaaggggc tggaatggat cggaattatt agtagtagtg gtagcacata ctacgcgagc 180
tgggcgaaag gccgattcac catctccaag acctcgacca cggtggatct gaaaatcgcc 240
agtccgacaa ccgaggacac ggccacctat ttctgtgcca gagatcacat ttataggtac 300
gatgactatg gtgattaccc tacctactac ggcatggacc cctggggccc aggcaccctg 360
gtcaccgtct cgagc 375

<210> SEQ ID NO 78
<211> LENGTH: 219
<212> TYPE: PRT
<213> ORGANISM: Artificial Sequence
<220> FEATURE:
<223> OTHER INFORMATION: Rabbit 10273 mIgG Light chain

<400> SEQUENCE: 78

Ala Val Val Leu Thr Gln Thr Pro Ser Pro Met Ser Ala Ala Val Gly
1 5 10 15

Gly Thr Val Thr Ile Ser Cys Gln Ser Ser Gln Ser Val Tyr Asn Asn
20 25 30

Asn Asp Leu Ala Trp Tyr Gln Gln Lys Pro Gly Gln Pro Pro Lys Leu
35 40 45

Leu Ile Tyr Arg Ala Ser Thr Leu Ala Ser Gly Val Pro Ser Arg Phe
50 55 60

Ser Gly Ser Gly Ser Gly Thr Gln Phe Thr Leu Thr Ile Ser Gly Val

-continued

```
65                  70                  75                  80

Gln Cys Asp Asp Ala Ala Thr Tyr Tyr Cys Leu Gly Gly Tyr Asp Asp
                85                  90                  95

Asp Val Asp Thr Tyr Thr Phe Gly Gly Gly Thr Glu Val Val Val Lys
            100                 105                 110

Arg Thr Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Cys
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215


<210> SEQ ID NO 79
<211> LENGTH: 449
<212> TYPE: PRT
<213> ORGANISM: Artificial Sequence
<220> FEATURE:
<223> OTHER INFORMATION: Rabbit 10273 mIgG Heavy Chain

<400> SEQUENCE: 79

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Gly
            20                  25                  30

Met Ser Trp Val Arg Gln Ala Pro Gly Lys Gly Leu Glu Trp Ile Gly
        35                  40                  45

Ile Ile Ser Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Asp His
                85                  90                  95

Ile Tyr Arg Tyr Asp Asp Tyr Gly Asp Tyr Pro Thr Tyr Tyr Gly Met
            100                 105                 110

Asp Pro Trp Gly Pro Gly Thr Leu Val Thr Val Ser Ser Ala Lys Thr
        115                 120                 125

Thr Pro Pro Ser Val Tyr Pro Leu Ala Pro Gly Ser Ala Ala Gln Thr
    130                 135                 140

Asn Ser Met Val Thr Leu Gly Cys Leu Val Lys Gly Tyr Phe Pro Glu
145                 150                 155                 160

Pro Val Thr Val Thr Trp Asn Ser Gly Ser Leu Ser Ser Gly Val His
                165                 170                 175

Thr Phe Pro Ala Val Leu Gln Ser Asp Leu Tyr Thr Leu Ser Ser Ser
            180                 185                 190

Val Thr Val Pro Ser Ser Thr Trp Pro Ser Glu Thr Val Thr Cys Asn
        195                 200                 205

Val Ala His Pro Ala Ser Ser Thr Lys Val Asp Lys Lys Ile Val Pro
```

```
    210                 215                 220

Arg Asp Cys Gly Cys Lys Pro Cys Ile Cys Thr Val Pro Glu Val Ser
225                 230                 235                 240

Ser Val Phe Ile Phe Pro Pro Lys Pro Lys Asp Val Leu Thr Ile Thr
                245                 250                 255

Leu Thr Pro Lys Val Thr Cys Val Val Val Asp Ile Ser Lys Asp Asp
            260                 265                 270

Pro Glu Val Gln Phe Ser Trp Phe Val Asp Asp Val Glu Val His Thr
        275                 280                 285

Ala Gln Thr Gln Pro Arg Glu Glu Gln Phe Asn Ser Thr Phe Arg Ser
    290                 295                 300

Val Ser Glu Leu Pro Ile Met His Gln Asp Trp Leu Asn Gly Lys Glu
305                 310                 315                 320

Phe Lys Cys Arg Val Asn Ser Ala Ala Phe Pro Ala Pro Ile Glu Lys
                325                 330                 335

Thr Ile Ser Lys Thr Lys Gly Arg Pro Lys Ala Pro Gln Val Tyr Thr
            340                 345                 350

Ile Pro Pro Pro Lys Glu Gln Met Ala Lys Asp Lys Val Ser Leu Thr
        355                 360                 365

Cys Met Ile Thr Asp Phe Phe Pro Glu Asp Ile Thr Val Glu Trp Gln
    370                 375                 380

Trp Asn Gly Gln Pro Ala Glu Asn Tyr Lys Asn Thr Gln Pro Ile Met
385                 390                 395                 400

Asp Thr Asp Gly Ser Tyr Phe Val Tyr Ser Lys Leu Asn Val Gln Lys
                405                 410                 415

Ser Asn Trp Glu Ala Gly Asn Thr Phe Thr Cys Ser Val Leu His Glu
            420                 425                 430

Gly Leu His Asn His His Thr Glu Lys Ser Leu Ser His Ser Pro Gly
        435                 440                 445

Lys
```

<210> SEQ ID NO 80
<211> LENGTH: 657
<212> TYPE: DNA
<213> ORGANISM: Artificial Sequence
<220> FEATURE:
<223> OTHER INFORMATION: Rabbit 10273 mIgG Light Chain Nucl.

<400> SEQUENCE: 80

```
gcagtcgtgc tgactcagac accatcaccc atgtctgcag ctgtgggagg cacagtcacc     60

atcagttgcc agtccagtca gagtgtttat aataataacg acttagcctg gtatcagcag    120

aaaccagggc agcctcctaa gctcctgatc tacagggcat ccactctggc atctggggtc    180

ccgtcgcggt tcagcggcag tggatctggg acacagttca ctctcaccat cagcggcgtg    240

cagtgtgacg atgctgccac ttactactgt ctaggcggtt atgatgatga tgttgatacg    300

tatactttcg gcggagggac cgaggtggtg gtcaaacgta cggatgctgc accaactgta    360

tccatcttcc caccatccag tgagcagtta acatctggag gtgcctcagt cgtgtgcttc    420

ttgaacaact tctaccccaa agacatcaat gtcaagtgga agattgatgg cagtgaacga    480

caaaatggcg tcctgaacag ttggactgat caggacagca aagactgcac ctacagcatg    540

agcagcaccc tcacgttgac caaggacgag tatgaacgac ataacagcta tacctgtgag    600

gccactcaca agacatcaac ttcacccatt gtcaagagct tcaacaggaa tgagtgt       657
```

<210> SEQ ID NO 81
<211> LENGTH: 1347
<212> TYPE: DNA
<213> ORGANISM: Artificial Sequence
<220> FEATURE:
<223> OTHER INFORMATION: Rabbit 10273 mIgG Heavy Chain nucl.

<400> SEQUENCE: 81

```
cagtcggtgg aggagtccgg gggtcgcctg gtcacgcctg ggacacccct gacactcacc     60
tgcacagtct ctggattctc cctcagtagc tatggaatga gctgggtccg ccaggctcca    120
gggaaggggc tggaatggat cggaattatt agtagtagtg gtagcacata ctacgcgagc    180
tgggcgaaag gccgattcac catctccaag acctcgacca cggtggatct gaaaatcgcc    240
agtccgacaa ccgaggacac ggccacctat ttctgtgcca gagatcacat ttataggtac    300
gatgactatg gtgattaccc tacctactac ggcatggacc cctggggccc aggcaccctg    360
gtcaccgtct cgagtgccaa aacgacaccc ccatctgtct atccactggc ccctggatct    420
gctgcccaaa ctaactccat ggtgaccctg ggatgcctgg tcaagggcta tttccctgag    480
ccagtgacag tgacctggaa ctctggatcc ctgtccagcg gtgtgcacac cttcccagct    540
gtcctgcagt ctgacctcta cactctgagc agctcagtga ctgtcccctc cagcacctgg    600
cccagcgaga ccgtcacctg caacgttgcc cacccggcca gcagcaccaa ggtggacaag    660
aaaattgtgc ccagggattg tggttgtaag ccttgcatat gtacagtccc agaagtatca    720
tctgtcttca tcttcccccc aaagcccaag gatgtgctca ccattactct gactcctaag    780
gtcacgtgtg ttgtggtaga catcagcaag gatgatcccg aggtccagtt cagctggttt    840
gtagatgatg tggaggtgca cacagctcag acgcaacccc gggaggagca gttcaacagc    900
actttccgct cagtcagtga acttcccatc atgcaccagg actggctcaa tggcaaggag    960
ttcaaatgca gggtcaacag tgcagctttc cctgccccca tcgagaaaac catctccaaa   1020
accaaaggca gaccgaaggc tccacaggtg tacaccattc cacctcccaa ggagcagatg   1080
gccaaggata aagtcagtct gacctgcatg ataacagact tcttccctga agacattact   1140
gtggagtggc agtggaatgg gcagccagcg gagaactaca agaacactca gcccatcatg   1200
gacacagatg gctcttactt cgtctacagc aagctcaatg tgcagaagag caactgggag   1260
gcaggaaata ctttcacctg ctctgtgtta catgagggcc tgcacaacca ccatactgag   1320
aagagcctct cccactctcc tggtaaa                                       1347
```

<210> SEQ ID NO 82
<211> LENGTH: 217
<212> TYPE: PRT
<213> ORGANISM: Artificial Sequence
<220> FEATURE:
<223> OTHER INFORMATION: Rabbit 10236 mIgG Light Chain

<400> SEQUENCE: 82

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80
```

```
Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys Arg Thr
            100                 105                 110

Asp Ala Ala Pro Thr Val Ser Ile Phe Pro Pro Ser Ser Glu Gln Leu
        115                 120                 125

Thr Ser Gly Gly Ala Ser Val Val Cys Phe Leu Asn Asn Phe Tyr Pro
    130                 135                 140

Lys Asp Ile Asn Val Lys Trp Lys Ile Asp Gly Ser Glu Arg Gln Asn
145                 150                 155                 160

Gly Val Leu Asn Ser Trp Thr Asp Gln Asp Ser Lys Asp Cys Thr Tyr
                165                 170                 175

Ser Met Ser Ser Thr Leu Thr Leu Thr Lys Asp Glu Tyr Glu Arg His
            180                 185                 190

Asn Ser Tyr Thr Cys Glu Ala Thr His Lys Thr Ser Thr Ser Pro Ile
        195                 200                 205

Val Lys Ser Phe Asn Arg Asn Glu Cys
    210                 215


<210> SEQ ID NO 83
<211> LENGTH: 438
<212> TYPE: PRT
<213> ORGANISM: Artificial Sequence
<220> FEATURE:
<223> OTHER INFORMATION: Rabbit 10236 mIgG Heavy Chain

<400> SEQUENCE: 83

Gln Ser Val Glu Glu Ser Gly Gly Arg Leu Val Thr Pro Gly Thr Pro
1               5                   10                  15

Leu Thr Leu Thr Cys Thr Val Ser Gly Phe Pro Leu Ser Asn Tyr Ala
            20                  25                  30

Met Ser Trp Val Arg Gln Ala Pro Gly Lys Gly Leu Glu Trp Ile Gly
        35                  40                  45

Asp Ile Tyr Pro Ser Asp Ile Ile Asp Tyr Ala Ser Trp Ala Lys Gly
    50                  55                  60

Arg Phe Thr Ile Ser Gln Thr Ser Thr Thr Val Glu Leu Lys Ile Thr
65                  70                  75                  80

Gly Pro Thr Thr Glu Asp Thr Ala Thr Tyr Phe Cys Ala Arg Asp Asn
                85                  90                  95

Asn Asp Tyr Gly Leu Asp Ile Trp Gly Pro Gly Thr Leu Val Thr Val
            100                 105                 110

Ser Ser Ala Lys Thr Thr Pro Pro Ser Val Tyr Pro Leu Ala Pro Gly
        115                 120                 125

Ser Ala Ala Gln Thr Asn Ser Met Val Thr Leu Gly Cys Leu Val Lys
    130                 135                 140

Gly Tyr Phe Pro Glu Pro Val Thr Val Thr Trp Asn Ser Gly Ser Leu
145                 150                 155                 160

Ser Ser Gly Val His Thr Phe Pro Ala Val Leu Gln Ser Asp Leu Tyr
                165                 170                 175

Thr Leu Ser Ser Ser Val Thr Val Pro Ser Ser Thr Trp Pro Ser Glu
            180                 185                 190

Thr Val Thr Cys Asn Val Ala His Pro Ala Ser Ser Thr Lys Val Asp
        195                 200                 205

Lys Lys Ile Val Pro Arg Asp Cys Gly Cys Lys Pro Cys Ile Cys Thr
    210                 215                 220
```

```
Val Pro Glu Val Ser Ser Val Phe Ile Phe Pro Pro Lys Pro Lys Asp
225                 230                 235                 240

Val Leu Thr Ile Thr Leu Thr Pro Lys Val Thr Cys Val Val Val Asp
                245                 250                 255

Ile Ser Lys Asp Asp Pro Glu Val Gln Phe Ser Trp Phe Val Asp Asp
            260                 265                 270

Val Glu Val His Thr Ala Gln Thr Gln Pro Arg Glu Glu Gln Phe Asn
        275                 280                 285

Ser Thr Phe Arg Ser Val Ser Glu Leu Pro Ile Met His Gln Asp Trp
    290                 295                 300

Leu Asn Gly Lys Glu Phe Lys Cys Arg Val Asn Ser Ala Ala Phe Pro
305                 310                 315                 320

Ala Pro Ile Glu Lys Thr Ile Ser Lys Thr Lys Gly Arg Pro Lys Ala
                325                 330                 335

Pro Gln Val Tyr Thr Ile Pro Pro Pro Lys Glu Gln Met Ala Lys Asp
            340                 345                 350

Lys Val Ser Leu Thr Cys Met Ile Thr Asp Phe Phe Pro Glu Asp Ile
        355                 360                 365

Thr Val Glu Trp Gln Trp Asn Gly Gln Pro Ala Glu Asn Tyr Lys Asn
    370                 375                 380

Thr Gln Pro Ile Met Asp Thr Asp Gly Ser Tyr Phe Val Tyr Ser Lys
385                 390                 395                 400

Leu Asn Val Gln Lys Ser Asn Trp Glu Ala Gly Asn Thr Phe Thr Cys
                405                 410                 415

Ser Val Leu His Glu Gly Leu His Asn His His Thr Glu Lys Ser Leu
            420                 425                 430

Ser His Ser Pro Gly Lys
        435
```

<210> SEQ ID NO 84
<211> LENGTH: 651
<212> TYPE: DNA
<213> ORGANISM: Artificial Sequence
<220> FEATURE:
<223> OTHER INFORMATION: Rabbit 10236 mIgG Light Chain nucl.

<400> SEQUENCE: 84

```
gcctatgata tgacccagac tccagcctct gtggaggtag ctgtgggagg cacagtcacc     60

atcaagtgcc aggccagtca gagcattagc agttggttag cctggtatca gcagaaacca    120

ggtcagcctc ccaagctcct gatctatctg gcatccactc tggcatctgg ggtctcatcg    180

cggttcaaag gcagtggatc tgggacacag ttcactctca ccatcagcgg cgtggagtgt    240

gccgatgctg ccacttacta ctgtcaacag ggttatacta atagtaatat tattaatact    300

ttcggcggag ggaccgaggt ggtggtcaaa cgtacggatg ctgcaccaac tgtatccatc    360

ttcccaccat ccagtgagca gttaacatct ggaggtgcct cagtcgtgtg cttcttgaac    420

aacttctacc ccaaagacat caatgtcaag tggaagattg atggcagtga acgacaaaat    480

ggcgtcctga acagttggac tgatcaggac agcaaagact gcacctacag catgagcagc    540

accctcacgt tgaccaagga cgagtatgaa cgacataaca gctatacctg tgaggccact    600

cacaagacat caacttcacc cattgtcaag agcttcaaca ggaatgagtg t             651
```

<210> SEQ ID NO 85
<211> LENGTH: 1386
<212> TYPE: DNA

<213> ORGANISM: Artificial Sequence
<220> FEATURE:
<223> OTHER INFORMATION: Rabbit 10236 mIgG Heavy Chain nucl.

<400> SEQUENCE: 85
cagtcggtgg aggagtccgg gggtcgcctg gtcacgcctg ggacacccct gacactcacc 60
tgcaccgtct ctgggttccc cctcagtaat tatgcaatga gctgggtccg ccaggctcca 120
gggaaggggc tggaatggat cggagacatt tatcctagtg atatcataga ctacgcgagc 180
tgggcgaaag gccgattcac catctcccaa acctcgacca cggtggagct gaaaatcacg 240
ggtccgacaa ccgaggacac ggccacctat ttctgtgcca gagacaacaa tgactatggt 300
ctggacatct ggggcccagg caccctggtc accgtctcga gtgccaaaac gacaccccca 360
tctgtctatc cactggcccc tggatctgct gcccaaacta actccatggt gaccctggga 420
tgcctggtca agggctattt ccctgagcca gtgacagtga cctggaactc tggatccctg 480
tccagcggtg tgcacacctt cccagctgtc ctgcagtctg acctctacac tctgagcagc 540
tcagtgactg tcccctccag cacctggccc agcgagaccg tcacctgcaa cgttgcccac 600
ccggccagca gcaccaaggt ggacaagaaa attgtgccca gggattgtgg ttgtaagcct 660
tgcatatgta cagtcccaga agtatcatct gtcttcatct tccccccaaa gcccaaggat 720
gtgctcacca ttactctgac tcctaaggtc acgtgtgttg tggtagacat cagcaaggat 780
gatcccgagg tccagttcag ctggtttgta gatgatgtgg aggtgcacac agctcagacg 840
caaccccggg aggagcagtt caacagcact ttccgctcag tcagtgaact tcccatcatg 900
caccaggact ggctcaatgg caaggagttc aaatgcaggg tcaacagtgc agctttccct 960
gcccccatcg agaaaaccat ctccaaaacc aaaggcagac cgaaggctcc acaggtgtac 1020
accattccac ctcccaagga gcagatggcc aaggataaag tcagtctgac ctgcatgata 1080
acagacttct tccctgaaga cattactgtg gagtggcagt ggaatgggca gccagcggag 1140
aactacaaga acactcagcc catcatggac acagatggct cttacttcgt ctacagcaag 1200
ctcaatgtgc agaagagcaa ctgggaggca ggaaatactt tcacctgctc tgtgttacat 1260
gagggcctgc acaaccacca tactgagaag agcctctccc actctcctgg taaatgatcc 1320
cagtgtcctt ggagccctct ggtcctacag gactctgaca cctacctcca cccctccctg 1380
tataaa 1386

<210> SEQ ID NO 86
<211> LENGTH: 214
<212> TYPE: PRT
<213> ORGANISM: Artificial Sequence
<220> FEATURE:
<223> OTHER INFORMATION: 10236 Light chain Fab

<400> SEQUENCE: 86

Ala Tyr Asp Met Thr Gln Thr Pro Ala Ser Val Glu Val Ala Val Gly
1 5 10 15

Gly Thr Val Thr Ile Lys Cys Gln Ala Ser Gln Ser Ile Ser Ser Trp
20 25 30

Leu Ala Trp Tyr Gln Gln Lys Pro Gly Gln Pro Pro Lys Leu Leu Ile
35 40 45

Tyr Leu Ala Ser Thr Leu Ala Ser Gly Val Ser Ser Arg Phe Lys Gly
50 55 60

Ser Gly Ser Gly Thr Gln Phe Thr Leu Thr Ile Ser Gly Val Glu Cys
65 70 75 80

-continued

```
Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys Arg Thr
            100                 105                 110

Pro Val Ala Pro Thr Val Leu Ile Phe Pro Pro Ala Ala Asp Gln Val
        115                 120                 125

Ala Thr Gly Thr Val Thr Ile Val Cys Val Ala Asn Lys Tyr Phe Pro
    130                 135                 140

Asp Val Thr Val Thr Trp Glu Val Asp Gly Thr Thr Gln Thr Thr Gly
145                 150                 155                 160

Ile Glu Asn Ser Lys Thr Pro Gln Asn Ser Ala Asp Cys Thr Tyr Asn
                165                 170                 175

Leu Ser Ser Thr Leu Thr Leu Thr Ser Thr Gln Tyr Asn Ser His Lys
            180                 185                 190

Glu Tyr Thr Cys Lys Val Thr Gln Gly Thr Thr Ser Val Val Gln Ser
        195                 200                 205

Phe Asn Arg Gly Asp Cys
    210
```

<210> SEQ ID NO 87
<211> LENGTH: 642
<212> TYPE: DNA
<213> ORGANISM: Artificial Sequence
<220> FEATURE:
<223> OTHER INFORMATION: 10236 Light Chain Fab nucl.

<400> SEQUENCE: 87

```
gcctatgata tgacccagac tccagcctct gtggaggtag ctgtgggagg cacagtcacc     60

atcaagtgcc aggccagtca gagcattagc agttggttag cctggtatca gcagaaacca    120

ggtcagcctc ccaagctcct gatctatctg gcatccactc tggcatctgg ggtctcatcg    180

cggttcaaag gcagtggatc tgggacacag ttcactctca ccatcagcgg cgtggagtgt    240

gccgatgctg ccacttacta ctgtcaacag ggttatacta atagtaatat tattaatact    300

ttcggcggag ggaccgaggt ggtggtcaaa cgtacgccag ttgcacctac tgtcctcatc    360

ttcccaccag ctgctgatca ggtggcaact ggaacagtca ccatcgtgtg tgtggcgaat    420

aaatactttc ccgatgtcac cgtcacctgg gaggtggatg gcaccaccca aacaactggc    480

atcgagaaca gtaaaacacc gcagaattct gcagattgta cctacaacct cagcagcact    540

ctgacactga ccagcacaca gtacaacagc cacaaagagt acacctgcaa ggtgacccag    600

ggcacgacct cagtcgtcca gagcttcaat aggggtgact gt                       642
```

<210> SEQ ID NO 88
<211> LENGTH: 217
<212> TYPE: PRT
<213> ORGANISM: Artificial Sequence
<220> FEATURE:
<223> OTHER INFORMATION: 10236 Heavy Chain Fab

<400> SEQUENCE: 88

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Pro Leu Ser Asn Tyr Ala
            20                  25                  30

Met Ser Trp Val Arg Gln Ala Pro Gly Lys Gly Leu Glu Trp Ile Gly
        35                  40                  45

Asp Ile Tyr Pro Ser Asp Ile Ile Asp Tyr Ala Ser Trp Ala Lys Gly
```

```
    50                  55                  60

Arg Phe Thr Ile Ser Gln Thr Ser Thr Thr Val Glu Leu Lys Ile Thr
65                  70                  75                  80

Gly Pro Thr Thr Glu Asp Thr Ala Thr Tyr Phe Cys Ala Arg Asp Asn
                85                  90                  95

Asn Asp Tyr Gly Leu Asp Ile Trp Gly Pro Gly Thr Leu Val Thr Val
            100                 105                 110

Ser Ser Gly Gln Pro Lys Ala Pro Ser Val Phe Pro Leu Ala Pro Cys
        115                 120                 125

Cys Gly Asp Thr Pro Ser Ser Thr Val Thr Leu Gly Cys Leu Val Lys
    130                 135                 140

Gly Tyr Leu Pro Glu Pro Val Thr Val Thr Trp Asn Ser Gly Thr Leu
145                 150                 155                 160

Thr Asn Gly Val Arg Thr Phe Pro Ser Val Arg Gln Ser Ser Gly Leu
                165                 170                 175

Tyr Ser Leu Ser Ser Val Val Ser Val Thr Ser Ser Ser Gln Pro Val
            180                 185                 190

Thr Cys Asn Val Ala His Pro Ala Thr Asn Thr Lys Val Asp Lys Thr
        195                 200                 205

Val Ala Pro Ser Thr Cys Ser Lys Pro
    210                 215
```

<210> SEQ ID NO 89
<211> LENGTH: 651
<212> TYPE: DNA
<213> ORGANISM: Artificial Sequence
<220> FEATURE:
<223> OTHER INFORMATION: 10236 Heavy Chain Fab nucl.

<400> SEQUENCE: 89

```
cagtcggtgg aggagtccgg gggtcgcctg gtcacgcctg ggacacccct gacactcacc     60

tgcaccgtct ctgggttccc cctcagtaat tatgcaatga gctgggtccg ccaggctcca    120

gggaaggggc tggaatggat cggagacatt tatcctagtg atatcataga ctacgcgagc    180

tgggcgaaag gccgattcac catctcccaa acctcgacca cggtggagct gaaaatcacg    240

ggtccgacaa ccgaggacac ggccacctat ttctgtgcca gagacaacaa tgactatggt    300

ctggacatct ggggcccagg caccctggtc accgtctcga gtgggcaacc taaggctcca    360

tcagtcttcc cactggcccc ctgctgcggg gacacaccca gctccacggt gaccctgggc    420

tgcctggtca aaggctacct cccggagcca gtgaccgtga cctggaactc gggcaccctc    480

accaatgggg tacgcacctt cccgtccgtc cggcagtcct caggcctcta ctcgctgagc    540

agcgtggtga gcgtgacctc aagcagccag cccgtcacct gcaacgtggc ccacccagcc    600

accaacacca aagtggacaa gaccgttgcg ccctcgacat gcagcaagcc c             651
```

<210> SEQ ID NO 90
<211> LENGTH: 216
<212> TYPE: PRT
<213> ORGANISM: Artificial Sequence
<220> FEATURE:
<223> OTHER INFORMATION: 10273 Light Chain Fab

<400> SEQUENCE: 90

```
Ala Val Val Leu Thr Gln Thr Pro Ser Pro Met Ser Ala Ala Val Gly
1               5                   10                  15

Gly Thr Val Thr Ile Ser Cys Gln Ser Ser Gln Ser Val Tyr Asn Asn
            20                  25                  30
```

```
Asn Asp Leu Ala Trp Tyr Gln Gln Lys Pro Gly Gln Pro Pro Lys Leu
        35                  40                  45

Leu Ile Tyr Arg Ala Ser Thr Leu Ala Ser Gly Val Pro Ser Arg Phe
    50                  55                  60

Ser Gly Ser Gly Ser Gly Thr Gln Phe Thr Leu Thr Ile Ser Gly Val
65                  70                  75                  80

Gln Cys Asp Asp Ala Ala Thr Tyr Tyr Cys Leu Gly Gly Tyr Asp Asp
                85                  90                  95

Asp Val Asp Thr Tyr Thr Phe Gly Gly Gly Thr Glu Val Val Val Lys
            100                 105                 110

Arg Thr Pro Val Ala Pro Thr Val Leu Ile Phe Pro Pro Ala Ala Asp
        115                 120                 125

Gln Val Ala Thr Gly Thr Val Thr Ile Val Cys Val Ala Asn Lys Tyr
    130                 135                 140

Phe Pro Asp Val Thr Val Thr Trp Glu Val Asp Gly Thr Thr Gln Thr
145                 150                 155                 160

Thr Gly Ile Glu Asn Ser Lys Thr Pro Gln Asn Ser Ala Asp Cys Thr
                165                 170                 175

Tyr Asn Leu Ser Ser Thr Leu Thr Leu Thr Ser Thr Gln Tyr Asn Ser
            180                 185                 190

His Lys Glu Tyr Thr Cys Lys Val Thr Gln Gly Thr Thr Ser Val Val
        195                 200                 205

Gln Ser Phe Asn Arg Gly Asp Cys
    210                 215
```

<210> SEQ ID NO 91
<211> LENGTH: 648
<212> TYPE: DNA
<213> ORGANISM: Artificial Sequence
<220> FEATURE:
<223> OTHER INFORMATION: 10273 Light Chain Fab nucl.

<400> SEQUENCE: 91

```
gcagtcgtgc tgactcagac accatcaccc atgtctgcag ctgtgggagg cacagtcacc      60

atcagttgcc agtccagtca gagtgtttat aataataacg acttagcctg gtatcagcag     120

aaaccagggc agcctcctaa gctcctgatc tacagggcat ccactctggc atctggggtc     180

ccgtcgcggt tcagcggcag tggatctggg acacagttca ctctcaccat cagcggcgtg     240

cagtgtgacg atgctgccac ttactactgt ctaggcggtt atgatgatga tgttgatacg     300

tatactttcg gcggagggac cgaggtggtg gtcaaacgta cgccagttgc acctactgtc     360

ctcatcttcc caccagctgc tgatcaggtg gcaactggaa cagtcaccat cgtgtgtgtg     420

gcgaataaat actttcccga tgtcaccgtc acctgggagg tggatggcac cacccaaaca     480

actggcatcg agaacagtaa aacaccgcag aattctgcag attgtaccta caacctcagc     540

agcactctga cactgaccag cacacagtac aacagccaca aagagtacac ctgcaaggtg     600

acccagggca cgacctcagt cgtccagagc ttcaataggg gtgactgt                  648
```

<210> SEQ ID NO 92
<211> LENGTH: 228
<212> TYPE: PRT
<213> ORGANISM: Artificial Sequence
<220> FEATURE:
<223> OTHER INFORMATION: 10273 Heavy Chain Fab

<400> SEQUENCE: 92

-continued

```
Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Gly
            20                  25                  30

Met Ser Trp Val Arg Gln Ala Pro Gly Lys Gly Leu Glu Trp Ile Gly
        35                  40                  45

Ile Ile Ser Ser Ser Gly Ser Thr Tyr Tyr Ala Ser Trp Ala Lys Gly
    50                  55                  60

Arg Phe Thr Ile Ser Lys Thr Ser Thr Thr Val Asp Leu Lys Ile Ala
65                  70                  75                  80

Ser Pro Thr Thr Glu Asp Thr Ala Thr Tyr Phe Cys Ala Arg Asp His
                85                  90                  95

Ile Tyr Arg Tyr Asp Asp Tyr Gly Asp Tyr Pro Thr Tyr Tyr Gly Met
            100                 105                 110

Asp Pro Trp Gly Pro Gly Thr Leu Val Thr Val Ser Ser Gly Gln Pro
        115                 120                 125

Lys Ala Pro Ser Val Phe Pro Leu Ala Pro Cys Cys Gly Asp Thr Pro
    130                 135                 140

Ser Ser Thr Val Thr Leu Gly Cys Leu Val Lys Gly Tyr Leu Pro Glu
145                 150                 155                 160

Pro Val Thr Val Thr Trp Asn Ser Gly Thr Leu Thr Asn Gly Val Arg
                165                 170                 175

Thr Phe Pro Ser Val Arg Gln Ser Ser Gly Leu Tyr Ser Leu Ser Ser
            180                 185                 190

Val Val Ser Val Thr Ser Ser Ser Gln Pro Val Thr Cys Asn Val Ala
        195                 200                 205

His Pro Ala Thr Asn Thr Lys Val Asp Lys Thr Val Ala Pro Ser Thr
    210                 215                 220

Cys Ser Lys Pro
225
```

<210> SEQ ID NO 93
<211> LENGTH: 684
<212> TYPE: DNA
<213> ORGANISM: Artificial Sequence
<220> FEATURE:
<223> OTHER INFORMATION: 10273 Heavy Chain Fab nucl.

<400> SEQUENCE: 93

```
cagtcggtgg aggagtccgg gggtcgcctg gtcacgcctg ggacacccct gacactcacc     60

tgcacagtct ctggattctc cctcagtagc tatggaatga gctgggtccg ccaggctcca    120

gggaaggggc tggaatggat cggaattatt agtagtagtg gtagcacata ctacgcgagc    180

tgggcgaaag gccgattcac catctccaag acctcgacca cggtggatct gaaaatcgcc    240

agtccgacaa ccgaggacac ggccacctat ttctgtgcca gagatcacat ttataggtac    300

gatgactatg gtgattaccc tacctactac ggcatggacc cctggggccc aggcaccctg    360

gtcaccgtct cgagtgggca acctaaggct ccatcagtct tcccactggc cccctgctgc    420

ggggacacac ccagctccac ggtgaccctg ggctgcctgg tcaaaggcta cctcccggag    480

ccagtgaccg tgacctggaa ctcgggcacc ctcaccaatg ggtacgcac cttcccgtcc     540

gtccggcagt cctcaggcct ctactcgctg agcagcgtgg tgagcgtgac ctcaagcagc    600

cagcccgtca cctgcaacgt ggcccaccca gccaccaaca ccaaagtgga caagaccgtt    660

gcgccctcga catgcagcaa gccc                                           684
```

```
<210> SEQ ID NO 94
<211> LENGTH: 316
<212> TYPE: PRT
<213> ORGANISM: Artificial Sequence
<220> FEATURE:
<223> OTHER INFORMATION: Human LEKTI D5 Fab H chain

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Gly Gly Gly Gly Ser Gly
65                  70                  75                  80

Gly Gly Gly Ser Arg Glu Ile Val Lys Leu Cys Ser Gln Tyr Gln Asn
                85                  90                  95

Gln Ala Lys Asn Gly Ile Leu Phe Cys Thr Arg Glu Asn Asp Pro Ile
            100                 105                 110

Arg Gly Pro Asp Gly Lys Met His Gly Asn Leu Cys Ser Met Cys Gln
        115                 120                 125

Ala Tyr Phe Gln Ala Glu Asn Glu Glu Lys Lys Lys Ala Glu Ala Arg
    130                 135                 140

Ala Arg Ser Gly Gly Gly Gly Gly Gly Gly Gly Ser Lys Asn Thr Val
145                 150                 155                 160

Tyr Leu Gln Met Asn Ser Leu Arg Ala Glu Asp Thr Ala Val Tyr Tyr
                165                 170                 175

Cys Ala Arg Thr Val Pro Gly Tyr Ser Thr Ala Pro Tyr Phe Asp Leu
            180                 185                 190

Trp Gly Gln Gly Thr Leu Val Thr Val Ser Ser Ala Ser Thr Lys Gly
        195                 200                 205

Pro Ser Val Phe Pro Leu Ala Pro Ser Ser Lys Ser Thr Ser Gly Gly
    210                 215                 220

Thr Ala Ala Leu Gly Cys Leu Val Lys Asp Tyr Phe Pro Glu Pro Val
225                 230                 235                 240

Thr Val Ser Trp Asn Ser Gly Ala Leu Thr Ser Gly Val His Thr Phe
                245                 250                 255

Pro Ala Val Leu Gln Ser Ser Gly Leu Tyr Ser Leu Ser Ser Val Val
            260                 265                 270

Thr Val Pro Ser Ser Ser Leu Gly Thr Gln Thr Tyr Ile Cys Asn Val
        275                 280                 285

Asn His Lys Pro Ser Asn Thr Lys Val Asp Lys Lys Val Glu Pro Lys
    290                 295                 300

Ser Cys His His His His His His His His His His
305                 310                 315


<210> SEQ ID NO 95
<211> LENGTH: 217
<212> TYPE: PRT
<213> ORGANISM: Artificial Sequence
<220> FEATURE:
<223> OTHER INFORMATION: Human LEKTI D5 Fab L chain

<400> SEQUENCE: 95
```

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215
```

<210> SEQ ID NO 96
<211> LENGTH: 217
<212> TYPE: PRT
<213> ORGANISM: Artificial Sequence
<220> FEATURE:
<223> OTHER INFORMATION: Rabbit/human chimeric chain (hCK S171C) 10236

<400> SEQUENCE: 96

```
Ala Tyr Asp Met Thr Gln Thr Pro Ala Ser Val Glu Val Ala Val Gly
1               5                   10                  15

Gly Thr Val Thr Ile Lys Cys Gln Ala Ser Gln Ser Ile Ser Ser Trp
            20                  25                  30

Leu Ala Trp Tyr Gln Gln Lys Pro Gly Gln Pro Pro Lys Leu Leu Ile
        35                  40                  45

Tyr Leu Ala Ser Thr Leu Ala Ser Gly Val Ser Ser Arg Phe Lys Gly
    50                  55                  60

Ser Gly Ser Gly Thr Gln Phe Thr Leu Thr Ile Ser Gly Val Glu Cys
65                  70                  75                  80

Ala Asp Ala Ala Thr Tyr Tyr Cys Gln Gln Gly Tyr Thr Asn Ser Asn
                85                  90                  95

Ile Ile Asn Thr Phe Gly Gly Gly Thr Glu Val Val Val Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140
```

-continued

Arg Glu Ala Lys Val Gln Trp Lys Val Asp Asn Ala Leu Gln Ser Gly
145 150 155 160

Asn Ser Gln Glu Ser Val Thr Glu Gln Asp Ser Lys Asp Cys Thr Tyr
165 170 175

Ser Leu Ser Ser Thr Leu Thr Leu Ser Lys Ala Asp Tyr Glu Lys His
180 185 190

Lys Val Tyr Ala Cys Glu Val Thr His Gln Gly Leu Ser Ser Pro Val
195 200 205

Thr Lys Ser Phe Asn Arg Gly Glu Cys
210 215

<210> SEQ ID NO 97
<211> LENGTH: 441
<212> TYPE: PRT
<213> ORGANISM: Artificial Sequence
<220> FEATURE:
<223> OTHER INFORMATION: Rabbit/human chimeric heavy chain 10236

<400> SEQUENCE: 97

Gln Ser Val Glu Glu Ser Gly Gly Arg Leu Val Thr Pro Gly Thr Pro
1 5 10 15

Leu Thr Leu Thr Cys Thr Val Ser Gly Phe Pro Leu Ser Asn Tyr Ala
20 25 30

Met Ser Trp Val Arg Gln Ala Pro Gly Lys Gly Leu Glu Trp Ile Gly
35 40 45

Asp Ile Tyr Pro Ser Asp Ile Ile Asp Tyr Ala Ser Trp Ala Lys Gly
50 55 60

Arg Phe Thr Ile Ser Gln Thr Ser Thr Thr Val Glu Leu Lys Ile Thr
65 70 75 80

Gly Pro Thr Thr Glu Asp Thr Ala Thr Tyr Phe Cys Ala Arg Asp Asn
85 90 95

Asn Asp Tyr Gly Leu Asp Ile Trp Gly Pro Gly Thr Leu Val Thr Val
100 105 110

Ser Ser Ala Ser Thr Lys Gly Pro Ser Val Phe Pro Leu Ala Pro Cys
115 120 125

Ser Arg Ser Thr Ser Glu Ser Thr Ala Ala Leu Gly Cys Leu Val Lys
130 135 140

Asp Tyr Phe Pro Glu Pro Val Thr Val Ser Trp Asn Ser Gly Ala Leu
145 150 155 160

Thr Ser Gly Val His Thr Phe Pro Ala Val Leu Gln Ser Ser Gly Leu
165 170 175

Tyr Ser Leu Ser Ser Val Val Thr Val Pro Ser Ser Ser Leu Gly Thr
180 185 190

Lys Thr Tyr Thr Cys Asn Val Asp His Lys Pro Ser Asn Thr Lys Val
195 200 205

Asp Lys Arg Val Glu Ser Lys Tyr Gly Pro Pro Cys Pro Pro Cys Pro
210 215 220

Ala Pro Glu Phe Leu Gly Gly Pro Ser Val Phe Leu Phe Pro Pro Lys
225 230 235 240

Pro Lys Asp Thr Leu Met Ile Ser Arg Thr Pro Glu Val Thr Cys Val
245 250 255

Val Val Asp Val Ser Gln Glu Asp Pro Glu Val Gln Phe Asn Trp Tyr
260 265 270

Val Asp Gly Val Glu Val His Asn Ala Lys Thr Lys Pro Arg Glu Glu
275 280 285

```
Gln Phe Asn Ser Thr Tyr Arg Val Val Ser Val Leu Thr Val Leu His
    290                 295                 300

Gln Asp Trp Leu Asn Gly Lys Glu Tyr Lys Cys Lys Val Ser Asn Lys
305                 310                 315                 320

Gly Leu Pro Ser Ser Ile Glu Lys Thr Ile Ser Lys Ala Lys Gly Gln
                325                 330                 335

Pro Arg Glu Pro Gln Val Tyr Thr Leu Pro Pro Ser Gln Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Arg Leu Thr Val Asp Lys Ser Arg Trp Gln Glu Gly Asn Val
                405                 410                 415

Phe Ser Cys Ser Val Met His Glu Ala Leu His Asn His Tyr Thr Gln
            420                 425                 430

Lys Ser Leu Ser Leu Ser Leu Gly Lys
        435                 440


<210> SEQ ID NO 98
<211> LENGTH: 308
<212> TYPE: PRT
<213> ORGANISM: Artificial Sequence
<220> FEATURE:
<223> OTHER INFORMATION: LEKTI-D5-Fc TEV

<400> SEQUENCE: 98

Glu Ile Val Lys Leu Cys Ser Gln Tyr Gln Asn Gln Ala Lys Asn Gly
1               5                   10                  15

Ile Leu Phe Cys Thr Arg Glu Asn Asp Pro Ile Arg Gly Pro Asp Gly
            20                  25                  30

Lys Met His Gly Asn Leu Cys Ser Met Cys Gln Ala Tyr Phe Gln Ala
        35                  40                  45

Glu Asn Glu Glu Lys Lys Lys Ala Glu Ala Arg Ala Arg Asn Leu Glu
    50                  55                  60

Glu Asn Leu Tyr Phe Gln Gly Val Asp Lys Lys Val Glu Pro Lys Ser
65                  70                  75                  80

Cys Asp Lys Thr His Thr Cys Pro Pro Cys Pro Ala Pro Glu Leu Leu
                85                  90                  95

Gly Gly Pro Ser Val Phe Leu Phe Pro Pro Lys Pro Lys Asp Thr Leu
            100                 105                 110

Met Ile Ser Arg Thr Pro Glu Val Thr Cys Val Val Val Asp Val Ser
        115                 120                 125

His Glu Asp Pro Glu Val Lys Phe Asn Trp Tyr Val Asp Gly Val Glu
    130                 135                 140

Val His Asn Ala Lys Thr Lys Pro Arg Glu Glu Gln Tyr Asn Ser Thr
145                 150                 155                 160

Tyr Arg Val Val Ser Val Leu Thr Val Leu His Gln Asp Trp Leu Asn
                165                 170                 175

Gly Lys Glu Tyr Lys Cys Lys Val Ser Asn Lys Ala Leu Pro Ala Pro
            180                 185                 190

Ile Glu Lys Thr Ile Ser Lys Ala Lys Gly Gln Pro Arg Glu Pro Gln
        195                 200                 205
```

Val Tyr Thr Leu Pro Pro Ser Arg Asp Glu Leu Thr Lys Asn Gln Val
    210                 215                 220

Ser Leu Thr Cys Leu Val Lys Gly Phe Tyr Pro Ser Asp Ile Ala Val
225                 230                 235                 240

Glu Trp Glu Ser Asn Gly Gln Pro Glu Asn Asn Tyr Lys Thr Thr Pro
                245                 250                 255

Pro Val Leu Asp Ser Asp Gly Ser Phe Phe Leu Tyr Ser Lys Leu Thr
            260                 265                 270

Val Asp Lys Ser Arg Trp Gln Gln Gly Asn Val Phe Ser Cys Ser Val
        275                 280                 285

Met His Glu Ala Leu His Asn His Tyr Thr Gln Lys Ser Leu Ser Leu
    290                 295                 300

Ser Pro Gly Lys
305

<210> SEQ ID NO 99
<211> LENGTH: 315
<212> TYPE: PRT
<213> ORGANISM: Artificial Sequence
<220> FEATURE:
<223> OTHER INFORMATION: LEKTI-D8Fc TEV

<400> SEQUENCE: 99

Glu Ala Ala Lys Glu Ile Cys Ser Glu Phe Arg Asp Gln Val Arg Asn
1               5                   10                  15

Gly Thr Leu Ile Cys Thr Arg Glu His Asn Pro Val Arg Gly Pro Asp
            20                  25                  30

Gly Lys Met His Gly Asn Lys Cys Ala Met Cys Ala Ser Val Phe Lys
        35                  40                  45

Leu Glu Glu Glu Glu Lys Lys Asn Asp Lys Glu Glu Lys Gly Lys Val
    50                  55                  60

Glu Ala Glu Lys Val Leu Glu Glu Asn Leu Tyr Phe Gln Gly Val Asp
65                  70                  75                  80

Lys Lys Val Glu Pro Lys Ser Cys Asp Lys Thr His Thr Cys Pro Pro
                85                  90                  95

Cys Pro Ala Pro Glu Leu Leu Gly Gly Pro Ser Val Phe Leu Phe Pro
            100                 105                 110

Pro Lys Pro Lys Asp Thr Leu Met Ile Ser Arg Thr Pro Glu Val Thr
        115                 120                 125

Cys Val Val Val Asp Val Ser His Glu Asp Pro Glu Val Lys Phe Asn
    130                 135                 140

Trp Tyr Val Asp Gly Val Glu Val His Asn Ala Lys Thr Lys Pro Arg
145                 150                 155                 160

Glu Glu Gln Tyr Asn Ser Thr Tyr Arg Val Val Ser Val Leu Thr Val
                165                 170                 175

Leu His Gln Asp Trp Leu Asn Gly Lys Glu Tyr Lys Cys Lys Val Ser
            180                 185                 190

Asn Lys Ala Leu Pro Ala Pro Ile Glu Lys Thr Ile Ser Lys Ala Lys
        195                 200                 205

Gly Gln Pro Arg Glu Pro Gln Val Tyr Thr Leu Pro Pro Ser Arg Asp
    210                 215                 220

Glu Leu Thr Lys Asn Gln Val Ser Leu Thr Cys Leu Val Lys Gly Phe
225                 230                 235                 240

Tyr Pro Ser Asp Ile Ala Val Glu Trp Glu Ser Asn Gly Gln Pro Glu
                245                 250                 255

-continued

```
Asn Asn Tyr Lys Thr Thr Pro Pro Val Leu Asp Ser Asp Gly Ser Phe
            260                 265                 270

Phe Leu Tyr Ser Lys Leu Thr Val Asp Lys Ser Arg Trp Gln Gln Gly
            275                 280                 285

Asn Val Phe Ser Cys Ser Val Met His Glu Ala Leu His Asn His Tyr
            290                 295                 300

Thr Gln Lys Ser Leu Ser Leu Ser Pro Gly Lys
305                 310                 315

<210> SEQ ID NO 100
<211> LENGTH: 651
<212> TYPE: DNA
<213> ORGANISM: Artificial Sequence
<220> FEATURE:
<223> OTHER INFORMATION: 10236 gL5 Light Chain nucl. Minus RS

<400> SEQUENCE: 100

gcgtatgaca tgactcagag cccgtccagc ctgtccgcgt ccgtgggaga tcgcgtgact      60

atcacgtgtc aggcctcaca atccattagc tcctggctgg cctggtacca gcagaagcca     120

gggaaggctc cgaagctgct gatctacctg gcctccaccc ttgcctccgg cgtgccttca     180

cggtttaaag gatccggctc gggaaccgac ttcaccctca ccatctcgtc gctccaaccc     240

gaggacttcg caacctacta ctgccaacag gggtatacca acagcaacat catcaacacc     300

ttcggtggcg gaactaaggt cgaaatcaag cgtacggtgg ccgctccctc cgtgttcatc     360

ttcccaccct ccgacgagca gctgaagtcc ggcaccgcct ccgtcgtgtg cctgctgaac     420

aacttctacc cccgcgaggc caaggtgcag tggaaggtgg acaacgccct gcagtccggc     480

aactcccagg aatccgtcac cgagcaggac tccaaggaca gcacctactc cctgtcctcc     540

accctgaccc tgtccaaggc cgactacgag aagcacaagg tgtacgcctg cgaagtgacc     600

caccagggcc tgtccagccc cgtgaccaag tccttcaacc ggggcgagtg c              651

<210> SEQ ID NO 101
<211> LENGTH: 651
<212> TYPE: DNA
<213> ORGANISM: Artificial Sequence
<220> FEATURE:
<223> OTHER INFORMATION: 10236 gL7 Light Chain nucl. Plus RS

<400> SEQUENCE: 101

gcgatcgaca tgactcagag cccgtccagc ctgtccgcgt ccgtgggaga tcgcgtgact      60

atcacgtgtc aggcctcaca atccattagc tcctggctgg cctggtacca gcagaagcca     120

gggaaggctc cgaagctgct gatctacctg gcctccaccc ttgcctccgg cgtgccttca     180

cggttttctg gatccggctc gggaaccgac ttcaccctca ccatctcgtc gctccaaccc     240

gaggacttcg caacctacta ctgccaacag gggtatacca acagcaacat catcaacacc     300

ttcggtggcg gaactaaggt cgaaatcaag cgtacggtgg ccgctccctc cgtgttcatc     360

ttcccaccct ccgacgagca gctgaagtcc ggcaccgcct ccgtcgtgtg cctgctgaac     420

aacttctacc cccgcgaggc caaggtgcag tggaaggtgg acaacgccct gcagtccggc     480

aactcccagg aatccgtcac cgagcaggac tccaaggaca gcacctactc cctgtcctcc     540

accctgaccc tgtccaaggc cgactacgag aagcacaagg tgtacgcctg cgaagtgacc     600

caccagggcc tgtccagccc cgtgaccaag tccttcaacc ggggcgagtg c              651

<210> SEQ ID NO 102
```

<211> LENGTH: 651
<212> TYPE: DNA
<213> ORGANISM: Artificial Sequence
<220> FEATURE:
<223> OTHER INFORMATION: 10236 gL8 Light chain nucl. Plus RS

<400> SEQUENCE: 102
gcgtatcaga tgactcagag cccgtccagc ctgtccgcgt ccgtgggaga tcgcgtgact 60
atcacgtgtc aggcctcaca atccattagc tcctggctgg cctggtacca gcagaagcca 120
gggaaggctc cgaagctgct gatctacctg gcctccaccc ttgcctccgg cgtgccttca 180
cggttttctg gatccggctc gggaaccgac ttcaccctca ccatctcgtc gctccaaccc 240
gaggacttcg caacctacta ctgccaacag ggtataccaa acagcaacat catcaacacc 300
ttcggtggcg gaactaaggt cgaaatcaag cgtacggtgg ccgctccctc cgtgttcatc 360
ttcccaccct ccgacgagca gctgaagtcc ggcaccgcct ccgtcgtgtg cctgctgaac 420
aacttctacc cccgcgaggc caaggtgcag tggaaggtgg acaacgccct gcagtccggc 480
aactcccagg aatccgtcac cgagcaggac tccaaggaca gcacctactc cctgtcctcc 540
accctgaccc tgtccaaggc cgactacgag aagcacaagg tgtacgcctg cgaagtgacc 600
caccagggcc tgtccagccc cgtgaccaag tccttcaacc ggggcgagtg c 651

<210> SEQ ID NO 103
<211> LENGTH: 651
<212> TYPE: DNA
<213> ORGANISM: Artificial Sequence
<220> FEATURE:
<223> OTHER INFORMATION: 10236 gL6 Light Chain nucl. Q24R Plus RS

<400> SEQUENCE: 103
gcgtatgaca tgactcagag cccgtccagc ctgtccgcgt ccgtgggaga tcgcgtgact 60
atcacgtgtc gggcctcaca atccattagc tcctggctgg cctggtacca gcagaagcca 120
gggaaggctc cgaagctgct gatctacctg gcctccaccc ttgcctccgg cgtgccttca 180
cggttttctg gatccggctc gggaaccgac ttcaccctca ccatctcgtc gctccaaccc 240
gaggacttcg caacctacta ctgccaacag ggtataccaa acagcaacat catcaacacc 300
ttcggtggcg gaactaaggt cgaaatcaag cgtacggtgg ccgctccctc cgtgttcatc 360
ttcccaccct ccgacgagca gctgaagtcc ggcaccgcct ccgtcgtgtg cctgctgaac 420
aacttctacc cccgcgaggc caaggtgcag tggaaggtgg acaacgccct gcagtccggc 480
aactcccagg aatccgtcac cgagcaggac tccaaggaca gcacctactc cctgtcctcc 540
accctgaccc tgtccaaggc cgactacgag aagcacaagg tgtacgcctg cgaagtgacc 600
caccagggcc tgtccagccc cgtgaccaag tccttcaacc ggggcgagtg c 651

<210> SEQ ID NO 104
<211> LENGTH: 651
<212> TYPE: DNA
<213> ORGANISM: Artificial Sequence
<220> FEATURE:
<223> OTHER INFORMATION: 10236 gL6  Light Chain nucl. Q24K Plus RS

<400> SEQUENCE: 104
gcgtatgaca tgactcagag cccgtccagc ctgtccgcgt ccgtgggaga tcgcgtgact 60
atcacgtgta aggcctcaca atccattagc tcctggctgg cctggtacca gcagaagcca 120
gggaaggctc cgaagctgct gatctacctg gcctccaccc ttgcctccgg cgtgccttca 180
cggttttctg gatccggctc gggaaccgac ttcaccctca ccatctcgtc gctccaaccc 240

-continued

```
gaggacttcg caacctacta ctgccaacag gggtatacca acagcaacat catcaacacc    300
ttcggtggcg gaactaaggt cgaaatcaag cgtacggtgg ccgctccctc cgtgttcatc    360
ttcccaccct ccgacgagca gctgaagtcc ggcaccgcct ccgtcgtgtg cctgctgaac    420
aacttctacc cccgcgaggc caaggtgcag tggaaggtgg acaacgccct gcagtccggc    480
aactcccagg aatccgtcac cgagcaggac tccaaggaca gcacctactc cctgtcctcc    540
accctgaccc tgtccaaggc cgactacgag aagcacaagg tgtacgcctg cgaagtgacc    600
caccagggcc tgtccagccc cgtgaccaag tccttcaacc ggggcgagtg c             651
```